US012753415B2

(12) United States Patent
Bate et al.

(10) Patent No.: US 12,753,415 B2
(45) Date of Patent: Oct. 6, 2026

(54) **MODIFICATION OF *BRASSINOSTEROID* RECEPTOR GENES TO IMPROVE YIELD TRAITS**

(71) Applicant: Pairwise Plants Services, Inc., Durham, NC (US)

(72) Inventors: Nicholas Bate, Raleigh, NC (US); Lolita George Mathew, Cary, NC (US); Devin O'Connor, Hillsborough, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 547 days.

(21) Appl. No.: 18/176,514

(22) Filed: Mar. 1, 2023

(65) Prior Publication Data

US 2024/0327858 A1 Oct. 3, 2024

Related U.S. Application Data

(60) Provisional application No. 63/315,646, filed on Mar. 2, 2022.

(51) Int. Cl.

*C12N 15/82* (2006.01)
*C07K 14/415* (2006.01)
*C12N 9/22* (2006.01)
*C12N 15/11* (2006.01)
*C12Q 1/6895* (2018.01)

(52) U.S. Cl.

CPC ........ *C12N 15/8261* (2013.01); *C07K 14/415* (2013.01); *C12N 9/22* (2013.01); *C12N 15/11* (2013.01); *C12N 15/8213* (2013.01); *C12Q 1/6895* (2013.01); *C12N 2310/20* (2017.05); *C12Q 2600/13* (2013.01); *C12Q 2600/156* (2013.01)

(58) Field of Classification Search

None

See application file for complete search history.

(56) References Cited

FOREIGN PATENT DOCUMENTS

| | | |
|---|---|---|
| WO | 2017054721 A1 | 4/2017 |
| WO | 2019076355 A1 | 4/2019 |
| WO | 2023019188 A1 | 2/2023 |

OTHER PUBLICATIONS

Liu, Guanqing, Yong Zhang, and Tao Zhang. "Computational approaches for effective CRISPR guide RNA design and evaluation." Computational and structural biotechnology journal 18 (2020): 35-44. (Year: 2020).*

Sun, Xianjun, et al. "Targeted mutagenesis in soybean using the CRISPR-Cas9 system." Scientific reports 5.1 (2015): 10342. Supplementary Information (Year: 2015).*

GenBank Accession NM_001359015.1 "Glycine max brassinosteroid receptor (BRI1A), mRNA" dated Apr. 29, 2021 https://www.ncbi.nlm.nih.gov/nucleotide/NM_001359015.1?report=genbank&log$=nuclalign&blast_rank=1&RID=ABXTHNSZ013 (Year: 2021).*

Zhang, Xiao-Hui, et al. "Off-target effects in CRISPR/Cas9-mediated genome engineering." Molecular therapy Nucleic acids 4 (2015). (Year: 2015).*

Zhang, Huawei, et al. "Genome editing of upstream open reading frames enables translational control in plants." Nature Biotechnology 36.9 (2018): 894-898. (Year: 2018).*

Sun, Xianjun, et al. "Targeted mutagenesis in soybean using the CRISPR-Cas9 system." Scientific reports 5.1 (2015): 10342. (Year: 2015).*

Zhang, Huawei, et al. "Genome editing of upstream open reading frames enables translational control in plants." Nature Biotechnology 36.9 (2018): 894-898. Supplementary Materials (Year: 2018).*

International Search Report and Written Opinion corresponding to International Application No. PCT/US2023/063415 mailed Jun. 1, 2021, 15 pages.

Divi, Uday K., et al., "Brassinosteroid: a biotechnological target for enhancing crop yield and stress tolerance", New Biotechnology, vol. 26, 2009, 131-136.

Gendron, Joshua M., et al., "Multiple mechanisms modulate Brassinosteroid signaling", Curr Opin Plant Biol. 10(5), 2007, 436-441.

Gruszka, Damian, "Exploring the Brassinosteroid Signaling in Monocots Reveals Novel Components of the Pathway and Implications for Plant Breeding", International journal of molecular sciences 21(1), 2020, 354.

Li, Jianming, et al., "Regulation of brassinosteroid signaling", Plant Science 12(1), 2007, 37-41.

Si, Xiaomin, et al., "Manipulating gene translation in plants by CRISPR-Cas9-mediated genome editing of upstream open reading frames", Nature Protocols vol. 15, No. 2, 2020, 338-363.

Srivastava, Ashish Kumar, et al., "UTR-Dependent Control of Gene Expression in Plants", Trends in Plant Science vol. 23, No. 3, 2017, 248-259.

Wang, Xuelu, et al., "Autoregulation and Homodimerization Are Involved in the Activation of the Plant Steroid Receptor BRI1", Developmental Cell, vol. 8, 2005, 855-865.

Wang, Shufen, et al., "Modification of Threonine-1050 of SlBRI1 regulates BR Signalling and increases fruit yield of tomato", BMC Plant Biology, 2019, 256.

Wu, Guo-Fan, et al., "Identification of Knockout of BRI1 Mutant in *Arabidopsis* Mediated by CRISPR/Cas9", Bulletin of Botanical Research (English Abstract only), 2021, 362-371.

(Continued)

*Primary Examiner* — Amjad Abraham
*Assistant Examiner* — Kelsey L McWilliams
(74) *Attorney, Agent, or Firm* — Myers Bigel, P.A.

(57) ABSTRACT

This invention relates to compositions and methods for modifying Brassinosteroid Insensitive-1 (BRI1) genes in plants, optionally to improve yield traits. The invention further relates to plants having increased improved yield traits produced using the methods and compositions of the invention.

4 Claims, No Drawings

Specification includes a Sequence Listing.

(56) References Cited

OTHER PUBLICATIONS

Yan, Liuhua, "High-efficiency genome editing in *Arabidopsis* using YAO promoter-driven CRISPR/Cas9 system", Molecular Plant, 2015, 1820-1823.

Yeap, Wan-Chin, et al., "An Efficient Clustered Regularly Interspaced Short Palindromic Repeat (CRISPR) / CRISPR-Associated Protein 9 Mutagenesis System for Oil Palm (*Elaeis guineesis*)", Frontiers in Plant Science vol. 12, 2021.

Zhang, Huawei, et al., "Genome editing of upstream open reading frames enables translational control in plants", Nature Biotechnology vol. 36, No. 9, 2018, 896.

* cited by examiner

MODIFICATION OF *BRASSINOSTEROID* RECEPTOR GENES TO IMPROVE YIELD TRAITS

STATEMENT OF PRIORITY

This application claims the benefit, under 35 U.S.C. § 119 (e), of U.S. Provisional Application No. 63/315,646 filed on Mar. 2, 2022, the entire contents of which is incorporated by reference herein.

STATEMENT REGARDING ELECTRONIC FILING OF A SEQUENCE LISTING

A Sequence Listing in XML format, entitled 1499-90_ST26.xml, 298,814 bytes in size, generated on Feb. 15, 2023 and filed herewith, is hereby incorporated by reference into the specification for its disclosures.

FIELD OF THE INVENTION

This invention relates to compositions and methods for modifying Brassinosteroid Insensitive-1 (BRI1) genes in plants, optionally to improve yield traits. The invention further relates to plants having increased improved yield traits produced using the methods and compositions of the invention.

BACKGROUND OF THE INVENTION

Intensive breeding across row crops has led to incremental increases in plant yield. However, genetic gain from breeding has started to plateau and assembling multiple small-effect genes in a breeding program has substantially increased research and development costs. Single gene solutions have been challenging for a complex trait such as yield, where background genetics and environment combine to reduce the impact of individual genes. Breeding has been successful by combining many individual genes with small contributing effects but is requiring greater resources to find unique combinations with improved effects. To increase the rate of yield gain, novel variation needs to be introduced in important genes and pathways that contribute to yield.

Transgenic approaches involving stable transformation to increase yield have largely been unsuccessful and there are no commercially relevant single gene approaches that have successfully created a step change in yield. Modifying hormone related pathways through GM approaches has not been fruitful because the simple over- or under-expression through transgene technology is not consistent with the fine-tuning effect required for improving plant yield.

The present invention addresses these shortcomings in the art by providing new compositions and methods for improving/enhancing yield traits in plants, including soybean, corn and other plant species.

SUMMARY OF THE INVENTION

One aspect of the invention provides a plant or plant part thereof comprising at least one mutation in an endogenous Brassinosteroid Insensitive-1 (BRI1) gene encoding a BRI1 polypeptide (brassinosteroid receptor polypeptide), optionally wherein the at least one mutation is a non-natural mutation.

A second aspect of the invention provides a plant cell, comprising an editing system comprising: (a) a CRISPR-Cas effector protein; and (b) a guide nucleic acid (e.g., gRNA, gDNA, crRNA, crDNA, sgRNA, sgDNA) comprising a spacer sequence with complementarity to an endogenous target gene encoding a Brassinosteroid Insensitive-1 (BRI1) polypeptide (a brassinosteroid receptor polypeptide).

A third aspect of the invention provides a plant cell comprising at least one mutation within an endogenous Brassinosteroid Insensitive-1 (BRI1) gene, wherein the at least one mutation is a substitution, insertion, or deletion that is introduced using an editing system that comprises a nucleic acid binding domain that binds to a target site in the endogenous BRI1 gene, optionally wherein the at least one mutation is a non-natural mutation.

A fourth aspect of the invention provides a method of producing/breeding a transgene-free edited plant, comprising: crossing the plant of the invention with a transgene free plant, thereby introducing the at least one mutation into the plant that is transgene-free; and selecting a progeny plant that comprises the at least one mutation and is transgene-free, thereby producing a transgene free edited plant.

A fifth aspect of the invention provides a method of providing a plurality of plants having one or more improved yield traits, optionally increased seed size (e.g., seed area and/or seed weight) and/or seed oil content, the method comprising planting two or more plants of the invention in a growing area, thereby providing a plurality of plants having one or more improved yield traits as compared to a plurality of control plants not comprising the at least one mutation.

A sixth aspect of the invention provides a method of generating variation in a region of a Brassinosteroid Insensitive-1 (BRI1) polypeptide, comprising: introducing an editing system into a plant cell, wherein the editing system is targeted to a region of a Brassinosteroid Insensitive-1 (BRI1) gene that encodes the region of the BRI1 polypeptide, and contacting the region of the BRI1 gene with the editing system, thereby introducing a mutation into the BRI1 gene and generating variation in the BRI1 polypeptide of the plant cell.

A seventh aspect provides a method for editing a specific site in the genome of a plant cell, the method comprising: cleaving, in a site-specific manner, a target site within an endogenous Brassinosteroid Insensitive-1 (BRI1) gene in the plant cell, the endogenous BRI1 gene: (a) comprising a sequence having at least 80% sequence identity to any one of the nucleotide sequences of SEQ ID NOs: 69, 70, 80, or 81, (b) comprising a region having at least 80% sequence identity to any one of the nucleotide sequences of SEQ ID NOs: 73-79 or 83-95, and/or (c) encoding an amino acid sequence having at least 80% sequence identity to any one of SEQ ID NOs: 71, 72 or 82 thereby generating an edit in the endogenous BRI1 gene of the plant cell and producing a plant cell comprising the edit in the endogenous BRI1 gene.

An eighth aspect provides a method for making a plant, comprising: (a) contacting a population of plant cells comprising an endogenous Brassinosteroid Insensitive-1 (BRI1) gene with a nuclease linked to a nucleic acid binding domain (e.g., editing system) that binds to a sequence (a) contacting a population of plant cells comprising an endogenous Brassinosteroid Insensitive-1 (BRI1) gene with a nuclease linked to a nucleic acid binding domain (e.g., editing system) that binds to a sequence (i) having at least 80% (e.g., 80, 81, 82, 83, 84, 85, 86, 87, 88, 89, 90, 91, 92, 93, 94, 95, 96, 97, 98, 99, or 100%) sequence identity to the nucleotide sequence of any one of SEQ ID NOs: 69, 70, 80 or 81, (ii) encoding an amino acid sequence having at least 80% sequence identity to any one of SEQ ID NOs: 71, 72 or 82, and/or (iii) comprising a region having at least 80% identity to the nucleotide sequence of any one of SEQ ID NOs: 73-79 or 83-95; (b) selecting a plant cell from the population in which an endogenous BRI1 gene has been mutated, thereby producing a plant cell comprising a mutation in the endogenous BRI1 gene; and (c) growing the selected plant cell into a plant.

A ninth aspect provides a method for improving one or more yield traits in a plant, comprising (a) contacting a plant cell comprising an endogenous Brassinosteroid Insensitive-1 (BRI1) gene with a nuclease targeting the endogenous BRI1 gene, wherein the nuclease is linked to a nucleic acid binding domain (e.g., editing system) that binds to a target site in the endogenous BRI1 gene, wherein the endogenous BRI1 gene: (i) comprises a sequence having at least 80% sequence identity to the nucleotide sequence of any one of SEQ ID NOs: 69, 70, 80 or 81; (ii) comprises a region having at least 80% identity to any one of the nucleotide sequences of SEQ ID NOs: 73-79 or 83-95; and/or (iii) encodes an amino acid sequence having at least 80% sequence identity to any one of SEQ ID NOs: 71, 72 or 82, to produce a plant cell comprising a mutation in the endogenous BRI1 gene to produce a plant cell comprising a mutation in the endogenous BRI1 gene; and (b) growing the plant cell into a plant comprising the mutation in the endogenous BRI1 gene, thereby producing a plant having a mutated endogenous BRI1 gene and one or more improved yield traits.

A tenth aspect provides producing a plant or part thereof comprising at least one cell having a mutated endogenous Brassinosteroid Insensitive-1 (BRI1) gene, the method comprising contacting a target site in an endogenous BRI1 gene in the plant or plant part with a nuclease comprising a cleavage domain and a nucleic acid binding domain, wherein the nucleic acid binding domain binds to a target site in the endogenous BRI1 gene, wherein the endogenous BRI1 gene (a) comprises a sequence having at least 80% sequence identity to the nucleotide sequence of any one of SEQ ID NOs: 69, 70, 80, or 81; (b) comprises a region having at least 80% sequence identity to any one of the nucleotide sequences of SEQ ID NOs: 73-79 or 83-95; and/or (c) encodes an amino acid sequence having at least 80% sequence identity to any one of SEQ ID NOs: 71, 72 or 82, thereby producing the plant or part thereof comprising at least one cell having a mutation in the endogenous BRI1 gene.

An eleventh aspect of the invention provides a method for producing a plant or part thereof comprising a mutated endogenous Brassinosteroid Insensitive-1 (BRI1) gene and exhibiting one or more improved yield traits, the method comprising contacting a target site in an endogenous BRI1 gene in the plant or plant part with a nuclease comprising a cleavage domain and a nucleic acid binding domain, wherein the nucleic acid binding domain binds to a target site in the endogenous BRI1 gene, wherein the endogenous BRI1 gene: (a) comprises a sequence having at least 80% sequence identity to the nucleotide sequence of any one of SEQ ID NOs: 69, 70, 80, or 81; (b) comprises a region having at least 80% sequence identity to any one of the nucleotide sequences of SEQ ID NOs: 73-79 or 83-95; and/or (c) encodes an amino acid sequence having at least 80% sequence identity to any one of SEQ ID NOs: 71, 72 or 82, thereby producing the plant or part thereof comprising an endogenous BRI1 gene having a mutation and exhibiting one or more improved yield traits.

A twelfth aspect provides a guide nucleic acid that binds to a target site in a Brassinosteroid Insensitive-1 (BRI1) gene, wherein the target site is in a region of the BRI1 gene located (a) from about nucleotide 2-213, 42-174, 62-154, 82-134, and/or 92-124 with reference to nucleotide position numbering of SEQ ID NO:69 (e.g., SEQ ID NOs: 73-79), and/or (b) from about nucleotide 1-267, 40-227, 70-195 and/or 100-168 with reference to nucleotide position numbering of SEQ ID NO:80 (e.g., SEQ ID NOs: 83-95).

In a thirteenth aspect, a system is provided comprising a guide nucleic acid of the invention and a CRISPR-Cas effector protein that associates with the guide nucleic acid. A system comprising the guide nucleic acid of the invention and a CRISPR-Cas effector protein that associates with the guide nucleic acid.

A fourteenth aspect provides a guide nucleic acid of the invention and a CRISPR-Cas effector protein that associates with the guide nucleic acid.

A fifteenth aspect provides a gene editing system comprising a CRISPR-Cas effector protein in association with a guide nucleic acid, wherein the guide nucleic acid comprises a spacer sequence that binds to an endogenous Brassinosteroid Insensitive-1 (BRI1) gene.

In a sixteenth aspect, a complex comprising a guide nucleic acid and a CRISPR-Cas effector protein comprising a cleavage domain is provided, wherein the guide nucleic acid binds to a target site in an endogenous Brassinosteroid Insensitive-1 (BRI1) gene, wherein the endogenous BRI1 gene: (a) comprises a sequence having at least 80% sequence identity to the nucleotide sequence of any one of SEQ ID NOs: 69, 70, 80, or 81; (b) comprises a region having at least 80% identity to the nucleotide sequence of any one of SEQ ID NOs: 73-79 or 83-95; and/or (c) encodes an amino acid sequence having at least 80% sequence identity to any one of SEQ ID NOs: 71, 72 or 82, wherein the cleavage domain cleaves a target strand in the BRI1 gene.

In a seventeenth aspect, an expression cassette is provided, the expression cassette comprising (a) a polynucleotide encoding CRISPR-Cas effector protein comprising a cleavage domain and (b) a guide nucleic acid that binds to a target site in an endogenous Brassinosteroid Insensitive-1 (BRI1) gene, wherein the guide nucleic acid comprises a spacer sequence that is complementary to and binds to (i) a portion of a nucleic acid having at least 80% sequence identity to any one of the nucleotide sequences of SEQ ID NOs: 69, 70, 80, or 81; (ii) a portion of a nucleic acid having at least 80% sequence identity to any one of SEQ ID NOs: 73-79 or 83-95; and/or (iii) a portion of a nucleic acid encoding an amino acid sequence having at least 80% sequence identity to any one of SEQ ID NOs: 71, 72 or 82.

In an eighteenth aspect, a nucleic acid encoding a hypomorphic mutation, a dominant mutation, and/or a semi-dominant mutation of a Brassinosteroid Insensitive-1 (BRI1) polypeptide is provided.

In a nineteenth aspect, a mutated endogenous BRI1 gene is provided that is produced by contacting a target site in an endogenous BRI1 gene in the plant or plant part with a nuclease comprising a cleavage domain and a nucleic acid binding domain, wherein the nucleic acid binding domain binds to a target site in the endogenous BRI1 gene, wherein the endogenous BRI1 gene: (a) comprises a sequence having at least 80% sequence identity to the nucleotide sequence of any one of SEQ ID NOs: 69, 70, 80, or 81; (b) comprises a region having at least 80% identity to any one of SEQ ID NOs: 73-79 or 83-95; and/or (c) encodes an amino acid sequence having at least 80% sequence identity to any one of SEQ ID NOs: 71, 72 or 82.

In another aspect, plants are provided that comprise in their genome one or more mutated Brassinosteroid Insensitive-1 (BRI1) genes produced by the methods of the invention.

A further aspect of the invention provides a corn plant or plant part thereof comprising at least one mutation in at least one endogenous Brassinosteroid Insensitive-1 (BRI1) gene having the gene identification number (gene ID) of GRMZM6G437417.

In an additional aspect, a soybean plant or plant part thereof is provided the soybean plant comprising at least one mutation in at least one endogenous Brassinosteroid Insensitive-1 (BRI1) gene having the gene identification number (gene ID) of Glyma.06g147600 and/or Glyma.04g218300

In a further aspect, a guide nucleic acid is provided that binds to a target nucleic acid within a Brassinosteroid Insensitive-1 (BRI1) gene having the gene identification number (gene ID) of Glyma.06g147600 and/or Glyma.04g218300. Another aspect of the invention provides a nucleic acid comprising a mutated Brassinosteroid Insensitive-1 (BRI1) gene, optionally wherein the at least one mutation disrupts an upstream open reading frame (uORF) (in a cis-regulatory element, e.g., in a promoter region) of the endogenous BRI1 gene.

A further aspect provides a mutated nucleic acid encoding a Brassinosteroid Insensitive-1 (BRI1) polypeptide, optionally wherein the mutation is in a cis-regulatory region of the BRI1 gene, wherein the mutation results in the BRI1 gene having increased expression, optionally wherein the mutated BRI1 gene comprises at least 90% sequence identity to any one of SEQ ID NOs: 101-117.

Further provided are plants comprising in their genome one or more Brassinosteroid Insensitive-1 (BRI1) genes having a mutation produced by the methods of the invention, optionally wherein the plant has a phenotype of one or more improved yield traits as compared to a plant devoid of the at least one mutation.

Further provided are polypeptides, polynucleotides, nucleic acid constructs, expression cassettes and vectors for making a plant of this invention.

These and other aspects of the invention are set forth in more detail in the description of the invention below.

BRIEF DESCRIPTION OF THE SEQUENCES

SEQ ID NOs: 1-17 are exemplary Cas12a amino acid sequences useful with this invention.

SEQ ID NOs: 18-20 are exemplary Cas12a nucleotide sequences useful with this invention.

SEQ ID NO:21-22 are exemplary regulatory sequences encoding a promoter and intron.

SEQ ID NOs: 23-29 are exemplary cytosine deaminase sequences useful with this invention.

SEQ ID NOs: 30-40 are exemplary adenine deaminase amino acid sequences useful with this invention.

SEQ ID NO:41 is an exemplary uracil-DNA glycosylase inhibitor (UGI) sequences useful with this invention.

SEQ ID NOs: 42-44 provide example peptide tags and affinity polypeptides useful with this invention.

SEQ ID NOs: 45-55 provide example RNA recruiting motifs and corresponding affinity polypeptides useful with this invention.

SEQ ID NOs: 56-57 are exemplary Cas9 polypeptide sequences useful with this invention.

SEQ ID NOs: 58-68 are exemplary Cas9 polynucleotide sequences useful with this invention.

SEQ ID NO:69 and SEQ ID NO:80 are example BRI1 genomic sequences from soybean.

SEQ ID NO:70 and SEQ ID NO:81 are example BRI1 coding sequences from soybean.

SEQ ID NOs: 71, 72 and 82 are example BRI1 polypeptide sequences from soybean.

SEQ ID NOs: 73-79 and SEQ ID NOs: 83-95 are example portions or regions of soybean BRI1 genomic and coding sequences from SEQ ID NO:69 and SEQ ID NO:80, respectively.

SEQ ID NOs: 96-100 are example spacer sequences for nucleic acid guides useful with this invention.

SEQ ID NOs: 101-117 are example edited BRI1 genes.

DETAILED DESCRIPTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise. For example, "a uORF" can mean one or more uORFs.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 5%, 10%, 15%, 20%, 25%, 50%, 75%, 100%, 150%, 200%, 300%, 400%, 500% or more as compared to a control. For example, a plant comprising a mutation in a Brassinosteroid Insensitive-1 (BRI1) gene as described herein can exhibit an improved yield trait (e.g., one or more improved yield traits; e.g., optionally increased seed size (e.g., seed area and/or seed weight) and/or increased seed oil content and) that is at least about 5% or greater than that of a control plant not comprising the same mutation. A control plant is typically the same plant as the edited plant, but the control plant has not been similarly edited and therefore is devoid of the mutation. A control plant maybe an isogenic plant and/or a wild type plant. Thus, a control plant can be the same breeding line, variety, or cultivar as the subject plant into which a mutation as described herein is introgressed, but the control breeding line, variety, or cultivar is free of the mutation. In some embodiments, a comparison between a plant of the invention and a control plant is made under the same growth conditions, e.g., the same environmental conditions (soil, hydration, light, heat, nutrients, and the like).

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In particular embodiments, the reduction can result in no or essentially no (i.e., an insignificant amount, e.g., less than about 10% or even 5%) detectable activity or amount.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

A "heterologous" or a "recombinant" nucleotide sequence is a nucleotide sequence not naturally associated with a host cell into which it is introduced, including non-naturally occurring multiple copies of a naturally occurring nucleotide sequence. A "heterologous" nucleotide/polypeptide may originate from a foreign species, or, if from the same species, is substantially modified from its native form in composition and/or genomic locus by deliberate human intervention.

A "native" or "wild type" nucleic acid, nucleotide sequence, polypeptide or amino acid sequence refers to a naturally occurring or endogenous nucleic acid, nucleotide sequence, polypeptide or amino acid sequence. In some contexts, a "wild type" nucleic acid is a nucleic acid that is not edited as described herein and can differ from an "endogenous" gene that may be edited as described herein (e.g., a mutated endogenous gene). In some contexts, a "wild type" nucleic acid (e.g., unedited) may be heterologous to the organism in which the wild type nucleic acid is found (e.g., a transgenic organism). As an example, a "wild type endogenous Brassinosteroid Insensitive-1 (BRI1) gene" is a BRI1 gene that is naturally occurring in or endogenous to the reference organism, e.g., a plant, e.g., a soybean plant, a maize plant, and may be subject to modification as described herein, after which, such a modified endogenous gene is no longer wild type.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "null allele" is a nonfunctional allele caused by a genetic mutation that results in a complete lack of production of the corresponding protein or produces a protein that is nonfunctional.

A "recessive mutation" is a mutation in a gene that produces a phenotype when homozygous but the phenotype is not observable when the locus is heterozygous.

A "dominant mutation" is a mutation in a gene that produces a mutant phenotype in the presence of a non-mutated copy of the gene. A dominant mutation may be a loss or a gain of function mutation, a hypomorphic mutation, a hypermorphic mutation or a weak loss of function or a weak gain of function.

A "dominant negative mutation" is a mutation that produces an altered gene product (e.g., having an aberrant function relative to wild type), which gene product adversely affects the function of the wild-type allele or gene product. For example, a "dominant negative mutation" may block a function of the wild type gene product. A dominant negative mutation may also be referred to as an "antimorphic mutation."

A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wildtype gene product.

A "hypomorphic mutation" is a mutation that results in a partial loss of gene function, which may occur through reduced expression (e.g., reduced protein and/or reduced RNA) or reduced functional performance (e.g., reduced activity), but not a complete loss of function/activity. A "hypomorphic" allele is a semi-functional allele caused by a genetic mutation that results in production of the corresponding protein that functions at anywhere between 1% and 99% of normal efficiency.

A "hypermorphic mutation" is a mutation that results in increased expression of the gene product and/or increased activity of the gene product.

As used herein, a "non-natural mutation" refers to a mutation that is generated though human intervention and differs from mutations found in the same gene that have occurred in nature (e.g., occurred naturally).

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one (e.g., one or more) progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms "cultivar" and "variety" refer to a group of similar plants that by structural or genetic features and/or performance can be distinguished from other varieties within the same species.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterologous" refers to a nucleotide/polypeptide that originates from a foreign species, or, if from the same species, is substantially modified from its native form in composition and/or genomic locus by deliberate human intervention.

A plant in which at least one (e.g., one or more, e.g., 1, 2, 3, or 4, or more) endogenous BRI1 gene is modified as described herein (e.g., comprises a modification as described herein) may have improved yield traits as compared to a plant that does not comprise the modification in the at least one BRI1 gene. As used herein, "improved yield traits" refers to any plant trait associated with growth, for example, biomass, yield, nitrogen use efficiency (NUE), inflorescence size/weight, fruit yield, fruit quality, fruit size, seed size (e.g., seed area, seed size), seed number, foliar tissue weight, nodulation number, nodulation mass, nodulation activity, number of seed heads, number of tillers, number of branches, number of flowers, number of tubers, tuber mass, bulb mass, number of seeds, total seed mass, rate of leaf emergence, rate of tiller/branch emergence, rate of seedling emergence, length of roots, number of roots, size and/or weight of root mass, or any combination thereof. Thus, in some aspects, "improved yield traits" may include, but is not limited to, increased inflorescence production, increased fruit production (e.g., increased number, weight and/or size of fruit), increased fruit quality, increased number, size and/or weight of roots, increased meristem size, increased seed size (e.g., seed area and/or seed weight), increased biomass, increased leaf size, increased nitrogen use efficiency, increased height, increased internode number and/or increased internode length as compared to a control plant or part thereof (e.g., a plant that does not comprise a mutated endogenous BRI1 nucleic acid (e.g., a mutated BRI1 gene)). In some aspects, improved yield traits can be expressed as quantity of grain produced per area of land (e.g., bushels per acre of land).

As used herein, an "increased yield" can mean an increase of at least 15% to about 100% (e.g., at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%), as compared to a control plant that is devoid of a mutation in an endogenous BRI1 gene as described herein. Increased yield may be evaluated according to any of the improved yield traits described herein, including, but not limited to, higher yield (bu/acre), increased biomass, increased plant height, increased stem diameter, increased leaf area, increased number of flowers, increased number of pods per node, increased number of pods per plant, increase number of seeds, increased number of seeds per pod, increased seed size, and/or increased seed weight (e.g., increase in 100-seed weight. In some embodiments, the increase in yield may be observed in a plant comprising a mutation in an endogenous BRI1 gene as described herein when the plant is experiencing abiotic stress such as when growing under conditions of drought, shade and/or low nitrogen as compared to a control plant growing under the same conditions but devoid of the mutation in an endogenous BRI1 gene.

As used herein, an "increased seed size" can mean a seed that is increased in area. In some embodiments, an seed may be increased in area by up to about 70% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, 50, 51, 52, 53, 54, 55, 56, 57, 58, 59, 60, 61, 62, 63, 64, 65, 66, 67, 68, 69, 70%) as compared to a seed from a control plant (e.g., a plant not comprising the mutation in an endogenous BRI1 gene as described herein). In some embodiments, an seed may be increased in weight by up to about 50% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, or 50%) as compared to a seed from a control plant (e.g., a plant not comprising the mutation in an endogenous BRI1 gene as described herein). In some embodiments, an increase in seed size can include an increase in both seed area and seed size.

As used herein a "control plant" means a plant that does not contain an edited BRI1 gene or genes as described herein that imparts an enhanced/improved trait (e.g., yield trait) or altered phenotype. A control plant is used to identify and select a plant edited as described herein and that has an enhanced trait or altered phenotype as compared to the control plant. A suitable control plant can be a plant of the parental line used to generate a plant comprising a mutated BRI1 gene(s), for example, a wild type plant devoid of an edit in an endogenous BRI1 gene as described herein. A suitable control plant can also be a plant that contains recombinant nucleic acids that impart other traits, for example, a transgenic plant having enhanced herbicide tolerance. A suitable control plant can in some cases be a progeny of a heterozygous or hemizygous transgenic plant line that is devoid of the mutated BRI1 gene as described herein, known as a negative segregant, or a negative isogenic line.

An enhanced trait (e.g., improved yield trait) may include, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, increased yield, increased nitrogen use efficiency, and increased water use efficiency as compared to a control plant. An altered phenotype may be, for example, plant height, biomass, canopy area, anthocyanin content, chlorophyll content, water applied, water content, and water use efficiency.

In some embodiments, a plant of this invention may comprise one or more improved yield traits including, but not limited to, higher yield (bu/acre), increased biomass, increased plant height, increased stem diameter, increased leaf area, increased number of flowers, increased number of pods, including an increased number of pods per node and/or an increased number of pods per plant, increased number of seeds per pod, increase number of seeds, increased seed size, and/or increased seed weight (e.g., increase in 100-seed weight) as compared to a control plant devoid of the at least one mutation As used herein a "trait" is a physiological, morphological, biochemical, or physical characteristic of a plant or particular plant material or cell. In some instances, this characteristic is visible to the human eye and can be measured mechanically, such as seed or plant size, weight, shape, form, length, height, growth rate and development stage, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. However, any technique can be used to measure the amount of, the comparative level of, or the difference in any selected chemical compound or macromolecule in the transgenic plants.

As used herein an "enhanced trait" means a characteristic of a plant resulting from mutations in a BRI1 gene(s) as described herein. Such traits include, but are not limited to, an enhanced agronomic trait characterized by enhanced plant morphology, physiology, growth and development, yield, nutritional enhancement, disease or pest resistance, or environmental or chemical tolerance. In some embodiments, an enhanced trait/altered phenotype may be, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, drought tolerance, increased water use efficiency, cold tolerance, increased nitrogen use efficiency, and increased yield. In some embodiments, a trait is increased yield under nonstress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, ear size, ear tip filling, kernel abortion, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), flowering time and duration, ear number, ear size, ear weight, seed number per ear or pod, seed size, composition of seed (starch, oil, protein) and characteristics of seed fill.

Also used herein, the term "trait modification" encompasses altering the naturally occurring trait by producing a detectable difference in a characteristic in a plant comprising a mutation in an endogenous BRI1 gene as described herein relative to a plant not comprising the mutation, such as a wild-type plant, or a negative segregant. In some cases, the trait modification can be evaluated quantitatively. For example, the trait modification can entail an increase or decrease in an observed trait characteristics or phenotype as compared to a control plant. It is known that there can be natural variations in a modified trait. Therefore, the trait modification observed entails a change of the normal distribution and magnitude of the trait characteristics or phenotype in the plants as compared to a control plant.

The present disclosure relates to a plant with improved economically relevant characteristics, more specifically increased yield. More specifically the present disclosure relates to a plant comprising a mutation(s) in a BRI1 gene(s) as described herein, wherein the plant has increased yield as compared to a control plant devoid of said mutation(s). In some embodiments, plants produced as described herein exhibit increased yield or improved yield trait components as compared to a control plant. In some embodiments, a plant of the present disclosure exhibits an improved trait that is related to yield, including but not limited to increased nitrogen use efficiency, increased nitrogen stress tolerance, increased water use efficiency and increased drought tolerance, as defined and discussed infra.

Yield can be defined as the measurable produce of economic value from a crop. Yield can be defined in the scope of quantity and/or quality. Yield can be directly dependent on several factors, for example, the number and size of organs, plant architecture (such as the number of branches, plant biomass, e.g., increased root biomass, steeper root angle and/or longer roots, and the like), flowering time and duration, grain fill period. Root architecture and development, photosynthetic efficiency, nutrient uptake, stress tolerance, early vigor, delayed senescence and functional stay green phenotypes may be factors in determining yield. Optimizing the above-mentioned factors can therefore contribute to increasing crop yield.

Reference herein to an increase/improvement in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens.

"Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination.

"Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor, for example, can be a combination of the ability of seeds to germinate and emerge after planting and the ability of the young plants to grow and develop after emergence. Plants having early vigor also show increased seedling survival and better establishment of the crop, which often results in highly uniform fields with the majority of the plants reaching the various stages of development at substantially the same time, which often results in increased yield. Therefore, early vigor can be determined by measuring various factors, such as kernel weight, percentage germination, percentage emergence, seedling growth, seedling height, root length, root and shoot biomass, canopy size and color and others.

Further, increased yield can also manifest as increased total seed yield, which may result from one or more of an increase in seed biomass (seed weight) due to an increase in the seed weight on a per plant and/or on an individual seed basis an increased number of, for example, flowers/panicles per plant; an increased number of pods; an increased number of nodes; an increased number of flowers ("florets") per panicle/plant; increased seed fill rate; an increased number of filled seeds; increased seed size (length, width, area, perimeter, and/or weight), which can also influence the composition of seeds; and/or increased seed volume, which can also influence the composition of seeds. In one embodiment, increased yield can be increased seed yield, for example, increased seed weight; increased number of filled seeds; and increased harvest index.

Increased yield can also result in modified architecture, or can occur because of modified plant architecture.

Increased yield can also manifest as increased harvest index, which is expressed as a ratio of the yield of harvestable parts, such as seeds, over the total biomass The disclosure also extends to harvestable parts of a plant such as, but not limited to, seeds, leaves, fruits, flowers, bolls, pods, siliques, nuts, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Typically, plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein, "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein, "water deficit" refers to the conditions or environments that provide less than optimal amounts of water needed for adequate/successful growth and development of plants.

As used herein, "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein with respect to nucleic acids, the term "fragment" or "portion" refers to a nucleic acid that is reduced in length relative (e.g., reduced by 1, 2, 3, 4, 5, 6, 7, 8, 9, 10, 11, 12, 13, 14, 15, 16, 17, 18, 19, 20, 20, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, or 900 or more nucleotides or any range or value therein) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a "portion" of a wild type CRISPR-Cas repeat sequence (e.g., a wild type CRISPR-Cas repeat; e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like).

In some embodiments, a nucleic acid fragment may comprise, consist essentially of or consist of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 285, 290, or 300 or more consecutive nucleotides, or any range or value therein, of a BRI1 nucleic acid, optionally a fragment of a BRI1 gene may be about 20, 21, 22, 23, 24, 25, 26, 27, 28, 29, 30, 31, 32, 33, 34, 35, 36, 37, 38, 39, 40, 41, 42, 43, 44, 45, 50, 51, 52, 53, 54, 55, 56, 57, 58, 59, 60, 61, 62, 63, 65, 65, 66, 67, 68, 69, 70, 75, 76, 77, 78, 79, 80, 85, 90, 91, 92, 93, 94, 95, 96, 97, 98, 99, 100, 105, 110, 115, 120, 121, 122, 123, 124, 125, 126, 127, 128, 129, 130, 131, 132, 133, 134, 135, 136, 137, 138, 139, 140, 145, 150, 155, 160, 165, 170, 175, 180, 181, 182, 183, 184, 185, 186, 187, 188, 189, 190, 195, 200, 205, 210, 211, 212, 213, 214, 215, 216, 217, 218, 219, 220, 225, 230, 235, 240, 245, 250, 255, 260, 261, 262, 263, 264, 265, 266, 267, 268, 269, or 270 or more consecutive nucleotides in length, or any range or value therein (e.g., a fragment or portion of any one of SEQ ID NOs: 69, 70, 80, or 81 (e.g., SEQ ID NOs: 73-79 or 83-95).

In some embodiments, a "sequence-specific nucleic acid binding domain" may bind to one or more fragments or portions of nucleotide sequences (e.g., DNA, RNA) encoding, for example, BRI1 polypeptides as described herein.

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, a polypeptide fragment may comprise, consist essentially of or consist of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 260, 270, 280, or 290 or more consecutive amino acids of a reference polypeptide.

In some embodiments, a deletion when comprised in a plant can result in the plant exhibiting one or more improved yield traits, as compared to a plant not comprising said deletion. A BRI1 gene may be edited in one or more than one location (and using one or more different editing tools), thereby providing a BRI1 gene comprising one or more than one mutation.

In some embodiments, a "portion" in reference to a nucleic acid means at least 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 141, 142, 143, 144, 145, 150, 160, 170, 180, 190, 200, 210, 220, 221, 222, 223, 224, 225, 230, 240, 250, 260, or 270 or more consecutive nucleotides from a gene (e.g., consecutive nucleotides from a BRI1 gene) (e.g., a fragment or portion of any one of SEQ ID NOs: 69, 70, 80, or 81 (e.g., SEQ ID NOs: 73-79 or 83-95).

As used herein with respect to nucleic acids, the term "functional fragment" refers to nucleic acid that encodes a functional fragment of a polypeptide. A "functional fragment" with respect to a polypeptide is a fragment of a polypeptide that retains one or more of the activities of the native reference polypeptide.

The term "gene," as used herein, refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, inversions and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue. A truncation can include a truncation at the C-terminal end of a polypeptide or at the N-terminal end of a polypeptide. A truncation of a polypeptide can be the result of a deletion of the corresponding 5' end or 3' end of the gene encoding the polypeptide. A frameshift mutation can occur when deletions or insertions of one or more base pairs are introduced into a gene, optionally resulting in an out-of-frame mutation or an in-frame mutation. Frameshift mutations in a gene can result in the production of a polypeptide that is longer, shorter or the same length as the wild type polypeptide depending on when the first stop codon occurs following the mutated region of the gene. As an example, an out-of-frame mutation that produces a premature stop codon can produce a polypeptide that is shorter that the wild type polypeptide, or, in some embodiments, the polypeptide may be absent/undetectable. In some embodiments, a mutation may be a DNA inversion, optionally a DNA inversion having a length of about 10 to about 2000 consecutive base pairs.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity) to the comparator nucleotide sequence.

Different nucleic acids or proteins having homology are referred to herein as "homologues." The term homologue includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994);

*Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent sequence identity" can refer to the percentage of identical amino acids in an amino acid sequence as compared to a reference polypeptide.

As used herein, the phrase "substantially identical," or "substantial identity" in the context of two nucleic acid molecules, nucleotide sequences, or polypeptide sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, about 100 nucleotides to about 200 nucleotides, about 100 nucleotides to about 300 nucleotides, about 100 nucleotides to about 400 nucleotides, about 100 nucleotides to about 500 nucleotides, about 100 nucleotides to about 600 nucleotides, about 100 nucleotides to about 800 nucleotides, about 100 nucleotides to about 900 nucleotides, or more in length, or any range therein, up to the full length of the sequence. In some embodiments, nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40, 50, 60, 70, or 80 nucleotides or more).

In some embodiments of the invention, the substantial identity exists over a region of consecutive amino acid residues of a polypeptide of the invention that is about 3 amino acid residues to about 20 amino acid residues, about 5 amino acid residues to about 25 amino acid residues, about 7 amino acid residues to about 30 amino acid residues, about 10 amino acid residues to about 25 amino acid residues, about 15 amino acid residues to about 30 amino acid residues, about 20 amino acid residues to about 40 amino acid residues, about 25 amino acid residues to about 40 amino acid residues, about 25 amino acid residues to about 50 amino acid residues, about 30 amino acid residues to about 50 amino acid residues, about 40 amino acid residues to about 50 amino acid residues, about 40 amino acid residues to about 70 amino acid residues, about 50 amino acid residues to about 70 amino acid residues, about 60 amino acid residues to about 80 amino acid residues, about 70 amino acid residues to about 80 amino acid residues, about 90 amino acid residues to about 100 amino acid residues, or more amino acid residues in length, and any range therein, up to the full length of the sequence. In some embodiments, polypeptide sequences can be substantially identical to one another over at least about 8 consecutive amino acid residues (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, 300, 350 or more amino acids in length or more consecutive amino acid residues). In some embodiments, two or more BRI1 polypeptides may be identical or substantially identical (e.g., at least 70% to 99.9% identical, e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% identical or any range or value therein) over at least 10 amino acids to about 350 amino acids or more.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG WISCONSIN PACKAGER (Accelrys Inc., San Diego, CA) software suite for sequence analysis. An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent and are different under different environmental parameters. An extensive guide to the hybridization of nucleic acids is found in Tijssen *Laboratory Techniques in Biochemistry and Molecular Biology—Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention (e.g., expression cassettes and/or vectors) may be codon optimized for expression. In some embodiments, the polynucleotides, nucleic acid constructs, expression cassettes, and/or vectors of the editing systems of the invention (e.g., comprising/encoding a sequence-specific nucleic acid binding domain (e.g., a sequence-specific nucleic acid binding domain (e.g., DNA binding domain) from a polynucleotide-guided endonuclease, a zinc finger nuclease, a transcription activator-like effector nuclease (TALEN), an Argonaute protein, and/or a CRISPR-Cas endonuclease (e.g., CRISPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, the codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acids, polynucleotides, expression cassettes, and/or vectors that have not been codon optimized.

In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a nucleic acid binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

As used herein, the term "linked," or "fused" in reference to polynucleotides, refers to the attachment of one polynucleotide to another. In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides. In some embodiments, a polynucleotide motif of a certain structure may be inserted within another polynucleotide sequence (e.g., extension of the hairpin structure in the guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in *Genetic Engineering of Plants*, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. Gene 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. Gene 403:132- 142 (2007)) and Pdca1 is induced by salt (Li et al. *Mol Biol. Rep.* 37:1143-1154 (2010)). In some embodiments, a promoter useful with this invention is RNA polymerase II (Pol II) promoter. In some embodiments, a U6 promoter or a 7SL promoter from *Zea mays* may be useful with constructs of this invention. In some embodiments, the U6c promoter and/or 7SL promoter from *Zea mays* may be useful for driving expression of a guide nucleic acid. In some embodiments, a U6c promoter, U6i promoter and/or 7SL promoter from *Glycine max* may be useful with constructs of this invention. In some embodiments, the U6c promoter, U6i promoter and/or 7SL promoter from *Glycine max* may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) Nature 313:810-812), CaMV 19S promoter (Lawton et al. (1987) *Plant Mol. Biol.* 9:315-324), nos promoter (Ebert et al. (1987) Proc. Natl. Acad. Sci USA 84:5745-5749), Adh promoter (Walker et al. (1987) *Proc. Natl. Acad. Sci. USA* 84:6624-6629), sucrose synthase promoter (Yang & Russell (1990) Proc. Natl. Acad. Sci. USA 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79:87-94), maize (Christensen et al., 1989. *Plant Molec. Biol.* 12:619-632), and *Arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231:150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP U.S. Pat. No. 255,378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9 (5): 297-306 (2015)), ZmSTK2_USP from maize (Wang et al. *Genome* 60 (6): 485-495 (2017)), LAT52 and LAT59 from tomato (Twell et al. *Development* 109 (3): 705-713 (1990)), Zm13 (U.S. Pat. No. 10,421,972), PLA2-8 promoter from *Arabidopsis* (U.S. Pat. No. 7,141,424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37 (8): 1108-1115), corn light harvesting complex promoter (Bansal et al. (1992) Proc. Natl. Acad. Sci. USA 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) Mol. Gen. Genet. 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), petunia chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron (see, e.g., SEQ ID NO:21 and SEQ ID NO:22).

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a one or more polynucleotides of the invention (e.g., a polynucleotide encoding a sequence-specific nucleic acid binding domain, a polynucleotide encoding a deaminase protein or domain, a polynucleotide encoding a reverse transcriptase protein or domain, a polynucleotide encoding a 5'-3' exonuclease polypeptide or domain, a guide nucleic acid and/or reverse transcriptase (RT) template), wherein polynucleotide(s) is/are operably associated with one or more control sequences (e.g., a promoter, terminator and the like). Thus, in some embodiments, one or more expression cassettes may be provided, which are designed to express, for example, a nucleic acid construct of the invention (e.g., a polynucleotide encoding a sequence-specific nucleic acid binding domain, a polynucleotide encoding a nuclease polypeptide/domain, a polynucleotide encoding a deaminase protein/domain, a polynucleotide encoding a reverse transcriptase protein/domain, a polynucleotide encoding a 5'-3' exonuclease polypeptide/domain, a polynucleotide encoding a peptide tag, and/or a polynucleotide encoding an affinity polypeptide, and the like, or comprising a guide nucleic acid, an extended guide nucleic acid, and/or RT template, and the like). When an expression cassette of the present invention comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter, or they may be different promoters. Thus, a polynucleotide encoding a sequence specific nucleic acid binding domain, a polynucleotide encoding a nuclease protein/domain, a polynucleotide encoding a CRISPR-Cas effector protein/domain, a polynucleotide encoding an deaminase protein/domain, a polynucleotide encoding a reverse transcriptase polypeptide/domain (e.g., RNA-dependent DNA polymerase), and/or a polynucleotide encoding a 5'-3' exonuclease polypeptide/domain, a guide nucleic acid, an extended guide nucleic acid and/or RT template when comprised in a single expression cassette may each be operably linked to a single promoter, or separate promoters in any combination.

An expression cassette comprising a nucleic acid construct of the invention may be chimeric, meaning that at least one (e.g., one or more) of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to, for example, a gene encoding a sequence-specific nucleic acid binding protein, a gene encoding a nuclease, a gene encoding a reverse transcriptase, a gene encoding a deaminase, and the like, or may be native to a host cell, or may be native to another source (e.g., foreign or heterologous to, for example, to a promoter, to a gene encoding a sequence-specific nucleic acid binding protein, a gene encoding a nuclease, a gene encoding a reverse transcriptase, a gene encoding a deaminase, and the like, or to the host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct (e.g., expression cassette(s)) comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g., autonomous replicating plasmid with an origin of replication). Additionally, included are shuttle vectors by which is meant a DNA vehicle capable, naturally or by design, of replication in two different host organisms, which may be selected from actinomycetes and related species, bacteria and eukaryotic (e.g., higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid or polynucleotide of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific nucleic acid binding protein (e.g., polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein)) and a deaminase or a nucleic acid construct encoding the same, under conditions whereby the sequence-specific nucleic acid binding protein, the reverse transcriptase and/or the deaminase are expressed and the sequence-specific nucleic acid binding protein binds to the target nucleic acid, and the reverse transcriptase and/or deaminase may be fused to either the sequence-specific nucleic acid binding protein or recruited to the sequence-specific nucleic acid binding protein (via, for example, a peptide tag fused to the sequence-specific nucleic acid binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions, and also RNA-protein interactions and chemical interactions may be used for protein-protein and protein-nucleic acid recruitment.

As used herein, “modifying” or “modification” in reference to a target nucleic acid includes editing (e.g., mutating), covalent modification, exchanging/substituting nucleic acids/nucleotide bases, deleting, cleaving, nicking, and/or altering transcriptional control of a target nucleic acid. In some embodiments, a modification may include one or more single base changes (SNPs) of any type.

“Introducing,” “introduce,” “introduced” (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms “transformation” or transfection” may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention. In some embodiments, a host cell or host organism may be transiently transformed with a polynucleotide/nucleic acid molecule of the invention.

“Transient transformation” in the context of a polynucleotide means that a polynucleotide is introduced into the cell and does not integrate into the genome of the cell.

By “stably introducing” or “stably introduced” in the context of a polynucleotide introduced into a cell is intended that the introduced polynucleotide is stably incorporated into the genome of the cell, and thus the cell is stably transformed with the polynucleotide.

“Stable transformation” or “stably transformed” as used herein means that a nucleic acid molecule is introduced into a cell and integrates into the genome of the cell. As such, the integrated nucleic acid molecule is capable of being inherited by the progeny thereof, more particularly, by the progeny of multiple successive generations. “Genome” as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)). General guides to various plant transformation methods known in the art include Miki et al. (“Procedures for Introducing Foreign DNA into Plants” in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via *Agrobacterium* transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

Phytohormones regulate plant growth and development as well as responses to the changes in the growing environment (for example in response to drought or other abiotic stresses). Phytohormone signals can be modulated through biosynthesis or breakdown of the phytohormone at a metabolic level, or through control of phytohormone signaling. Brassinosteroids are a class of polyhydroxylated steroidal phytohormones that are growth promoting phytohormones in plants. Brassinolide was the first brassinosteroid isolated, and since then, over 70 additional brassinosteroid compounds have been isolated from plants. Brassinosteroid phytohormones have been associated with yield and abiotic stress in plants (Divi and Krishna 2009 *New Biotechnology* 26 (3-4), 131-136; Gruszka 2020 *Intl. J. Molecular Sci.* 21 (1), 354. Brassinosteroid signaling in plants is tightly controlled by multiple layers of transcriptional and post-transcriptional regulation (Li and Jin 2007 *Trends Plant Sci.* 12 (1): 37-41; Gendron and Wang 2007 *Curr. Opin. Plant Biol.* 10 (5), 436-441).

The present invention is directed to modification of a brassinosteroid gene, Brassinosteroid Insensitive-1 (BRI1), in plants through editing technology to provide plants that exhibit one or more improved yield traits. Mutations that may be useful for producing plants with one or more improved yield traits include, for example, substitutions, deletions, and/or insertions. In some aspects, a mutation generated by the editing technology can be a point mutation. In some embodiments, the BRI1 polypeptide comprises a cis-regulatory region (e.g., a promoter region comprising one or more upstream open reading frames (uORFs)) in which a mutation is generated, optionally wherein the mutation increases expression of the BRI1 gene. A mutation in at least one upstream open reading frame (uORF) within a promoter region or a cis-regulator region of a BRI1 gene as described herein results in increased expression of the BRI1 gene by disrupting the inhibition of the expression of the BRI1 gene associated with the uORFs. Without wishing to be limited by any particular theory, the increased expression of BRI1 gene may lead to enhanced binding of BR hormone and thus efficient intracellular phosphorylation relay cascade. This in turn may promote the activity and stability of the plant-specific transcription factors BZR1 (BRASSINAZOLE RESISTANT 1) and BES1 (BRI1-EMS-SUPPRESSOR 1), which directly control the transcription of BR-responsive genes involved in reproductive meristem developmental events in the plant.

In some embodiments, the invention provides a plant or plant part thereof comprising at least one mutation in an endogenous Brassinosteroid Insensitive-1 (BRI1) gene encoding a BRI1 polypeptide (brassinosteroid receptor polypeptide), optionally wherein the at least one non-natural mutation disrupts one or more upstream open reading frames (uORF) (in a cis-regulatory element, e.g., in a promoter region) of the endogenous BRI1 gene), optionally wherein the at least one mutation is a non-natural mutation.

In some embodiments, the invention provides a plant cell comprising at least one mutation within an endogenous Brassinosteroid Insensitive-1 (BRI1) gene, wherein the mutation is a substitution, insertion, deletion or inversion that is introduced using an editing system that comprises a nucleic acid binding domain that binds to a target site in the endogenous BRI1 gene), optionally wherein the at least one mutation is a non-natural mutation.

In some embodiments, a plant cell is provided, the plant cell comprising an editing system, the editing system comprising: (a) a CRISPR-Cas effector protein; and (b) a guide nucleic acid (e.g., gRNA, gDNA, crRNA, crDNA, sgRNA, sgDNA) comprising a spacer sequence with complementarity to an endogenous target gene encoding a BRI1 protein. The editing system may be used to generate a mutation in the endogenous target gene encoding a BRI1 polypeptide. In some embodiments, the mutation is a non-natural mutation. In some embodiments, a guide nucleic acid of an editing system may comprise the nucleotide sequence (a spacer sequence, e.g., one or more spacers) of any of SEQ ID NO:96, SEQ ID NO: 97, SEQ ID NO:98, SEQ ID NO: 99 and/or SEQ ID NO:100, or any combination thereof.

A mutation in a BRI1 gene of the plant, plant part thereof or the plant cell useful for this invention may be any type of mutation, including a base substitution, a base deletion, and/or a base insertion. In some embodiments, a mutation may comprise a base substitution to an A, a T, a G, or a C. In some embodiments, a mutation may be a deletion of at least one base pair (e.g., 1 base pair to about 270 base pairs; e.g., about 1, 2, 3, 4, 5, 6, 7, 8, 9, 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 141, 142, 143, 144, 145, 150, 160, 170, 180, 190, 200, 210, 220, 221, 222, 223, 224, 225, 230, 240, 250, 260, or 270, and any range or value therein). In some embodiments, the at least one mutation may be a non-natural mutation.

An endogenous BRI1 gene useful with this invention (e.g., an endogenous target gene) may be any BRI1 gene that encodes a Brassinosteroid Insensitive-1 (BRI1) polypeptide. In some embodiments, an endogenous BRI1 gene (e.g., endogenous target gene) may (a) (i) comprise a nucleic acid sequence having at least 80% (e.g., 80, 81, 82, 83, 84, 85, 86, 87, 88, 89, 90, 91, 92, 93, 94, 95, 96, 97, 98, 99, or 100%) sequence identity to any one of SEQ ID NOs: 69, 70, 80, or 81, or (ii) a region having at least 80% sequence identity to any one of SEQ ID NOs: 73-79 or 83-95, and/or (b) encode a BRI1 polypeptide having at least 80% sequence identity to any one of SEQ ID NOs: 71, 72 or 82.

The types of editing tools that may be used to generate these and other mutations in BRI1 genes include any base editors or cutters, which are guided to a target site using spacers having at least 80% complementarity to a portion of a BRI1 gene as described herein.

In some embodiments, a mutation of a BRI1 gene may be located at the 5' end of the endogenous BRI1 gene that encodes the BRI1 polypeptide, optionally wherein the mutation may be 5' of the BRI1 gene ATG start site for translation. In some embodiments, the mutation at the 5' end of the BRI1 gene may be in a region of the gene that is transcribed into a mRNA, but may be 5' of the ATG start site for the translation of the BRI1 polypeptide. As an example, the mutation may be in the cis-regulatory region, e.g., promoter region, of the BRI1 gene, optionally in one or more uORFs located in the cis-regulatory region/promoter region of the BRI1 gene, wherein the mutation disrupts the one or more uORFs, resulting in a modified BRI1 transcript (mRNA) (e.g., the mRNA comprises one or more disrupted uORFs). In some embodiments, a disruption of a uORF of a BRI1 gene as described herein results in increased production of the encoded BRI1 polypeptide. In some embodiments, the disruption of one or more uORFs of a BRI1 gene may be a modification in an ATG located in the uORF (e.g., an insertion, substitution or deletion of at least one base pair (e.g., 1, 2, or 3 base pairs) of the ATG of the uORF). In some embodiments, one or more uORFs of a BRI1 gene may be disrupted by a deletion, insertion or substitution, optionally a deletion of about 2 to about 270 base pairs. In some embodiments, a mutation or edit in an endogenous BRI1 gene may result in a hypomorphic mutation, a dominant mutation, and/or a semi-dominant mutation.

In some embodiments, a mutation of a BRI1 gene may be within a portion or region of the endogenous BRI1 gene located (a) from about nucleotide 2-213, 42-174, 62-154, 82-134, and/or 92-124 with reference to nucleotide position numbering of SEQ ID NO:69 (e.g., SEQ ID NOs: 73-79), and/or (b) from about nucleotide 1-267, 40-227, 70-195 and/or 100-168 with reference to nucleotide position numbering of SEQ ID NO:80 (e.g., SEQ ID NOs: 83-95).

In some embodiments, a mutated BRI1 gene may comprise at least 90% identity to any one of SEQ ID NOs: 101-117. In some embodiments, a plant or part thereof may comprise a mutated BRI1 gene having at least 90% sequence identity to any one of SEQ ID NOs: 101-117, optionally wherein mutated BRI1 gene may be a hypomorphic mutation, a dominant mutation, and/or a semi-dominant mutation.

In some embodiments, a plant (e.g., a soybean plant) comprising at least one (e.g., one or more) mutation in an endogenous BRI1 exhibits one or more improved yield traits as compared to a plant devoid of the at least one mutation (e.g., an isogenic plant (e.g., wild type unedited plant or a null segregant). In some embodiments, the one or more improved yield traits can include, but is not limited to, higher yield (bu/acre), increased biomass, increased plant height, increased stem diameter, increased leaf area, increased number of flowers, increased number of pods per node, increased number of pods per plant, increase number of seeds, increased number of seeds per pod, increased seed size, and/or increased seed weight (e.g., increase in 100-seed weight) as compared to a control plant devoid of the at least one mutation. In some embodiments, a plant may be regenerated from a plant part and/or plant cell of the invention comprising a mutation in a BRI1 gene as described herein, wherein the regenerated plant comprises the mutation in the endogenous BRI1 gene and a phenotype of improvement in one or more yield traits, as compared to a plant devoid of the same mutation in the BRI1 gene.

In some embodiments, a plant cell is provided, the plant cell comprising at least one (e.g., one or more) mutation within an endogenous Brassinosteroid Insensitive-1 (BRI1) gene, wherein the mutation is a substitution, insertion, or deletion that is introduced using an editing system that comprises a nucleic acid binding domain that binds to a target site in the endogenous BRI1 gene. In some embodiments, the substitution, insertion, or deletion results in, for example, a mutation in a cis-regulatory region that affects the expression of the BRI1 gene, optionally wherein the mutation is in one or more uORFs in promoter region of the BRI1 gene. In some embodiments, the at least one mutation may be a non-natural mutation. In some embodiments, the at least one mutation is a point mutation. In some embodiments, the at least one mutation within the BRI1 gene is an insertion and/or a deletion. In some embodiments, the at least one mutation may be a hypomorphic mutation, dominant, and/or a semi-dominant mutation. In some embodiments, the at least one mutation results in a mutated BRI1 gene having at least 90% sequence identity to any one of SEQ ID NOs: 101-117.

In some embodiments, the target site in the BRI1 gene of the plant cell is within a region of the BRI1 gene located (a) from about nucleotide 2-213, 42-174, 62-154, 82-134, and/or 92-124 with reference to nucleotide position numbering of SEQ ID NO:69 (e.g., SEQ ID NOs: 73-79), and/or (b) from about nucleotide 1-267, 40-227, 70-195 and/or 100-168 with reference to nucleotide position numbering of SEQ ID NO:80 (e.g., SEQ ID NOs: 83-95).

In some embodiments, the mutation may be made following cleavage by an editing system that comprises a nuclease and a nucleic acid binding domain that binds to a target site within a sequence having least 80% sequence identity to a sequence encoding of any one of SEQ ID NOs: 69, 70, 80, or 81 or having at least 80% sequence identity to a sequence encoding any one of SEQ ID NOs: 73-79 or 83-95, and a mutation within a BRI1 gene is made following cleavage by the nuclease. In some embodiments, the at least one mutation may result in a modified ATG site in a uORF of the BRI1 gene (the site is no longer ATG). In some embodiments, the at least one mutation may be a deletion of a portion of or an entire uORF of the BRI1 gene. In some embodiments, the at least one mutation may be a non-natural mutation. In some embodiments, the at least one mutation may result in a hypomorphic mutation, dominant, and/or a semi-dominant mutation in the endogenous BRI1 gene. In some embodiments, the at least one mutation results in a mutated BRI1 gene having at least 90% sequence identity to any one of SEQ ID NOs: 101-117.

In some embodiments, a plant cell may be regenerated into a plant that comprises the at least one mutation (e.g., a non-natural mutation), optionally wherein the plant regenerated from the plant cell exhibits a phenotype of at least one (one or more) improved yield trait when compared to a wild-type plant not comprising/devoid of the allele (e.g., an isogenic wild type plant), optionally wherein the one or more improved yield traits includes, but is not limited to, higher yield (bu/acre), increased biomass, increased plant height, increased stem diameter, increased leaf area, increased number of flowers, increased number of pods per node, increased number of pods per plant, increase number of seeds, increased number of seeds per pod, increased seed size, and/or increased seed weight (e.g., increase in 100-seed weight) as compared to a control plant devoid of the at least one mutation. In some embodiments, the regenerated plant comprises a mutated BRI1 gene having at least 90% sequence identity to any one of SEQ ID NOs: 101-117.

In some embodiments, a method of producing/breeding a transgene-free edited plant (e.g., a soybean plant) is provided, the method comprising: crossing a plant of the present invention (e.g., a plant comprising one or more mutations (e.g., non-natural mutations) in one or more BRI1 genes and having one or more improved yield traits) with a transgene free plant, thereby introducing the mutation into the plant that is transgene-free; and selecting a progeny plant that comprises the mutation and is transgene-free, thereby producing a transgene free edited plant.

Also provided herein is a method of providing a plurality of plants (e.g., soybean plants) having one or more improved yield traits, the method comprising planting two or more plants of the invention (e.g., 2, 3, 4, 5, 6, 7, 8, 9, 10, 50, 100, 1000 or more plants comprising one or more mutations (e.g., non-natural mutations) in one or more BRI1 genes and having one or more improved yield traits) in a growing area (e.g., a field (e.g., a cultivated field, an agricultural field), a growth chamber, a greenhouse, a recreational area, a lawn, and/or a roadside and the like), thereby providing a plurality of plants having one or more improved yield traits as compared to a plurality of control plants devoid of the mutation.

The invention further provides a method of generating variation in a region of a Brassinosteroid Insensitive-1 (BRI1) transcript, comprising: introducing an editing system into a plant cell, wherein the editing system is targeted to a region of a Brassinosteroid Insensitive-1 (BRI1) gene that encodes the region of the BRI1 polypeptide, and contacting the region of the BRI1 gene with the editing system, thereby introducing a mutation into the BRI1 gene and generating variation in the BRI1 transcript of the plant cell. In some embodiments, the BRI1 gene comprises a nucleotide sequence having at least 80% sequence identity to any one of SEQ ID NOs: 69, 70, 80, or 81 and/or encodes an amino acid sequence having at least 80% sequence identity to any one of SEQ ID NOs: 71, 72 or 82, and the mutation is made following cleavage by the editing system that comprises a nuclease and a nucleic acid binding domain that binds to a target site within a sequence having at least 80% sequence identity to any one of the nucleotide sequences of SEQ ID NOs: 69, 70, 80, or 81.

In some embodiments, the region of the BRI1 gene that is targeted for generating variation in a BRI1 transcript (mRNA) comprises at least 80% sequence identity to any one of the nucleotide sequences of SEQ ID NOs: 73-79 or 83-95 and/or is located (a) from about nucleotide 2-213, 42-174, 62-154, 82-134, and/or 92-124 with reference to nucleotide position numbering of SEQ ID NO:69 (e.g., SEQ ID NOs: 73-79), and/or (b) from about nucleotide 1-267, 40-227, 70-195 and/or 100-168 with reference to nucleotide position numbering of SEQ ID NO:80 (e.g., SEQ ID NOs: 83-95). In some embodiments, contacting the region of the endogenous BRI1 gene in the plant cell with the editing system produces a plant cell comprising in its genome an edited BRI1 gene, the method further comprising (a) regenerating a plant from the plant cell; (b) selfing the plant to produce progeny plants (E1); (c) assaying the progeny plants of (b) for one or more improved yield traits; and (d) selecting the progeny plants exhibiting a phenotype of one or more improved yield traits as compared to a control plant. In some embodiments, the method may further comprise (e) selfing the selected progeny plants of (d) to produce progeny plants (E2); (f) assaying the progeny plants of (e) for one or more improved yield traits; and (g) selecting the progeny plants exhibiting a phenotype of one or more improved yield traits as compared to a control plant, optionally repeating (e) through (g) one or more additional times.

In some embodiments, a method for editing a specific site in the genome of a plant cell is provided, the method comprising: cleaving, in a site-specific manner, a target site within an endogenous Brassinosteroid Insensitive-1 (BRI1) gene in the plant cell, the endogenous BRI1 gene: (a) comprising a sequence having at least 80% sequence identity to any one of the nucleotide sequences of SEQ ID NOs: 69, 70, 80, or 81, (b) comprising a region having at least 80% sequence identity to any one of the nucleotide sequences of SEQ ID NOs: 73-79 or 83-95, and/or (c) encoding an amino acid sequence having at least 80% sequence identity to any one of SEQ ID NOs: 71, 72 or 82, thereby generating an edit in the endogenous BRI1 gene of the plant cell and producing a plant cell comprising the edit in the endogenous BRI1 gene.

In some embodiments, the edit results in a mutation, including but not limited to a deletion, substitution, or insertion. In some embodiments, the edit results in a non-natural mutation. In some embodiments, an edit in an endogenous BRI1 gene may result in hypomorphic mutation, dominant, and/or a semi-dominant mutation. In some embodiments, the edit may be a nucleotide substitution to an A, a T, a G, or a C. In some embodiments, an edit results in variation in the BRI1 transcript produced from the BRI1 gene, optionally in one or more uORFs of the BRI1 transcript. As an example, an edit may result in variation in a sequence of the BRI1 gene having at least 80% identity to any one of SEQ ID NOs: 73-79 or 83-95 and/or is located (a) from about nucleotide 2-213, 42-174, 62-154, 82-134, and/or 92-124 with reference to nucleotide position numbering of SEQ ID NO:69 (e.g., SEQ ID NOs: 73-79), and/or (b) from about nucleotide 1-267, 40-227, 70-195 and/or 100-168 with reference to nucleotide position numbering of SEQ ID NO:80 (e.g., SEQ ID NOs: 83-95), thereby resulting in a BRI1 transcript having one or more modified (optionally deleted) uORF regions. In some embodiments, the edit is in an ATG site of the BRI1 gene and in the BRI1 transcript transcribed from the BRI1 gene. In some embodiments, the edit produced a modified BRI1 gene having at least 90% sequence identity to any one of SEQ ID NOs: 101-117.

In some embodiments, a method of editing may further comprise regenerating a plant from the plant cell comprising the edit in the endogenous BRI1 gene, thereby producing a plant comprising the edit in its endogenous BRI1 gene and having a phenotype of one or more improved yield traits when compared to a control plant that is devoid of the edit, optionally wherein the regenerated plant comprises a mutated BRI1 gene having at least 90% sequence identity to any one of SEQ ID NOs: 101-117.

In some embodiments, a method for making a plant is provided, the method comprising (a) contacting a population of plant cells comprising an endogenous Brassinosteroid Insensitive-1 (BRI1) gene with a nuclease linked to a nucleic acid binding domain (e.g., editing system) that binds to a sequence (i) having at least 80% (e.g., 80, 81, 82, 83, 84, 85, 86, 87, 88, 89, 90, 91, 92, 93, 94, 95, 96, 97, 98, 99, or 100%) sequence identity to the nucleotide sequence of any one of SEQ ID NOs: 69, 70, 80 or 81, (ii) encoding an amino acid sequence having at least 80% sequence identity to any one of SEQ ID NOs: 71, 72 or 82, and/or (iii) comprising a region having at least 80% identity to the nucleotide sequence of any one of SEQ ID NOs: 73-79 or 83-95; (b) selecting a plant cell from the population in which an endogenous BRI1 gene has been mutated, thereby producing a plant cell comprising a mutation in the endogenous BRI1 gene; and (c) growing the selected plant cell into a plant.

In some embodiments, a method of improving one or more yield traits in a plant is provided, the method comprising (a) contacting a plant cell comprising an endogenous Brassinosteroid Insensitive-1 (BRI1) gene with a nuclease targeting the endogenous BRI1 gene, wherein the nuclease is linked to a nucleic acid binding domain (e.g., editing system) that binds to a target site in the endogenous BRI1 gene, wherein the endogenous BRI1 gene: (i) comprises a sequence having at least 80% sequence identity to the nucleotide sequence of any one of SEQ ID NOs: 69, 70, 80 or 81; (ii) comprises a region having at least 80% identity to any one of the nucleotide sequences of SEQ ID NOs: 73-79 or 83-95; and/or (iii) encodes an amino acid sequence having at least 80% sequence identity to any one of SEQ ID NOs: 71, 72 or 82, to produce a plant cell comprising a mutation in the endogenous BRI1 gene; and (b) growing the plant cell into a plant comprising the mutation in the endogenous BRI1 gene, thereby producing a plant have a mutated endogenous BRI1 gene and one or more improved yield traits.

In some embodiments, a method for producing a plant or part thereof comprising at least one cell having a mutated endogenous BRI1 gene is provided, the method comprising contacting a target site in an endogenous BRI1 gene in the plant or plant part with a nuclease comprising a cleavage domain and a nucleic acid binding domain, wherein the nucleic acid binding domain binds to a target site in the endogenous BRI1 gene, wherein the endogenous BRI1 gene (a) comprises a sequence having at least 80% sequence identity to the nucleotide sequence of any one of SEQ ID NOs: 69, 70, 80, or 81; (b) comprises a region having at least 80% sequence identity to any one of the nucleotide sequences of SEQ ID NOs: 73-79 or 83-95; and/or (c) encodes an amino acid sequence having at least 80% sequence identity to any one of SEQ ID NOs: 71, 72 or 82, thereby producing the plant or part thereof comprising at least one cell having a mutation in the endogenous BRI1 gene.

Also provided herein is a method for producing a plant or part thereof comprising a mutated endogenous Brassinosteroid Insensitive-1 (BRI1) gene and exhibiting one or more improved yield traits, the method comprising contacting a target site in an endogenous BRI1 gene in the plant or plant part with a nuclease comprising a cleavage domain and a nucleic acid binding domain, wherein the nucleic acid binding domain binds to a target site in the endogenous BRI1 gene, wherein the endogenous BRI1 gene: (a) comprises a sequence having at least 80% sequence identity to the nucleotide sequence of any one of SEQ ID NOs: 69, 70, 80, or 81; (b) comprises a region having at least 80% sequence identity to any one of the nucleotide sequences of SEQ ID NOs: 73-79 or 83-95; and/or (c) encodes an amino acid sequence having at least 80% sequence identity to any one of SEQ ID NOs: 71, 72 or 82, thereby producing the plant or part thereof comprising an endogenous BRI1 gene having a mutation and exhibiting one or more improved yield traits, optionally wherein the one or more improved yield traits includes, but is not limited to, higher yield (bu/acre), increased biomass, increased plant height, increased stem diameter, increased leaf area, increased number of flowers, increased number of pods per node, increased number of pods per plant, increase number of seeds, increased number of seeds per pod, increased seed size, and/or increased seed weight (e.g., increase in 100-seed weight) as compared to a control plant devoid of the at least one mutation.

In some embodiments, a nuclease may cleave an endogenous BRI1 gene, thereby introducing the mutation into the endogenous BRI1 gene. A nuclease useful with the invention may be any nuclease that can be utilized to edit/modify a target nucleic acid. Such nucleases include, but are not limited to a zinc finger nuclease, transcription activator-like effector nucleases (TALEN), endonuclease (e.g., Fok1) and/or a CRISPR-Cas effector protein. Likewise, any nucleic acid binding domain useful with the invention may be any DNA binding domain or RNA binding domain that can be utilized to edit/modify a target nucleic acid. Such nucleic acid binding domains include, but are not limited to, a zinc finger, transcription activator-like DNA binding domain (TAL), an argonaute and/or a CRISPR-Cas effector DNA binding domain.

In some embodiments, a nucleic acid binding domain (e.g., DNA binding domain) is comprised in a nucleic acid binding polypeptide. A "nucleic acid binding protein" or "nucleic acid binding polypeptide" as used herein refers to a polypeptide that binds and/or is capable of binding a nucleic acid in a site- and/or sequence-specific manner. In some embodiments, a nucleic acid binding polypeptide may be a sequence-specific nucleic acid binding polypeptide (e.g., a sequence-specific DNA binding domain) such as, but not limited to, a sequence-specific binding polypeptide and/or domain from, for example, a polynucleotide-guided endonuclease, a CRISPR-Cas effector protein (e.g., a CRISPR-Cas endonuclease), a zinc finger nuclease, a transcription activator-like effector nuclease (TALEN) and/or an Argonaute protein. In some embodiments, a nucleic acid binding polypeptide comprises a cleavage polypeptide (e.g., a nuclease polypeptide and/or domain) such as, but not limited to, an endonuclease (e.g., Fok1), a polynucleotide-guided endonuclease, a CRISPR-Cas endonuclease, a zinc finger nuclease, and/or a transcription activator-like effector nuclease (TALEN). In some embodiments, the nucleic acid binding polypeptide associates with and/or is capable of associating with (e.g., forms a complex with) one or more nucleic acid molecule(s) (e.g., forms a complex with a guide nucleic acid as described herein) that can direct or guide the nucleic acid binding polypeptide to a specific target nucleotide sequence (e.g., a gene locus of a genome) that is complementary to the one or more nucleic acid molecule(s) (or a portion or region thereof), thereby causing the nucleic acid binding polypeptide to bind to the nucleotide sequence at the specific target site. In some embodiments, the nucleic acid binding polypeptide is a CRISPR-Cas effector protein as described herein. In some embodiments, reference is made to specifically to a CRISPR-Cas effector protein for simplicity, but a nucleic acid binding polypeptide as described herein may be used. In some embodiments, a polynucleotide and/or a nucleic acid construct of the invention can be an "expression cassette" or can be comprised within an expression cassette.

In some embodiments, a method of editing an endogenous BRI1 gene in a plant or plant part is provided, the method comprising contacting a target site in an endogenous BRI1 gene in the plant or plant part with a cytosine base editing system comprising a cytosine deaminase and a nucleic acid binding domain that binds to a target site in the endogenous BRI1 gene, wherein the endogenous BRI1 gene: (a) comprises a sequence having at least 80% sequence identity to the nucleotide sequence of any one of SEQ ID NOs: 69, 70, 80, or 81; (b) comprises a region having at least 80% sequence identity to any one of the nucleotide sequences of SEQ ID NOs: 73-79 or 83-95; and/or (c) encodes an amino acid sequence having at least 80% sequence identity to any one of SEQ ID NOs: 71, 72 or 82, thereby editing the endogenous BRI1 gene in the plant or part thereof and producing a plant or part thereof comprising at least one cell having a mutation in the endogenous BRI1 gene.

In some embodiments, a method of editing an endogenous BRI1 gene in a plant or plant part is provided, the method comprising contacting a target site in an BRI1 gene in the plant or plant part with an adenosine base editing system comprising an adenosine deaminase and a nucleic acid binding domain that binds to a target site in the BRI1 gene, the BRI1 gene (a) comprises a sequence having at least 80% sequence identity to the nucleotide sequence of any one of SEQ ID NOs: 69, 70, 80, or 81; (b) comprises a region having at least 80% sequence identity to any one of the nucleotide sequences of SEQ ID NOs: 73-79 or 83-95; and/or (c) encodes an amino acid sequence having at least 80% sequence identity to any one of SEQ ID NOs: 71, 72 or 82, thereby editing the endogenous BRI1 gene in the plant or part thereof and producing a plant or part thereof comprising at least one cell having a mutation in the endogenous BRI1 gene.

In some embodiments, a method of creating a mutation in an endogenous Brassinosteroid Insensitive-1 (BRI1) gene in a plant, comprising: (a) targeting a gene editing system to a portion of the BRI1 gene that comprises a nucleotide sequence having at least 90% sequence identity to any one of SEQ ID NOs: 73-79 or 83-95; and (b) selecting a plant that comprises a modification located in a region of the one or more BRI1 genes having at least 90% identity to the nucleotide sequence of any one of SEQ ID NOs: 73-79 or 83-95.

In some embodiments, a method of creating a mutation in an Brassinosteroid Insensitive-1 (BRI1) gene in a plant is provided, comprising: (a) targeting a gene editing system to a portion of the BRI1 gene that is located from about nucleotide 2-213, 42-174, 62-154, 82-134, and/or 92-124 with reference to nucleotide position numbering of SEQ ID NO: 69 (e.g., SEQ ID NOs: 73-79), and/or (b) from about nucleotide 1-267, 40-227, 70-195 and/or 100-168 with reference to nucleotide position numbering of SEQ ID NO:80 (e.g., SEQ ID NOs: 83-95).

In some embodiments, a method of detecting a mutant BRI1 gene (a mutation in an endogenous BRI1 gene) in a plant is provided, the method comprising detecting in the genome of the plant a BR1 gene having at least one mutation within a region having at least 80% sequence identity to a nucleotide sequence of any one of SEQ ID NOs: 73-79 or 83-95. In some embodiments, the mutant BRI1 gene that is detected may comprise a nucleic acid sequence having at least 90% sequence identity to any one of SEQ ID NOs: 101-117.

In some embodiments, a mutation provided by methods of the invention may be a non-natural mutation. In some embodiments, the mutation may be a substitution, an insertion and/or a deletion, optionally wherein the insertion or deletion is an in-frame insertion or in-frame deletion. In some embodiments, a mutation in an endogenous BRI1 gene may result in a hypomorphic mutation, a dominant mutation, and/or a semi-dominant mutation. In some embodiments, a mutation may be a deletion of about 1 base pair to about 270 consecutive base pairs, optionally wherein the deletion disrupts at least one upstream open reading frame (uORF) (in a cis-regulatory element, e.g., in a promoter region) of the endogenous BRI1 gene, optionally wherein the at least one uORF is located from about nucleotide 2-213, 42-174, 62-154, 82-134, and/or 92-124 with reference to nucleotide position numbering of SEQ ID NO: 69 (e.g., SEQ ID NOs: 73-79), and/or (b) from about nucleotide 1-267, 40-227, 70-195 and/or 100-168 with reference to nucleotide position numbering of SEQ ID NO:80 (e.g., SEQ ID NOs: 83-95). In some embodiments, the mutation results in a modified BRI1 transcript. In some embodiments, the mutation results in a mutated BRI1 gene having at least 90% sequence identity to any one of SEQ ID NOs: 101-117, optionally the mutation may be a hypomorphic mutation, a dominant mutation, and/or a semi-dominant mutation.

In some embodiments, a method of detecting a mutant BRI1 gene is provide, the method comprising detecting in the genome of a plant an endogenous BRI1 gene encoding a BRI1 polypeptide comprising a mutation in a cis-regulator region, optionally in a uORF located from about nucleotide 2-213, 42-174, 62-154, 82-134, and/or 92-124 with reference to nucleotide position numbering of SEQ ID NO:69 (e.g., SEQ ID NOs: 74-79), and/or (b) from about nucleotide 1-267, 40-227, 70-195 and/or 100-168 with reference to nucleotide position numbering of SEQ ID NO:80 (e.g., SEQ ID NOs: 83-95). In some embodiments, a method of detecting a mutant BRI1 gene is provide, the method comprising detecting in the genome of a plant a mutated BRI1 transcript, wherein the mutation is in one or more uORFs of the transcript. In some embodiments, the mutated BRI1 gene that is detected may comprise at least 90% sequence identity to any one of SEQ ID NOs: 101-117.

In some embodiments, the present invention provides a method of producing a plant comprising a mutation in an endogenous Brassinosteroid Insensitive-1 (BRI1) gene and at least one polynucleotide of interest, the method comprising crossing a plant of the invention comprising at least one mutation in an endogenous BRI1 gene (a first plant) with a second plant that comprises the at least one polynucleotide of interest to produce progeny plants; and selecting progeny plants comprising at least one mutation in the BRI1 gene and the at least one polynucleotide of interest, thereby producing the plant comprising a mutation in an endogenous BRI1 gene and at least one polynucleotide of interest.

The present invention further provides a method of producing a plant comprising a mutation in an endogenous BRI1 gene and at least one polynucleotide of interest, the method comprising introducing at least one polynucleotide of interest into a plant of the present invention comprising at least one mutation in a BRI1 gene, thereby producing a plant comprising at least one mutation in a BRI1 gene and at least one polynucleotide of interest. In some embodiments, the plant is a corn plant. In some embodiments, the plant is a soybean plant.

In some embodiments, also provided is a method of producing a plant comprising a mutation in an endogenous BRI1 gene and exhibiting a phenotype of improved yield traits, improved plant architecture and/or improved defense traits, the method comprising crossing a first plant, which is a plant of the present invention comprising at least one mutation in a BRI1 gene, with a second plant that exhibits a phenotype of improved yield traits, improved plant architecture and/or improved defense traits; and selecting progeny plants comprising the mutation in the BRI1 gene and a phenotype of improved yield traits, improved plant architecture and/or improved defense traits, thereby producing the plant comprising a mutation in an endogenous BRI1 gene and exhibiting a phenotype of improved yield traits, improved plant architecture and/or improved defense traits as compared to a control plant.

Further provided is a method of controlling weeds in a container (e.g., pot, or seed tray and the like), a growth chamber, a greenhouse, a field, a recreational area, a lawn, or on a roadside, the method comprising applying an herbicide to one or more (a plurality) plants of the invention growing in a container, a growth chamber, a greenhouse, a field, a recreational area, a lawn, or on a roadside, thereby controlling the weeds in the container, the growth chamber, the greenhouse, the field, the recreational area, the lawn, or on the roadside in which the one or more plants are growing.

In some embodiments, a method of reducing insect predation on a plant is provided, the method comprising applying an insecticide to one or more plants of the invention, optionally, wherein the one or more plants are growing in a container, a growth chamber, a greenhouse, a field, a recreational area, a lawn, or on a roadside, thereby reducing insect predation on the one or more plants.

In some embodiments, a method of reducing fungal disease on a plant is provided, the method comprising applying a fungicide to one or more plants of the invention, optionally, wherein the one or more plants are growing in a container, a growth chamber, a greenhouse, a field, a recreational area, a lawn, or on a roadside, thereby reducing fungal disease on the one or more plants.

A polynucleotide of interest may be any polynucleotide that can confer a desirable phenotype or otherwise modify the phenotype or genotype of a plant. In some embodiments, a polynucleotide of interest may be polynucleotide that confers herbicide tolerance, insect resistance, nematode resistance, disease resistance, increased yield, increased nutrient use efficiency or abiotic stress resistance.

Thus, plants or plant cultivars which are to be treated with preference in accordance with the invention include all plants which, through genetic modification, received genetic material which imparts particular advantageous useful properties ("traits") to these plants. Examples of such properties are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products.

Further examples of such properties are an increased resistance against animal and microbial pests, such as against insects, arachnids, nematodes, mites, slugs and snails owing, for example, to toxins formed in the plants. Among DNA sequences encoding proteins which confer properties of tolerance to such animal and microbial pests, in particular insects, mention will particularly be made of the genetic material from *Bacillus thuringiensis* encoding the Bt proteins widely described in the literature and well known to those skilled in the art. Mention will also be made of proteins extracted from bacteria such as *Photorhabdus* (WO97/17432 and WO98/08932). In particular, mention will be made of the Bt Cry or VIP proteins which include the CrylA, CryIAb, CryIAc, CryIIA, CryIIIA, CryIIIB2, Cry9c Cry2Ab, Cry3Bb and CryIF proteins or toxic fragments thereof and also hybrids or combinations thereof, especially the CrylF protein or hybrids derived from a CrylF protein (e.g. hybrid CrylA-CrylF proteins or toxic fragments thereof), the CrylA-type proteins or toxic fragments thereof, preferably the CrylAc protein or hybrids derived from the CrylAc protein (e.g. hybrid CrylAb-CrylAc proteins) or the CrylAb or Bt2 protein or toxic fragments thereof, the Cry2Ae, Cry2Af or Cry2Ag proteins or toxic fragments thereof, the CrylA.105 protein or a toxic fragment thereof, the VIP3Aa19 protein, the VIP3Aa20 protein, the VIP3A proteins produced in the COT202 or COT203 cotton events, the VIP3 Aa protein or a toxic fragment thereof as described in Estruch et al. (1996), Proc Natl Acad Sci USA. 28; 93 (11): 5389-94, the Cry proteins as described in WO2001/47952, the insecticidal proteins from Xenorhabdus (as described in WO98/50427), *Serratia* (particularly from *S. entomophila*) or *Photorhabdus* species strains, such as Tc-proteins from *Photorhabdus* as described in WO98/08932. Also any variants or mutants of any one of these proteins differing in some amino acids (1-10, preferably 1-5) from any of the above named sequences, particularly the sequence of their toxic fragment, or which are fused to a transit peptide, such as a plastid transit peptide, or another protein or peptide, is included herein.

Another and particularly emphasized example of such properties is conferred tolerance to one or more herbicides, for example imidazolinones, sulphonylureas, glyphosate or phosphinothricin. Among DNA sequences encoding proteins (i.e., polynucleotides of interest) which confer properties of tolerance to certain herbicides on the transformed plant cells and plants, mention will be particularly be made to the bar or PAT gene or the *Streptomyces coelicolor* gene described in WO2009/152359 which confers tolerance to glufosinate herbicides, a gene encoding a suitable EPSPS (5-Enolpyruvylshikimat-3-phosphat-Synthase) which confers tolerance to herbicides having EPSPS as a target, especially herbicides such as glyphosate and its salts, a gene encoding glyphosate-n-acetyltransferase, or a gene encoding glyphosate oxidoreductase. Further suitable herbicide tolerance traits include at least one ALS (acetolactate synthase) inhibitor (e.g. WO2007/024782), a mutated *Arabidopsis* ALS/AHAS gene (e.g. U.S. Pat. No. 6,855,533), genes encoding 2,4-D-monooxygenases conferring tolerance to 2,4-D (2,4-dichlorophenoxyacetic acid) and genes encoding Dicamba monooxygenases conferring tolerance to dicamba (3,6-dichloro-2-methoxybenzoic acid).

Further examples of such properties are increased resistance against phytopathogenic fungi, bacteria and/or viruses owing, for example, to systemic acquired resistance (SAR), systemin, phytoalexins, elicitors and also resistance genes and correspondingly expressed proteins and toxins.

Particularly useful transgenic events in transgenic plants or plant cultivars which can be treated with preference in accordance with the invention include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control-herbicide tolerance, deposited as PTA-6233, described in WO2005/103266 or US-A 2005-216969); Event 3006-210-23 (cotton, insect control-herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control-herbicide tolerance, deposited as ATCC PTA-11508, described in WO 11/075593); Event 43A47 (corn, insect control-herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLR1 (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control-herbicide tolerance, deposited as ATCC PTA 11384, described in US-A 2006-070139); Event DAS-59132 (corn, insect control-herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-I (brinjal, insect control, not deposited, described in WO 07/091277); Event Fil 17 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO98/044140); Event GHB119 (cotton, insect control-herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLINl (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait—herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control—herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MSl 1 (oilseed rape, pollination control-herbicide tolerance, deposited as ATCC PTA-850 or PTA-2485, described in WO2001/031042); Event MS8 (oilseed rape, pollination control-herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control-herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control-herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control-herbicide tolerance, not deposited, described in US-A 2005-039226 or WO2004/099447); Event VIP1034 (corn, insect control-herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession No PTA-11041) optionally stacked with event EE-GM1/LL27 or event EE-GM2/LL55 (WO2011/063413A2), event DAS-68416-4 (soybean, herbicide tolerance, ATCC Accession No PTA-10442, WO2011/066360A1), event DAS-68416-4 (soybean, herbicide tolerance, ATCC Accession No PTA-10442, WO2011/066384A1), event DP-040416-8 (corn, insect control, ATCC Accession No PTA-11508, WO2011/075593A1), event DP-043A47-3 (corn, insect control, ATCC Accession No PTA-11509, WO2011/075595A1), event DP-004114-3 (corn, insect control, ATCC Accession No PTA-11506, WO2011/084621A1), event DP-032316-8 (corn, insect control, ATCC Accession No PTA-11507, WO2011/084632A1), event MON-88302-9 (oilseed rape, herbicide tolerance, ATCC Accession No PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, Accession No PTA-11336, WO2012075426A2), event 8291.45.36.2 (soybean, stacked herbicide tolerance, Accession No. PTA-11335, WO2012075429A2), event SYHT0H2 (soybean, ATCC Accession No PTA-11226, WO2012/082548A2), event MON88701 (cotton, ATCC Accession No PTA-11754, WO2012/134808A1), event KK179-2 (alfalfa, ATCC Accession No PTA-11833, WO2013/003558A1), event pDAB8264.42.32.1 (soybean, stacked herbicide tolerance, ATCC Accession No PTA-11993, WO2013/010094A1), event MZDT09Y (corn, ATCC Accession No PTA-13025, WO2013/012775A1).

The genes/events (e.g., polynucleotides of interest), which impart the desired traits in question, may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails, as well as the increased resistance of the plants to one or more herbicides.

Commercially available examples of such plants, plant parts or plant seeds that may be treated with preference in accordance with the invention include commercial products, such as plant seeds, sold or distributed under the GENUITY®, DROUGHTGARD®, SMARTSTAX®, RIB COMPLETER, ROUNDUP READY®, VT DOUBLE PRO®, VT TRIPLE PRO®, BOLLGARD IIR, ROUNDUP READY 2 YIELD®, YIELDGARD®, ROUNDUP READY® 2 XTEND™, INTACTA RR2 PRO®, VISTIVE GOLD®, and/or XTENDFLEX™ trade names.

A BRI1 gene useful with this invention includes any BRI1 gene in which a mutation as described herein can confer improvement in one or more yield traits in a plant or part thereof comprising the mutation. In some embodiments, an endogenous BRI1 gene (a) comprises a sequence having at least 80% sequence identity to the nucleotide sequence of any one of SEQ ID NOs: 69, 70, 80, or 81; (b) comprises a region having at least 80% identity to any one of SEQ ID NOs: 73-79 or 83-95; (c) encodes an amino acid sequence having at least 80% sequence identity to any one of SEQ ID NOs: 71, 72, or 82. A mutation in an endogenous BRI1 gene in a plant may be a base substitution, a base deletion and/or a base insertion, optionally a non-natural mutation. In some embodiments, a mutation in an endogenous BRI1 gene in a plant may result in a plant having the phenotype of one or more improved yield traits as compared to a control plant devoid of the edit/mutation, optionally wherein the improved yield trait can include but is not limited to, higher yield (bu/acre), increased biomass, increased plant height, increased stem diameter, increased leaf area, increased number of flowers, increased number of pods per node, increased number of pods per plant, increase number of seeds, increased number of seeds per pod, increased seed size, and/or increased seed weight (e.g., increase in 100-seed weight). In some embodiments, a mutation in an endogenous BRI1 gene may be a base substitution, a base deletion and/or a base insertion of at least 1 nucleotide to about 270 nucleotides (e.g., about 1, 2, 3, 4, 5, 6, 7, 8, 9, 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 141, 142, 143, 144, 145, 150, 160, 170, 180, 190, 200, 210, 220, 221, 222, 223, 224, 225, 230, 240, 250, 260, or 270, and any range or value therein), optionally where the mutation may result in a substitution, a deletion and/or an insertion in the uORF region of the gene and transcript. In some embodiments, the at least one mutation may be a point mutation, optionally a base substitution to an A, a T, a G, or a C. In some embodiments, the mutation may be generated in the BRI1 gene in a location (a) from about nucleotide 2-213, 42-174, 62-154, 82-134, and/or 92-124 with reference to nucleotide position numbering of SEQ ID NO:69 (e.g., SEQ ID NOs: 73-79), and/or (b) from about nucleotide 1-267, 40-227, 70-195 and/or 100-168 with reference to nucleotide position numbering of SEQ ID NO:80 (e.g., SEQ ID NOs: 83-95). In some embodiments, a mutation in a BRI1 gene may be a deletion of one base pair to about 250 base pairs, wherein at least an ATG site in the uORF is deleted. In some embodiments, a mutation in a BRI1 gene (a mutated BRI1 gene) may comprise at least 90% sequence identity to any one of SEQ ID NOs: 101-117.

In some embodiments, a mutation in an endogenous BRI1 gene may be made following cleavage by an editing system that comprises a nuclease and a nucleic acid binding domain that binds to a target site within a target nucleic acid (e.g., a BRI1 gene), the target nucleic acid comprising a sequence having at least 80% sequence identity to any one of the nucleotide sequences of SEQ ID NOs: 69, 70, 80, or 81, and/or encoding an amino acid sequence having at least 80% sequence identity to any one of SEQ ID NOs: 71, 72 or 82, optionally wherein the target site is located in a region of the BRI1 gene: the region comprising a sequence having at least 90% identity to any one of SEQ ID NOs: 73-79 or 83-95.

Further provided are guide nucleic acids (e.g., gRNA, gDNA, crRNA, crDNA) that bind to a target site in a Brassinosteroid Insensitive-1 (BRI1) gene, wherein the target site is in a region of the BRI1 gene located (a) from about nucleotide 2-213, 42-174, 62-154, 82-134, and/or 92-124 with reference to nucleotide position numbering of SEQ ID NO:69 (e.g., SEQ ID NOs: 73-79), and/or (b) from about nucleotide 1-267, 40-227, 70-195 and/or 100-168 with reference to nucleotide position numbering of SEQ ID NO:80 (e.g., SEQ ID NOs: 83-95). In some embodiments, the guide nucleic acid comprises a spacer comprising any one of the nucleotide sequences of SEQ ID NOs: 96-100.

In some embodiments, a soybean plant or plant part thereof is provided comprising at least one mutation in at least one endogenous Brassinosteroid Insensitive-1 (BRI1) gene having the gene identification number (gene ID) of Glyma.06g147600 (SEQ ID NO:69) and/or Glyma.04g218300 (SEQ ID NO:80), optionally wherein the mutation is a non-natural mutation. In some embodiments, a soybean plant or plant part thereof is provided comprising a mutated BRI1 gene having at least 90% sequence identity to any one of SEQ ID NOs: 101-117.

In some embodiments, a guide nucleic acid is provided that binds to a target nucleic acid in a Brassinosteroid Insensitive-1 (BRI1) gene having the gene identification number (gene ID) of Glyma.06g147600 (SEQ ID NO:69) and/or Glyma.04g218300 (SEQ ID NO: 80).

In some embodiments, a system is provided comprising a guide nucleic acid comprising a spacer (e.g., one or more spacers) having the nucleotide sequence of any one of SEQ ID NOs: 96-100, and a CRISPR-Cas effector protein that associates with the guide nucleic acid. In some embodiments, the system may further comprise a tracr nucleic acid that associates with the guide nucleic acid and a CRISPR-Cas effector protein, optionally wherein the tracr nucleic acid and the guide nucleic acid are covalently linked. As used herein, "a CRISPR-Cas effector protein in association with a guide nucleic acid" refers to the complex that is formed between a CRISPR-Cas effector protein and a guide nucleic acid in order to direct the CRISPR-Cas effector protein to a target site in a gene.

The invention further provides a gene editing system comprising a CRISPR-Cas effector protein in association with a guide nucleic acid and the guide nucleic acid comprises a spacer sequence that binds to a Brassinosteroid Insensitive-1 (BRI1) gene, optionally wherein the BRI1 gene (a) comprises a sequence having at least 80% sequence identity to the nucleotide sequence of any one of SEQ ID NOs: 69, 70, 80, or 81; (b) comprises a region having at least 80% sequence identity to any one of the nucleotide sequences of SEQ ID NOs: 73-79 or 83-95; and/or (c) encodes an amino acid sequence having at least 80% sequence identity to any one of SEQ ID NOs: 71, 72 or 82. In some embodiments, a spacer sequence of the guide nucleic acid may comprise the nucleotide sequence of any of SEQ ID NOs: 96-100. In some embodiments, the gene editing system may further comprise a tracr nucleic acid that associates with the guide nucleic acid and a CRISPR-Cas effector protein, optionally wherein the tracr nucleic acid and the guide nucleic acid are covalently linked.

The present invention further provides a complex comprising a CRISPR-Cas effector protein comprising a cleavage domain and a guide nucleic acid, wherein the guide nucleic acid binds to a target site in an endogenous Brassinosteroid Insensitive-1 (BRI1) gene, wherein the endogenous BRI1 gene: (a) comprises a sequence having at least 80% sequence identity to the nucleotide sequence of any one SEQ ID NOs: 69, 70, 80, or 81; (b) comprises a region having at least 80% sequence identity to any one of the nucleotide sequences of SEQ ID NOs: 73-79 or 83-95; and/or (c) encodes an amino acid sequence having at least 80% sequence identity to any one of SEQ ID NOs: 71, 72 or 82, wherein the cleavage domain cleaves a target strand in the BRI1 gene.

In some embodiments, an expression cassette(s) is/are provided that comprise (a) a polynucleotide encoding CRISPR-Cas effector protein comprising a cleavage domain and (b) a guide nucleic acid that binds to a target site in an endogenous Brassinosteroid Insensitive-1 (BRI1) gene, wherein the guide nucleic acid comprises a spacer sequence that is complementary to and binds to (i) a portion of a nucleic acid having at least 80% sequence identity to any one of the nucleotide sequences of SEQ ID NOs: 69, 70, 80, or 81; (ii) a portion of a nucleic acid having at least 80% sequence identity to any one of SEQ ID NOs: 73-79 or 83-95; and/or (iii) a portion of a nucleic acid encoding an amino acid sequence having at least 80% sequence identity to any one of SEQ ID NOs: 71, 72 or 82.

In some embodiments a modified Brassinosteroid Insensitive-1 (BRI1) gene or transcript is provided comprising a mutation in cis-regulatory regions (e.g., promoter region, e.g., one or more uORFa) located: (a) from about nucleotide 2-213, 42-174, 62-154, 82-134, and/or 92-124 with reference to nucleotide position numbering of SEQ ID NO:69 (e.g., SEQ ID NOs: 73-79), and/or (b) from about nucleotide 1-267, 40-227, 70-195 and/or 100-168 with reference to nucleotide position numbering of SEQ ID NO:80 (e.g., SEQ ID NOs: 83-95), optionally wherein when present in a plant or plant part the mutated BRI1 gene/transcript results in the plant comprising a phenotype of one or more improved yield traits as compared to a plant or plant part devoid of the mutation. In some embodiments, a mutated BRI1 transcript may be produced from a mutated BRI1 gene having at least 90% sequence identity to any one of SEQ ID NOs: 101-117.

Nucleic acid constructs of the invention (e.g., a construct comprising a sequence specific nucleic acid binding domain (e.g., sequence specific DNA binding domain), a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids (e.g., endogenous BRI1 genes) and/or their expression.

Any plant comprising an endogenous BRI1 gene that is capable of conferring at least one improved yield trait when modified as described herein may be modified (e.g., mutated, e.g., base edited, cleaved, nicked, etc.) as described herein (e.g., using the polypeptides, polynucleotides, RNPs, nucleic acid constructs, expression cassettes, and/or vectors of the invention) to improve one or more yield traits in the plant. A plant exhibiting an improved yield trait may show an improvement of about 5% to about 100% (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% or more or any range or value therein; e.g., about 5% to about 10%, about 5% to about 15%, about 5% to about 20%, about 10% to about 50%, about 10% to about 80%, about 10% to about 90%, about 10% to about 100%, about 20% to about 50%, about 20% to about 80%, about 20% to about 90%, about 20% to about 100%, about 30% to about 50%, about 30% to about 80%, about 30% to about 90%, about 30% to about 100%, about 50% to about 100%, about 75% to about 100% or more, and any range or value therein) in the yield trait as compared to a plant or part thereof that is devoid of the mutated endogenous BRI1 gene.

An editing system useful with this invention can be any site-specific (sequence-specific) genome editing system now known or later developed, which system can introduce mutations in a target specific manner. For example, an editing system (e.g., site- or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or more polypeptides and/or one or more polynucleotides that when expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (DNA binding domain), a nuclease, and/or other polypeptide, and/or a polynucleotide.

In some embodiments, an editing system may comprise one or more sequence-specific nucleic acid binding domains (DNA binding domains) that can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN). In some embodiments, an editing system can comprise one or more polypeptides that include, but are not limited to, a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but is not limited to, a CRISPR array (CRISPR guide) nucleic acid, extended guide nucleic acid, and/or a reverse transcriptase template.

In some embodiments, a method of modifying or editing a Brassinosteroid Insensitive-1 (BRI1) gene may comprise contacting a target nucleic acid (e.g., a nucleic acid encoding a BRI1 polypeptide) with a base-editing fusion protein (e.g., a sequence specific DNA binding protein (e.g., a CRISPR-Cas effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing a locus within the target nucleic acid. In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific nucleic acid binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, a method of modifying or editing a Brassinosteroid Insensitive-1 (BRI1) gene may comprise contacting a target nucleic acid (e.g., a nucleic acid encoding a BRI1 polypeptide) with a sequence-specific nucleic acid binding fusion protein (e.g., a sequence-specific DNA binding protein (e.g., a CRISPR-Cas effector protein or domain) fused to a peptide tag, a deaminase fusion protein comprising a deaminase domain (e.g., an adenine deaminase and/or a cytosine deaminase) fused to an affinity polypeptide that is capable of binding to the peptide tag, and a guide nucleic acid, wherein the guide nucleic acid is capable of guiding/targeting the sequence-specific nucleic acid binding fusion protein to the target nucleic acid and the sequence-specific nucleic acid binding fusion protein is capable of recruiting the deaminase fusion protein to the target nucleic acid via the peptide tag-affinity polypeptide interaction, thereby editing a locus within the target nucleic acid. In some embodiments, the sequence-specific nucleic acid binding fusion protein may be fused to the affinity polypeptide that binds the peptide tag and the deaminase may be fused to the peptide tag, thereby recruiting the deaminase to the sequence-specific nucleic acid binding fusion protein and to the target nucleic acid. In some embodiments, the sequence-specific binding fusion protein, deaminase fusion protein, and guide nucleic acid may be comprised in one or more expression cassettes. In some embodiments, the target nucleic acid may be contacted with a sequence-specific binding fusion protein, deaminase fusion protein, and an expression cassette comprising a guide nucleic acid. In some embodiments, the sequence-specific nucleic acid binding fusion proteins, deaminase fusion proteins and guides may be provided as ribonucleoproteins (RNPs).

In some embodiments, methods such as prime editing may be used to generate a mutation in an endogenous BRI1 gene. In prime editing, RNA-dependent DNA polymerase (reverse transcriptase, RT) and reverse transcriptase templates (RT template) are used in combination with sequence specific nucleic acid binding domains that confer the ability to recognize and bind the target in a sequence-specific manner, and which can also cause a nick of the PAM-containing strand within the target. The nucleic acid binding domain may be a CRISPR-Cas effector protein and in this case, the CRISPR array or guide RNA may be an extended guide that comprises an extended portion comprising a primer binding site (PSB) and the edit to be incorporated into the genome (the template). Similar to base editing, prime editing can take advantages of the various methods of recruiting proteins for use in the editing to the target site, such methods including both non-covalent and covalent interactions between the proteins and nucleic acids used in the selected process of genome editing.

As used herein, a "CRISPR-Cas effector protein" is a protein or polypeptide or domain thereof that cleaves or cuts a nucleic acid, binds a nucleic acid (e.g., a target nucleic acid and/or a guide nucleic acid), and/or that identifies, recognizes, or binds a guide nucleic acid as defined herein. In some embodiments, a CRISPR-Cas effector protein may be an enzyme (e.g., a nuclease, endonuclease, nickase, etc.) or portion thereof and/or may function as an enzyme. In some embodiments, a CRISPR-Cas effector protein refers to a CRISPR-Cas nuclease polypeptide or domain thereof that comprises nuclease activity or in which the nuclease activity has been reduced or eliminated, and/or comprises nickase activity or in which the nickase has been reduced or eliminated, and/or comprises single stranded DNA cleavage activity (ss DNAse activity) or in which the ss DNAse activity has been reduced or eliminated, and/or comprises self-processing RNAse activity or in which the self-processing RNAse activity has been reduced or eliminated. A CRISPR-Cas effector protein may bind to a target nucleic acid.

In some embodiments, a sequence-specific nucleic acid binding domain may be a CRISPR-Cas effector protein. In some embodiments, a CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g., Cas9 nickase, Cas12a nickase.

A CRISPR Cas9 effector protein or CRISPR Cas9 effector domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes, S. thermophilus*), *Lactobacillus* spp., *Bifidobacterium* spp., *Kandleria* spp., *Leuconostoc* spp., Oenococcus spp., *Pediococcus* spp., *Weissella* spp., and/or *Olsenella* spp. Example Cas9 sequences include, but are not limited to, the amino acid sequences of SEQ ID NO: 56 and SEQ ID NO:57 or the nucleotide sequences of SEQ ID NOs: 58-68.

In some embodiments, the CRISPR-Cas effector protein may be a Cas9 polypeptide derived from *Streptococcus pyogenes* and recognizes the PAM sequence motif NGG, NAG, NGA (Mali et al, Science 2013; 339 (6121): 823-826). In some embodiments, the CRISPR-Cas effector protein may be a Cas9 polypeptide derived from *Streptococcus* thermophiles and recognizes the PAM sequence motif NGGNG and/or NNAGAAW (W=A or T) (See, e.g., Horvath et al, Science, 2010; 327 (5962): 167-170, and Deveau et al, J Bacteriol 2008; 190 (4): 1390-1400). In some embodiments, the CRISPR-Cas effector protein may be a Cas9 polypeptide derived from *Streptococcus mutans* and recognizes the PAM sequence motif NGG and/or NAAR (R=A or G) (See, e.g., Deveau et al, J BACTERIOL 2008; 190 (4): 1390-1400). In some embodiments, the CRISPR-Cas effector protein may be a Cas9 polypeptide derived from *Streptococcus aureus* and recognizes the PAM sequence motif NNGRR (R=A or G). In some embodiments, the CRISPR-Cas effector protein may be a Cas9 protein derived from *S. aureus*, which recognizes the PAM sequence motif N GRRT (R=A or G). In some embodiments, the CRISPR-Cas effector protein may be a Cas9 polypeptide derived from *S. aureus*, which recognizes the PAM sequence motif N GRRV (R=A or G). In some embodiments, the CRISPR-Cas effector protein may be a Cas9 polypeptide that is derived from *Neisseria meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the CRISPR-Cas effector protein may be a Cas13a protein derived from Leptotrichia shahii, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease see, e.g., amino acid sequences of SEQ ID NOs: 1-17, nucleic acid sequences of SEQ ID NOs: 18-20. Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. *Nat. Biotechnol.* 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally occurring cytosine deaminase, including but not limited to a primate (e.g., a human, monkey, chimpanzee, gorilla), a dog, a cow, a rat or a mouse. Thus, in some embodiments, a cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same (e.g., SEQ ID NO:27, SEQ ID NO: 28 or SEQ ID NO:29). In some embodiments, the cytosine deaminase may be an APOBEC1 deaminase having the amino acid sequence of SEQ ID NO:23. In some embodiments, the cytosine deaminase may be an APOBEC3A deaminase having the amino acid sequence of SEQ ID NO:24. In some embodiments, the cytosine deaminase may be an CDA1 deaminase, optionally a CDA1 having the amino acid sequence of SEQ ID NO:25. In some embodiments, the cytosine deaminase may be a FERNY deaminase, optionally a FERNY having the amino acid sequence of SEQ ID NO:26. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NO:23, SEQ ID NO:24, SEQ ID NO:25 or SEQ ID NO:26 (e.g., at least 80%, at least 85%, at least 90%, at least 92%, at least 95%, at least 96%, at least 97%, at least 98%, at least 99%, or at least 99.5% identical to the amino acid sequence of SEQ ID NO: 23, SEQ ID NO:24, SEQ ID NO:25, SEQ ID NO:26, SEQ ID NO:27, SEQ ID NO:28 or SEQ ID NO:29). In some embodiments, a polynucleotide encoding a cytosine deaminase may be codon optimized for expression in a plant and the codon optimized polypeptide may be about 70% to 99.5% identical to the reference polynucleotide.

In some embodiments, a nucleic acid construct of this invention may further encode a uracil glycosylase inhibitor (UGI) (e.g., uracil-DNA glycosylase inhibitor) polypeptide/domain. Thus, in some embodiments, a nucleic acid construct encoding a CRISPR-Cas effector protein and a cytosine deaminase domain (e.g., encoding a fusion protein comprising a CRISPR-Cas effector protein domain fused to a cytosine deaminase domain, and/or a CRISPR-Cas effector protein domain fused to a peptide tag or to an affinity polypeptide capable of binding a peptide tag and/or a deaminase protein domain fused to a peptide tag or to an affinity polypeptide capable of binding a peptide tag) may further encode a uracil-DNA glycosylase inhibitor (UGI), optionally wherein the UGI may be codon optimized for expression in a plant. In some embodiments, the invention provides fusion proteins comprising a CRISPR-Cas effector polypeptide, a deaminase domain, and a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and a UGI may be fused to any combination of peptide tags and affinity polypeptides as described herein, thereby recruiting the deaminase domain and UGI to the CRISPR-Cas effector polypeptide and a target nucleic acid. In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:41 or a polypeptide having about 70% to about 99.5% sequence identity to the amino acid sequence of SEQ ID NO:41 (e.g., at least 80%, at least 85%, at least 90%, at least 92%, at least 95%, at least 96%, at least 97%, at least 98%, at least 99%, or at least 99.5% identical to the amino acid sequence of SEQ ID NO:41). For example, in some embodiments, a UGI domain may comprise a fragment of the amino acid sequence of SEQ ID NO:41 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:41. In some embodiments, a UGI domain may be a variant of a known UGI (e.g., SEQ ID NO:41) having about 70% to about 99.5% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% sequence identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO: 30. In some embodiments, a mutated/evolved *E. coli* TadA* comprises the amino acid sequence of SEQ ID NOs: 31-40 (e.g., SEQ ID NOs: 31, 32, 33, 34, 35, 36, 37, 38, 39 or 40). In some embodiments, a polynucleotide encoding a TadA/TadA* may be codon optimized for expression in a plant.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a sequence-specific nucleic acid binding protein and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt function; and/or generation of point mutations in genomic DNA to disrupt splice junctions.

The nucleic acid constructs of the invention encoding a base editor comprising a sequence-specific nucleic acid binding protein and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt function; and/or generation of point mutations in genomic DNA to disrupt splice junctions.

The nucleic acid constructs of the invention comprising a CRISPR-Cas effector protein or a fusion protein thereof may be used in combination with a guide RNA (gRNA, CRISPR array, CRISPR RNA, crRNA), designed to function with the encoded CRISPR-Cas effector protein or domain, to modify a target nucleic acid. A guide nucleic acid useful with this invention comprises at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex (e.g., a CRISPR-Cas effector fusion protein (e.g., CRISPR-Cas effector domain fused to a deaminase domain and/or a CRISPR-Cas effector domain fused to a peptide tag or an affinity polypeptide to recruit a deaminase domain and optionally, a UGI) to the target nucleic acid, wherein the target nucleic acid may be modified (e.g., cleaved or edited) or modulated (e.g., modulating transcription) by the deaminase domain.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made, and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids Res.* 35 (Web Server issue): W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to the same region (e.g., 5' end)

of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g., protospacer) (e.g., a portion of consecutive nucleotides of a sequence (a) having at least 80% sequence identity to any one of SEQ ID NOs: 69, 70, 80, or 81, or SEQ ID NOs: 73-79 or 83-95; and/or (b) encoding an amino acid sequence having at least 80% sequence identity to any one of SEQ ID NOs: 71, 72 or 82). In some embodiments, a spacer sequence (e.g., one or more spacers) may include, but is not limited to, the nucleotide sequences of any one of SEQ ID NOs: 96-100. The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length.

In some embodiments, the 5' region of a spacer sequence of a guide nucleic acid may be identical to a target DNA, while the 3' region of the spacer may be substantially complementary to the target DNA (such as for a Type V CRISPR-Cas), or the 3' region of a spacer sequence of a guide nucleic acid may be identical to a target DNA, while the 5' region of the spacer may be substantially complementary to the target DNA (such as for a Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

```
  5'-NNNNNNNNNNNNNNNNNNNN-3' RNA Spacer
       ||||||||||||||||||
3'AAANNNNNNNNNNNNNNNNNNN-5' Target strand

5'TTTNNNNNNNNNNNNNNNNNNN-3' Non-target strand
```

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR- Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention (e.g., one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct comprising a CRISPR-Cas effector protein and a deaminase domain (e.g., a fusion protein)) or the components for base editing (e.g., a CRISPR-Cas effector protein fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

Fusion proteins of the invention may comprise sequence-specific nucleic acid binding domains (e.g., sequence-specific DNA binding domains), CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26 (5): 910-924 (2017)); Gilbreth (*Curr Opin Struc Biol* 22 (4): 413-420 (2013)), U.S. Pat. No. 9,982,053, each of which are incorporated by reference in their entireties for the teachings relevant to affibodies, anticalins, monobodies and/or DARPins. Example peptide tag sequences and their affinity polypeptides include, but are not limited to, the amino acid sequences of SEQ ID NOs: 42-In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases). Example RNA recruiting motifs and their affinity polypeptides include, but are not limited to, the sequences of SEQ ID NOs: 45-55.

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat-spacer-extended portion (RT template-primer binding site)-RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide Pumilio/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide Pumilio/fem-3 mRNA binding factor (PUF).

In some embodiments, the components for recruiting polypeptides and nucleic acids may those that function through chemical interactions that may include, but are not limited to, rapamycin-inducible dimerization of FRB-FKBP; Biotin-streptavidin; SNAP tag; Halo tag; CLIP tag; DmrA-DmrC heterodimer induced by a compound; bifunctional ligand (e.g., fusion of two protein-binding chemicals together, e.g., dihyrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

Further provided herein are cells comprising one or more polynucleotides, guide nucleic acids, nucleic acid constructs, expression cassettes or vectors of the invention.

The nucleic acid constructs of the invention (e.g., a construct comprising a sequence specific DNA binding domain, a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids and/or their expression.

A target nucleic acid of any plant or plant part (or groupings of plants, for example, into a genus or higher order classification) may be modified (e.g., mutated, e.g., base edited, cleaved, nicked, etc.) using the polypeptides, polynucleotides, ribonucleoproteins (RNPs), nucleic acid constructs, expression cassettes, and/or vectors of the invention including an angiosperm, a gymnosperm, a monocot, a dicot, a C3, C4, CAM plant, a bryophyte, a fern and/or fern ally, a microalgae, and/or a macroalgae. A plant and/or plant part that may be modified as described herein may be a plant and/or plant part of any plant species/variety/cultivar. In some embodiments, a plant that may be modified as described herein is a monocot. In some embodiments, a plant that may be modified as described herein is a dicot.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

Any plant comprising an endogenous Brassinosteroid Insensitive-1 (BRI1) gene may be modified as described herein to improve one or more yield traits. Non-limiting examples of plants that may be modified as described herein may include, but are not limited to, turf grasses (e.g., bluegrass, bentgrass, ryegrass, fescue), feather reed grass, tufted hair grass, miscanthus, arundo, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, Chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, papaya, and lychee, a field crop plant such as clover, alfalfa, timothy, evening primrose, meadow foam, corn/maize (field, sweet, popcorn), hops, jojoba, buckwheat, safflower, quinoa, wheat, rice, barley, rye, millet, sorghum, oats, triticale, sorghum, tobacco, kapok, a leguminous plant (beans (e.g., green and dried), lentils, peas, soybeans), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), *Cannabis* (e.g., *Cannabis sativa, Cannabis indica*, and *Cannabis ruderalis*), lauraceae (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, or sunflower.

In some embodiments, a plant that may be modified as described herein may include, but is not limited to, soybean, canola, corn, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, or a *Brassica* spp (e.g., *B. napus, B. oleracea, B. rapa, B. juncea*, and/or *B. nigra*). In some embodiments, a plant that may be modified as described herein is a dicot. In some embodiments, a plant that may be modified as described herein is soybean (i.e., *Glycine max*).

The invention will now be described with reference to the following examples. It should be appreciated that these examples are not intended to limit the scope of the claims to the invention but are rather intended to be exemplary of certain embodiments. Any variations in the exemplified methods that occur to the skilled artisan are intended to fall within the scope of the invention.

EXAMPLES

Example 1. Editing Strategy

A strategy to generate edits in the 5' regulatory region of the soybean BRI1 genes of Glyma.06g147600 (SEQ ID NO:72) and Glyma.04g218300 (SEQ ID NO:83) to remove or modify upstream open reading frames (uORF(s)) which are present in the transcript of the BRI1 gene. To generate a range of alleles, CRISPR guide nucleic acids comprising one or more spacers (SEQ ID NOs: 99-103) having complementarity to targets within both of the BRI1 soybean genes were designed and placed into a construct for editing.

Lines carrying edits in the BRI1 genes were screened and those showing edits in the targeted gene were advanced to the next generation.

The lines carrying edits in the BRI1 genes were grouped into two classes. Genotype 1 contains lines with edits in the uORF of the soybean gene Glyma. 06g147600 (SEQ ID NO: 69), and genotype 2 contains lines with edits in the uORF of the soybean gene Glyma.04g218300 (SEQ ID NO:80). Genotype 1 lines included CE160306 (SEQ ID NO: 101, SEQ ID NO:102), CE160313 (SEQ ID NO:103, SEQ ID NO:104), CE160326 (SEQ ID NO:105), CE160327 (SEQ ID NO:106, SEQ ID NO:107) and genotype 2 lines included CE160331 (SEQ ID NO:108, SEQ ID NO:109), CE160334 (SEQ ID NO:110), CE160349 (SEQ ID NO:111), CE160355 (SEQ ID NO:112), CE160374 (SEQ ID NO:113, SEQ ID NO:114), CE160392 (SEQ ID NO:115, SEQ ID NO:116) and CE160403 (SEQ ID NO: 117). The edited alleles in each of genotype 1 and genotype 2 represent a range of deletions in the uORF region of the targeted gene which were expected to remove the "ATG" start site of at least one uORF in the BRI1 gene.

Example 2. Phenotype Evaluation

The E0 plants described in Example 1 were allowed to set E1 seed. The E1 seed was collected and planted and the resulting E1 plants were evaluated at the R6 growth stage for plant architectural features that may be indicative of an increase in yield, as well as seed counts which are a direct indication of plant yield. The plant phenotypes measured included plant height (measured in cm), number of nodes on the mainstem, number of branches, pods on branches, pods on mainstem, pod per node on the mainstem, pods per plant, seeds per pod and seeds per plant. Results are summarized in Table 2 and Table 3, which demonstrate that the edits obtained in the BRI1 genes are altering plant architecture and may affect plant yield. Results are summarized in Table 5 for the genotypes described in Table 4 for individual plant genotypes where the "ATG" of at least 1 uORF associated with a target BRI1 gene was altered.

TABLE 2

| E1 progeny from | Plant height (standard deviation) | Nodes on mainstem (standard deviation) | Branches per plant (standard deviation) | Pods on branches (standard deviation) | Pods on mainstem (standard deviation) | Pods per node mainstem (standard deviation) | Pods per plant (standard deviation) |
|---|---|---|---|---|---|---|---|
| Genotype 1 | 107.4 (6.2) | 18.8* (0.8) | 6.7 (2.2) | 78 (15) | 49 (6) | 2.6 (0.4) | 127 (17) |
| Genotype 2 | 103 (9) | 19.4 (0.5) | 6.5 (2.1) | 65 (27) | 47 (12) | 2.4 (0.6) | 112 (35) |

TABLE 2-continued

| E1 progeny from | Plant height (standard deviation) | Nodes on mainstem (standard deviation) | Branches per plant (standard deviation) | Pods on branches (standard deviation) | Pods on mainstem (standard deviation) | Pods per node mainstem (standard deviation) | Pods per plant (standard deviation) |
|---|---|---|---|---|---|---|---|
| Unedited/WT control | 107.6 (5.7) | 20 (0.7) | 7 (1.1) | 72 (13) | 44 (9) | 2.2 (0.4) | 116 (18) |
| Null segregant | 103.2 (4.7) | 20.2 (0.8) | 7 (1.7) | 83 (18) | 40 (6) | 2 (0.3) | 123 (20) |

TABLE 3

| E1 progeny from | Seeds per plant (standard deviation) | Seeds per pod (standard deviation) |
|---|---|---|
| Genotype 1 | 249.2 (49.0) | 1.98 (0.4) |
| Genotype 2 | 222.5 (78.2) | 1.98 (0.3) |
| Unedited/WT control | 274.9 (45.6) | 2.38 (0.2) |
| Null segregant | 263.2 (59.5) | 2.13 (0.3) |

TABLE 4

| Genotypes | | |
|---|---|---|
| Genotype | edit | description |
| Genotype 1A (SEQ ID NOs: 103 and 104) | Compound heterozygous with one allele having a 17 bp deletion at position 75-91 (inclusive) of SEQ ID NO: 69; and the second allele having a 8 bp deletion at position 79-86 (inclusive) of SEQ ID NO: 69 | The "ATG" of uORF1 associated with Glyma.06g147600 is deleted in one allele and thus the deletion of the "ATG" is heterozygous |
| Genotype 1B (SEQ ID NO: 105) | Homozygous for 12 bp deletion at position 76-82 (inclusive) of SEQ ID NO: 69 | Edit deletes a portion of uORF1 associated with Glyma.06g147600 and does not affect the "ATG" of uORF1 |
| Genotype 2A (SEQ ID NOs: 108 and 109) | Heterozygous with one allele having a 24 bp deletion at position 6-29 (inclusive) of SEQ ID NO: 80; and the second allele having a 7 bp deletion at position 11-17 (inclusive) of SEQ ID NO: 80 | Both alleles delete the "ATG" of uORF1 associated with Glyma.04g218300 |
| Genotype 2B (SEQ ID NO: 111) | Homozygous for 199 bp deletion at position 8-206 (inclusive) of SEQ ID NO: 80 | Edit deletes uORF1-4 (including "ATG" for all four) associated with Glyma.04g218300 |
| Genotype 2C (SEQ ID NO: 117) | Homozygous for 11 bp deletion at position 7-17 (inclusive), and 4 bp deletion at position 153-156 (inclusive) and 14 bp deletion at position 193-206 (inclusive) of SEQ ID NO: 80 | Edit deletes "ATG" from uORF1 and uORF5 associated with Glyma.04g218300 |
| Genotype 2D (SEQ ID NOs: 115-116) | Heterozygous with one allele having a 152 bp deletion at position 8-159 (inclusive); and the second allele having a 10 bp deletion at position 8-17 (inclusive) of SQ ID NO: 80 | The edit results in the homozygous deletion of the "ATG" in uORF1 in both alleles of Glyma.04g218300; and the heterozygous deletion of the "ATG" from uORFs 2-4 in one allele of Glyma.04g218300 |
| Genotype 2E (SEQ ID NOs: 113-114) | Heterozygous with one allele having a 85 bp deletion at position 1-85 (inclusive); and the second allele havinga 4 bp deletion at position 9-12 (inclusive) of SEQ ID NO: 80 | Edit results in heterozygous deletion of "ATG" of uORF1 and uORF2 associated with Glyma.04g218300 |

TABLE 5

| Mean values individual genotypes | | | | | | | | | |
|---|---|---|---|---|---|---|---|---|---|
| Genotype (number of plants) | Plant Height | Nodes on Main stem | Number of branches | Pods on branches | Pods on Main stem | Pods per node on main stem | Pods per plant | Seeds per plant | Seeds per pod |
| 1A (2) | 109.5 | 18.5 | 9 | 90 | 50.5 | 2.74 | 140.5 | 273 | 1.99 |
| 1B (3) | 100.0 | 18.66 | 6 | 68.67 | 50.66 | 2.71 | 119.33 | 217.33 | 1.83 |
| 2A (2) | 105.5 | 19 | 5 | 49 | 47.50 | 2.5 | 96.50 | 214 | 2.22 |
| 2B (3) | 108.6 | 19.33 | 9 | 78.67 | 54.66 | 2.82 | 133.33 | 246 | 1.83 |
| 2C (1) | 95 | 19 | 6 | 33 | 32 | 1.68 | 65 | 101 | 1.55 |
| 2D (1) | 105 | 20 | 4 | 93 | 40 | 2 | 133 | 289 | 2.17 |
| 2E (1) | 87 | 20 | 7 | 62 | 43 | 2.15 | 105 | 224 | 2.13 |
| Null segregant control (6) | 103.2 | 20.17 | 7 | 82.50 | 40.33 | 2.00 | 122.83 | 263.17 | 2.13 |
| Unedited wild type control (9) | 107.6 | 20 | 7 | 72.11 | 43.67 | 2.18 | 115.78 | 274.89 | 2.38 |

The foregoing is illustrative of the present invention and is not to be construed as limiting thereof. The invention is defined by the following claims, with equivalents of the claims to be included therein.

What is claimed is:

1. A guide nucleic acid comprising a spacer having at least 90% complementarity to a target site in a soybean Brassinosteroid Insensitive-1 (BRI1) gene, wherein the target site is in a region of the soybean BRI1 gene located (a) from about nucleotide 2-213 with reference to nucleotide position numbering of SEQ ID NO:69 and the spacer has at least 90% complementarity to a sequence in any one of the nucleotide sequences of SEQ ID NOs: 74-79, and/or (b) from about nucleotide 1-267 with reference to nucleotide position numbering of SEQ ID NO:80 and the spacer has at least 90% complementarity to a sequence in any one of the nucleotide sequences of SEQ ID NOs: 84-95.

2. The guide nucleic acid of claim 1, wherein the spacer comprises any one of the nucleotide sequences of SEQ ID NOs: 96-100.

3. The guide nucleic acid of claim 1, wherein the region of the soybean BRI1 gene is located from about nucleotide 42-174, 62-154, 82-134, or 92-124 with reference to nucleotide position numbering of SEQ ID NO:69.

4. The guide nucleic acid of claim 1, wherein the region of the soybean BRI1 gene is located from about nucleotide 40-227, 70-195 or 100-168 with reference to nucleotide position numbering of SEQ ID NO:80.

* * * * *

SEQUENCE LISTING

```
Sequence total quantity: 117
SEQ ID NO: 1            moltype = AA  length = 1228
FEATURE                 Location/Qualifiers
source                  1..1228
                        mol_type = protein
                        note = Lachnospiraceae bacterium
                        organism = unidentified
SEQUENCE: 1
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                    1228

SEQ ID NO: 2            moltype = AA  length = 1307
FEATURE                 Location/Qualifiers
source                  1..1307
                        mol_type = protein
                        organism = Acidaminococcus sp.
SEQUENCE: 2
MTQFEGFTNL YQVSKTLRFE LIPQGKTLKH IQEQGFIEED KARNDHYKEL KPIIDRIYKT  60
YADQCLQLVQ LDWENLSAAI DSYRKEKTEE TRNALIEEQA TYRNAIHDYF IGRTDNLTDA  120
INKRHAEIYK GLFKAELFNG KVLKQLGTVT TTEHENALLR SFDKFTTYFS GFYENRKNVF  180
SAEDISTAIP HRIVQDNFPK FKENCHIFTR LITAVPSLRE HFENVKKAIG IFVSTSIEEV  240
FSFPFYNQLL TQTQIDLYNQ LLGGISREAG TEKIKGLNEV LNLAIQKNDE TAHIIASLPH  300
RFIPLFKQIL SDRNTLSFIL EEFKSDEEVI QSFCKYKTLL RNENVLETAE ALFNELNSID  360
LTHIFISHKK LETISSALCD HWDTLRNALY ERRISELTGK ITKSAKEKVQ RSLKHEDINL  420
QEIISAAGKE LSEAFKQKTS EILSHAHAAL DQPLPTTLKK QEEKEILKSQ LDSLLGLYHL  480
LDWFAVDESN EVDPEFSARL TGIKLEMEPS LSFYNKARNY ATKKPYSVEK FKLNFQMPTL  540
```

-continued

```
ASGWDVNKEK NNGAILFVKN GLYYLGIMPK QKGRYKALSF EPTEKTSEGF DKMYYDYFPD  600
AAKMIPKCST QLKAVTAHFQ THTTPILLSN NFIEPLEITK EIYDLNNPEK EPKKFQTAYA  660
KKTGDQKGYR EALCKWIDFT RDFLSKYTKT TSIDLSSLRP SSQYKDLGEY YAELNPLLYH  720
ISFQRIAEKE IMDAVETGKL YLFQIYNKDF AKGHHGKPNL HTLYWTGLFS PENLAKTSIK  780
LNGQAELFYR PKSRMKRMAH RLGEKMLNKK LKDQKTPIPD TLYQELYDYV NHRLSHDLSD  840
EARALLPNVI TKEVSHEIIK DRRFTSDKFF FHVPITLNYQ AANSPSKFNQ RVNAYLKEHP  900
ETPIIGIDRG ERNLIYITVI DSTGKILEQR SLNTIQQFDY QKKLDNREKE RVAARQAWSV  960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN              1307

SEQ ID NO: 3            moltype = AA  length = 1241
FEATURE                 Location/Qualifiers
source                  1..1241
                        mol_type = protein
                        organism = Butyrivibrio proteoclasticus
SEQUENCE: 3
MLLYENYTKR NQITKSLRLE LRPQGKTLRN IKELNLLEQD KAIYALLERL KPVIDEGIKD  60
IARDTLKNCE LSFEKLYEHF LSGDKKAYAK ESERLKKEIV KTLIKNLPEG IGKISEINSA  120
KYLNGVLYDF IDKTHKDSEE KQNILSDILE TKGYLALFSK FLTSRITTLE QSMPKRVIEN  180
FEIYAANIPK MQDALERGAV SFAIEYESIC SVDYYNQILS QEDIDSYNRL ISGIMDEDGA  240
KEKGINQTIS EKNIKIKSEH LEEKPFRILK QLHKQILEER EKAFTIDHID SDEEVVQVTK  300
EAFEQTKEQW ENIKKINGFY AKDPGDITLF IVVGPNQTHV LSQLIYGEHD RIRLLLEEYE  360
KNTLEVLPRR TKSEDARYDK FVNAVPKKVA KESHTFDGLQ KMTGDDRLFI LYRDELARNY  420
MRIKEAYGTF ERDILKSRRG IKGNRDVQES LVSFYDELTK FRSALRIINS GNDEKADPIF  480
YNTFDGIFEK ANRTYKAENL CRNYVTKSPA DDARIMASCL GTPARLRTHW WNGEENFAIN  540
DVAMIRRGDE YYYFVLTPDV KPVDLKTKDE TDAQIFVQRK GAKSFLGLPK ALFKCILEPY  600
FESPEHKNDK NCVIEEYVSK PLTIDRRAYD IFKNGTFKKT NIGIDGLTEE KFKDDCRYLI  660
DVYKEFIAVY TRYSCFNMSG LKRADEYNDI GEFFSDVDTR LCTMEWIPVS FERINDMVDK  720
KEGLLFLVRS MFLYNRPRKP YERTFIQLFS DSNMEHTSML LNSRAMIQYR AASLPRRVTH  780
KKGSILVALR DSNGEHIPMH IREAIYKMKN NFDISSEDFI MAKAYLAEHD VAIKKANEDI  840
IRNRRYTEDK FFLSLSYTKN ADISARTLDY INDKVEEDTQ DSRMAVIVTR NLKDLTYVAV  900
VDEKNNVLEE KSLNEIDGVN YRELLKERTK IKYHDKTRLW QYDVSSKGLK EAYVELAVTQ  960
ISKLATKYNA VVVVESMSST FKDKFSFLDE QIFKAFEARL CARMSDLSFN TIKEGEAGSI  1020
SNPIQVSNNN GNSYQDGVIY FLNNAYTRTL CPDTGFVDVF DKTRLITMQS KRQFFAKMKD  1080
IRIDDGEMLF TFNLEEYPTK RLLDRKEWTV KIAGDGSYFD KDKGEYVYVN DIVREQIIPA  1140
LLEDKAVFDG NMAEKFLDKT AISGKSVELI YKWFANALYG IITKKDGEKI YRSPITGTEI  1200
DVSKNTTYNF GKKFMFKQEY RGDGDFLDAF LNYMQAQDIA V                    1241

SEQ ID NO: 4            moltype = AA  length = 1238
FEATURE                 Location/Qualifiers
source                  1..1238
                        mol_type = protein
                        organism = Candidatus Methanoplasma termitum
SEQUENCE: 4
MNNYDEFTKL YPIQKTIRFE LKPQGRTMEH LETFNFFEED RDRAEKYKIL KEAIDEYHKK  60
FIDEHLTNMS LDWNSLKQIS EKYYKSREEK DKKVFLSEQK RMRQEIVSEF KKDDRFKDLF  120
SKKLFSELLK EEIYKKGNHQ EIDALKSFDK FSGYFIGLHE NRKNMYSDGD EITAISNRIV  180
NENFPKFLDN LQKYQEARKK YPEWIIKAES ALVAHNIKMD IVFSLEYFNK VLNQEGIQRY  240
NLALGGYVTK SGEKMMGLND ALNLAHQSEK SSKGRIHMTP LFKQILSEKE SFSYIPDVFT  300
EDSQLLPSIG GFFAQIENDK DGNIFDRALE LISSYAEYDT ERIYIRQADI NRVSNVIFGE  360
WGTLGGLMRE YKADSINDIN LERTCKKVDK WLDSKEFALS DVLEAIDRTG NNDAFNEYIS  420
KMRTAREKID AARKEMKFIS EKISGDEESI HIIKTLLDSV QQFLHFFNLF KARQDIPLDG  480
AFYAEFDEVH SKLFAIVPLY NKVRNYLTKN NLNTKKIKLN FKNPTLANGW DQNKVYDYAS  540
LIFLRDGNYY LGIINPKRKK NIKFEQGSGN GPFYRKMVYK QIPGPNKNLR PVFLTSTKGK  600
KEYKPSKEII EGYEADKHIR GDKFDLDFCH KLIDFFKESI EKHKDWSKFN FYFSPTESYG  660
DISEFYLDVE KQGYRMHFEN ISAETIDEYV EKGDLFLFQI YNKDFVKAAT GKKDMHTIYW  720
NAAFSPENLQ DVVVKLNGEA ELFYRDKSDI KEIVHREGEI LVNRTYNGRT PVPDKIHKKL  780
TDYHNGRTKD LGEAKEYLDK VRYFKAHYDI TKDRRYLNDK IYFHVPLTLN FKANGKKNLN  840
KMVIEKFLSD EKAHIIGIDR GERNLLYYSI IDRSGKIIDQ QSLNVIDGFD YREKLNQREI  900
EMKDARQSWN AIGKIKDLKE GYLSKAVHEI TKMAIQYNAI VVMEELNYGF KRGRFKVEKQ  960
IYQKFENMLI DKMNYLVFKD APDESPGGVL NAYQLTNPLE SFAKLGKQTG ILFYVPAAYT  1020
SKIDPTTGFV NLFNTSSKTN AQERKEFLQK FESISYSAKD GGIFAFAFDY RKFGTSKTDH  1080
KNVWTAYTNG ERMRYIKEKK RNELFDPSKE IKEALTSSGI KYDGGQNILP DILRSNNNGL  1140
IYTMYSSFIA AIQMRVYDGK EDYIISPIKN SKGEFFRTDP KRRELPIDAD ANGAYNIALR  1200
GELTMRAIAE KFDPDSEKMA KLELKHKDWF EFMQTRGD                        1238

SEQ ID NO: 5            moltype = AA  length = 1281
FEATURE                 Location/Qualifiers
source                  1..1281
                        mol_type = protein
                        organism = Eubacterium eligens
SEQUENCE: 5
MNGNRSIVYR EFVGVIPVAK TLRNELRPVG HTQEHIIQNG LIQEDELRQE KSTELKNIMD  60
DYYREYIDKS LSGVTDLDFT LLFELMNLVQ SSPSKDNKKA LEKEQSKMRE QICTHLQSDS  120
NYKNIFNAKL LKEILPDFIK NYNQYDVKDK AGKLETLALF NGFSTYFTDF FEKRKNVFTK  180
```

-continued

```
EAVSTSIAYR IVHENSLIFL ANMTSYKKIS EKALDEIEVI EKNNQDKMGD WELNQIFNPD  240
FYNMVLIQSG IDFYNEICGV VNAHMNLYCQ QTKNNYNLFK MRKLHKQILA YTSTSFEVPK  300
MFEDDMSVYN AVNAFIDETE KGNIIGKLKD IVNKYDELDE KRIYISKDFY ETLSCFMSGN  360
WNLITGCVEN FYDENIHAKG KSKEEKVKKA VKEDKYKSIN DVNDLVEKYI DEKERNEFKN  420
SNAKQYIREI SNIITDTETA HLEYDDHISL IESEEKADEM KKRLDMYMNM YHWAKAFIVD  480
EVLDRDEMFY SDIDDIYNIL ENIVPLYNRV RNYVTQKPYN SKKIKLNFQS PTLANGWSQS  540
KEFDNNAIIL IRDNKYYLAI FNAKNKPDKK IIQGNSDKKN DNDYKKMVYN LLPGANKMLP  600
KVFLSKKGIE TFKPSDYIIS GYNAHKHIKT SENFDISFCR DLIDYFKNSI EKHAEWRKYE  660
FKFSATDSYS DISEFYREVE MQGYRIDWTY ISEADINKLD EEGKIYLFQI YNKDFAENST  720
GKENLHTMYF KNIFSEENLD KIIKLNGQAE LFYRRASVKN PVKHKKDSVL VNKTYKNQLD  780
NGDVVRIPIP DDIYNEIYKM YNGYIKESDL SEAAKEYLDK VEVRTAQKDI VKDYRYTVDK  840
YFIHTPITIN YKVTARNNVN DMVVKYIAQN DDIHVIGIDR GERNLIYISV IDSHGNIVKQ  900
KSYNILNNYD YKKKLVEKEK TREYARKNWK SIGNIKELKE GYISGVVHEI AMLIVEYNAI  960
IAMEDLNYGF KRGRFKVERQ VYQKFESMLI NKLNYFASKE KSVDEPGGLL KGYQLTYVPD  1020
NIKNLGKQCG VIFYVPAAFT SKIDPSTGFI SAFNFKSIST NASRKQFFMQ FDEIRYCAEK  1080
DMFSFGFDYN NFDTYNITMG KTQWTVYTNG ERLQSEFNNA RRTGKTKSIN LTETIKLLLE  1140
DNEINYADGH DIRIDMEKMD EDKKSEFFAQ LLSLYKLTVQ MRNSYTEAEE QENGISYDKI  1200
ISPVINDEGE FFDSDNYKES DDKECKMPKD ADANGAYCIA LKGLYEVLKI KSEWTEDGFD  1260
RNCLKLPHAE WLDFIQNKRY E                                            1281

SEQ ID NO: 6            moltype = AA  length = 1300
FEATURE                 Location/Qualifiers
source                  1..1300
                        mol_type = protein
                        organism = Francisella novicida
SEQUENCE: 6
MSIYQEFVNK YSLSKTLRFE LIPQGKTLEN IKARGLILDD EKRAKDYKKA KQIIDKYHQF  60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKVNY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
AFKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                        1300

SEQ ID NO: 7            moltype = AA  length = 1206
FEATURE                 Location/Qualifiers
source                  1..1206
                        mol_type = protein
                        note = Lachnospiraceae sp.
                        organism = unidentified
SEQUENCE: 7
MYYESLTKQY PVSKTIRNEL IPIGKTLDNI RQNNILESDV KRKQNYEHVK GILDEYHKQL  60
INEALDNCTL PSLKIAAEIY LKNQKEVSDR EDFNKTQDLL RKEVVEKLKA HENFTKIGKK  120
DILDLLEKLP SISEDDYNAL ESFRNFYTYF TSYNKVRENL YSDKEKSSTV AYRLINENFP  180
KFLDNVKSYR FVKTAGILAD GLGEEEQDSL FIVETFNKTL TQDGIDTYNS QVGKINSSIN  240
LYNQKNQKAN GFRKIPKMKM LYKQILSDRE ESFIDEFQSD EVLIDNVESY GSVLIESLKS  300
SKVSAFFDAL RESKGKNVYV KNDLAKTAMS VIVFENWRTF DDLLNQEYDL ANENKKKDDK  360
YFEKRQKELK KNKSYSLEHL CNLSEDSCNL IENYIHQISD DIENIIINNE TFLRIVINEH  420
DRSRKLAKNR KAVKAIKDFL DSIKVLEREL KLINSSGQEL EKDLIVYSAH EELLVELKQV  480
DSLYNMTRNY LTKKPFSTEK VKLNFNRSTL LNGWDRNKET DNLGVLLLKD GKYYLGIMNT  540
SANKAFVNPP VAKTEKVFKK VDYKLLPVPN QMLPKVFFAK SNIDFYNPSS EIYSNYKKGT  600
HKKGNMFSLE DCHNLIDFFK ESISKHEDWS KFGFKFDTQA SYNDISEFYR EVEKQGYKLT  660
YTDIDETYIN DLIERNELYL FQIYNKDFSM YSKGKLNLHT LYFMMLFDQR NIDDVVYKLN  720
GEAEVFYRPA SISEDELIIH KAGEEIKNKN PNRARTKETS TFSYDIVKDK RYSKDKFTLH  780
IPITMNFGVD EVKRFNDAVN SAIRIDENVN VIGIDRGERN LLYVVVIDSK GNILEQISLN  840
SIINKEYDIE TDYHALLDER EGGRDKARKD WNTVENIRDL KAGLYLQVVN VVAKLVLKYN  900
AIICLEDLNF GFKRGRQKVE KQVYQKFEKM LIDKLNYLVI DKSREQTSPK ELGGALNALQ  960
LTSKFKSFKE LGKQSGVIYY VPAYLTSKID PTTGFANLFY MKCENVEKSK RFFDGFDFIR  1020
FNALENVFEF GFDYRSFTQR ACGINSKWTV CTNGERIIKY RNPDKNNMFD EKVVVVTDEM  1080
KNLFEQYKIP YEDGRNVKDM IISNEEAEFY RRLYRLLQQT LQMRNSTSDG TRDYIISPVK  1140
NKREAYFNSE LSDGSVPKDA DANGAYNIAR KGLWVLEQIR QKSEGEKINL AMTNAEWLEY  1200
AQTHLL                                                             1206

SEQ ID NO: 8            moltype = AA  length = 1233
```

```
FEATURE               Location/Qualifiers
source                1..1233
                      mol_type = protein
                      note = Lachnospiraceae sp.
                      organism = unidentified
SEQUENCE: 8
MDYGNGQFER RAPLTKTITL RLKPIGETRE TIREQKLLEQ DAAFRKLVET VTPIVDDCIR  60
KIADNALCHF GTEYDFSCLG NAISKNDSKA IKKETEKVEK LLAKVLTENL PDGLRKVNDI  120
NSAAFIQDTL TSFVQDDADK RVLIQELKGK TVLMQRFLTT RITALTVWLP DRVFENFNIF  180
IENAEKMRIL LDSPLNEKIM KFDPDAEQYA SLEFYGQCLS QKDIDSYNLI ISGIYADDEV  240
KNPGINEIVK EYNQQIRGDK DESPLPKLKK LHKQILMPVE KAFFVRVLSN DSDARSILEK  300
ILKDTEMLPS KIIEAMKEAD AGDIAVYGSR LHELSHVIYG DHGKLSQIIY DKESKRISEL  360
METLSPKERK ESKKRLEGLE EHIRKSTYTF DELNRYAEKN VMAAYIAAVE ESCAEIMRKE  420
KDLRTLLSKE DVKIRGNRHN TLIVKNYFNA WTVFRNLIRI LRRKSEAEID SDFYDVLDDS  480
VEVLSLTYKG ENLCRSYITK KIGSDLKPEI ATYGSALRPN SRWWSPGEKF NVKFHTIVRR  540
DGRLYYFILP KGAKPVELED MDGDIECLQM RKIPNPTIFL PKLVFKDPEA FFRDNPEADE  600
FVFLSGMKAP VTITRETYEA YRYKLYTVGK LRDGEVSEEE YKRALLQVLT AYKEFLENRM  660
IYADLNFGFK DLEEYKDSSE FIKQVETHNT FMCWAKVSSS QLDDLVKSGN GLLFEIWSER  720
LESYYKYGNE KVLRGYEGVL LSILKDENLV SMRTLLNSRP MLVYRPKESS KPMVVHRDGS  780
RVVDRFDKDG KYIPPEVHDE LYRFFNNLLI KEKLGEKARK ILDNKKVKVK VLESERVKWS  840
KFYDEQFAVT FSVKKNADCL DTTKDLNAEV MEQYSESNRL ILIRNTTDIL YYLVLDKNGK  900
VLKQRSLNII NDGARDVDWK ERFRQVTKDR NEGYNEWDYS RTSNDLKEVY LNYALKEIAE  960
AVIEYNAILI IEKMSNAFKD KYSFLDDVTF KGFETKKLAK LSDLHFRGIK DGEPCSFTNP  1020
LQLCQNDSNK ILQDGVIFMV PNSMTRSLDP DTGFIFAIND HNIRTKKAKL NFLSKFDQLK  1080
VSSEGCLIMK YSGDSLPTHN TDNRVWNCCC NHPITNYDRE TKKVEFIEEP VEELSRVLEE  1140
NGIETDTELN KLNERENVPG KVVDAIYSLV LNYLRGTVSG VAGQRAVYYS PVTGKKYDIS  1200
FIQAMNLNRK CDYYRIGSKE RGEWTDFVAQ LIN                             1233

SEQ ID NO: 9          moltype = AA  length = 1227
FEATURE               Location/Qualifiers
source                1..1227
                      mol_type = protein
                      note = Lachnospiraceae sp.
                      organism = unidentified
SEQUENCE: 9
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI ANINKCPKNI FKINTEVRVL LKHDDNPYVI GIDRGERNLL  840
YIVVVDGKGN IVEQYSLNEI INNFNGIRIK TDYHSLLDKK EKERFEARQN WTSIENIKEL  900
KAGYISQVVH KICELVEKYD AVIALEDLNS GFKNSRVKVE KQVYQKFEKM LIDKLNYMVD  960
KKSNPCATGG ALKGYQITNK FESFKSMSTQ NGFIFYIPAW LTSKIDPSTG FVNLLKTKYT  1020
SIADKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IASNKEWLEY AQTSVKH                                   1227

SEQ ID NO: 10         moltype = AA  length = 1264
FEATURE               Location/Qualifiers
source                1..1264
                      mol_type = protein
                      organism = Leptospira inadai
SEQUENCE: 10
MEDYSGFVNI YSIQKTLRFE LKPVGKTLEH IEKKGFLKKD KIRAEDYKAV KKIIDKYHRA  60
YIEEVFDSVL HQKKKKDKTR FSTQFIKEIK EFSELYYKTE KNIPDKERLE ALSEKLRKML  120
VGAFKGEFSE EVAEKYNKNL FSKELIRNEI EKFCETDEER KQVSNFKSFT TYFTGFHSNR  180
QNIYSDEKKS TAIGYRIIHQ NLPKFLDNLK IIESIQRRFK DFPWSDLKKN LKKIDKNIKL  240
TEYFSIDGFV NVLNQKGIDA YNTILGGKSE ESGEKIQGLN EYINLYRQKN NIDRKNPLNV  300
KILFKQILGD RETKSFIPEA FPDDQSVLNS ITEFAKYLKL DKKKSIIAE LKKFLSSFNR  360
YELDGIYLAN DNSLASISTF LFDDWSFIKK SVSFKYDESV GDPKKKIKSP LKYEKEKEKW  420
LKQKYYTISF LNDAIESYSK SQDEKRVKIR LEAYFAEFKS KDDAKKQFDL LERIEEAYAI  480
VEPLLGAEYP RDRNLKADKK EVGKIKDFLD SIKSLQFFLK PLLSAEIFDE KDLGFYNQLE  540
GYYEEIDISG HLYNKVRNYL TGKIYSKEKF KLNFENSTLL KGWDENREVA NLCVIFREDQ  600
KYYLGVMDKE NNTILSDIPK VKPNELFYEK MVYKLIPTPH MQLPRIIFSS DNLSIYNPSK  660
SILKIREAKS FKEGKNFKLK DCHKFIDFYK ESISKNEDWS RFDFKFSKTS SYENISEFYR  720
EVERQGYNLD FKKVSKFYID SLVEDGKLYL FQIYNKDFSI FSKGKPNLHT IYFRSLFSKE  780
NLKDVCLKLN GEAEMFFRKK SINYDEKKKR EGHHPELFEK LKYPILKDKR YSEDKFQFHL  840
PISLNFKSKE RLNFNLKVNE FLKRNKDINI IGIDRGERNL LYLVMINQKG EILKQTLLDS  900
MQSGKGRPEI NYKEKLQEKE IERDKARKSW GTVENIKELK EGYLSIVIHQ ISKLMVENNA  960
```

```
IVVLEDLNIG FKRGRQKVER QVYQKFEKML IDKLNFLVFK ENKPTEPGGV LKAYQLTDEF  1020
QSFEKLSKQT GFLFYVPSWN TSKIDPRTGF IDFLHPAYEN IEKAKQWINK FDSIRFNSKM  1080
DWFEFTADTR KFSENLMLGK NRVWVICTTN VERYFTSKTA NSSIQYNSIQ ITEKLKELFV  1140
DIPFSNGQDL KPEILRKNDA VFFKSLLFYI KTTLSLRQNN GKKGEEEKDF ILSPVVDSKG  1200
RFFNSLEASD DEPKDADANG AYHIALKGLM NLLVLNETKE ENLSRPKWKI KNKDWLEFVW  1260
ERNR                                                              1264

SEQ ID NO: 11           moltype = AA  length = 1373
FEATURE                 Location/Qualifiers
source                  1..1373
                        mol_type = protein
                        organism = Moraxella bovoculi
SEQUENCE: 11
MLFQDFTHLY PLSKTVRFEL FIDRTLEHIH AKNFLSQDET MADMHQKVKV ILDDYHRDFI  60
ADMMGEVKLT KLAEFYDVYL KFRKNPKDDE LQKAQLKDLQ AVLRKEIVKP IGNGGKYKAG  120
YDRLFGAKLF KDGKELGDLA KFVIAQEGES SPKLAHLAHF EKFSTYFTGF HDNRKNMYSD  180
EDKHTAIAYR LIHENLPRFI DNLQILTTIK QKHSALYDQI INELTASGLD VSLASHLDGY  240
HKLLTQEGIT AYNTLLGGIS GEAGSPKIQG INELINSHHN QHCHKSERIA KLRPLHKQIL  300
SDGMSVSFLP SKFADDSEMC QAVNEFYRHY ADVFAKVQSL FDGFDDHQKD GIYVEHKNLN  360
ELSKQAFGDF ALLGRVLDGY YVDVVNPEFN ERFAKAKTDN AKAKLTKEKD KFIKGVHSLA  420
SLEQAIEHYT ARHDDESVQA GKLGQYFKHG LAGVDNPIQK IHNNHSTIKG FLERERPAGE  480
RALPKIKSGK NPEMTQLRQL KELLDNALNV AHFAKLLTTK TTLDNQDGNF YGEFGVLYDE  540
LAKIPTLYNK VRDYLSQKPF STEKYKLNFG NPTLLNGWDL NKEKDNFGVI LQKDGCYYLA  600
LLDKAHKKVF DNAPNTGKSI YQKMIYKYLE VRKQFPKVFF SKEAIAINYH PSKELVEIKD  660
KGRQRSDDER LKLYRFILEC LKIHPKYDKK FEGAIGDIQL FKKDKKGREV PISEKDLFKD  720
INGIFSSKPK LEMEDFFIGE FKRYNPSQDL VDQYNIYKKI DSNDNRKKEN FYNNHPKFKK  780
DLVRYYYESM CKHEEWEESF EFSKKLQDIG CYVDVNELFT EIETRRLNYK ISFCNINADY  840
IDELVEQGQL YLFQIYNKDF SPKAHGKPNL HTLYFKALFS EDNLADPIYK LNGEAQIFYR  900
KASLDMNETT IHRAGEVLEN KNPDNPKKRQ FVYDIIKDKR YTQKDFMLHV PITMNFGVQG  960
MTIKEFNKKV NQSIQQYDEV NVIGIDRGER HLLYLTVINS KGEILEQCSL NDITTASANG  1020
TQMTTPYHKI LDKREIERLN ARVGWGEIET IKELKSGYLS HVVHQISQLM LKYNAIVVLE  1080
DLNFGFKRGR FKVEKQIYQN FENALIKKLN HLVLKDKADD EIGSYKNALQ LTNNFTDLKS  1140
IGKQTGFLFY VPAWNTSKID PETGFVDLLK PRYENIQASQ AFFGKFDKIC YNADKDYFEF  1200
HIDYAKFTDK AKNSRQIWTI CSHGDKRYVY DKTANQNKGA AKGINVNDIL KSLFARHHIN  1260
EKQPNLVMDI CQNNDKEFHK SLMYLLKTLL ALRYSNASSD EDFILSPVAN DEGVFFNSAL  1320
ADDTQPQNAD ANGAYHIALK GLWLLNELKN SDDLNKVKLA IDNQTWLNFA QNR         1373

SEQ ID NO: 12           moltype = AA  length = 1352
FEATURE                 Location/Qualifiers
source                  1..1352
                        mol_type = protein
                        note = Parcubacteria bacterium
                        organism = unidentified
SEQUENCE: 12
MENIFDQFIG KYSLSKTLRF ELKPVGKTED FLKINKVFEK DQTIDDSYNQ AKFYFDSLHQ  60
KFIDAALASD KTSELSFQNF ADVLEKQNKI ILDKKREMGA LRKRDKNAVG IDRLQKEIND  120
AEDIIQKEKE KIYKDVRTLF DNEAESWKTY YQEREVDGKK ITESKADLKQ KGADFLTAAG  180
ILKVLKYEFP EEKEKEFQAK NQPSLFVEEK ENPGQKRYIF DSFDKFAGYL TKFQQTKKNL  240
YAADGTSTAV ATRIADNFII FHQNTKVFRD KYKNNHTDLG FDEENIFEIE RYKNCLLQRE  300
IEHIKNENSY NKIIGRINKK IKEYRDQKAK DTKLTKSDFP FFKNLDKQIL GEVEKEKQLI  360
EKTREKTEED VLIERFKEFI ENNEERFTAA KKLMNAFCNG EFESEYEGIY LKNKAINTIS  420
RRWFVSDRDF ELKLPQQKSK NKSEKNEPKV KKFISIAEIK NAVEELDGDI FKAVFYDKKI  480
IAQGGSKLEQ FLVIWKYEFE YLFRDIEREN GEKLLGYDSC LKIAKQLGIF PQEKEAREKA  540
TAVIKNYADA GLGIFQMMKY FSLDDKDRKN TPGQLSTNFY AEYDGYYKDF EFIKYYNEFR  600
NFITKKPFDE DKIKLNFENG ALLKGWDENK EYDFMGVILK KEGRLYLGIM HKNHRKLFQS  660
MGNAKGDNAN RYQKMIYKQI ADASKDVPRL LLTSKKAMEK FKPSQEILRI KKEKTFKRES  720
KNFSLRDLHA LIEYYRNCIP QYSNWSFYDF QFQDTGKYQN IKEFTDDVQK YGYKISFRDI  780
DDEYINQALN EGKMYLFEVV NKDIYNTKNG SKNLHTLYFE HILSAENLND PVFKLSGMAE  840
IFQRQPSVNE REKITTQKNQ CILDKGDRAY KYRRYTEKKI MFHMSLVLNT GKGEIKQVQF  900
NKIINQRISS SDNEMRVNVI GIDRGEKNLL YYSVVKQNGE IIEQASLNEI NGVNYRDKLI  960
EREKERLKNR QSWKPVVKIK DLKKGYISHV IHKICQLIEK YSAIVVLEDL NMRFKQIRGG  1020
IERSVYQQFE KALIDKLGYL VFKDNRDLRA PGGVLNGYQL SAPFVSFEKM RKQTGILFYT  1080
QAEYTSKTDP ITGFRKNVYI SNSASLDKIK EAVKKFDAIG WDGKEQSYFF KYNPYNLADE  1140
KYKNSTVSKE WAIFASAPRI RRQKGEDGYW KYDRVKVNEE FEKLLKVWNF VNPKATDIKQ  1200
EIIKKIKAGD LQGEKELDGR LRNFWHSFIY LFNLVLELRN SFSLQIKIKA GEVIAVDEGV  1260
DFIASPVKPF FTTPNPYIPS NLCWLAVENA DANGAYNIAR KGVMILKKIR EHAKKDPEFK  1320
KLPNLFISNA EWDEAARDWG KYAGTTALNL DH                                1352

SEQ ID NO: 13           moltype = AA  length = 1260
FEATURE                 Location/Qualifiers
source                  1..1260
                        mol_type = protein
                        organism = Porphyromonas creviorricanis
SEQUENCE: 13
MDSLKDFTNL YPVSKTLRFE LKPVGKTLEN IEKAGILKED EHRAESYRRV KKIIDTYHKV  60
FIDSSLENMA KMGIENEIKA MLQSFCELYK KDHRTEGEDK ALDKIRAVLR GLIVGAFTGV  120
CGRRENTVQN EKYESLFKEK LIKEILPDFV LSTEAESLPF SVEEATRSLK EFDSFTSYFA  180
GFYENRKNIY STKPQSTAIA YRLIHENLPK FIDNILVFQK IKEPIAKELE HIRADFSAGG  240
YIKKDERLED IFSLNYYIHV LSQAGIEKYN ALIGKIVTEG DGEMKGLNEH INLYNQQRGR  300
```

```
EDRLPLFRPL YKQILSDREQ LSYLPESFEK DEELLRALKE FYDHIAEDIL GRTQQLMTSI  360
SEYDLSRIYV RNDSQLTDIS KKMLGDWNAI YMARERAYDH EQAPKRITAK YERDRIKALK  420
GEESISLANL NSCIAFLDNV RDCRVDTYLS TLGQKEGPHG LSNLVENVFA SYHEAEQLLS  480
FPYPEENNLI QDKDNVVLIK NLLDNISDLQ RFLKPLWGMG DEPDKDERFY GEYNYIRGAL  540
DQVIPLYNKV RNYLTRKPYS TRKVKLNFGN SQLLSGWDRN KEKDNSCVIL RKGQNFYLAI  600
MNNRHKRSFE NKMLPEYKEG EPYFEKMDYK FLPDPNKMLP KVFLSKKGIE IYKPSPKLLE  660
QYGHGTHKKG DTFSMDDLHE LIDFFKHSIE AHEDWKQFGF KFSDTATYEN VSSFYREVED  720
QGYKLSFRKV SESYVYSLID QGKLYLFQIY NKDFSPCSKG TPNLHTLYWR MLFDERNLAD  780
VIYKLDGKAE IFFREKSLKN DHPTHPAGKP IKKKSRQKKG EESLFEYDLV KDRRYTMDKF  840
QFHVPITMNF KCSAGSKVND MVNAHIREAK DMHVIGIDRG ERNLLYICVI DSRGTILDQI  900
SLNTINDIDY HDLLESRDKD RQQEHRNWQT IEGIKELKQG YLSQAVHRIA ELMVAYKAVV  960
ALEDLNMGFK RGRQKVESSV YQQFEKQLID KLNYLVDKKK RPEDIGGLLR AYQFTAPFKS  1020
FKEMGKQNGF LFYIPAWNTS NIDPTTGFVN LFHVQYENVD KAKSFFQKFD SISYNPKKDW  1080
FEFAFDYKNF TKKAEGSRSM WILCTHGSRI KNFRNSQKNG QWDSEEFALT EAFKSLFVRY  1140
EIDYTADLKT AIVDEKQKDF FVDLLKLFKL TVQMRNSWKE KDLDYLISPV AGADGRFFDT  1200
REGNKSLPKD ADANGAYNIA LKGLWALRQI RQTSEGGKLK LAISNKEWLQ FVQERSYEKD  1260

SEQ ID NO: 14          moltype = AA  length = 664
FEATURE                Location/Qualifiers
source                 1..664
                       mol_type = protein
                       organism = Prevotella disiens
SEQUENCE: 14
NSYKEDKKRL NKVIIAYIEQ IKQTNIKKSI IESISKYPNI SDDDKVTPSS LLEKIKKVSI  60
DSYNGILSFK SFQSVNKEVI DNLLKTISPL KNKAEFLDLI NKDYQIFTEV QAVIDEICKQ  120
KTFIYFPISN VELEKEMGDK DKPLCLFQIS NKDLSFAKTF SANLRKKRGA ENLHTMLFKA  180
LMEGNQDNLD LGSGAIFYRA KSLDGNKPTH PANEAIKCRN VANKDKVSLF TYDIYKNRRY  240
MENKFLFHLS IVQNYKAAND SAQLNSSATE YIRKADDLHI IGIDRGERNL LYYSVIDMKG  300
NIVEQDSLNI IRNNDLETDY HDLLDKREKE RKANRQNWEA VEGIKDLKKG YLSQAVHQIA  360
QLMLKYNAII ALEDLGQMFV TRGQKIEKAV YQQFEKSLVD KLSYLVDKKR PYNELGGILK  420
AYQLASSITK NNSDKQNGFL FYVPAWNTSK IDPVTGFTDL LRPKAMTIKE AQDFFGAFDN  480
ISYNDKGYFE FETNYDKFKI RMKSAQTRWT ICTFGNRIKR KKDKNYWNYE EVELTEEFKK  540
LFKDSNIDYE NCNLKEEIQN KDNRKFFDDL IKLLQLTLQM RNSDDKGNDY IISPVANAEG  600
QFFDSRNGDK KLPLDADANG AYNIARKGLW NIRQIKQTKN KDDLNLSISS TEWLDFVREK  660
PYLK                                                              664

SEQ ID NO: 15          moltype = AA  length = 1484
FEATURE                Location/Qualifiers
VARIANT                1073
                       note = Xaa can be any naturally occurring amino acid
source                 1..1484
                       mol_type = protein
                       note = Peregrinibacteria bacterium
                       organism = unidentified
SEQUENCE: 15
MSNFFKNFTN LYELSKTLRF ELKPVGDTLT NMKDHLEYDE KLQTFLKDQN IDDAYQALKP  60
QFDEIHEEFI TDSLESKKAK EIDFSEYLDL FQEKKELNDS EKKLRNKIGE TFNKAGEKWK  120
KEKYPQYEWK KGSKIANGAD ILSCQDMLQF IKYKNPEDEK IKNYIDDTLK GFFTYFGGFN  180
QNRANYYETK KEASTAVATR IVHENLPKFC DNVIQFKHII KRKKDGTVEK TERKTEYLNA  240
YQYLKNNNKI TQIKDAETEK MIESTPIAEK IFDVYYFSSC LSQKQIEEYN RIIGHYNLLI  300
NLYNQAKRSE GKHLSANEKK YKDLPKFKTL YKQIGCGKKK DLFYTIKCDT EEEANKSRNE  360
GKESHSVEEI INKAQEAINK YFKSNNDCEN INTVPDFINY ILTKENYEGV YWSKAAMNTI  420
SDKYFANYHD LQDRLKEAKV FQKADKKSED DIKIPEAIEL SGLFGVLDSL ADWQTTLFKS  480
SILSNEKLKI ITDSQTPSEA LLKMIFNDIE KNMESFLKET NDIITLKKYK GNKEGTEKIK  540
QWFDYTLAIN RMLKYFLVKE NKIKGNSLDT NISEALKTLI YSDDAEWFKW YDALRNYLTQ  600
KPQDEAKENK LKLNFDNPSL AGGWDVNKEC SNFCVILKDK NEKKYLAMIK KGENTLFQKE  660
WTEGRGKNLT KKSNPLFEIN NCEILSKMEY DFWADVSKMI PKCSTQLKAV VNHFKQSDNE  720
FIFPIGYKVT SGEKFREECK ISKQDFELNN KVFNKNELSV TAMRYDLSST QEKQYIKAFQ  780
KEYWELLFKQ EKRDTKLTNN EIFNEWINFC NKKYSELLSW ERKYKDALTN WINFCKYFLS  840
KYPKTTLFNY SFKESENYNS LDEFYRDVDI CSYKLNINTT INKSILDRLV EEGKLYLFEI  900
KNQDSNDGKS IGHKNNLHTI YWNAIFENFD NRPKLNGEAE IFYRKAISKD KLGIVKGKKT  960
KNGTWIIKNY RFSKEKFILH VPITLNFCSN NEYVNDIVNT KFYNFSNLHF LGIDRGEKHL  1020
AYYSLVNKNG EIVDQGTLNL PFTDKDGNQR SIKKEKYFYN KQEDKWEAKE VDXWNYNDLL  1080
DAMASNRDMA RKNWQRIGTI KEAKNGYVSL VIRKIADLAV NNERPAFIVL EDLNTGFKRS  1140
RQKIDKSVYQ KFELALAKKL NFLVDKNAKR DEIGSPTKAL QLTPPVNNYG DIENKKQAGI  1200
MLYTRANYTS QTDPATGWRK TIYLKAGPEE TTYKKDGKIK NKSVKDQIIE TFTDIGFDGK  1260
DYYFEYDKGE FVDEKTGEIK PKKWRLYSGE NGKSLDRFRG EREKDKYEWK IDKIDIVKIL  1320
DDLFVNFDKN ISLLKQLKEG VELTRNNEHG TGESLRFAIN LIQQIRNTGN NERDNDFILS  1380
PVRDENGKHF DSREYWDKET KGEKISMPSS GDANGAFNIA RKGIIMNAHI LANSDSKDLS  1440
LFVSDEEWDL HLNNKTEWKK QLNIFSSRKA MAKRKKKRPA ATKK                  1484

SEQ ID NO: 16          moltype = AA  length = 1245
FEATURE                Location/Qualifiers
source                 1..1245
                       mol_type = protein
                       organism = Porphyromonas macacae
SEQUENCE: 16
MKTQHFFEDF TSLYSLSKTI RFELKPIGKT LENIKKNGLI RRDEQRLDDY EKLKKVIDEY  60
HEDFIANILS SFSFSEEILQ SYIQNLSISE ARAKIEKTMR DTLAKAFSED ERYKSIFKKE  120
```

```
LVKKDIPVWC PAYKSLCKKF DNFTTSLVPF HENRKNLYTS NEITASIPYR IVHVNLPKFI  180
QNIEALCELQ KKMGADLYLE MMENLRNVWP SFVKTPDDLC NLKTYNHLMV QSSISEYNRF  240
VGGYSTEDGT KHQGINEWIN IYRQRNKEMR LPGLVFLHKQ ILAKVDSSSF ISDTLENDDQ  300
VFCVLRQFRK LFWNTVSSKE DDAASLKDLF CGLSGYDPEA IYVSDAHLAT ISKNIFDRWN  360
YISDAIRRKT EVLMPRKKES VERYAEKISK QIKKRQSYSL AELDDLLAHY SEESLPAGFS  420
LLSYFTSLGG QKYLVSDGEV ILYEEGSNIW DEVLIAFRDL QVILDKDFTE KKLGKDEEAV  480
SVIKKALDSA LRLRKFFDLL SGTGAEIRRD SSFYALYTDR MDKLKGLLKM YDKVRNYLTK  540
KPYSIEKFKL HFDNPSLLSG WDKNKELNNL SVIFRQNGYY YLGIMTPKGK NLFKTLPKLG  600
AEEMFYEKME YKQIAEPMLM LPKVFFPKKT KPAFAPDQSV VDIYNKKTFK TGQKGFNKKD  660
LYRLIDFYKE ALTVHEWKLF NFSFSPTEQY RNIGEFFDEV REQAYKVSMV NVPASYIDEA  720
VENGKLYLFQ IYNKDFSPYS KGIPNLHTLY WKALFSEQNQ SRVYKLCGGG ELFYRKASLH  780
MQDTTVHPKG ISIHKKNLNK KGETSLFNYD LVKDKRFTED KFFFHVPISI NYKNKKITNV  840
NQMVRDYIAQ NDDLQHGIDR GERNLLYISR IDTRGNLLEQ FSLNVIESDK GDLRTDYQKI  900
LGDREQERLR RRQEWKSIES IKDLKDGYMS QVVHKICNMV VEHKAIVVLE NLNLSFMKGR  960
KKVEKSVYEK FERMLVDKLN YLVVDKKNLS NEPGGLYAAY QLTNPLFSFE ELHRYPQSGI  1020
LFFVDPWNTS LTDPSTGFVN LLGRINYTNV GDARKFFDRF NAIRYDGKGN ILFDLDLSRF  1080
DVRVETQRKL WTLTTFGSRI AKSKKSGKWM VERIENLSLC FLELFEQFNI GYRVEKDLKK  1140
AILSQDRKEF YVRLIYLFNL MMQIRNSDGE EDYILSPALN EKNLQFDSRL IEAKDLPVDA  1200
DANGAYNVAR KGLMVVQRIK RGDHESIHRI GRAQWLRYVQ EGIVE                 1245

SEQ ID NO: 17          moltype = AA  length = 1250
FEATURE                Location/Qualifiers
source                 1..1250
                       mol_type = protein
                       organism = Smithella sp.
SEQUENCE: 17
MQTLFENFTN QYPVSKTLRF ELIPQGKTKD FIEQKGLLKK DEDRAEKYKK VKNIIDEYHK  60
DFIEKSLNGL KLDGLEKYKT LYLKQEKDDK DKKAFDKEKE NLRKQIANAF RNNEKFKTLF  120
AKELIKNDLM SFACEEDKKN VKEFEAFTTY FTGFHQNRAN MYVADEKRTA IASRLIHENL  180
PKFIDNIKIF EKMKKEAPEL LSPFNQTLKD MKDVIKGTTL EEIFSLDYFN KTLTQSGIDI  240
YNSVIGGRTP EEGKTKIKGL NEYINTDFNQ KQTDKKKRQP KFKQLYKQIL SDRQSLSFIA  300
EAFKNDTEIL EAIEKFYVNE LLHFSNEGKS TNVLDAIKNA VSNLESFNLT KMYFRSGASL  360
TDVSRKVFGE WSIINRALDN YYATTYPIKP REKSEKYEER KEKWLKQDFN VSLIQTAIDE  420
YDNETVKGKN SGKVIADYFA KFCDDKETDL IQKVNEGYIA VKDLLNTPCP ENEKLGSNKD  480
QVKQIKAFMD SIMDIMHFVR PLSLKDTDKE KDETFYSLFT PLYDHLTQTI ALYNKVRNYL  540
TQKPYSTEKI KLNFENSTLL GGWDLNKETD NTAIILRKDN LYYLGIMDKR HNRIFRNVPK  600
ADKKDFCYEK MVYKLLPGAN KMLPKVFFSQ SRIQEFTPSA KLLENYANET HKKGDNFNLN  660
HCHKLIDFFK DSINKHEDWK NFDFRFSATS TYADLSGFYH EVEHQGYKIS FQSVADSFID  720
DLVNEGKLYL FQIYNKDFSP FSKGKPNLHT LYWKMLFDEN NLKDVVYKLN GEAEVFYRKK  780
SIAEKNTTIH KANESIINKN PDNPKATSTF NYDIVKDKRY TIDKFQFHIP ITMNFKAEGI  840
FNMNQRVNQF LKANPDINII GIDRGERHLL YYALINQKGK ILKQDTLNVI ANEKQKVDYH  900
NLLDKKEGDR ATARQEWGVI ETIKELKEGY LSQVIHKLTD LMIENNAIIV MEDLNFGFKR  960
GRQKVEKQVY QKFEKMLIDK LNYLVDKNKK ANELGGLLNA FQLANKFESF QKMGKQNGFI  1020
FYVPAWNTSK TDPATGFIDF LKPRYENLNQ AKDFFEKFDS IRLNSKADYF EFAFDFKNFT  1080
EKADGGRTKW TVCTTNEDRY QWNRALNNNR GSQEKYDITA ELKSLFDGKV DYKSGKDLKQ  1140
QIASQESADF FKALMKNLSI TLSLRHNNGE KGDNEQDYIL SPVADSKGRF FDSRKADDDM  1200
PKNADANGAY HIALKGLWCL EQISKTDDLK KVKLAISNKE WLEFVQTLKG            1250

SEQ ID NO: 18          moltype = DNA  length = 3987
FEATURE                Location/Qualifiers
source                 1..3987
                       mol_type = other DNA
                       organism = synthetic construct
SEQUENCE: 18
atggccggga gcaagaagcg ccggataaag caggacacgc agttcgaggg cttcaccaac  60
ctgtaccaag tctccaagac gctccggttc gagcttatcc cgcaagggaa gaccctgaaa  120
cacatccagg aacaaggttt catcgaggag gacaaggccc gcaacgacca ctacaaggag  180
ctcaagccca taatcgatcg gatctacaag acgtacgccg accagtgcct ccaactggtg  240
cagctcgact gggagaacct gagcgccgcc attgacagct accgcaagga aaagacggag  300
gagacgcgca acgcccttat tgaggagcaa gccacctacc gcaacgccat ccacgactac  360
ttcatcggcc gcaccgacaa cctgacggac gcgatcaaca agcgccacgc ggaaatctac  420
aagggccttt tcaaggccga gctcttcaac gggaaggtcc taaaacagct cgggactgtc  480
acgacaaccg agcatgagaa cgccctcctt cgcagcttcg acaagttcac cacatacttc  540
tcgggcttct accggaaccg caagaacgtt ttcagcgccg aggacatctc caccgccatc  600
ccgcacagga tcgtccagga caacttcccc aagttcaagg agaactgcca catcttcacg  660
cgcctgatta cagccgtacc ttcacttcgt gagcacttcg agaacgtcaa aaaggccatc  720
gggatcttcg tctccacgtc catcgaggag gtattctctt tcccgttcta taaccagctc  780
ctgacccaga cgcagatcga cctctacaac cagctactgg gcggcatcag ccgggaggcc  840
gggaccgaga aaataaaggg cctcaacgaa gttctcaacc tggccatcca gaagaacgac  900
gagaccgcgc atatcatcgc atccctgccg catcgcttca ttcctttgtt caagcagata  960
ttgagcgacc ggaacaccct ctcgttcatc ctcgaagaat tcaagagcga cgaggaggtc  1020
attcagtctt tctgcaagta caagacgctc ctacggaatg agaatgtgct ggagaccgcg  1080
gaggcactct tcaatgagct gaactccatt gacctgaccc acatcttcat tagccacaag  1140
aaactggaga cgatctccag cgccctgtgc gaccactggg acactctccg caacgccctc  1200
tacgaacgcc ggatctccga acttaccggc aagataacta agtcggctaa ggagaaggtg  1260
caacggagcc tcaagcacga ggacatcaac cttcaggaaa tcatctcagc cgcgggcaag  1320
gagctgagcg aggcgtttaa gcagaaaaca tcggagatac tgagccacgc gcacgcggcc  1380
ctggatcaac cgctgccgac gactctcaag aagcaagagg agaaggaaat ccttaagtcc  1440
cagctcgact cgctgctcgg cctctatcac ttgctcgact ggttcgcggt tgatgagtcc  1500
```

```
aacgaggtgg acccggagtt ctccgcgcgc ctcacgggta ttaagctgga gatggagcca  1560
agcttaagct tctacaacaa ggcccgcaac tacgcgacca aaaaaccgta ctcagtcgag  1620
aaattcaagc tgaatttcca gatgcctaca ttggcgaggg ggtgggacgt gaaccgcgag  1680
aagaacaatg gagccatcct gttcgtcaaa aatgggttgt actacctggg catcatgccc  1740
aagcagaagg gccgttacaa ggccctgtca ttcgagccta ccgagaagac ctcggagggc  1800
ttcgacaaga tgtactacga ctatttcccg gacgccgcca agatgatccc gaagtgctcc  1860
acgcagctca aagccgtcac ggcccacttc cagacgcata ccacgccgat acttctgagc  1920
aacaacttca ttgagccgct agagatcacg aaggagatat acgacctaaa caaccccgaa  1980
aaggagccca agaagttcca gacagcctac gctaagaaga caggtgatca gaagggatat  2040
agggaggcac tctgcaagtg gatcgacttc acgcgcgact tcctgtcgaa atatacaaag  2100
acgaccagca ttgacctaag ttctctccgc ccatcctccc agtacaagga tctgggcgag  2160
tattatgcgg agctgaaccc attgctgtac cacatcagct tccagaggat cgccgagaag  2220
gagattatgg acgcggtgga gacggggaaa ctatacctgt tccaaatata taacaaggac  2280
ttcgctaaag ggcaccacgg gaagcccaac ctgcacacac tctactggac gggcttgttt  2340
tcgccagaaa atttggccaa gacttcgatc aagctcaacg gccaggcgga gttgttttac  2400
cgtcccaagt ctcgcatgaa gcgcatggcg catcgcctcg gagagaaaat gcttaacaag  2460
aagctcaagg atcagaagac gcccatacct gatacgttgt accaggaatt gtacgactac  2520
gtgaaccacc gcctatcgca cgacctctca gacgaggccc gcgccctcct cccaaacgtg  2580
attactaagg aggtttccca tgaaataatc aaggaccgac ggttcaccag cgacaaattt  2640
tttttccacg tgcctatcac gctcaattac caggcggcca actccccatc gaagttcaac  2700
cagcgcgtga acgcctacct taaggagcac ccggagaccc caatcatcgg gatcgaccgt  2760
ggcgagcgga acctgatcta tattacggtg atcgatagca ccgggaagat cctggagcag  2820
cgctccctga acacaatcca gcagtttgac taccagaaga aactcgacaa ccgggagaag  2880
gagcgcgtcg cagcccggca agcatggagt gtggtcggca ccataaagga cctgaaacag  2940
ggttacctaa gtcaagttat ccacgagatc gttgacctga tgatacacta tcaagccgta  3000
gtcgtgctgg agaacctcaa cttcgggttt aagtccaagc gcaccggcat cgcggagaag  3060
gcggtgtacc agcagttcga gaagatgctg atcgacaagc tgaactgcct ggtgctcaag  3120
gactaccctg cggagaaggt cggcggggtc ttgaacccgt accagctaac cgaccagttc  3180
acgagcttcg ccaaaatggg cacgcagtcc ggattcttgt tttatgtccc ggctccatat  3240
acaagtaaga tcgacccgct gacagggttt gttgacccat tcgtgtggaa gaccatcaag  3300
aaccacgaga gcaggaaaca cttcttagag ggcttcgact tcctgcatta cgacgttaag  3360
acaggcgact tcatcctgca cttcaagatg aaccgcaacc tgtcgttcca gaggggcctg  3420
cccggcttca tgcccgcctg ggatatcgtc tttgagaaga atgagacgca gttcgacgcg  3480
aaggggacgc cgttcatcgc tggaaagcgg atcgtgccgg tcatcgagaa ccaccgcttc  3540
acgggtcgct accgagattt ataccccgcc aacgaactaa ttgcgctgct ggaggagaag  3600
gggatcgtgt tccgagatgg cagcaacatt ctcccgaagc tgctggagaa cgacgactcg  3660
cacgctattg acacgatggt cgccctcata cggagcgtgc ttcagatgcg gaacagtaac  3720
gctgccacgg gcgaggacta cattaactcc cccgtccgcg acctcaacgg ggtctgcttc  3780
gatagccgct tccagaaccc ggagtggcct atggatgcgg acgcgaacgg ggcctaccac  3840
atcgccctca agggccaact cctgctcaac cacttgaagg aaagcaaaga cctcaaattg  3900
cagaatggca tcagtaacca ggactggctc gcgtacatcc aggaactgag aaacgggtcc  3960
aagaagcggc gtatcaagca agattga                                     3987
```

```
SEQ ID NO: 19          moltype = DNA  length = 3987
FEATURE                Location/Qualifiers
source                 1..3987
                       mol_type = other DNA
                       organism = synthetic construct
SEQUENCE: 19
atggcgggaa gcaaaaagcg ccggattaag caagacacgc agttcgaggg cttcacgaac  60
ctctaccaag tcagcaagac cctccggttc gagctgatac cacagggaaa gacgctcaag  120
cacatccagg aacagggctt catcgaggag gacaaggcgc gcaacgacca ctacaaggag  180
ttgaaaccga tcatcgaccg catctacaag acgtacgccg accagtgcct ccagctcgtg  240
cagctcgact gggagaacct ctccgccgcc attgactcgt accggaagga gaagactgag  300
gagacccgca acgccctgat cgaggagcaa gcaacctacc ggaacgccat ccacgactac  360
ttcatcggcc gcaccgacaa cctcaccgac gcgatcaaca agcggcacgc ggagatatac  420
aaagggctgt tcaaggcgga gctgttcaac ggcaaggtgc tcaagcagct agggacggtg  480
accacgaccg agcacgagaa cgcgctcctc cgcagcttcg acaagttcac cacctacttc  540
agcggcttct accggaaccg caagaatgtg ttcagcgcgg aggacatcag cacggccatc  600
ccgcaccgca tcgtccagga caacttcccg aagttcaagg agaactgcca catcttcacc  660
cgcctgataa ccgccgtccc ctccctgcgg gagcacttcg agaacgtcaa aaaggcaatt  720
gggatcttcg tctcgaccag cattgaggag gtgttcagct tccccttcta caaccagctc  780
ctcacccaga cgcagatcga cctgtacaat cagttgctcg gcgggataag ccgcgaggcg  840
ggaaccgaaa aaatcaaggg gctgaacgaa gtgttgaacc tcgccatcca gaagaacgac  900
gagaccgcgc acatcatcgc ctccctgccc caccggttca tcccgctgtt caagcagatc  960
ctctctgacc ggaacaccct gtccttcatt cttgaggagt tcaagtcgga cgaggaggtc  1020
atccagagct tctgcaagta caagacgctg ctacggaacg agaacgtgct ggagacggcg  1080
gaggcactgt tcaacgagct aaacagcatc gacctcacgc acatcttcat cagtcacaag  1140
aaactggaga ccatctcctc cgcgctgtgc gaccactggg acacgctcag gaacgcgctc  1200
tacgagcgcc gaatcagtga gctgacgggc aagatcacga agtccgcgaa ggagaaggtg  1260
cagcggtccc tcaagcacga ggacatcaac ctccaggaga tcatctcagc ggctgggaaa  1320
gagctgtccg aggcgttcaa gcagaaaacg agcgaaatcc tgtcccacgc gcacgcggcc  1380
ctggatcagc ctctgccgac gaccctcaag aaacaagaag aaaaggaaat cctcaagtcg  1440
cagctcgact cgctgctggg cctgtaccat ctcctcgact ggttcgccgt ggacgagagc  1500
aacgaggtgg accccgagtt ctccgcgcgg cttacgggga tcaagctgga gatggagccc  1560
agcctgtcct tctacaacaa ggcgcgcaac tacgccacca agaagcccta cagcgtggag  1620
aagttcaagc tcaacttcca gatgcccact ctcgcacgtg ggtgggacgt caaccgcgaa  1680
aaaaataatg ggcgatcct gttcgtcaag aacggcctgt actacttggg catcatgccg  1740
aaacagaagg gccgctacaa ggccctgagc ttcgaaccga ccgagaaaac gagcgagggg  1800
```

```
ttcgacaaga tgtactacga ctacttcccc gacgccgcga agatgattcc aaagtgctcc  1860
acgcagctta aggccgtgac ggcccacttc cagacgcaca cgaccccgat cctcctcagc  1920
aacaacttca tcgagcccct ggagatcacg aaggagatat acgacctgaa caacccggag  1980
aaggagccca agaaattcca gaccgcctac gccaagaaga caggcgacca aaagggttac  2040
agggaggccc tctgcaagtg gatcgacttc actagggact tcctgtccaa gtacaccaag  2100
actacctcta tcgacctgtc cagcctccgc ccgtcgtccc agtacaaaga tttgggcgag  2160
tattacgcgg agctgaaccc actgctctac cacatcagct tccagcgcat cgcggagaag  2220
gagatcatgg acgcagtgga gacgggcaag ctatacctat ttcagatata caacaaagac  2280
ttcgctaagg gacaccacgg caagcctaac ctgcacaccc tctactggac ggggctcttc  2340
agcccggaga acctcgccaa gacctcgatc aagctcaacg gccaggccga gctgttctac  2400
cggcccaagt cccgcatgaa gcggatggcc caccggctcg gggagaaaat gctcaacaag  2460
aaattgaagg accaaaaaac gccgataccc gacaccctat accaggagct gtacgactat  2520
gtgaaccacc gcctgagcca cgacctcagc gacgaggcgc gggccctcct gccgaacgtc  2580
atcacaaagg aggtcagcca cgagatcatc aaggaccggc gcttcacctc cgacaagttt  2640
ttctttcacg tgcccatcac gctcaactac caggccgcca actcgccgtc caagttcaac  2700
cagcgcgtga acgcctacct caaggagcac cccgagaccc cgatcatcgg gattgaccga  2760
ggggagcgga acctcatcta catcaccgtc atcgacagca ccgggaagat ccttgaacag  2820
cggtcgctca acaccatcca gcagttcgac taccagaaga aactcgacaa ccgggagaag  2880
gagagagtgg cggcccgcca ggcttggtcc gtcgtcggga cgattaagga cttgaaacaa  2940
ggttacctgt cgcaagtgat ccacgagatc gttgacctga tgatccacta ccaagccgtc  3000
gtggtcctgg agaacctcaa cttcggcttc aagagcaaac gaaccggcat cgcggagaag  3060
gccgtgtacc agcagttcga aaaaatgctg atcgacaagc tgaactgcct cgtgctcaag  3120
gactaccccg ctgagaaggt cggcggggtg ctgaacccgt accagctcac tgaccagttc  3180
accagcttcg caaagatggg cacccagtcc ggcttcctgt tctacgtgcc tgcgccatac  3240
acctcgaaga tcgacccgct caccgggttc gtggacccct tcgtctggaa gaccatcaag  3300
aaccacgaga gccgcaagca cttcctggag ggcttcgact tcctccacta cgacgtcaag  3360
accggggact tcatcctgca cttcaagatg aaccgcaacc tcagtttcca gcgcggcctg  3420
ccggggttca tgcccgcttg ggatatagtc ttcgagaaga atgagacgca gttcgacgcg  3480
aagggcaccc cgttcatcgc cgggaagcgc atcgtgccgg tcatcgagaa ccaccggttc  3540
accgggcgct accgcgacct atacccggcg aacgagttga tcgccctcct ggaggagaag  3600
ggcatcgtgt tccgcgacgg ctccaacatc ctcccgaagc tgctcgaaaa cgacgactcc  3660
cacgccatcg acacgatggt cgcgctgatc cggtcggtgc tccagatgcg gaactccaac  3720
gccgcgacgg gcgaggacta catcaacagt ccggtccgcg atctgaacgg cgtctgcttc  3780
gactcccggt tccagaaccc cgagtggccg atggacgcgg acgcgaacgg cgcataccac  3840
atcgccctaa aagggcaatt gctgctcaac cacctcaagg aatccaaaga cctaaagctc  3900
cagaacggca tctccaacca ggactggctg gcgtacatcc aggaactgcg gaacgggagc  3960
aaaaaacgtc ggatcaagca agattga                                    3987

SEQ ID NO: 20          moltype = DNA  length = 3987
FEATURE                Location/Qualifiers
source                 1..3987
                       mol_type = other DNA
                       organism = synthetic construct
SEQUENCE: 20
atggcgggct ccaagaaacg ccggattaag caagataccc agttcgaggg gttcacgaac  60
ctctaccaag tgagcaagac cctccgattc gaactgattc ctcaggggaa gaccctcaag  120
cacatccagg agcaagggtt catcgaggag gacaaggcgc ggaacgacca ctacaaggaa  180
ctcaaaccca tcatcgaccg catctacaag acctacgccg atcagtgcct ccagctcgtg  240
cagttggact gggagaacct cagcgcggcc attgactcct accggaagga gaaaacggag  300
gagacgcgca acgcgctcat cgaggaacag gcaacctatc gcaacgccat ccacgactac  360
ttcatcggga ggactgacaa cctcactgac gcgattaaca agcgccacgc ggagatatac  420
aagggactct tcaaagcgga gctgtttaac ggcaaggttc tcaagcaact cggcactgtg  480
accacgaccg agcatgagaa cgccctgctc cgctccttcg acaagttcac cacctacttc  540
tccgggttct accgcaaccg caagaatgtc ttcagcgcgg aggacatcag cacggccatt  600
ccacatcgaa tcgtccaaga taacttcccg aagttcaagg agaactgcca catcttcacc  660
cgactcatta ctgctgtacc gtcgttacgc gaacacttcg agaacgtcaa gaaggcaatt  720
ggaatcttcg tctctacgtc aatagaggag gtgttcagct tccctttcta caaccagctc  780
cttacgcaga cccagataga cctgtacaat cagctcctcg gtgggatcag ccgggaggcg  840
gggactgaga agattaaagg gctcaacgag gtcttgaacc tggccatcca aaaaaacgat  900
gagacggcgc acatcatcgc ctcgctgccc caccggttca tcccgctgtt caagcagatc  960
ctcagtgaca ggaacacctt gagctttatc ctagaggagt tcaagagcga cgaggaggtg  1020
atccagagct tctgcaagta caaaaccctg ctgaggaacg agaacgtcct ggagacggcg  1080
gaggcgctgt tcaacgagct gaactctatc gacttaactc acatattcat ctcgcacaag  1140
aagctggaga ctattagctc tgcactctgc gaccactggg acaccctccg caacgcgctc  1200
tacgagcgcc gcatctcgga gctgaccggg aagatcacca aatccgcgaa ggaaaaggtc  1260
cagcgttccc tcaaacacga ggatattaac ttacaggaga ttatctcagc ggctgggaag  1320
gagttgtcag aggcgttcaa gcagaaaact tccgagatcc tgagccacgc gcacgcagcg  1380
ctcgaccagc ctctgcccac caccctcaaa aagcaggaag aaaaagagat cctcaagagc  1440
cagttggact ccctgctggg gctctatcac cttctcgact ggttcgccgt cgatgagtcg  1500
aacgaggtgg accccgagtt ctccgcccgg ctgaccggca tcaagctaga gatggagccg  1560
tccctcagct tctacaataa ggcccgcaac tacgcgacca aaaaacccta cagcgtggag  1620
aagttcaagc tgaacttcca gatgccgacc ttagcacgcg gttgggacgt aaacagggag  1680
aagaacaatg gagccatcct gttcgtcaag aacgggcttt actacctcgg gataatgccc  1740
aagcagaagg gccgctacaa ggccctttcc ttcgagccga cggagaaaac ctccgagggg  1800
ttcgacaaga tgtactacga ctacttcccc gacgccgcca agatgatccc gaagtgctca  1860
acgcagctaa aagccgtgac cgcccacttc cagacccaca cgacgccgat cctgctgagc  1920
aacaacttca tcgagcccct tgagatcact aaggagatat acgacctgaa caaccccgag  1980
aaggagccca agaagtttca aaccgcctac gccaaaaaaa ctggcgacca aaagggctac  2040
agggaggcgc tgtgtaagtg gatcgacttc acacgcgact tcctttcgaa gtatacgaag  2100
```

```
acaacctcta ttgacctgag cagcctgcgt cctagctccc agtacaaaga tttgggcgag  2160
tactacgcgg agcttaatcc actactctac cacatctcat tccagcgcat cgctgagaag  2220
gaaatcatgg acgcggtgga gacaggcaaa ctgtacctct tccagatata caacaaagac  2280
ttcgctaagg ggcaccacgg gaagcccaac cttcatacgc tctactggac gggcctattc  2340
agccccgaaa atctggccaa gacctccatc aagctgaacg gccaagcgga gctgttctac  2400
agacccaaga gccggatgaa gcggatggcc cacaggctcg gcgagaaaat gcttaacaaa  2460
aagttgaagg accagaaaac ccctatcccc gacaccctct accaggaact gtacgactac  2520
gtgaaccaca ggctctcgca cgacctttcc gacgaggccc gtgccctact cccgaacgtc  2580
attaccaaag aggtttcgca cgagatcatc aaggaccggc ggttcacgag cgacaagttt  2640
ttctttcacg tccccatcac ccttaactac caggcggcca actccccatc caagttcaac  2700
cagcgtgtga atgcctacct caaggagcac ccagagaccc cgatcattgg gatcgaccgg  2760
ggcgagcgga acctgatcta catcaccgtc atcgactcga cgggcaagat tcttgagcag  2820
agatcgttga ataccataca gcagttcgac taccagaaga aactcgacaa ccgcgagaag  2880
gagcgcgtgg cggcccgcca ggcgtggtcc gtcgttggga cgattaagga cttgaaacaa  2940
ggttatctgt cccaagtcat ccacgagatc gttgatctga tgatccacta tcaggcagtg  3000
gtggtgctgg agaatctcaa cttcggcttc aagagtaagc ggacgggaat cgccgagaag  3060
gccgtgtacc agcagttcga gaagatgctg atcgacaagc tcaactgcct tgtgctgaaa  3120
gactacccgg ccgagaaggt cggcggcgtc ctcaacccgt accaacttac cgaccagttc  3180
acctccttcg ccaagatggg cactcagtcc gggttcttgt tctacgtccc cgcaccttac  3240
acctctaaga tcgaccctct gactggcttc gtagatccat tcgtgtggaa gaccattaag  3300
aaccacgaga gccgcaagca cttcctggag ggcttcgact tcctgcacta cgacgtgaag  3360
accggggact tcatccttca cttcaagatg aaccggaacc tcagcttcca gcggggcctg  3420
ccggggttca tgcccgcctg ggacatcgtg ttcgagaaga acgagaccca gttcgacgcg  3480
aagggcacgc ccttcatcgc cgggaagcgt atcgtgccgg tgatcgagaa ccatcgtttc  3540
acgggtcgct accgtgacct ctacccggcg aacgagctta tcgcactcct ggaggagaag  3600
ggcatcgtct tccgggacgg ctccaacatc ctcccgaaac tgctggaaaa cgacgactct  3660
cacgccatcg acacgatggt ggccctcatc cggtccgtgc tccaaatgcg gaacagcaac  3720
gccgccaccg gtgaggacta catcaacagc ccggtccggg atctgaacgg ggtgtgcttc  3780
gattcgcggt tccagaatcc tgagtggccg atggacgcgg atgcaaacgg ggcgtaccac  3840
atcgcgctca agggccagtt acttctgaac caccttaagg agtctaaaga tttgaaactc  3900
cagaacggga tctcgaacca ggactggctg gcctacatcc aagagttgcg gaacggcagc  3960
aagaagcggc ggattaagca agattag                                      3987

SEQ ID NO: 21          moltype = DNA  length = 1592
FEATURE                Location/Qualifiers
source                 1..1592
                       mol_type = other DNA
                       organism = Medicago truncatula
SEQUENCE: 21
actgttaata atttttaaac gtcagcgcac taaaaaaacg aaaagacgga cacgtgaaaa  60
taaaaaacac acactagttt atgacgcaat actattttac ttatgatttg ggtacattag  120
acaaaaccgt gaaagagatg tatcagctat gaaacctgta tacttcaata cagagactta  180
ctcatatcgg atacgtacgc acgaagtatc atattaatta ttttaatttt taataaatat  240
tttatcggat acttatgtga tactctacat atacacaagg atatttctaa gatactttat  300
agatacgtat cctagaaaaa catgaagagt aaaaaagtga gacaatgttg taaaaattca  360
ttataaatgt atatgattca attttagata tgcatcagta taattgattc tcgatgaaac  420
acttaaaatt atatttcttg tggaagaacg tagcgagaga ggtgattcag ttagacaaca  480
ttaaataaaa ttaatgttaa gttcttttaa tgatgtttct ctcaatatca catcatatga  540
aaatgtaata tgatttataa gaaaattttt aaaaaattta ttttaataat cacatgtact  600
attttttaaa aattgtatct tttataataa tacaataata aagagtaatc agtgttaatt  660
tttcttcaaa tataagtttt attataaatc attgttaacg tatcataagt cattaccgta  720
tcgtatctta attttttttt aaaaaccgct aattcacgta cccgtattgt attgtacccg  780
cacctgtatc acaatcgatc ttagttagaa gaattgtctc gaggcggtgc aagacagcat  840
ataatagacg tggactctct tataccaaac gttgtcgtat cacaaagggt taggtaacaa  900
gtcacagttt gtccacgtgt cacgttttaa ttggaagagg tgccgttggc gtaatataac  960
agccaatcga tttttgctat aaaagcaaat caggtaaact aaacttcttc attcttttct  1020
tccccatcgc tacaaaaccg gttcctttgg aaaagagatt cattcaaacc tagcacccaa  1080
ttccgtttca aggtataatc tactttctat tcttcgatta ttttattatt attagctact  1140
atcgtttaat cgatcttttc ttttgatccg tcaaatttaa attcaattag ggttttgttc  1200
ttttctttca tctgattgaa atccttctga attgaaccgt ttacttgatt ttactgttta  1260
ttgtatgatt taatcctttg tttttcaaag acagtcttta gattgtgatt aggggttcat  1320
ataaattttt agatttggat ttttgtattg tatgattcaa aaaatacgtc ctttaattag  1380
attagtacat ggatattttt tacccgattt attgattgtc agggagaatt tgatgagcaa  1440
gttttttga tgtctgttgt aaattgaatt gattataatt gctgatctgc tgcttccagt  1500
tttcataacc catattcttt taaccttgtt gtacacacaa tgaaaaattg gtgattgatt  1560
catttgtttt tctttgtttt ggattataca gg                                1592

SEQ ID NO: 22          moltype = DNA  length = 2000
FEATURE                Location/Qualifiers
source                 1..2000
                       mol_type = other DNA
                       organism = Zea mays
SEQUENCE: 22
gtcgtgcccc tctctagaga taaagagcat tgcatgtcta aagtataaaa aattaccaca  60
tatttttttg tcacacttat ttgaagtgta gtttatctat ctctatacat atatttaaac  120
ttcactctac aaataatata gtctataata ctaaaataat attagtgttt tagaggatca  180
tataaataaa ctgctagaca tggtctaaag gataattgaa tattttgaca atctacagtt  240
ttatcttttt agtgtgcatg tgatctctct gttttttttg caaatagctt gacctatata  300
atacttcatc cattttatta gtacatccat ttaggattta gggttgatgg tttctataga  360
```

```
ctaattttta gtacatccat tttattcttt ttagtctcta aattttttaa aactaaaact  420
ctattttagt tttttattta ataatttaga tataaaatga aataaaataa attgactaca  480
aataaaacaa ataccettta agaaataaaa aaactaagca aacattttte ttgtttcgag  540
tagataatga caggctgttc aacgccgtcg acgagtctaa cggacaccaa ccagcgaacc  600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg ctttcccttc ctcgcccgcc  840
gtaataaata gacacccect ccacaccctc tttccccaac ctcgtgttcg ttcggagcgc  900
acacacacgc aaccagatct cccccaaatc cagccgtcgg cacctccgct tcaaggtacg  960
ccgctcatcc tccccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag gatactgttt  1140
caagctacct ggtggattta ttaattttgt atctgtatgt gtgtgccata catcttcata  1200
gttacgagtt taagatgatg gatggaaata tcgatctagg ataggtatac atgttgatgc  1260
gggttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc                                              2000
```

```
SEQ ID NO: 23          moltype = AA  length = 228
FEATURE                Location/Qualifiers
source                 1..228
                       mol_type = protein
                       organism = Rattus norvegicus
SEQUENCE: 23
SSETGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLK              228
```

```
SEQ ID NO: 24          moltype = AA  length = 199
FEATURE                Location/Qualifiers
source                 1..199
                       mol_type = protein
                       organism = Homo sapiens
SEQUENCE: 24
MEASPASGPR HLMDPHIFTS NFNNGIGRHK TYLCYEVERL DNGTSVKMDQ HRGFLHNQAK  60
NLLCGFYGRH AELRFLDLVP SLQLDPAQIY RVTWFISWSP CFSWGCAGEV RAFLQENTHV  120
RLRIFAARIY DYDPLYKEAL QMLRDAGAQV SIMTYDEFKH CWDTFVDHQG CPFQPWDGLD  180
EHSQALSGRL RAILQNQGN                                               199
```

```
SEQ ID NO: 25          moltype = DNA  length = 621
FEATURE                Location/Qualifiers
source                 1..621
                       mol_type = other DNA
                       organism = Petromyzon marinus
SEQUENCE: 25
acagatgcag agtatgtgag aattcacgaa aagctggaca tctatacctt caagaagcag  60
ttctttaaca ataagaagtc tgtgagccat aggtgctacg tgctgttcga gctgaagaga  120
aggggtgaaa gaagggcatg tttttggggg tatgctgtga acaagcccca gtctggaact  180
gagagaggca ttcacgccga aattttcagc atcagaaagg tggaggaata cctgagggat  240
aaccctggac agtttacaat taattggtat tctagctggt ctccatgcgc tgactgtgcc  300
gagaagatcc tggaatggta caaccaggag ctgagaggaa atggccatac cctgaagatt  360
tgggcctgca agctgtacta tgaaaagaac gcaagaaatc agatcggact gtggaacctg  420
agggataatg gtgtggggct gaacgtgatg gtgtccgagc actatcagtg ctgtagaaag  480
atttcattc agtcctcaca taatcagctg aacgagaata gatggctgga aaagactctg  540
aagagggctg agaagagaag gtccgaactg tcaattatga tccaggtgaa gatcctgcac  600
accactaagt cacctgccgt g                                            621
```

```
SEQ ID NO: 26          moltype = AA  length = 160
FEATURE                Location/Qualifiers
source                 1..160
                       mol_type = protein
                       organism = synthetic construct
SEQUENCE: 26
FERNYDPREL RKETYLLYEI KWGKSGKLWR HWCQNNRTQH AEVYFLENIF NARRFNPSTH  60
CSITWYLSWS PCAECSQKIV DFLKEHPNVL EIYVARLYYH EDERNRQGLR DLVNSGVTIR  120
IMDLPDYNYC WKTFVSDQGG DEDYWPGHFA PWIKQYSLKL                        160
```

```
SEQ ID NO: 27          moltype = AA  length = 207
FEATURE                Location/Qualifiers
source                 1..207
                       mol_type = protein
                       organism = synthetic construct
SEQUENCE: 27
TDAEYVRIHE KLDIYTFKKQ FSNNKKSVSH RCYVLFELKR RGERRACFWG YAVNKPQSGT  60
ERGIHAEIFS IRKVEEYLRD NPGQFTINWY SSWSPCADCA EKILEWYNQE LRGNGHTLKI  120
WVCKLYYEKN ARNQIGLWNL RDNGVGLNVM VSEHYQCCRK IFIQSSHNQL NENRWLEKTL  180
KRAEKRRSEL SIMFQVKILH TTKSPAV                                    207

SEQ ID NO: 28          moltype = AA  length = 228
FEATURE                Location/Qualifiers
source                 1..228
                       mol_type = protein
                       organism = synthetic construct
SEQUENCE: 28
SSKTGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPNVT LFIYIARLYH  120
LANPRNRQGL RDLISSGVTI QIMTEQESGY CWHNFVNYSP SNESHWPRYP HLWVRLYVLE  180
LYCIILGLPP CLNILRRKQS QLTSFTIALQ SCHYQRLPPH ILWATGLK              228

SEQ ID NO: 29          moltype = AA  length = 162
FEATURE                Location/Qualifiers
source                 1..162
                       mol_type = protein
                       organism = synthetic construct
SEQUENCE: 29
SFERNYDPRE LRKETYLLYE IKWGKSGKLW RHWCQNNRTQ HAEVYFLENI FNARRFNPST  60
HCSITWYLSW SPCAECSQKI VDFLKEHPNV NLEIYVARLY YPENERNRQG LRDLVNSGVT  120
IRIMDLPDYN YCWKTFVSDQ GGDEDYWPGH FAPWIKQYSL KL                    162

SEQ ID NO: 30          moltype = AA  length = 166
FEATURE                Location/Qualifiers
source                 1..166
                       mol_type = protein
                       organism = Escherichia coli
SEQUENCE: 30
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTD                166

SEQ ID NO: 31          moltype = AA  length = 166
FEATURE                Location/Qualifiers
source                 1..166
                       mol_type = protein
                       organism = synthetic construct
SEQUENCE: 31
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC AALLCYFFRM PRQVFNAQKK AQSSTD                166

SEQ ID NO: 32          moltype = AA  length = 166
FEATURE                Location/Qualifiers
source                 1..166
                       mol_type = protein
                       organism = synthetic construct
SEQUENCE: 32
SEVEFSHEYW MRHALTLAKR AWDEREVPVG AVLVLNNRVI GEGWNRSIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC AALLCYFFRM RRQVFNAQKK AQSSTD                166

SEQ ID NO: 33          moltype = AA  length = 166
FEATURE                Location/Qualifiers
source                 1..166
                       mol_type = protein
                       organism = synthetic construct
SEQUENCE: 33
SEVEFSHEYW MRHALTLAKR ALDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC NALLCYFFRM RRQVFNAQKK AQSSTD                166

SEQ ID NO: 34          moltype = AA  length = 166
FEATURE                Location/Qualifiers
source                 1..166
                       mol_type = protein
                       organism = synthetic construct
SEQUENCE: 34
SEVEFSHEYW MRHALTLAKR ALDEREVPVG AVLVLNNRVI GEGWNRAIGL HDPTAHAEIM  60
```

-continued

```
ALRQGGLVMQ NYRLIDATLY VTFEPCVMCA GAMIHSRIGR VVFGVRNAKT GAAGSLMDVL  120
HYPGMNHRVE ITEGILADEC NALLCYFFRM PRQVFNAQKK AQSSTD                 166

SEQ ID NO: 35          moltype = AA  length = 1763
FEATURE                Location/Qualifiers
source                 1..1763
                       mol_type = protein
                       organism = synthetic construct
SEQUENCE: 35
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLIDATLYVT FEPCVMCAGA MIHSRIGRVV  300
FGVRNAKTGA AGSLMDVLHY PGMNHRVEIT EGILADECAA LLCYFFRMPR QVFNAQKKAQ  360
SSTDSGGSSG GSSGSETPGT SESATPESSG GSSGGSDKKY SIGLAIGTNS VGWAVITDEY  420
KVPSKKFKVL GNTDRHSIKK NLIGALLFDS GETAEATRLK RTARRRYTRR KNRICYLQEI  480
FSNEMAKVDD SFFHRLEESF LVEEDKKHER HPIFGNIVDE VAYHEKYPTI YHLRKKLVDS  540
TDKADLRLIY LALAHMIKFR GHFLIEGDLN PDNSDVDKLF IQLVQTYNQL FEENPINASG  600
VDAKAILSAR LSKSRRLENL IAQLPGEKKN GLFGNLIALS LGLTPNFKSN FDLAEDAKLQ  660
LSKDTYDDDL DNLLAQIGDQ YADLFLAAKN LSDAILLSDI LRVNTEITKA PLSASMIKRY  720
DEHHQDLTLL KALVRQQLPE KYKEIFFDQS KNGYAGYIDG GASQEEFYKF IKPILEKMDG  780
TEELLVKLNR EDLLRKQRTF DNGSIPHQIH LGELHAILRR QEDFYPFLKD NREKIEKILT  840
FRIPYYVGPL ARGNSRFAWM TRKSEETITP WNFEEVVDKG ASAQSFIERM TNFDKNLPNE  900
KVLPKHSLLY EYFTVYNELT KVKYVTEGMR KPAFLSGEQK KAIVDLLFKT NRKVTVKQLK  960
EDYFKKIECF DSVEISGVED RFNASLGTYH DLLKIIKDKD FLDNEENEDI LEDIVLTLTL  1020
FEDREMIEER LKTYAHLFDD KVMKQLKRRR YTGWGRLSRK LINGIRDKQS GKTILDFLKS  1080
DGFANRNFMQ LIHDDSLTFK EDIQKAQVSG QGDSLHEHIA NLAGSPAIKK GILQTVKVVD  1140
ELVKVMGRHK PENIVIEMAR ENQTTQKGQK NSRERMKRIE EGIKELGSQI LKEHPVENTQ  1200
LQNEKLYLYY LQNGRDMYVD QELDINRLSD YDVDHIVPQS FLKDDSIDNK VLTRSDKNRG  1260
KSDNVPSEEV VKKMKNYWRQ LLNAKLITQR KFDNLTKAER GGLSELDKAG FIKRQLVETR  1320
QITKHVAQIL DSRMNTKYDE NDKLIREVKV ITLKSKLVSD FRKDFQFYKV REINNYHHAH  1380
DAYLNAVVGT ALIKKYPKLE SEFVYGDYKV YDVRKMIAKS EQEIGKATAK YFFYSNIMNF  1440
FKTEITLANG EIRKRPLIET NGETGEIVWD KGRDFATVRK VLSMPQVNIV KKTEVQTGGF  1500
SKESILPKRN SDKLIARKKD WDPKKYGGFD SPTVAYSVLV VAKVEKGKSK KLKSVKELLG  1560
ITIMERSSFE KNPIDFLEAK GYKEVKKDLI IKLPKYSLFE LENGRKRMLA SAGELQKGNE  1620
LALPSKYVNF LYLASHYEKL KGSPEDNEQK QLFVEQHKHY LDEIIEQISE FSKRVILADA  1680
NLDKVLSAYN KHRDKPIREQ AENIIHLFTL TNLGAPAAFK YFDTTIDRKR YTSTKEVLDA  1740
TLIHQSITGL YETRIDLSQL GGD                                          1763

SEQ ID NO: 36          moltype = AA  length = 1565
FEATURE                Location/Qualifiers
source                 1..1565
                       mol_type = protein
                       organism = synthetic construct
SEQUENCE: 36
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNSKR GAAGSLMNVL  120
NYPGMNHRVE ITEGILADEC AALLCDFYRM PRQVFNAQKK AQSSINSGGS SGGSSGSETP  180
GTSESATPES SGGSSGGSDK KYSIGLAIGT NSVGWAVITD EYKVPSKKFK VLGNTDRHSI  240
KKNLIGALLF DSGETAEATR LKRTARRRYT RRKNRICYLQ EIFSNEMAKV DDSFFHRLEE  300
SFLVEEDKKH ERHPIFGNIV DEVAYHEKYP TIYHLRKKLV DSTDKADLRL IYLALAHMIK  360
FRGHFLIEGD LNPDNSDVDK LFIQLVQTYN QLFEENPINA SGVDAKAILS ARLSKSRRLE  420
NLIAQLPGEK KNGLFGNLIA LSLGLTPNFK SNFDLAEDAK LQLSKDTYDD DLDNLLAQIG  480
DQYADLFLAA KNLSDAILLS DILRVNTEIT KAPLSASMIK RYDEHHQDLT LLKALVRQQL  540
PEKYKEIFFD QSKNGYAGYI DGGASQEEFY KFIKPILEKM DGTEELLVKL NREDLLRKQR  600
TFDNGSIPHQ IHLGELHAIL RRQEDFYPFL KDNREKIEKI LTFRIPYYVG PLARGNSRFA  660
WMTRKSEETI TPWNFEEVVD KGASAQSFIE RMTNFDKNLP NEKVLPKHSL LYEYFTVYNE  720
LTKVKYVTEG MRKPAFLSGE QKKAIVDLLF KTNRKVTVKQ LKEDYFKKIE CFDSVEISGV  780
EDRFNASLGT YHDLLKIIKD KDFLDNEENE DILEDIVLTL TLFEDREMIE ERLKTYAHLF  840
DDKVMKQLKR RRYTGWGRLS RKLINGIRDK QSGKTILDFL KSDGFANRNF MQLIHDDSLT  900
FKEDIQKAQV SGQGDSLHEH IANLAGSPAI KKGILQTVKV VDELVKVMGR HKPENIVIEM  960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                              1565

SEQ ID NO: 37          moltype = AA  length = 1565
FEATURE                Location/Qualifiers
source                 1..1565
                       mol_type = protein
                       organism = synthetic construct
```

```
SEQUENCE: 37
SEVEFSHEYW MRHALTLAKR ARDEREVPVG AVLVLNNRVI GEGWNRAIGL HDPTAHAEIM  60
ALRQGGLVMQ NYRLYDATLY STFEPCVMCA GAMIHSRIGR VVFGVRNAKT GAAGSLMDVL  120
HHPGMNHRVE ITEGILADEC AALLCRFFRM PRRVFNAQKK AQSSTDSGGS SGGSSGSETP  180
GTSESATPES SGGSSGGSDK KYSIGLAIGT NSVGWAVITD EYKVPSKKFK VLGNTDRHSI  240
KKNLIGALLF DSGETAEATR LKRTARRRYT RRKNRICYLQ EIFSNEMAKV DDSFFHRLEE  300
SFLVEEDKKH ERHPIFGNIV DEVAYHEKYP TIYHLRKKLV DSTDKADLRL IYLALAHMIK  360
FRGHFLIEGD LNPDNSDVDK LFIQLVQTYN QLFEENPINA SGVDAKAILS ARLSKSRRLE  420
NLIAQLPGEK KNGLFGNLIA LSLGLTPNFK SNFDLAEDAK LQLSKDTYDD DLDNLLAQIG  480
DQYADLFLAA KNLSDAILLS DILRVNTEIT KAPLSASMIK RYDEHHQDLT LLKALVRQQL  540
PEKYKEIFFD QSKNGYAGYI DGGASQEEFY KFIKPILEKM DGTEELLVKL NREDLLRKQR  600
TFDNGSIPHQ IHLGELHAIL RRQEDFYPFL KDNREKIEKI LTFRIPYYVG PLARGNSRFA  660
WMTRKSEETI TPWNFEEVVD KGASAQSFIE RMTNFDKNLP NEKVLPKHSL LYEYFTVYNE  720
LTKVKYVTEG MRKPAFLSGE QKKAIVDLLF KTNRKVTVKQ LKEDYFKKIE CFDSVEISGV  780
EDRFNASLGT YHDLLKIIKD KDFLDNEENE DILEDIVLTL TLFEDREMIE ERLKTYAHLF  840
DDKVMKQLKR RRYTGWGRLS RKLINGIRDK QSGKTILDFL KSDGFANRNF MQLIHDDSLT  900
FKEDIQKAQV SGQGDSLHEH IANLAGSPAI KKGILQTVKV VDELVKVMGR HKPENIVIEM  960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                             1565

SEQ ID NO: 38           moltype = AA  length = 364
FEATURE                 Location/Qualifiers
source                  1..364
                        mol_type = protein
                        organism = synthetic construct
SEQUENCE: 38
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLIDATLYVT FEPCVMCAGA MIHSRIGRVV  300
FGVRNAKTGA AGSLMDVLHY PGMNHRVEIT EGILADECAA LLCYFFRMPR QVFNAQKKAQ  360
SSTD                                                              364

SEQ ID NO: 39           moltype = AA  length = 167
FEATURE                 Location/Qualifiers
source                  1..167
                        mol_type = protein
                        organism = synthetic construct
SEQUENCE: 39
MSEVEFSHEY WMRHALTLAK RARDEREVPV GAVLVLNNRV IGEGWNRAIG LHDPTAHAEI  60
MALRQGGLVM QNYRLYDATL YSTFEPCVMC AGAMIHSRIG RVVFGVRNAK TGAAGSLMDV  120
LHHPGMNHRV EITEGILADE CAALLCRFFR MPRRVFNAQK KAQSSTD               167

SEQ ID NO: 40           moltype = AA  length = 167
FEATURE                 Location/Qualifiers
source                  1..167
                        mol_type = protein
                        organism = synthetic construct
SEQUENCE: 40
MSEVEFSHEY WMRHALTLAK RARDEREVPV GAVLVLNNRV IGEGWNRAIG LHDPTAHAEI  60
MALRQGGLVM QNYRLIDATL YVTFEPCVMC AGAMIHSRIG RVVFGVRNSK RGAAGSLMNV  120
LNYPGMNHRV EITEGILADE CAALLCDFYR MPRQVFNAQK KAQSSIN               167

SEQ ID NO: 41           moltype = AA  length = 83
FEATURE                 Location/Qualifiers
source                  1..83
                        mol_type = protein
                        note = Bacillus phage AR9
                        organism = unidentified
SEQUENCE: 41
TNLSDIIEKE TGKQLVIQES ILMLPEEVEE VIGNKPESDI LVHTAYDEST DENVMLLTSD  60
APEYKPWALV IQDSNGENKI KML                                          83

SEQ ID NO: 42           moltype = AA  length = 24
FEATURE                 Location/Qualifiers
source                  1..24
                        mol_type = protein
                        organism = synthetic construct
SEQUENCE: 42
```

```
EELLSKNYHL ENEVARLKKG SGSG                                        24

SEQ ID NO: 43          moltype = AA  length = 241
FEATURE                Location/Qualifiers
source                 1..241
                       mol_type = protein
                       organism = synthetic construct
SEQUENCE: 43
EEELLSKNYH LENEVARLKK GSGSGEELLS KNYHLENEVA RLKKGSGSGE ELLSKNYHLE  60
NEVARLKKGS GSGEELLSKN YHLENEVARL KKGSGSGEEL LSKNYHLENE VARLKKGSGS  120
GEELLSKNYH LENEVARLKK GSGSGEELLS KNYHLENEVA RLKKGSGSGE ELLSKNYHLE  180
NEVARLKKGS GSGEELLSKN YHLENEVARL KKGSGSGEEL LSKNYHLENE VARLKKGSGS  240
G                                                                 241

SEQ ID NO: 44          moltype = AA  length = 277
FEATURE                Location/Qualifiers
source                 1..277
                       mol_type = protein
                       organism = synthetic construct
SEQUENCE: 44
MGPDIVMTQS PSSLSASVGD RVTITCRSST GAVTTSNYAS WVQEKPGKLF KGLIGGTNNR  60
APGVPSRFSG SLIGDKATLT ISSLQPEDFA TYFCALWYSN HWVFGQGTKV ELKRGGGGSG  120
GGGSGGGGSS GGGSEVKLLE SGGGLVQPGG SLKLSCAVSG FSLTDYGVNW VRQAPGRGLE  180
WIGVIWGDGI TDYNSALKDR FIISKDNGKN TVYLQMSKVR SDDTALYYCV TGLFDYWGQG  240
TLVTVSSYPY DVPDYAGGGG GSGGGGSGGG GSGGGGS                          277

SEQ ID NO: 45          moltype = DNA  length = 66
FEATURE                Location/Qualifiers
source                 1..66
                       mol_type = other DNA
                       organism = Saccharomyces bayanus
SEQUENCE: 45
ttcttgtcgt acttatagat cgctacgtta tttcaatttt gaaaatctga gtcctgggag  60
tgcgga                                                            66

SEQ ID NO: 46          moltype = AA  length = 605
FEATURE                Location/Qualifiers
source                 1..605
                       mol_type = protein
                       organism = Homo sapiens
SEQUENCE: 46
MSGWESYYKT EGDEEAEEEQ EENLEASGDY KYSGRDSLIF LVDASKAMFE SQSEDELTPF  60
DMSIQCIQSV YISKIISSDR DLLAWFYGTE KDKNSVNFKI YVLQELDNPG AKRILELDQF  120
KGQQGQKRFQ DMMGHGSDYS LSEVLWVCAN LFSDVQFKMS HKRIMLFTNE DNPHGNDSAK  180
ASRARTKAGD LRDTGIFLDL HLKKPGGFDI SLFYRDIISI AEDEDLRVHF EESSKLEDLL  240
RKVRAKETRK RALSRLKLKL NKDIVISVGI YNLVQKALKP PPIKLYRETN EPVKTKTRTF  300
NTSTGGLLLP SDTKRSQIYG SRQIILEKEE TEELKRFDDP GLMLMGFKPL VLLKKHHYLR  360
PSLFVYPEES LVIGSSTLFS ALLIKCLEKE VAALCRYTPR RNIPPYFVAL VPQEEELDDQ  420
KIQVTPPGFQ LVFLPFADDK RKMPFTEKIM ATPEQVGKMK AIVEKLRFTY RSDSFENPVL  480
QQHFRNLEAL ALDLMEPEQA VDLTLPKVEA MNKRLGSLVD EFKELVYPPD YNPEGKVTKR  540
KHDNEGSGSK RPKVEYSEEE LKTHISKGTL GKFTVPLKEA CRAYGLKSGL KKQELLEALT  600
KHFQD                                                             605

SEQ ID NO: 47          moltype = AA  length = 482
FEATURE                Location/Qualifiers
source                 1..482
                       mol_type = protein
                       organism = synthetic construct
SEQUENCE: 47
MVRSGNKAAW LCMDVGFTMS NSIPGIESPF EQAKKVITMF VQRQVFAENK DEIALVLFGT  60
DGTDNPLSGG DQYQNITVHR HLMLPDFDLL EDIESKIQPG SQQADFLDAL IVSMDVIQHE  120
TIGKKFEKRH IEIFTDLSSR FSKSQLDIII HSLKKCDISE RHSIHWPCRL TIGSNLSIRI  180
AAYKSILQER VKKTTWDAKT LKKEDIQKET VYCLNDDDET EVLKEDIIQG FRYGSDIVPF  240
SKVDEEQMKY KSEGKCFSVL GFCKSSQVQR RFFMGNQVLK VFAARDDEAA AVALSSLIHA  300
LDDLDIWAIV RYAYDKRANP QVGVAFPHIK HNYECLVYVQ LPFMEDLRQY MFSSLKNSKK  360
YAPTEAQLNA VDALIDSMSL AKKDEKTDTL EDLFPTTKIP NPRFQRLFQC LLHRALHPRE  420
PLPPIQQHIW NMLNPPAEVT TKSQIPLSKI KTLFPLIEAK KKDQVTAQEI FQDNHEDGPT  480
AK                                                                482

SEQ ID NO: 48          moltype = DNA  length = 10
FEATURE                Location/Qualifiers
source                 1..10
                       mol_type = other DNA
                       organism = Methanobacterium thermoautotrophicum
SEQUENCE: 48
aatttttgga                                                        10

SEQ ID NO: 49          moltype = AA  length = 83
FEATURE                Location/Qualifiers
```

```
source                  1..83
                        mol_type = protein
                        organism = Methanobacterium thermoautotrophicum
SEQUENCE: 49
GSVIDVSSQR VNVQRPLDAL GNSLNSPVII KLKGDREFRG VLKSFDLHMN LVLNDAEELE  60
DGEVTRRLGT VLIRGDNIVY ISP                                         83

SEQ ID NO: 50           moltype = DNA  length = 25
FEATURE                 Location/Qualifiers
source                  1..25
                        mol_type = other DNA
                        organism = Bacteriophage MS2
SEQUENCE: 50
gcgcacatga ggatcaccca tgtgc                                       25

SEQ ID NO: 51           moltype = AA  length = 116
FEATURE                 Location/Qualifiers
source                  1..116
                        mol_type = protein
                        organism = Bacteriophage MS2
SEQUENCE: 51
MASNFTQFVL VDNGGTGDVT VAPSNFANGI AEISSNSRSQ AYKVTCSVRQ SSAQNRKYTI  60
KVEVPKGAWR SYLNMELTIP IFATNSDCEL IVKAMQGLLK DGNPIPSAIA ANSGIY      116

SEQ ID NO: 52           moltype = DNA  length = 26
FEATURE                 Location/Qualifiers
source                  1..26
                        mol_type = other DNA
                        organism = Bacteriophage PP7
SEQUENCE: 52
ataaggagtt tatatggaaa ccctta                                      26

SEQ ID NO: 53           moltype = AA  length = 127
FEATURE                 Location/Qualifiers
source                  1..127
                        mol_type = protein
                        organism = Bacteriophage PP7
SEQUENCE: 53
MSKTIVLSVG EATRTLTEIQ STADRQIFEE KVGPLVGRLR LTASLRQNGA KTAYRVNLKL  60
DQADWDCSTS VCGELPKVRY TQVWSHDVTI VANSTEASRK SLYDLTKSLV ATSQVEDLVV  120
NLVPLGR                                                           127

SEQ ID NO: 54           moltype = DNA  length = 19
FEATURE                 Location/Qualifiers
source                  1..19
                        mol_type = other DNA
                        organism = Shigella phage
SEQUENCE: 54
ctgaatgcct gcgagcatc                                              19

SEQ ID NO: 55           moltype = AA  length = 62
FEATURE                 Location/Qualifiers
source                  1..62
                        mol_type = protein
                        organism = Shigella phage
SEQUENCE: 55
MKSIRCKNCN KLLFKADSFD HIEIRCPRCK RHIIMLNACE HPTEKHCGKR EKITHSDETV  60
RY                                                                62

SEQ ID NO: 56           moltype = AA  length = 1367
FEATURE                 Location/Qualifiers
source                  1..1367
                        mol_type = protein
                        organism = synthetic construct
SEQUENCE: 56
DKKYSIGLAI GTNSVGWAVI TDEYKVPSKK FKVLGNTDRH SIKKNLIGAL LFDSGETAEA  60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
```

```
VPQSFLKDDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM  1020
IAKSEQEIGK ATAKYFFYSN IMNFFKTEIT LANGEIRKRP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD                1367

SEQ ID NO: 57          moltype = AA  length = 1367
FEATURE                Location/Qualifiers
source                 1..1367
                       mol_type = protein
                       organism = synthetic construct
SEQUENCE: 57
DKKYSIGLAI GTNSVGWAVI TDEYKVPSKK FKVLGNTDRH SIKKNLIGAL LFDSGETAEA  60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLADDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PALESEFVYG DYKVYDVRKM  1020
IAKSEQEIGK ATAKYFFYSN IMNFFKTEIT LANGEIRKAP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD                1367

SEQ ID NO: 58          moltype = DNA  length = 4101
FEATURE                Location/Qualifiers
source                 1..4101
                       mol_type = other DNA
                       organism = synthetic construct
SEQUENCE: 58
gacaagaagt acagcatcgg gctggcgatc gggaccaact ccgtcggctg ggctgtgatt  60
accgacgagt acaaggtgcc atccaagaag ttcaaggtcc tcggcaacac tgaccggcac  120
agcattaaga agaacctgat tggggcgctg ctgttcgatt cgggggagac tgcggaggcg  180
accaggctga agcggactgc gcgccggagg tacaccagga ggaagaatcg gatctgctac  240
ctccaggaga ttttctcgaa tgagatggcc aaggtggacg attccttctt ccatcgcctg  300
gaggagtcgt tcctcgttga ggaggacaag aagcatgaga ggcatcccat tttcgggaat  360
atcgttgacg aggtggctta ccatgagaag tacccgacca tctaccatct gcggaagaag  420
ctcgtcgatt cgaccgataa ggccgacctg cggctgatct acctggccct cgcgcacatg  480
attaagttcc ggggccattt cctcatcgag ggcgacctca acccggacaa ctcggacgtg  540
gataagctct tcattcagct cgtgcagaca tacaaccagc tcttcgagga gaatcccatt  600
aacgcctcgg gggtcgacgc taaggctatt ctctcggctc ggctgtcgaa gtcgcgccgg  660
ctggagaatc tcattgccca gctcccaggc gagaagaaga acggcctctt cggcaacctg  720
attgccctgt cgctggggct cacaccgaat ttcaagtcga acttcgacct cgccgaggac  780
gctaagctcc agctcagcaa ggatacttac gatgatgacc tcgataacct gctcgcccag  840
attggggatc agtacgcgga tctgttcctc gcggccaaga atctcagcga tgctattctc  900
ctgtcggaca ttctccgcgt caacacagag attactaagg ccccactgtc ggcgagcatg  960
attaagaggt acgatgagca tcatcaggac ctgacactgc tcaaggcgct ggtccggcag  1020
cagctccccg agaagtacaa ggagattttc ttcgatcagt caaagaatgg gtacgcgggc  1080
tacattgatg gcggcgcgtc ccaggaggag ttctacaagt tcattaagcc catcctggag  1140
aagatggacg ggaccgagga gctgctggtg aagctcaatc gggaggacct gctccggaag  1200
cagcgcacat tcgacaatgg ctcgattcct caccagattc acctgggcga gctgcacgcc  1260
attctccgca ggcaggagga cttctacccg ttcctcaagg acaaccgcga gaagatcgag  1320
aagatcctga ccttccggat tccatactac gtggggccgc tcgcgcgggg gaactcccgg  1380
ttcgcgtgga tgactcgcaa gtccgaagaa acgattacac cgtggaattt cgaggaggtc  1440
gtcgacaagg gcgctagtgc gcagtcattc attgagagga tgaccaattt cgataagaac  1500
ctgcctaacg agaaggtgct gccgaagcat tcgctgctct acgagtactt caccgtttac  1560
aatgagctga ccaaggtgaa gtatgtgact gagggcatga ggaagccagc gttcctgagc  1620
ggcgagcaga agaaggctat cgtggacctg ctcttcaaga ctaaccggaa ggtgactgtg  1680
aagcagctca aggaggacta cttcaagaag attgagtgct tcgattccgt tgagattagc  1740
ggggtggagg atcggttcaa tgcttcgctc gggacatacc acgatctcct gaagatcatt  1800
aaggataagg acttcctcga caacgaggag aacgaggaca ttctcgaaga tattgtcctg  1860
accctcaccc tcttcgagga tcgggagatg atcgaggaga ggctcaagac atacgctcat  1920
ctgttcgatg ataaggtcat gaagcagctg aagcgcaggc ggtacacagg gtgggggcgg  1980
```

```
ctgagccgga agctgatcaa cgggattcgg gataagcagt ccgggaagac aattctcgac  2040
ttcctcaagt ccgacgggtt cgctaaccgg aacttcatgc agctcattca tgatgactcg  2100
ctgacattca aggaggatat tcagaaggcg caggtttcgg ggcagggcga ctcgctccac  2160
gagcatattg cgaatctggc gggctccccc gcgattaaga agggcattct gcaaaccgtc  2220
aaggtggttg atgagctggt caaggtcatg gggcggcata agccagagaa tattgtcatc  2280
gagatggcgc gggagaatca gaccacacag aaggggcaga agaactcacg ggagcggatg  2340
aagcgcatcg aggagggcat caaggagctg ggtcgcaga tcctgaagga gcatcccgtg   2400
gagaacactc agctgcaaaa tgagaagctg tacctctact acctccagaa cgggagggac  2460
atgtatgtgg atcaggagct ggatattaat aggctgagcg attacgatgt cgaccacatt  2520
gtcccacagt cgttcctgaa ggacgacagc attgacaaca aggtgctgac ccgctcggat  2580
aagaacaggg gcaagagcga taatgttcca agcgaggagg ttgtgaagaa gatgaagaac  2640
tactggcggc agctcctgaa cgcgaagctc atcacacagc ggaagttcga caacctcacc  2700
aaggctgagc gcgggggcct gagcgagctg gacaaggcgg ggttcattaa gaggcagctg  2760
gtcgagacac ggcagattac aaagcatgtt gcgcagattc tcgattcccg gatgaacacc  2820
aagtacgatg agaacgataa gctgattcgg gaggtcaagg taattaccct gaagtccaag  2880
ctggtgtccg acttcaggaa ggacttccag ttctacaagg ttcgggagat caacaactac  2940
caccacgcgc atgatgccta cctcaacgcg gtcgtgggga ccgctctcat caagaagtac  3000
ccaaagctgg agtcagagtt cgtctacggg gattacaagg tttacgacgt gcggaagatg  3060
atcgctaaga gcgagcagga gattggcaag gctaccgcta agtacttctt ctactccaac  3120
atcatgaact tcttcaagac agagattacc ctcgcgaatg gcgagatccg gaagaggccc  3180
ctcatcgaga caaatgggga gacaggggag attgtctggg ataaggggcg ggatttcgcg  3240
accgtccgga aggtcctgtc gatgccccag gttaatattg tcaagaagac tgaggtccag  3300
actggcggct tctcaaagga gtcgattctc ccaaagagga actccgataa gctcattgct  3360
cggaagaagg attgggaccc caagaagtac ggggggattcg actcccccac tgttgcttac 3420
tctgttctgg ttgttgctaa ggtggagaag gggaagtcga agaagctgaa gagcgtgaag  3480
gagctgctcg ggattacaat tatggagagg tcatccttcg agaagaatcc catcgacttc  3540
ctggaggcca agggctacaa ggaggtgaag aaggacctga ttattaagct gcccaagtac  3600
tcgctcttcg agctggagaa tgggcggaag cggatgctgg cgtccgcggg ggagctgcaa  3660
aaggggaacg agctggcgct cccctccaag tatgtgaact tcctctacct ggcgtcgcac  3720
tacgagaagc tgaaggggtc cccagaggat aatgagcaga agcagctctt cgtcgagcag  3780
cataagcact acctggacga gattatcgag cagattagcg agttctcgaa gcgggtcatc  3840
ctcgcggatg cgaacctgga taaggtgctc agcgcctaca ataagcaccg ggacaagccg  3900
attcgggagc aggcggagaa tattattcac ctcttcacac tcaccaacct cggggcacca  3960
gctgcgttca agtacttcga cactactatc gaccggaagc ggtacacctc gacgaaggag  4020
gtgctcgacg ccaccctcat tcaccagtcg atcacaggcc tgtacgagac acggattgac  4080
ctgtcccagc tcgggggcga c                                            4101

SEQ ID NO: 59          moltype = DNA  length = 4101
FEATURE                Location/Qualifiers
source                 1..4101
                       mol_type = other DNA
                       organism = synthetic construct
SEQUENCE: 59
gacaagaagt actccattgg cctggcgatt gggacaaact cggtggggtg ggccgtgatt  60
acggatgagt acaaggtccc aagcaagaag ttcaaggtcc tcgggaacac agatcggcat  120
tcgattaaga agaatctcat tggggcgctc ctcttcgact cgggggagac agcggaggct  180
accaggctca agcggacagc caggcggcgg tacacaaggc ggaagaatcg catctgctac  240
ctccaggaga ttttctcgaa tgagatggcg aaggtggacg acagcttctt ccatcggctg  300
gaggagtcct tcctggtgga ggaggataag aagcacgaga ggcatccaat tttcgggaac  360
atcgtggacg aggttgcgta ccatgagaag taccctacaa tctaccatct gcggaagaag  420
ctggttgact ccacagacaa ggcggacctg aggctgatct acctcgctct ggcccacatg  480
attaagttcc gcgggcattt cctgatcgag ggggacctga atcccgacaa ttcggatgtg  540
gacaagctct tcatccagct ggtgcagacc tacaaccagc tgttcgagga gaatcccatc  600
aatgcgtcgg gcgttgacgc taaggccatt ctgtccgcta ggctgtcgaa gagcaggagg  660
ctggagaacc tgatcgccca gctgccaggc gagaagaaga atgggctctt cgggaatctg  720
attgcgctct ccctggggct gacaccgaac ttcaagagca atttcgatct ggctgaggac  780
gcgaagctcc agctctcgaa ggacacttac gacgatgacc tcgataacct cctcgcgcag  840
atcggggacc agtacgctga tctcttcctc gccgctaaga acctctcgga tgctatcctg  900
ctctccgaca ttctccgggt taataccgag attacaaagg ccccactgtc ggcgtccatg  960
atcaagcggt acgatgagca tcatcaggat ctcaccctgc tcaaggccct cgtgcggcag  1020
cagctgcccg agaagtacaa ggagattttc ttcgaccaga gcaagaatgg gtacgctggc  1080
tacattgacg gcggggcctc acaggaggag ttctacaagt tcatcaagcc aatcctggag  1140
aagatggatg ggacagagga gctgctggtg aagctcaacc gggaggatct gctcaggaag  1200
cagcggacgt tcgacaacgg gtcgattccc catcagatcc acctggggga gctgcacgcg  1260
atcctgcgcc ggcaggagga tttctaccct ttcctgaagg ataatcggga gaagatcgag  1320
aagattctca ccttccggat tccctactac gtcgggccac tcgcgcgggg caatagcagg  1380
ttcgcctgga tgacacggaa gagcgaggag acaatcaccc cctggaactt cgaggaggtt  1440
gtcgacaagg gggcgtccgc ccagtcattc attgagcgga tgaccaattt cgacaagaat  1500
ctgccaaatg agaaggttct cccaaagcat agcctcctct acgagtactt cactgtttac  1560
aacgagctga ccaaggtgaa gtatgtgacc gagggcatgc ggaagcccgc gttcctgtcc  1620
ggcgagcaga agaaggccat tgtggacctc ctgttcaaga ccaatcgcaa ggtcacagtc  1680
aagcagctca aggaggatta cttcaagaag atcgagtgct tcgactcggt tgagattagc  1740
ggggtggagg atcggttcaa cgcgagcctc ggcacttacc acgacctcct gaagatcatc  1800
aaggataagg acttcctcga caacgaggag aacgaggata ttctggagga catcgtgctc  1860
accctgacgc tgttcgagga tcgggagatg atcgaggagc gcctgaagac ctacgctcat  1920
ctcttcgatg ataaggtcat gaagcagctg aagaggaggc ggtacaccgg gtggggccgc  1980
ctgagcagga agctcattaa cggatcagg gacaagcaga gcggcaagac catcctggac   2040
ttcctcaaga gcgatggctt cgccaaccgg aatttcatgc agctcatcca cgacgactcc  2100
ctcaccttca aggaggacat tcagaaggct caggtcagcg gccagggcga ctcgctgcat  2160
```

```
gagcacatcg ctaacctggc gggcagccca gccatcaaga agggcatcct ccagacagtg  2220
aaggtcgtgg atgagctggt gaaggtcatg ggccggcata agcccgagaa tattgtgatt  2280
gagatggcgc gggagaatca gaccactcag aagggccaga agaactcgcg ggagcgcatg  2340
aagaggatcg aggaggggat taaggagctg ggcagccaga ttctcaagga gcaccccgtg  2400
gagaataccc agctccagaa cgagaagctg tacctctact acctccagaa tgggcgggac  2460
atgtatgttg atcaggagct ggacatcaat cgcctctcgg attacgacgt ggaccacatc  2520
gtgccccaga gcttcctgaa ggatgatagc atcgacaata aggtcctgac ccgctccgac  2580
aagaatcgcg gcaagagcga caacgtgccg agcgaggagg tcgtgaagaa gatgaagaac  2640
tactggcggc agctgctgaa cgcgaagctc attacacagc ggaagttcga taacctgacg  2700
aaggcggaga ggggcggcct ctccgagctg gacaaggcgg gcttcattaa gaggcagctc  2760
gtggagactc gccagatcac caagcacgtg gctcagatcc tcgatagccg gatgaatacg  2820
aagtacgatg agaatgacaa gctcatccgg gaggtgaagg taatcaccct gaagtcaaag  2880
ctcgttagcg atttccggaa ggacttccag ttctacaagg tgcgggagat taacaactac  2940
catcatgcgc acgatgcgta cctcaatgcg gtggtgggca cagccctgat taagaagtac  3000
cccaagctgg agagcgagtt cgtctacggg gactacaagg tgtacgatgt tcggaagatg  3060
atcgccaaga gcgagcagga gattgggaag gccaccgcta agtacttctt ctactcgaat  3120
attatgaatt tcttcaagac cgagatcaca ctcgctaatg gggagattcg gaagcggccc  3180
ctcatcgaga ctaacgggga gactggcgag attgtgtggg acaaggggcg cgacttcgct  3240
accgtgcgca aggtcctctc gatgccccag gttaatattg ttaagaagac agaggtgcag  3300
acgggcgggt tctccaagga gtctatcctg ccgaagcgga actcggacaa gctgatcgcc  3360
cgcaagaagg attgggaccc caagaagtac gggggattcg atagcccaac cgtggcttac  3420
agcgtcctgg tggtcgccaa ggttgagaag gggaagtcga agaagctcaa gagcgttaag  3480
gagctgctgg gcatcaccat catggagcgg tccagcttcg agaagaatcc tatcgacttc  3540
ctggaggcta aggggtacaa ggaggtcaag aaggacctga tcattaagct gcccaagtac  3600
tctctgttcg agctggagaa cgggaggaag cggatgctgg cgtctgctgg cgagctacag  3660
aagggcaatg agctggcgct cccctcgaag tatgtcaact tcctctacct ggcttcccat  3720
tacgagaagc tgaagggctc gcccgaggat aatgagcaga agcagctctt cgtggagcag  3780
cacaagcact acctcgacga gatcattgag cagatttcgg agttctcgaa gcgggtcatt  3840
ctcgcggacg cgaacctcga caaggtcctc tcggcgtaca acaagcaccg ggacaagccc  3900
atccgggagc aggccgagaa cattatccac ctcttcacac tgaccaacct cggcgctccc  3960
gccgcgttca agtacttcga caccaccatt gaccgcaaga gatacacatc caccaaggag  4020
gtgctggacg cgaccctcat ccaccagagc atcacaggcc tctacgagac acggatcgac  4080
ctctcgcagc tcgggggcga t                                            4101
```

```
SEQ ID NO: 60          moltype = DNA  length = 4092
FEATURE                Location/Qualifiers
source                 1..4092
                       mol_type = other DNA
                       organism = synthetic construct
SEQUENCE: 60
gacaagaagt actcgatcgg cctggcgatt ggcacaaaca gcgtggggtg ggctgtgatc  60
actgatgagt acaaggtgcc atcgaagaag ttcaaggtgc tggggaatac agaccggcat  120
tcgatcaaga agaatctcat tggcgctctc ctcttcgatt ccggcgagac tgctgaggcg  180
acccgcctga agcgcaccgc ccggcggcgc tacactcggc ggaagaatag gatttgctac  240
ctccaggaga ttttctcgaa tgagatggcc aaggtggatg acagcttctt ccaccgcctg  300
gaggagtcgt tcctggtcga ggaggacaag aagcatgagc ggcaccctat cttcgggaat  360
atcgttgatg aggtcgccta ccacgagaag taccccacta tctaccatct ccgcaagaag  420
ctcgtggaca gcacagataa ggccgacctc cgcctgatct acctcgccct cgcgcacatg  480
attaagttcc gggggcactt cctcattgag gggggatctga atcccgataa ctccgacgtg  540
gacaagctgt tcatccagct ggtgcagaca tacaaccagc tgttcgagga gaatcccatc  600
aacgcgagcg gcgtggacgc taaggccatt ctgtcggcta ggctctcgaa gtcgaggcgg  660
ctggagaacc tgattgcgca gctccccggc gagaagaaga acgggctgtt cgggaatctc  720
atcgccctct ccctcggcct cacaccaaac ttcaagagca atttcgacct ggctgaggac  780
gctaagctgc aactctcaaa ggatacatac gatgacgacc tggacaatct cctggctcag  840
atcggcgacc agtacgctga cctgttcctc gcggccaaga atctgtcgga cgcgattctc  900
ctcagcgaca tcctgcgcgt caataccgag attacgaagg ctccactgtc tgcgtcaatg  960
attaagcggt acgatgagca tcaccaggat ctgaccctcc tgaaggcgct cgtgcggcag  1020
cagctgcccg agaagtacaa ggagattttc ttcgatcaga gcaagaatgg ctacgccggc  1080
tacatcgacg gggcgcgag ccaggaggag ttctacaagt tcatcaagcc catcctggag  1140
aagatggacg gcaccgagga gctactcgtg aagctcaatc gggaggatct cctccggaag  1200
cagcggacat tcgataacgg gtctatccca caccagatcc acctcggcga gctgcatgcg  1260
attctgcggc ggcaggagga tttctaccct ttcctgaagg acaaccggga gaagatcgag  1320
aagatcctca cattccggat tccatactac gtcggccccc tggcgagggg caatagccgg  1380
ttcgcgtgga tgacaaggaa gtccgaggag actattaccc cgtggaattt cgaggaggtg  1440
gttgacaagg gcgcttccgc gcagagcttc attgagcgga tgacaaactt cgacaagaat  1500
ctccccaacg agaaggtcct gccgaagcat agcctcctgt acgagtactt caccgtctac  1560
aatgagctaa ctaaggtcaa gtatgtgaca gagggcatga ggaagccagc cttcctctca  1620
ggcgagcaga agaaggccat tgtggacctc ctgttcaaga caaaccgcaa ggtgacagtg  1680
aagcagctga aggaggatta cttcaagaag attgagtgct tcgactcagt ggagatttca  1740
ggcgtggagg atcggttcaa cgcgagcctg gggacttacc acgacctgct gaagattatt  1800
aaggacaagg acttcctgga taacgaggag aatgaggaca tcctggagga tattgtgctc  1860
accctcaccc tgttcgagga cagggagatg attgaggaga ggctcaagac ctacgcgcac  1920
ctgttcgatg acaaggtcat gaagcagctg aagaggcggc gctacactgg gtggggccgc  1980
ctgtcgcgga agctgatcaa cggcattcgg gataagcagt ccgggaagac cattctggat  2040
ttcctgaagt cggacggctt cgccaacagg aatttcatgc agctgatcca cgacgactcc  2100
ctcaccttca aggaggacat tcagaaggcc caggttagcg gccaggggga ctcactccac  2160
gagcatattg ccaatctggc cggctctcca gctatcaaga agggcatcct gcaaacagtt  2220
aaggttgttg acgagctggt taaggtcatg ggcggcata agcccgagaa cattgtcatc  2280
gagatggctc gggagaacca gacaactcag aagggccaga agaactccag ggagcgcatg  2340
```

```
aagcggattg aggagggcat taaggagctg gggtcccaga tcctcaagga gcaccctgtc  2400
gagaacactc agctgcaaaa cgagaagctc tacctgtact acctccagaa cgggcgggat  2460
atgtatgtgg atcaggagct ggacatcaac aggctctccg actacgacgt ggatcacatt  2520
gtcccacagt ctttcctcaa ggatgattcc atcgacaaca aggtgctgac gcgcagcgac  2580
aagaataggg ggaagtcgga caacgttccg agcgaggagg tcgtgaagaa gatgaagaat  2640
tactggaggc agctcctgaa tgcgaagctg atcactcaga ggaagttcga caatctgaca  2700
aaggcggaga ggggcggct ctcggagctg gataaggcgg gcttcatcaa gcggcagctc  2760
gttgaaaccc ggcagatcac caagcatgtc gcccagatcc tcgatagccg catgaacacc  2820
aagtacgatg agaacgacaa gctcattcgg gaggttaagg tcattacgct gaagtccaag  2880
ctcgtcagcg acttcaggaa ggatttccag ttctacaagg ttcgggagat taacaactac  2940
caccacgcgc atgatgcgta cctgaacgct gttgtcggca ctgctctcat caagaagtac  3000
ccaaagctgg agtccgagtt cgtctacggg gactacaagg tctacgatgt ccggaagatg  3060
atcgccaagt cggagcagga gatcgggaag gctactgcga agtacttctt ctacagcaac  3120
attatgaatt tcttcaagac ggagattacg ctggcgaacg gggagattag gaagaggccc  3180
ctcattgaga ctaatgggga gacaggcgag attgtttggg acaagggccg cgacttcgcg  3240
actgtgcgga aggtcctgtc catgccacag gtgaatattg ttaagaagac agaggtgcag  3300
actgggggct tctcgaagga gagcattctc ccaaagcgga acagcgataa gctcatcgcg  3360
cgcaagaagg attgggaccc taagaagtac ggcggcttcg attctcccac tgtggcctac  3420
tccgttctcg tggttgccaa ggttgagaag gggaagtcga agaagctgaa gtcggtcaag  3480
gagctgctcg ggattacaat catggagcgg agcagcttcg agaagaaccc tattgatttc  3540
ctggaggcca agggctacaa ggaggttaag aaggatctca ttatcaagct ccctaagtac  3600
tctctgttcg agctggagaa tggccggaag aggatgctgg cctcggctgg cgagctacag  3660
aaggggaatg agctggccct cccgtcgaag tatgtgaatt tcctgtacct cgcgtcgcac  3720
tacgagaagc tcaagggcag cccggaggat aatgagcaga agcagctctt cgtggagcag  3780
cataagcact acctggacga gatcattgag cagatcagcg agttctcgaa gcgggttatt  3840
ctggctgatg ctaacctgga caaggttctg agcgcctaca ataagcatcg cgacaagccg  3900
attcgcgagc aggcggagaa tattatccac ctgttcaccc tcactaacct cggggctccc  3960
gcggccttca agtacttcga taccacaata gataggaagc ggtacacctc gacgaaggag  4020
gtcctcgacg ccacactcat ccatcagtcg attacaggcc tgtacgagac acggattgac  4080
ctctcgcagc tg                                                      4092

SEQ ID NO: 61           moltype = DNA  length = 4101
FEATURE                 Location/Qualifiers
source                  1..4101
                        mol_type = other DNA
                        organism = synthetic construct
SEQUENCE: 61
gacaagaagt attccatagg cctggctatc ggcaccaaca gcgtgggctg ggccgtcatc  60
accgacgagt acaaagtgcc gagtaaaaag ttcaaagtgc tcggcaacac cgaccgccac  120
tccataaaga aaaacctgat cggggcgctc ctgttcgaca gcggcgagac ggcggaggcc  180
acccgcttga aacgcacggc ccgacggcgc tacacgcggc gcaagaaccg gatctgttac  240
ctacaggaga ttttctctaa cgagatggcg aaggtggacg actcgttctt tcaccgcctc  300
gaagagtcct tcctcgtgga ggaggacaag aaacacgagc gccacccgat cttcggcaac  360
atcgtggacg aggtggccta ccacgagaag tacccgacca tctaccacct ccggaagaaa  420
ctcgtggaca gcacggacaa ggccgacctg aggctcatct acctcgccct ggcgcacatg  480
attaagttcc ggggccactt cctgatcgag ggcgacctga acccggacaa cagcgacgtg  540
gacaagctgt tcatccagct agtccagacc tacaaccagc ttttcgagga aaaccccatc  600
aacgccagcg gggtggacgc gaaggcgatc ctgtccgccc ggctgagcaa gtcccggcgg  660
ctggagaacc tcatcgcgca gttgcccggc gagaagaaga acgggctgtt cgggaacctg  720
atcgccctct ccctggggct caccccgaac ttcaagtcca acttcgacct cgccgaggac  780
gccaaactac agctgagcaa ggacacctac gacgacgacc tcgacaacct gctggcccag  840
atcggggacc agtacgcaga cctgttcctc gccgccaaga acctctccga cgccatcctg  900
ctgtcggaca tcctgcgggt gaacacggag atcacgaagg ccccgctctc ggcctcgatg  960
attaaacgct acgacgagca ccaccaggac ttgaccctcc tcaaggcgct ggtccgccag  1020
cagcttcccg agaagtacaa ggaaatcttt ttcgatcaga gcaagaacgg gtacgccggg  1080
tacatcgacg gcggggcgtc ccaggaggag ttctacaagt tcatcaagcc catcctggag  1140
aaaatggacg ggaccgagga gctgctcgtg aagctcaacc gcgaagattt gctccgcaag  1200
cagcgcacgt tcgacaacgg gtcgatcccg caccagatcc acctgggcga gctgcacgcg  1260
atcctcaggc gtcaggaaga cttctacccc ttcctcaagg acaaccgcga gaagatagag  1320
aagattctga ccttcagaat tccttattac gtgggcccgc tggctcgggg caactcgcgc  1380
ttcgcctgga tgacgcgcaa gtccgaggag accatcaccc cgtggaactt cgaggaggtg  1440
gtggataagg gtgcctcggc ccagtccttc atcgagcgga tgaccaactt cgacaagaac  1500
ctgccgaacg agaaggtgct ccccaagcac agcctgctct acgaatattt cacggtgtac  1560
aacgagctga cgaaggtcaa gtacgtgacc gagggaatga ggaaacctgc attcctctcc  1620
ggggagcaga agaaagccat agtcgacctc ctgttcaaga ccaaccggaa ggtcaccgtc  1680
aagcagctca aggaggacta cttcaagaag atcgagtgct tcgattcagt ggagatcagc  1740
ggcgtcgagg accggttcaa cgccagcctg ggcacctacc acgacctgct caagatcatc  1800
aaggacaagg acttcctcga caacgaggag aacgaggaca tcctggagga catcgtgctg  1860
accctgacgc tcttcgagga ccgcgagatg atcgaggagc gcctcaagac ctacgcccac  1920
ctgttcgacg acaaggtgat gaagcagctc aagcggcgga gatatactgg gtggggccgc  1980
ctctcccgga agctcattaa cggtatcagg gataagcagt ccgggaagac gatcctcgac  2040
ttcctcaagt cggacgggtt cgccaaccgc aacttcatgc agctcatcca cgacgactcc  2100
ctgacgttca aggaggacat ccagaaggcc caagtgtctg gtcaaggtga ctcgctccac  2160
gagcacatcg ccaacctcgc gggcagcccg gccatcaaga agggaatact ccagaccgtc  2220
aaggtggtgg acgagctggt gaaggtcatg ggccgccaca agccggagaa catcgtcatc  2280
gagatggcgc gggagaacca gaccacgcag aaggggcaga aaaatagccg tgagcgcatg  2340
aagcgcatcg aggaggggat taaggagttg ggcagccaga tcctcaagga gcaccctgtg  2400
gagaacacgc agttgcaaaa cgagaagctc tacctgtact acctccagaa cgggagggat  2460
atgtacgtgg accaagaact ggacatcaac cgcctgtccg actacgacgt ggaccacatc  2520
```

```
gtgccgcaga gcttcctcaa ggacgacagc atcgacaaca aggtgctcac ccggtccgac  2580
aagaatcggg gcaagtccga caacgtgccc agcgaggagg tcgtcaaaaa gatgaaaaac  2640
tactggcgac aactactgaa cgccaagctc atcacccagc gcaagttcga caacctcaca  2700
aaagccgagc gcggcgggtt gagcgagctg gacaaggccg ggttcatcaa gcgccagctc  2760
gtcgagacgc gccagatcac gaagcacgtc gcgcagatac tcgacagccg gatgaacacc  2820
aagtacgacg agaacgacaa gctcatccgg gaggtgaagg tcatcaccct caagtcgaag  2880
ctcgtgagcg acttccgcaa ggacttccag ttctacaagg tccgggagat caacaactac  2940
caccacgccc acgatgctta tcttaacgcc gtggtgggga cggccctcat taagaaatac  3000
ccgaagctgg agtcggagtt cgtgtacggc gactacaagg tgtacgacgt caggaagatg  3060
atcgccaagt ccgaacagga gatcgggaag gccacggcga aatacttctt ctacagcaac  3120
atcatgaact tcttcaagac cgagatcacc ctcgccaacg gcgagatccg caagcgcccg  3180
ctcatcgaga cgaacgggga gaccggcgag atcgtctggg acaaggggcg cgacttcgcc  3240
actgtgcgga aggtgctgtc gatgccccag gtcaacatcg tcaagaagac ggaggtccag  3300
acgggcgggt tcagcaagga gagcatcctg ccgaagcgca acagcgacaa gctgatcgcc  3360
cgcaaaaagg actgggatcc aaaaaagtac ggcggcttcg acagccccac cgtcgcctac  3420
agcgtcctcg tcgtcgctaa agtcgagaag ggcaagtcca aaaagctcaa gagcgtcaag  3480
gagctgctcg ggatcaccat catggagcgg tccagcttcg agaagaaccc aattgatttc  3540
ctggaggcga agggctacaa ggaggtcaag aaagacctca tcataaagct gccgaagtac  3600
tcactcttcg agctggagaa cggcgcaag cggatgctgg cgtcggccgg agagctccaa  3660
aagggcaacg agctggcgct gccgagcaag tacgtgaact tcctctacct ggcgtcccac  3720
tacgagaagc tcaagggcag tccagaggat aacgagcaga agcagctatt cgtggagcag  3780
cacaagcact acctggacga gatcatcgag cagatcagcg agttctccaa gcgcgtcatc  3840
ctggcggacg ccaacctgga caaggtgctg tccgcgtaca acaagcaccg cgacaagccg  3900
atccgcgagc aagccgagaa catcatccac ctgttcaccc tcacgaacct cggggcaccc  3960
gccgccttca aatatttcga cacgaccatc gaccgcaagc gctacaccag cacgaaggag  4020
gtgctcgacg ccaccctgat ccaccagagc atcaccgggc tgtacgagac ccgcatcgac  4080
ctctcgcagc tcggcgggga c                                            4101

SEQ ID NO: 62          moltype = DNA  length = 4101
FEATURE                Location/Qualifiers
source                 1..4101
                       mol_type = other DNA
                       organism = synthetic construct
SEQUENCE: 62
gacaagaagt acagtattgg attggccatc gggacgaaca gcgtgggctg ggccgtcatc  60
accgacgagt acaaggtgcc atccaagaag tttaaggttc tggggaatac cgaccgccac  120
tcgatcaaga aaaatctcat cggggcgctg cttttcgaca gcggcgagac ggcggaagcg  180
acgcggctca agcggacggc tcgtcgccgt tacacccggc gtaagaaccg catctgttac  240
ctccaggaga tattcagcaa cgagatggcg aaggtggacg actccttttt ccaccgtctt  300
gaggagtcct tcctggtcga ggaggacaag aagcacgagc gccacccgat cttcgggaac  360
atcgtggacg aggtggccta ccacgagaag taccccacga tctaccacct ccgcaaaaaa  420
ctcgtggact caactgacaa ggccgatttg aggcttatct acctcgccct cgcccacatg  480
attaagttcc gtgggcactt cctaatcgag ggtgacctca accccgacaa ctctgacgtg  540
gacaagctgt tcatccagct tgtgcagacc tacaatcagc tctttgagga gaatccgatc  600
aacgcatctg gtgtggacgc aaaggccatc ctcagcgcgc ggctgagcaa gtctaggcgg  660
ttggagaacc tgatcgccca actgcccggc gagaagaaaa atggcctctt cggcaacctg  720
atcgccctgt cgctggggct cacgccgaac ttcaagagta actttgacct ggcggaggac  780
gctaagctcc agctatctaa ggacacatac gacgacgacc tggacaacct gctggcccag  840
atcggcgacc agtacgccga cctcttccta gccgccaaga acctgtccga cgccatcctc  900
ctcagcgaca tcctgcgcgt gaacacggag atcacgaagg ctccgctcag cgcctccatg  960
attaagcggt acgacgagca ccaccaagac ctaactttac tcaaagccct cgtgcggcag  1020
cagcttcccg agaagtacaa agagatattt tttgatcagt ccaagaacgg ttatgcgggc  1080
tacatcgacg gcggcgcgag ccaggaggag ttctacaagt tcatcaagcc catcctggag  1140
aagatggacg gcacggagga gctgctcgtg aagctcaacc gtgaagacct cctgcgaaag  1200
cagcgaacct tcgacaacgg ttcgatcccg caccagatcc acctcgggga gctgcacgcc  1260
atcctgaggc gacaggagga cttctaccct ttcctaaagg acaaccgcga gaagattgaa  1320
aaaatcctga cgtttcgcat accctactac gtcggcccgc tggcgcgcgg caactcccgg  1380
ttcgcctgga tgacccgtaa gagcgaggag acgatcaccc cgtggaactt cgaggaggtc  1440
gtggacaagg gcgcgagcgc gcagagcttc atcgagcgca tgaccaactt cgacaagaac  1500
ctcccgaacg agaaggtgct cccaaagcac tccctcctgt acgagtattt caccgtgtac  1560
aacgagttga caaaggtgaa gtacgtgacg gagggaatgc ggaagcctgc gttcctctcg  1620
ggcgagcaga agaaggcaat cgtggacctg ctcttcaaga ccaaccggaa ggtgacggtg  1680
aagcagctca aggaggacta cttcaaaaaa atcgagtgct tcgactccgt ggagataagc  1740
ggcgtggagg accgattcaa cgcctccctc ggcacctacc acgacctcct taagatcatc  1800
aaggacaagg acttcctgga caacgaggag aacgaggaca tcctggagga catcgtgctc  1860
accctgaccc tcttcgagga ccgggagatg atcgaggagc gcctcaagac gtacgcccac  1920
ttgttcgacg acaaggtgat gaagcagctc aagcggcggc gatacaccgg gtggggccgc  1980
ctatcccgca aacttatcaa cggcatccgc gacaagcagt ccggcaagac gatcctggat  2040
ttcctcaagt cggacgggtt cgccaaccgg aacttcatgc agctcatcca cgacgacagc  2100
ctcacgttca aggaggacat ccagaaggcc caagtgagcg gtcaagggga cagcctccac  2160
gagcacattg cgaaccttgc tgggagccct gcgatcaaga aggggatatt gcaaaccgtg  2220
aaggtcgtgg acgagttggt gaaggtcatg gggcgacaca agcccgagaa catcgtgatc  2280
gagatggcca gggaaaatca gaccacgcag aagggccaaa aaaacagccg cgagcggatg  2340
aagcggatcg aggagggcat caaggagctg gggtcgcaga tcctcaagga gcacccggtg  2400
gagaacacgc agctccagaa cgagaagctg tacctctatt acctacagaa cgggcgggat  2460
atgtacgtgg accaggagct agacatcaac cgcctgtccg actacgacgt ggaccatatc  2520
gtcccgcagt cgttcttgaa ggacgacagc atcgacaaca aggtgctcac aagatcggat  2580
aagaatcgag gcaagtccga caacgtgccc tcggaggagg tggtcaagaa aatgaaaaac  2640
tactggcggc agttgctgaa cgccaagctc attacgcagc ggaagttcga caacctgacg  2700
```

```
aaggctgaac gtggtgggct cagcgagcta gacaaggcgg ggttcatcaa gcggcagctc  2760
gtcgagaccc ggcagatcac caagcacgtg gcgcagatcc tggactcgcg catgaacacc  2820
aagtacgacg agaacgacaa gctcatccgt gaggtgaagg tcatcaccct taagtctaag  2880
ctggtcagtg acttccgcaa ggacttccag ttctacaagg tccgggagat caacaactac  2940
caccacgcgc acgacgccta cctcaacgcg gtggtgggga cggcgcttat taagaaatat  3000
cccaagctgg aaagcgagtt cgtttacggc gactacaagg tgtacgacgt ccgcaagatg  3060
atcgcaaagt cggaacagga aatcggaaag gcgacggcca aatatttctt ttactccaac  3120
atcatgaatt tttttaagac ggagatcacc ctggcgaacg gggagatccg caagcggccc  3180
ctcatcgaga ccaacgggga gacgggcgag atcgtctggg acaagggccg ggacttcgcc  3240
accgtgcgga aggtgctttc tatgcctcaa gtcaatatcg tcaaaaagac agaggtgcag  3300
accggcgggt tcagcaagga gtctatcctg ccgaagcgca actcggacaa gctcatcgcg  3360
cgcaagaaag actgggaccc caaaaaatat ggcgggttcg actcgccgac cgtcgcctac  3420
agcgtcctcg tggtggctaa ggtcgagaag ggcaagagca aaaagctaaa gtcggtgaag  3480
gagctgctgg gcatcaccat catggagcgc tcgtctttcg agaagaatcc aatcgacttc  3540
ctagaggcga aggggtacaa ggaggtcaaa aaggatctta tcatcaaact gccgaagtac  3600
agtctgttcg agctggagaa cggcggaaag cggatgctgg ctagtgcggg cgagttgcag  3660
aagggcaacg agttggcact gccctccaag tacgtgaact tcctgtacct ggcctcccac  3720
tacgagaagc tcaaggggag ccccgaggac aacgagcaga agcagctatt cgtcgagcag  3780
cacaagcact acctggacga gatcatcgag cagatcagtg agttctccaa gcgggtcatc  3840
ctcgcggacg ccaacctgga caaggtgctg agcgcgtaca acaagcacag ggacaagcca  3900
atcagggaac aggccgagaa catcatccac ctgttcaccc tgaccaacct gggtgcaccg  3960
gctgccttca agtactttga cacgaccatc gaccggaagc gctacacctc cacgaaggag  4020
gtgctggacg ccacgctgat ccaccagagc atcaccgggc tctacgagac acggatcgac  4080
ctgagccagc ttggcgggga c                                            4101
```

```
SEQ ID NO: 63          moltype = DNA  length = 4092
FEATURE                Location/Qualifiers
source                 1..4092
                       mol_type = other DNA
                       organism = synthetic construct
SEQUENCE: 63
gacaaaaagt attccattgg actcgctatc ggcacgaaca gcgtcgggtg ggcggtcatc  60
actgacgagt acaaggtgcc gagcaagaag tttaaggtgc tgggaaacac cgacaggcac  120
tcgatcaaga aaaatcttat cggggcccta ctcttcgact ccggagaaac cgccgaggcc  180
acccggttga agcgcacggc ccgccgtcgc tacaccaggc gcaagaaccg gatctgctac  240
ctccaggaga tattcagcaa tgagatggcg aaggtggacg actcgttttt tcacaggcta  300
gaggagtctt tcctcgtgga ggaggacaag aaacacgagc gccaccccat cttcggcaac  360
atcgtggatg aggtggcata tcacgagaag tacccaacca tctaccacct ccgcaaaaag  420
ctcgtggact ctaccgacaa ggccgacctc cgtctgatct acctcgcgct ggcccacatg  480
attaagttcc gaggacactt tctgatcgag ggcgacctga acccagacaa cagcgacgtg  540
gacaagctgt tcatccaact tgtccagacc tacaatcagc tcttcgagga gaaccctatc  600
aacgcctcgg gcgtggacgc gaaggccatc ctgtccgccc gcctgagcaa gtcgcggcgg  660
ctggagaacc tgatcgccca gctccccggc gaaaaaaaga acggcctctt cggcaacctc  720
atcgcgttgt cgctggggct caccccgaac ttcaagtcca acttcgacct ggccgaggac  780
gctaaactcc agctctcgaa ggatacctac gacgacgacc tcgacaacct gctggcccag  840
atcggcgacc agtacgcgga ccttttcctg gcggccaaga acctgagcga cgcgatcctc  900
cttagcgaca tactccgtgt gaacaccgag atcacgaagg ccccgctctc cgcgtccatg  960
attaagcgct acgacgagca ccaccaagac cttaccctgc ttaaggcgct ggtcaggcag  1020
cagttaccgg agaagtacaa ggagatcttt tttgatcaat ctaagaacgg ttacgccggg  1080
tacatcgacg gcggcgcgtc ccaggaggag ttctacaagt tcatcaagcc gatcttggag  1140
aaaatggacg ggaccgagga gctgctcgtg aagctcaacc gcgaagacct cctccgcaag  1200
cagcgcacct tcgacaacgg gagcatcccg caccagatcc acctgggaga gctgcacgcg  1260
atcctgcgga gacaagagga cttctacccc ttcctcaagg acaaccggga gaagattgaa  1320
aaaatactta cttttcgtat cccgtactac gtcgggcccc ttgcgagggg caactccaga  1380
ttcgcgtgga tgacccgcaa gtccgaggag accatcaccc cgtggaactt cgaggaggtg  1440
gtggacaagg gcgcgtcggc ccagtcgttc atcgagcgca tgaccaactt cgacaagaac  1500
cttccgaacg agaaggtgct cccgaagcac agcctgctct acgaatattt tactgtgtac  1560
aacgagctga cgaaggtcaa gtacgttacg gaggggatga ggaagcccgc cttcctctcc  1620
ggcgagcaga agaaagccat tgtggatctc ctgttcaaga ccaaccgcaa ggtgacggtg  1680
aaacagctca aagaggacta cttcaagaag atcgagtgct tcgactccgt agagatcagc  1740
ggggtcgagg accgcttcaa cgcctcgctg ggcacgtacc acgacctgct aaagattatc  1800
aaggacaaag acttcctaga caatgaggag aacgaggaca ttctggagga catcgtgctg  1860
actctgacgc tgttcgaaga ccgcgagatg atcgaggagc ggcttaagac gtacgcccac  1920
ctgttcgacg acaaggtgat gaagcagttg aaacggcggc gctacaccgg gtggggccgc  1980
ctctcccgca agctcatcaa cggcatccgc gacaagcagt cggggaagac gatcctggac  2040
ttcctcaaga gcgacggctt cgccaaccga aacttcatgc agctaatcca cgacgacagc  2100
ctgacgttca aggaggacat ccagaaggcc caagtgagcg gccagggaga ctcgctacac  2160
gagcatatcg ccaacctggc tggcagcccg gcgattaaga aaggaatcct ccaaaccgtc  2220
aaagtggtgg acgagctggt gaaggtgatg ggccgccaca agcccgagaa cattgtgatc  2280
gagatggcgc gggagaacca gacgacgcag aagggccaaa aaaatagcag ggaaaggatg  2340
aagcgaatag aggaggggat caaggagctg gggagccaga ttctcaaaga gcacccggtc  2400
gagaacacac agctccagaa cgagaagctg tacctctact acctccaaaa cggccgcgat  2460
atgtacgtgg accaggaact agacatcaac cggctgagcg actatgacgt ggaccacatc  2520
gtgccgcagt ccttcctcaa ggacgactcg attgacaaca aagtgctcac tagatccgac  2580
aagaacagag gcaagagcga taacgtcccg tcggaggagg tcgtcaagaa aatgaaaaac  2640
tactggcggc agctcctaaa cgccaagctc atcacgcagc gtaagttcga caacctgacg  2700
aaggcggagc ggggcgggct gagcgagctg gacaaagcgg ggttcatcaa gcggcagctc  2760
gttgagacgc ggcagatcac aaagcacgtc gcgcaaatcc tcgactcccg catgaacacc  2820
aagtacgacg agaacgacaa gctcatccgg gaggtgaagg tcattaccct taaatcgaag  2880
```

```
ctcgtcagcg actttcgtaa ggacttccag ttctacaagg tcagagagat caacaactac  2940
caccacgccc acgacgccta tctgaacgcc gtggtgggca ccgcgcttat taagaagtac  3000
cccaagctgg agtccgagtt cgtgtacggc gactacaagg tttatgacgt caggaagatg  3060
atcgccaagt cggaacagga gatcggaaaa gctaccgcca aatatttctt ctatagcaac  3120
atcatgaact tcttcaaaac cgagatcacc ctcgccaacg gcgagatccg gaagcgcccg  3180
ctcatcgaga ccaacgggga gaccggggag atcgtctggg acaaggggcg ggacttcgct  3240
actgtccgaa aggtgctctc catgccacaa gtgaatatcg tcaagaaaac agaggtgcag  3300
accggagggt tcagtaagga gtccatcctg cccaagcgga actccgacaa gctaattgct  3360
cgcaaaaagg attgggatcc taaaaaatat ggcggcttcg actcgcccac ggtcgcctac  3420
tctgtgctgg tcgtggcgaa ggtggagaag ggcaagtcca agaagctcaa gagcgtcaag  3480
gagctgctgg ggatcacgat catggagcgt agttcgtttg agaagaatcc catcgacttc  3540
ctggaggcta agggctacaa ggaggtcaaa aaggacctca tcattaagct gccgaagtac  3600
agcctcttcg agctggagaa cgggcggaag cgtatgctcg cctccgctgg ggagttacaa  3660
aaggggaacg agctggcgct gccgtctaag tacgtcaact tcctgtacct ggcctcccac  3720
tacgagaagc tcaaggggtc gccggaggac aacgagcaga agcagctctt cgtagagcag  3780
cacaagcact acctggacga gatcatcgag cagatttcag agttctcaaa gcgggtcatc  3840
ctcgccgacg ccaacctgga caaggtgctc tcggcctaca acaagcaccg ggacaagccg  3900
atccgcgaac aggccgaaaa catcatccac ctgttcacgc tcaccaacct cggtgccccg  3960
gcggccttca agtactttga cacgaccatc gaccggaagc gctatacctc gacgaaggag  4020
gtgctggacg ccaccctgat ccaccagtcc atcaccgggc tttacgagac ccggatcgac  4080
ctctcgcagc ta                                                      4092

SEQ ID NO: 64          moltype = DNA  length = 4101
FEATURE                Location/Qualifiers
source                 1..4101
                       mol_type = other DNA
                       organism = synthetic construct
SEQUENCE: 64
gacaagaagt atagtattgg actcgccatc ggaaccaact ctgtggggtg ggctgttatt  60
acagatgaat ataaggtgcc atccaaaaag tttaaagttc tgggcaatac tgatagacac  120
tcaatcaaga agaatctgat aggtgcactt ctgtttgata gtggagagac tgccgaggca  180
accagactta aaaggactgc aagaagaaga tataccagaa gaaagaatag gatttgctat  240
ttgcaggaaa tcttcagcaa cgaaatggcc aaggttgatg actcattttt ccataggttg  300
gaggagagtt ttcttgtgga ggaagataag aagcacgaaa gacacccaat tttcgggaat  360
atagtggacg aggtggctta tcatgagaag tatcccacta tctaccacct gagaaagaaa  420
cttgtggact caaccgataa ggctgatctt aggcttatat acttggccct tgcacatatg  480
atcaaattca ggggccattt tcttatcgaa ggcgatctta atcccgataa ctcagatgtg  540
gacaagctgt ttatacaact tgtgcaaacc tacaatcaac tcttcgagga gaatcccatt  600
aacgcctccg gcgtggatgc aaaagccata ctgtcagcca gactgagcaa aagtaggaga  660
ctggagaatc ttatagccca actgcccggt gaaaagaaga atgggctctt cggaaatctg  720
atcgctcttt cattggggtt gacacccaac tttaagagta actttgactt ggcagaagat  780
gcaaagttgc agctcagtaa agacacatat gacgatgacc ttgacaatct cttggcacaa  840
ataggggatc aatacgctga ccttttcctc gctgccaaga acctcagcga cgctatactg  900
ttgtccgaca ttcttagggt taataccgaa attacaaagg cccctcttag tgcaagtatg  960
atcaaaaggt atgatgagca tcaccaagac cttacactgc tgaaggctct ggttagacag  1020
caactccctg aaaagtataa ggaaatattc ttcgaccaaa gtaagaacgg gtacgccggt  1080
tatattgatg gggcgcaag tcaagaagaa ttttacaaat tcatcaagcc aattcttgaa  1140
aagatggacg ggactgagga attgctggtg aaactgaata gagaggacct tcttagaaaa  1200
cagaggacat ttgacaatgg gtccatccca caccagattc atctggggga actccacgca  1260
atattgagga gacaagaaga cttttaccca ttccttaagg ataatagaga gaaaatcgaa  1320
aaaatcctga ctttcaggat tccttactat gttgggccac tggccagggg gaactcaaga  1380
ttcgcttgga tgacaaggaa gtcagaagaa accataaccc cttggaattt tgaagaggtg  1440
gttgataagg gggcatcagc ccagtctttc atagagagga tgaccaactt tgataaaaat  1500
cttccaaatg agaaggtttt gccaaaacat agtcttttgt acgagtactt tactgtttat  1560
aacgaattga ccaaggtgaa gtatgtgacc gagggaatga ggaagccagc atttttgtcc  1620
ggggagcaaa agaaagcaat cgttgatctt ctcttcaaga ccaacagaaa agtgaccgtg  1680
aaacaactga aggaagacta cttcaaaaag atagaatgtt tcgattcagt ggaaattagc  1740
ggtgttgaag acaggttcaa tgcttcattg ggtacttacc acgacctgtt gaagataatc  1800
aaagacaagg actttctcga taatgaggag aacgaagaca tcttggaaga cattgtgctt  1860
acactcactt tgtttgagga cagggaaatg attgaggaaa gactcaaaac ttacgctcat  1920
ttgtttgatg ataaggttat gaaacaacta aaaagaagaa ggtacaccgg ctggggaaga  1980
ttgagtagga aactgatcaa cggtattaga gataaacaat ccggaaagac tatcctcgat  2040
ttccttaaga gtgatggctt tgcaaatagg aattttatgc agctgattca tgacgactca  2100
cttaccttca aagaagacat ccaaaaagct caggtgtctg ggcaaggcga cagtctgcat  2160
gaacatatag ctaacttggc tgggagtccc gccatcaaga aggggatact tcaaacagtt  2220
aaagttgtgg acgaattggt gaaggtaatg ggaaggcaca agcctgaaaa tatagtgata  2280
gaaatggcaa gggaaaatca aacaacccag aagggacaga agaacagtag ggaaaggatg  2340
aaaaggatag aagaggggat caaagagctt ggtagccaga tcctcaagga acatccagtg  2400
gagaataccc aacttcaaaa cgagaaactc tatttgtact acttgcagaa cggaagagat  2460
atgtatgtgg accaagagct tgatattaac aggctgagcg attatgacgt tgaccacata  2520
gtgccccaat cattcctcaa ggatgactct attgataata aggtgctgac aaggagtgac  2580
aagaatagag ggaaatccga caacgttcca tccgaggaag ttgtgaagaa gatgaagaac  2640
tactggaggc agttgctgaa cgctaagctc attacccaga ggaaattcga taacctgacc  2700
aaagcagaga gaggcgggct gagcgaactc gataaagcag gtttcatcaa gagacaactc  2760
gtggagacta ggcaaattac taagcacgtg gctcaaatac tcgacagcag gatgaacaca  2820
aagtacgacg agaacgacaa gctcattaga gaggttaagg ttattactct gaaaagtaaa  2880
ttggttagcg atttcagaaa ggatttccaa ttctataagg ttagagagat caacaattat  2940
catcatgcac atgatgccta tctgaatgct gtggttggta cagcccttat caagaagtac  3000
cctaagctag agagcgagtt tgtgtacgga gattataagg tgtatgatgt gaggaaaatg  3060
```

```
atcgctaaaa gtgagcaaga gattggaaag gctaccgcca aatacttctt ttattccaat  3120
attatgaatt tcttcaagac agaaatcacc ctggctaacg gcgagataag gaagaggccg  3180
cttatcgaaa ctaatgggga gacaggcgaa atagtgtggg acaaagggag ggatttcgca  3240
actgtgagga aggttttgag catgcctcag gtgaatatcg ttaagaaaac cgaagttcaa  3300
actggagggt tctctaagga aagcattctc cccaagagga actccgacaa gctgattgct  3360
agaaagaaag actgggaccc caagaagtat ggcggattcg actcacccac tgtggcatat  3420
agcgttctcg tggtggcaaa ggttgaaaag ggtaaatcca aaaaactcaa atccgtgaag  3480
gaactccttg gcataactat tatggaaagg agtagctttg aaaagaatcc catcgacttt  3540
ctcgaagcta agggctataa ggaagttaag aaggacctta taatcaaact tccaaaatac  3600
tcccttttg agttggaaaa cggcagaaag agaatgttgg ccagtgccgg ggagcttcaa  3660
aagggcaacg aactggctct gcctagcaaa tatgtgaact ttttgtatct ggcatcacac  3720
tacgagaaac ttaaaggctc tcctgaggac aacgagcaaa aacagctctt tgttgaacag  3780
cataagcact acctcgacga gattattgag cagatcagcg agttctcaaa gagagttatt  3840
ctggctgacg ctaatcttga caaggttttg tccgcttaca acaaacacag ggataagcca  3900
atcagggagc aggcagaaaa cataatccat ctctttaccc tgacaaacct cggtgccccc  3960
gctgctttca agtattttga tactaccatt gacaggaaga gatatacttc cactaaggaa  4020
gtgctcgacg caaccctcat acaccaaagt atcacaggcc tctatgaaac taggatagat  4080
ttgtctcaac ttgggggcga t                                            4101
```

```
SEQ ID NO: 65          moltype = DNA  length = 4101
FEATURE                Location/Qualifiers
source                 1..4101
                       mol_type = other DNA
                       organism = synthetic construct
SEQUENCE: 65
gacaaaaagt attccatcgg gcttgctatc ggaaccaact ctgtggggtg ggcagttatt  60
accgacgaat acaaggtgcc cagcaagaag tttaaggttc tggggaacac agatagacat  120
agcataaaga aaaacctgat aggcgcactg ttgttcgact ccggggaaac agccgaagct  180
accaggctga agagaactgc aagaagaagg tacaccagaa gaaaaaacag aatatgttat  240
ctccaagaga ttttctctaa cgagatggcc aaggtggacg actcattctt tcacagactg  300
gaagaatctt tccttgtgga agaagataag aaacacgaga ggcaccctat ttttggcaat  360
atcgtggatg aggtggctta ccacgaaaaa taccctacaa tataccacct caggaaaaaa  420
ttggttgata gtacagacaa ggccgacctc aggctcatct atttggccct ggcccatatg  480
attaaattca gggggcactt tctcatcgag ggagatttga accccgacaa cagtgatgtt  540
gataagctct ttattcagct cgtgcagact tacaatcagt tgtttgagga aaaccccatt  600
aatgcttccg gggtggacgc caaggcaatc ctttctgcaa gactctcaaa gtcaaggaga  660
ctcgaaaatc tgatagcaca gcttccagga gagaagaaga acgggctctt tggaaacctg  720
atcgctctgt cactcggact cacacccaat ttcaaaagca attttgattt ggcagaggac  780
gctaagctgc aactcagtaa ggatacctac gacgatgact tggataatct gctcgcacaa  840
attggggacc agtatgcaga cctgtttctc gcagctaaga acttgagtga cgccatattg  900
ctcagtgaca tcctcagggt taataccgag attacaaaag ctccactctc tgcaagcatg  960
atcaagaggt atgacgagca ccatcaagac ctgacactcc ttaaggcgtt ggttaggcag  1020
caacttcctg aaaagtataa ggaaatcttc ttcgatcaaa gcaaaaacgg ctacgccggc  1080
tatatagacg gggagcatc ccaagaagaa ttttataagt tcataaaacc tatattggag  1140
aagatggacg ggacagagga attgctcgtg aaactgaaca gggaggatct cctcaggaag  1200
caaaggacct tcgacaatgg ctccatccca catcagattc acctcggcga actgcacgca  1260
atactgagaa gacaagagga cttttatcct ttcctgaagg acaacaggga gaaaatcgag  1320
aaaatcttga cattcagaat cccatactac gttgggcctc tggccagagg taacagtagg  1380
ttcgcctgga tgactaggaa atcagaggag actattacac cctggaactt tgaagaagtt  1440
gttgataagg gagcttcagc acaatcattc atcgaaagaa tgacaaactt tgacaaaaat  1500
ctgcctaatg agaaagtgct cccaaaacat tccctgctgt atgagtattt taccgtttat  1560
aacgagctta ccaaggtgaa atacgttact gaaggtatga gaaagccagc ttttctttca  1620
ggggagcaaa agaaggctat cgtggatctt ctctttaaga ccaacagaaa ggttaccgtg  1680
aagcagctta aggaagacta ctttaaaaag atcgagtgtt ttgactcagt ggaaataagc  1740
ggtgttgaag atagattcaa cgcatccttg ggaacttatc atgatcttct taagataatc  1800
aaggataaag actttctcga caacgaggaa aacgaagata tactggagga catagttctg  1860
acacttactt tgttcgagga tagggagatg atcgaggaaa gactgaaaac atatgctcac  1920
cttttcgacg acaaagttat gaaacaactc aagagaagga gatatacagg gtgggggaga  1980
ttgagcagga aactgattaa tggtatcaga gacaaacagt caggaaaaac aatactcgac  2040
tttttgaaat cagacgggtt cgcaaatagg aatttcatgc agcttataca cgacgattca  2100
cttactttta aagaggacat tcaaaaggct caagttagtg gacaaggtga ctccctccac  2160
gaacacatcg caaatctcgc tggcagccct gcaattaaga agggtatact ccagacagtt  2220
aaggttgttg acgagctggt taaagtgatg ggaagacaca aaccccgagaa catagtgata  2280
gagatggcca gggaaaacca aaccactcaa aaagggcaga aaaattccag agagaggatg  2340
aaaaggattg aagaaggtat caaggagctg ggtagccaaa ttctgaaaga acatcctgtg  2400
gaaaacactc aactccagaa tgagaaactc tatctgtact atctgcaaaa tgggagagat  2460
atgtatgtgg accaggaact ggacataaac aggctctcag attacgatgt ggatcatatc  2520
gtgccacagt cctttcttaa ggatgatagc atcgacaata aggtgcttac caggtccgac  2580
aagaacaggg gaaagtcaga taacgtgcct tctgagaag ttgttaaaaa gatgaagaac  2640
tactggagac agctgcttaa cgctaagctc ataacacaga ggaagtttga caacttgacc  2700
aaggccgaga gaggcggact ctcagaattg gataaggcag ggttcataaa aaggcagctg  2760
gtggaaacaa ggcagataac taaacatgtg gctcagatcc tcgatagtag gatgaataca  2820
aaatacgatg agaacgacaa gctcataagg gaggttaaag tgataactct gaaatccaaa  2880
ctggttagcg attttaggaa ggatttccag ttttacaaag ttagggagat caacaattat  2940
catcacgccc acgatgccta cttgaacgca gttgtgggta ctgcacttat caaaaagtac  3000
cctaagctgg aatccgagtt tgtttatgga gactataagg tgtacgacgt tagaaaaatg  3060
attgcaaagt cagagcagga gatagggaaa gccactgcaa aatatttctt ttatagcaat  3120
atcatgaatt tctttaagac agaaatcaca ctggccaatg ggaaaataag gaagaggccc  3180
ctgatcgaaa ctaatggcga gacaggggag attgtgtggg ataaaggtag ggactttgca  3240
```

```
acagtgagga aagtgctgag catgccccaa gttaatatcg ttaaaaagac cgaggttcaa  3300
acagggggct ttagtaagga aagcattttg cccaagagga atagtgacaa attgattgct  3360
aggaaaaaag attgggaccc caaaaagtat ggcggatttg atagccccac tgttgcttac  3420
tccgtgctcg tggttgcaaa ggtggagaag ggaaagagca agaaactgaa gtcagttaag  3480
gaactccttg gtatcactat catggaaaga agctcctttg agaagaaccc tattgacttc  3540
ctggaggcta aagggtacaa agaggttaag aaagacctta tcattaaatt gcccaaatat  3600
agtcttttcg agcttgaaaa cggaagaaag aggatgcttg catccgctgg cgaattgcaa  3660
aagggcaatg agcttgctct cccttccaag tatgtgaact tcctttatct tgcctcacac  3720
tatgaaaaac tcaaaggttc acccgaagac aacgaacaaa agcaactatt tgtggaacaa  3780
cacaagcact acctggacga aatcattgag caaatttctg agttttcaaa aagggtaatc  3840
ttggctgacg caaatctcga caaagttttg tcagcttaca acaaacatag agataagcca  3900
attagagagc aagctgagaa tatcatccat ctgtttaccc tgactaacct tggagcgcct  3960
gctgctttta aatatttcga caccacaatc gacaggaaga ggtacactag cactaaggaa  4020
gttctcgacg ccaccctcat ccaccagagt attacaggcc tgtacgagac aagaattgat  4080
ctttctcaac ttggtggtga c                                            4101

SEQ ID NO: 66          moltype = DNA  length = 4101
FEATURE                Location/Qualifiers
source                 1..4101
                       mol_type = other DNA
                       organism = synthetic construct
SEQUENCE: 66
gataagaagt actcaatcgg tctggcaatc ggaaccaact ctgtgggttg ggcagtgatt  60
acagatgagt ataaggtgcc aagcaaaaaa ttcaaggtgc tgggtaatac cgacagacac  120
agcattaaga agaatttgat tggagcactc ctctttgact caggggaaac agcagaggca  180
acaaggctga agaggacagc aaggcggagg tacacaaggc ggaaaaacag gatatgctac  240
ctccaggaaa tctttagcaa cgagatggct aaagtggatg atagcttttt ccatagactc  300
gaagaatcct ttcttgttga agaggacaaa aagcatgaaa ggcatcccat cttcggcaat  360
atagttgatg aggttgcata ccatgagaag taccccacaa tctaccacct cagaaagaaa  420
cttgtggact ccacagataa agcagacctg aggctcatat acctcgcact cgcacacatg  480
atcaagttca gagggcactt tctcatcgaa ggtgacctga atccagataa ttcagatgtg  540
gataaactgt ttatacagct ggtgcaaaca tacaaccaac ttttcgagga aaacccaatc  600
aatgcctccg gtgttgatgc aaaggccatc ctgtcagcaa gactcagcaa aagcaggcgg  660
ctcgaaaacc tcatcgccca gcttcccggt gaaaagaaga acgggctctt tggtaatctc  720
atcgcattga gccttggtct tactccaaac ttcaagagca attttgatct ggcagaggat  780
gctaaactgc aactctcaaa ggacacatat gacgatgacc ttgacaatct gttggcccag  840
atcggggacc aatatgcaga cctcttcctg gccgcaaaga atctgtcaga tgcaatcctc  900
ttgtccgaca tactgagagt taacactgag atcacaaagg cacctctgtc cgcctccatg  960
attaagagat acgatgagca tcaccaggat ctgactttgc tcaaagccct cgttagacag  1020
cagttgccag aaaagtacaa agaaatattc tttgatcaat caaaaaacgg atatgcaggg  1080
tacatcgacg gtggggcaag ccaggaagag ttctacaaat tcatcaaacc tatcctggaa  1140
aagatggatg ggacagaaga gctgctggtt aagctgaata gggaagacct cctcagaaag  1200
cagaggacat ttgataacgg gagcatccct catcaaatcc acctcggtga actccatgct  1260
atcctgagaa ggcaggaaga cttttatcca tttttgaagg acaataggga gaaaatcgaa  1320
aaaatcctga cattcagaat cccatactac gttggtcctc tggcaagagg taacagtagg  1380
ttcgcatgga tgacaaggaa aagcgaggag acaatcacac cctggaattt tgaggaagtt  1440
gttgacaagg gtgccagcgc acaatccttt atcgaaagaa tgacaaattt cgacaagaat  1500
ctgcctaacg aaaaggttct cccaaagcat tcactcctgt acgaatattt tacagtttat  1560
aacgaactga ctaaagttaa atacgttacc gagggtatga ggaagccagc attcctttcc  1620
ggggaacaga agaaagctat tgtggacctc ctgttcaaga caaatagaaa agtgacagtt  1680
aagcaactca aagaggatta cttcaaaaag atcgaatgtt ttgactctgt ggagatcagc  1740
ggggtggagg atagattcaa cgccagcctg ggtacatatc atgatctcct gaaaatcatt  1800
aaagacaagg acttccttga caacgaggag aacgaggaca ttctggaaga cattgttctg  1860
accctcacac tctttgagga tagggagatg attgaggaaa gactgaagac ctacgcccac  1920
ctctttgacg ataaagtgat gaaacagctc aagagaagaa ggtatacagg ttgggggaga  1980
ctgagcagga agttgatcaa tggattaggg gacaaacagt ccgggaaaac aatcctcgat  2040
tttctgaagt cagacggttt cgcaaacaga aattttatgc agctcattca cgatgacagc  2100
ttgacattca aggaagacat ccaaaaggct caagtgagcg gccaagggga tagcctccac  2160
gagcatattg caaatctggc aggttcacca gccatcaaaa agggcatact tcagacagtt  2220
aaggttgtgg acgaattggt taaagttatg ggcaggcata agccagagaa tatcgttatc  2280
gaaatggcaa gggagaacca aacaactcaa aaagggcaga aaaatagcag agagaggatg  2340
aaaagaatcg aggaagggat caaggaactt gggtcccaaa tcctcaagga gcacccagtt  2400
gaaaatactc aactgcaaaa cgagaagctc tatctctact atctccaaaa cgggagggat  2460
atgtatgttg accaggagct ggatattaac agactgtcag attatgatgt tgatcatatc  2520
gtgccccagt cattcctgaa ggacgattcc atcgacaaca aagttctcac aaggtccgat  2580
aaaaacaggg gcaagtccga taacgttcca agcgaagaag tggtgaaaaa gatgaaaaac  2640
tattggagac aacttctgaa tgcaaagttg attactcaga gaaagtttga caacctcaca  2700
aaagcagaaa gaggcgggct tagcgaactc gataaggcag ggtttatcaa aagacagctg  2760
gttgagacaa ggcagatcac aaaacatgtg gcacagatcc ttgactcaag gatgaatacc  2820
aagtatgatg agaatgataa gttgatcagg gaggttaaag ttatcacact caaatccaaa  2880
ctggtgtcag acttcaggaa agactttcaa ttttataagg tgagggagat caataactac  2940
caccatgcac atgacgccta cctgaacgca gtggtgggta cagcattgat taaaaaatac  3000
cctaagctgg agtctgagtt tgtgtacggg gactacaagg tgtacgacgt gaggaaaatg  3060
atagccaagt ccgagcagga gatcgggaaa gcaacagcta agtatttctt ttacagtaat  3120
atcatgaatt tctttaaaac tgagattact ctggcaaacg gggagatcag gaaaagaccc  3180
ctcatcgaga ctaatggtga aacaggtgag atcgtttggg acaaggggag ggattttgct  3240
actgttagaa aagttctgag tatgccacaa gtgaatattg tgaaaaagac agaagttcag  3300
acaggtgggt tctccaaaga atccatcctg cccaagagaa attcagacaa gctcatcgca  3360
agaaagaagg actgggaccc taagaagtac ggaggatttg acagccccac cgtggcctat  3420
```

```
tccgtgcttg ttgtggcaaa ggtggagaaa gggaagagca aaaaactgaa atccgtgaaa  3480
gaactgctgg gaattaccat catggaaaga agctcctttg agaagaaccc aatcgacttc  3540
ctggaagcaa aaggatataa ggaagtgaaa aaggacctca ttatcaagct cccaaaatac  3600
tcacttttcg agttggagaa cggtagaaag aggatgctgg caagcgcagg ggaacttcag  3660
aaaggcaatg agctggcatt gccatcaaag tatgtgaact tcctctactt ggccagccat  3720
tacgagaaac ttaaaggtag cccagaagat aacgagcaaa aacagctctt tgtggaacag  3780
cataagcatt atctggatga gatcatagaa caaatctcag agttttccaa gagagttatc  3840
ctcgcagatg caaacctgga taaggttctc tcagcctata ataagcatag agacaagcca  3900
attagagagc aagcagagaa cattatccac ttgttcactc ttacaaacct gggggcacca  3960
gccgccttca aatatttcga tacaacaata gacagaaaga ggtataccag caccaaagaa  4020
gttctcgacg ccacactgat ccatcaatca atcacaggcc tttacgaaac taggatcgac  4080
ttgtcacaac tgggtgggga t                                             4101
```

```
SEQ ID NO: 67          moltype = DNA  length = 3307
FEATURE                Location/Qualifiers
source                 1..3307
                       mol_type = other DNA
                       organism = synthetic construct
SEQUENCE: 67
gagcaaggac acctacgacg acgacttgga caacctattg gcccagatag gtgaccagta  60
tgcagacctc ttccttgcgg ccaagaactt gagtgacgct atactgctca gtgacatcct  120
gagggtgaac actgagatca ctaaggcccc tctctctgcc tcaatgatta agcgttacga  180
cgagcatcac caggatctca ccctgcttaa ggcccttgtt cggcagcagc tccctgagaa  240
gtacaaggag atatttttg accagtctaa gaacggctac gccggttaca ttgacggtgg  300
ggcaagccag gaggagttct acaagttcat caagccgatc cttgagaaga tggacggcac  360
cgaggagcta cttgtcaagt tgaaccggga agacctgctc cggaaacagc gtacattcga  420
caacggcagc atccctcacc agatccacct gggcgaacta cacgccatcc tccgacgtca  480
ggaggacttc tatccattct tgaaagataa cagggaaaaa atcgaaaaaa tacttacgtt  540
tcgaatacct tactacgtgg ggccccttgc tcggggaaac tccagattcg catggatgac  600
caggaagtca gaggagacca tcacaccctg gaactttgag gaggtggttg acaaaggtgc  660
ttctgcccag tccttcattg agcggatgac taacttcgac aagaacctgc ccaacgagaa  720
ggtgctgcca aagcacagcc tgctctacga atactttact gtgtacaatg agctgacgaa  780
ggtgaagtac gtgacagagg ggatgcggaa gcccgctttc ctgagcggcg agcaaaaaaa  840
agcaatcgtg gacctactgt tcaagaccaa ccgaaaggtg acagtgaagc agctcaagga  900
ggactacttc aaaaaaatcg agtgcttcga ctctgttgag ataagcggcg tggaggaccg  960
attcaacgcc tcattgggaa cctatcacga cctgctcaag atcattaagg acaaggactt  1020
cctggataat gaggagaatg aggacatcct ggaggatatt gtgctgaccc ttactctatt  1080
cgaggacagg gagatgatcg aggagcgact caagacctac gctcacctgt tcgacgacaa  1140
ggttatgaag caattgaagc gtaggcgata cacggggtgg ggaagactct cccgaaaact  1200
gataaacggc atcagggaca agcagtcagg gaagacgatc ttggacttcc tgaaatccga  1260
cgggttcgcc aaccgcaact tcatgcagct cattcacgac gactcactaa cgttcaaaga  1320
ggacattcag aaggctcaag tcagtggaca aggcgactcc ctgcacgagc acattgcaaa  1380
ccttgcgggc tccccggcga ttaaaaaggg cattctccaa acggttaagg tggtggacga  1440
gctggtgaag gtgatgggcc gacacaagcc tgagaacatc gtgatcgaga tggccaggga  1500
gaaccagact acccagaagg gtcagaagaa ctctcgggaa cgtatgaagc gtattgagga  1560
ggggattaag gagttgggct ctcaaatcct caaggagcac cctgtggaga acactcagct  1620
ccaaaacgag aagctgtacc tgtactacct gcaaaacggg cgcgatatgt acgtggatca  1680
ggagttggac atcaacaggc ttagcgatta cgacgtggac cacatcgtgc cacagtcatt  1740
cttaaaggac gacagcatcg acaacaaggt tctgacgagg agcgacaaga atcgagggaa  1800
aagtgacaat gttccatccg aggaggtggt caagaaaatg aagaactatt ggcgtcagct  1860
tctgaacgcc aagctcatca cccagcggaa attcgacaac ctgactaagg ctgagcgagg  1920
cggactctcc gagcttgaca aggctggctt catcaagcgg cagttggtcg aaacccgaca  1980
gataacgaag cacgttgccc agatacttga ctcccgtatg aacaccaagt acgacgagaa  2040
cgacaagctc atcagggagg tgaaggtcat taccttaag tccaaactcg tcagcgactt  2100
tcgtaaggac ttccagttct acaaggtgcg cgagatcaat aactaccacc acgcacacga  2160
cgcctacctg aacgcagtgg ttggaaccgc gttgattaaa aagtacccca agttggagtc  2220
ggagttcgtt tacggggact acaaggtgta cgacgttcgg aagatgatcg ccaagtctga  2280
acaggagatc gggaaagcaa ccgccaagta tttcttctat agcaacatca tgaacttctt  2340
taaaaccgag atcacacttg ccaatggcga gatccgtaag aggccgctga tcgagacaaa  2400
tggggagact ggcgagatcg tgtgggacaa gggccgcgac ttcgcaaccg ttcggaaagt  2460
cttgtccatg cctcaagtca acatcgtcaa gaagactgag gtgcaaacag gcgggttctc  2520
gaaggagtcc atactgccca agaggaactc agacaagctc atagcacgca aaaaagactg  2580
ggatccaaag aaatacggcg ggttcgactc gccgacagtc gcatactccg tgttagtggt  2640
ggctaaagtg gaaaagggga agtccaagaa gctcaagtcc gtcaaggagt tgctcgggat  2700
caccattatg gaacggtcct cattcgagaa gaatcccatt gacttcctag aggcgaaggg  2760
ctacaaagag gtcaaaaagg acctaattat taagctcccc aagtattcac tcttcgaact  2820
tgaaaatggt cgtaagcgga tgttggcaag cgctggagag cttcagaagg ggaacgagct  2880
tgcactgcct tccaagtacg tgaacttcct gtacctcgcc tctcattacg agaagttgaa  2940
gggctcaccg gaggacaacg agcagaagca gttgttcgtg gagcagcaca agcactacct  3000
cgacgagatc attgagcaga taagtgagtt cagcaaacgg gtgatccttg ccgacgctaa  3060
cctggacaag gtgctgagcg cctacaacaa gcacagagac aagccgatcc gagagcaagc  3120
ggagaacatc atacacctgt tcaccctcac gaacctcggg gctcccgcag ccttcaaata  3180
ttttgacacg accatcgacc gtaaacgcta cactagcacg aaggaggtgc tggacgctac  3240
ccttatccac cagtccatca ccggcctgta cgagacgaga atcgacttgt cgcagctcgg  3300
tggtgac                                                             3307
```

```
SEQ ID NO: 68          moltype = DNA  length = 4101
FEATURE                Location/Qualifiers
source                 1..4101
```

```
                        mol_type = other DNA
                        organism = synthetic construct
SEQUENCE: 68
gacaaaaaat actcaattgg tctggcaatt gggaccaaca gtgtcggatg ggccgtgatt  60
accgacgagt acaaggtgcc gtccaaaaaa ttcaaggtgc ttgggaacac cgaccgccac  120
tcgatcaaga aaaacctaat cggtgcgttg cttttcgaca gtggggagac cgccgaggca  180
acacgcttaa aacgcacagc taggaggaga tatacacggc gcaagaaccg aatatgctac  240
ttacaggaga tattctccaa tgagatggcg aaggtggacg actctttctt ccatcggctt  300
gaggaatcct tcctggtcga ggaggacaag aagcacgagc gacacccgat attcgggaac  360
atcgttgatg aggtggcgta ccacgagaag tacccaacga tataccactt acgcaagaag  420
ctcgtggact ctacggacaa ggccgacttg cgccttatct acttggcact ggcccacatg  480
attaagttcc gaggccactt ccttatcgag ggtgacctga accccgataa ctccgacgtg  540
gacaagctct tcatccaact cgtccagaca tacaaccagc tattcgagga gaatcctatc  600
aacgcctctg ggtggacgc taaagctatc ctctcagccc gcctgtcaaa gtcgaggagg  660
ttggagaacc taatcgccca gcttccaggc gagaagaaaa atgggctgtt cggaaacctt  720
atcgcactct cactgggcct aaccccgaac ttcaagtcca acttcgacct ggcagaggac  780
gcgaaattgc agttgtcgaa agacacctat gacgatgacc tggacaacct gttggcccag  840
ataggggacc agtacgccga cctgttccta gcggccaaga acctgtccga cgccatcttg  900
ctgtcggata tactgcgggt gaacaccgag atcactaaag cacctctctc cgccagcatg  960
attaagcgtt acgacgagca ccaccaagat ttgaccctgc taaaggcact tgtacggcag  1020
cagcttcccg agaagtacaa ggagatcttt ttcgaccaaa gcaagaacgg ctacgccggg  1080
tacatcgacg gaggtgccag ccaggaggag ttctacaagt tcattaagcc catcctggag  1140
aagatggacg ggactgagga actacttgtg aagctgaacc gggaagactt actacggaag  1200
cagcgtacct tcgacaacgg ttctatccca catcagatcc atcttgggga gttgcacgcg  1260
atcctgcgac gccaggagga cttttacccc ttcctgaaag acaaccgcga gaaaatcgag  1320
aagatactga ccttcagaat accttactac gtcggacccc ttgcgcgagg caactcaaga  1380
ttcgcgtgga tgaccaggaa atcagaggag accatcacac cctggaattt cgaggaggtg  1440
gttgacaagg gtgcctccgc ccagtccttt atcgaacgaa tgaccaactt cgacaagaac  1500
ttgcccaacg agaaggtgct ccccaaacac agcctcctct acgaatattt cacagtgtac  1560
aacgagctta ctaaagttaa gtatgttact gagggcatga ggaaacccgc cttcctgtca  1620
ggcgagcaga agaaagctat tgtggacctc cttttcaaga ccaaccggaa ggtgacagtg  1680
aagcagctca aggaggacta cttcaagaag atagagtgct tcgacagcgt ggagatcagc  1740
ggggtggagg acagattcaa tgcctctctc ggaacatacc acgacttgct taagatcatc  1800
aaggacaagg acttcctcga caacgaggaa aacgaggata ttctggagga tattgttctg  1860
actcttaccc tgttcgagga ccgggagatg atcgaggagc gtctcaagac ctacgcccac  1920
ctgttcgacg acaaagttat gaagcagctc aagcgtcgga gatataccgg atggggccgt  1980
ctgtctcgga agctcatcaa cgggatcagg gacaagcagt cagggaagac gatcttagac  2040
ttccttaagt ctgacggctt cgccaacagg aacttcatgc agttgatcca cgacgacagc  2100
cttaccttca aggaggacat ccagaaggcc caagtgagtg gccagggtga cagcctccac  2160
gagcatattg ctaatcttgc gggttcccca gcgattaaaa agggcatact tcaaaccgtt  2220
aaggtggtgg acgagcttgt caaggtgatg gggcgacaca agcccgagaa catcgtgatc  2280
gagatggcca gggagaacca gaccacccag aagggggcaga agaatagccg agaacgcatg  2340
aagcgcatcg aggaggggat taaggagcta gggagccaga tcctcaagga acatcccgtc  2400
gagaacaccc agctccagaa cgagaagcta tacctctact acttgcaaaa cgggagggat  2460
atgtacgtgg atcaggagtt ggacattaac cgcctaagcg actacgacgt agatcacatc  2520
gtgcctcagt cattcctcaa agacgacagc attgacaaca aagtcttgac ccgatccgac  2580
aagaaccgag gaaaatccga caatgtgccc tcagaggagg tcgtcaagaa aatgaagaac  2640
tattggaggc agctacttaa cgccaaactc ataacccagc ggaagttcga caacctgaca  2700
aaggctgagc ggggtgggct cagcgagctt gacaaggctg gcttcatcaa gcggcagttg  2760
gtggagacaa gacagataac gaagcacgtg gctcagatcc tggactctcg catgaacacg  2820
aagtacgacg agaacgacaa attgatccgc gaggtcaagg ttattacgct caagagcaaa  2880
cttgtcagcg atttccgcaa ggacttccag ttctacaagg tgagggagat taacaactac  2940
caccatgcac atgatgccta cttgaacgca gtggtgggga ccgcgcttat taaaaagtac  3000
cctaagttgg agtcagagtt cgtttatggg gactacaagg tgtacgacgt ccggaagatg  3060
attgcaaagt ctgaacagga aatcgggaag gccaccgcca aatatttctt ctacagtaac  3120
attatgaatt tttttaagac tgaaattact ctcgcaaacg gcgagatcag gaagcgtccc  3180
ctcatcgaga caaacgggga gaccggggag atagtctggg acaaggggcg ggacttcgct  3240
acggtgagga aggtgctctc gatgccacaa gtgaacatcg tcaaaaagac agaggtgcag  3300
accggtggct tctcaaagga gtcaatcctg ccaaaacgta acagcgacaa gctcatcgcc  3360
cgcaagaaag actgggaccc taagaagtat ggtgggttcg actcaccgac ggtcgcatac  3420
tccgttctgg tcgtggcaaa ggtggaaaag ggcaagtcca aaaaactgaa atccgtgaag  3480
gagttgcttg gcattaccat catggaacgc agcagcttcg agaagaaccc cattgacttc  3540
ctggaggcta aagggtacaa ggaggtcaag aaagatttaa ttattaagct acctaagtac  3600
agcttgttcg agctggagaa cggccgaaaa cgaatgctcg catccgccgg ggaacttcaa  3660
aagggcaacg agcttgcgct gccctccaag tacgtgaact tcctgtactt ggcatcccac  3720
tacgagaaac tcaagggtag cccagaggac aacgagcaga agcagctatt cgtggagcag  3780
cacaagcact acctcgacga gataatcgag cagatcagtg agttcagtaa gcgggtgata  3840
ctcgcggacg ccaacttgga caaggtgctt agtgcctaca acaagcaccg tgacaagccc  3900
atccgagaac aggctgagaa catcatccac cttttcactc tgacaaacct cggtgctccc  3960
gccgccttca aatacttcga cactaccatc gacaggaagc gctacacatc tacgaaggaa  4020
gttcttgacg ctacgcttat tcatcagtct atcacagggc tgtacgagac aaggatcgac  4080
cttagccaac tcggcgggga t                                            4101

SEQ ID NO: 69           moltype = DNA  length = 4401
FEATURE                 Location/Qualifiers
source                  1..4401
                        mol_type = genomic DNA
                        organism = Glycine max
SEQUENCE: 69
```

-continued

```
gacttttgac tctctctctc tctctctcta cagtagtagt agtagtattc attcatattc  60
atacttgata tcatgtcaca cacacactat ctctctctct ctctctctaa tggcagagct  120
agctcagacc cttaacacag accacagcct ctgagagaaa ccactctcac tctcactctc  180
cttaaccttt caccttccat atctggcgaa aatgaaagct ctgtacagaa gctctctctt  240
gctcctcttc ttcctctccg tctgttctgc atcttcttct tcggttccca ctctgcaact  300
cctaagcttc aaaaactctc tcccgaaccc aaccctgctc ccgaactggc tcccgaacca  360
aagcccatgc tcattcaccg gcatcacctg caacgacacc cagcacctca cttccataga  420
cctctccggc gtccctctca ccacaaacct caccgtcatc gccaccttcc tcctcaccct  480
cgacaacctc cagtcactct ccttaaaatc caccaacctc tccggccccg ccgccatgcc  540
tcctcctctc tcccactcca agtgcgcctc cacattaacc tccctagatc tatcacaaaa  600
cgccctctcc ggttccctca acgacatgtc gtttctctcc tcctgctcca acctccaatc  660
cctcaatctc tccagcaacc ttcttgaatt cgactcctct cactggaagc tccacctcct  720
cgtcgccgac ttttcctaca acaagatttc cggccccggt atcctcccct ggcttctcaa  780
ccctgaaatc gaacacctcg ctctgaaagg caacaaagtc accggcgaaa ccgacttctc  840
cggttccaat tctctccagt ttttagacct ttcttccaac aacttttctg ttacgcttcc  900
tactttcggc gagtgttctt cgcttgagta tttggacctc tccgccaaca agtacttcgg  960
cgacattgct cgcactctct cgccttgcaa gaacctcgtt tacttaaact tctccagcaa  1020
ccagttctcc ggtccggttc cttcccttcc ctccggttcg ctacagttcg tgtaccttgc  1080
ttcaaaccac ttccacggcc agattcctct ccccctcgcc gacctctgct ccactctcct  1140
ccagctcgat ctctcctcca acaacctctc aggcgctctc ccgaagcctt cggcgcttgc  1200
acttctcttc agtccttcga catctccagc aacctcttcg ccggtgcgct gcctatggac  1260
gttctcacgc aaatgaaaag cctcaaagag ctcgcggtgg cgttcaacgc gttccttggt  1320
cccctccgg agtctctgac gaagctctcc actttagagt cgctggatct tagctccaac  1380
aacttcagcg gctcaatccc gacaacgctg tgcggtggtg acgctgggaa taataatatt  1440
ctgaaggaac tttacctgca gaacaaccgg ttcacgggtt ttattccacc cacgctcagc  1500
aactgttcaa acctcgttgc tttggacttg agtttcaact tcctcacggg aactattcct  1560
ccaagcctag ggtctctttc caagcttaaa gacttgatca tctggctcaa ccagctccat  1620
ggagaaatac cgcaggagct catgtatctg aaaagcctcg agaatttgat cctggatttc  1680
aacgacttga ctgggaacat tccctctggg cttgttaact gcaccaagct gaactggatc  1740
tccctctcca acaacaggct cagcggcgag attccgcggt ggattgggaa gctttctaat  1800
ctcgccatac ttaagctcag taataactct ttctccggcc ggattccgcc ggagctcggc  1860
gattgtacta gtttaatatg gttggatctg aatactaata tgctcaccgg gcccattccg  1920
ccggagctgt tcaagcagtc ggggaagatc gcggtgaatt tcatcagtgg gaagacgtat  1980
gtgtatataa agaacgatgg gagcaaagag tgtcatggtg cggggaactt gctggagttt  2040
gccgggatca gtcagcagca gttgaacagg atttcgacga ggaacccgtg caatttcact  2100
agggtttatg gaggtaagtt gcagccaacg tttaaccata atggttctat gatatttttg  2160
gatatctcgc acaacatgtt gtcagggagt attcccaagg agattggggc catgtactat  2220
ttgtacattc tcaatttggg tcataataat gtgtctggga gcattcctca agagcttggg  2280
aagatgaaga atctcaacat ccttgatctc tcaagtaata gactggaggg gcaaattcct  2340
cagagtctca cggggctttc cttgctcact gagattgacc tgtcgaataa cttgcttacg  2400
gggacgattc ctgagtcggg tcaatttgat actttccctg cggcgagatt tcagaacaac  2460
tctggtctct gtggagttcc tctcggccca tgtggttcgg acccggcgaa taacgggaat  2520
gcgcaacata tgaagtctca caggaggcag gcttctctgg tggggagtgt ggccatgggt  2580
ttgttgtttt ccctcttctg cgtctttggt ttgatcatta ttgccattga gaccaggaag  2640
aggaggaaga agaaggaggc tgctcttgaa gcctatgctg atggtaattt gcattcgggt  2700
cctgccaacg tgagctggaa gcacaccagt acccgggaag cgcttagcat aaaccttgca  2760
acgtttaaga ggccgctcag gaggcttact tttgcggacc ttcttgacgc taccaatggc  2820
tttcacaatg atagtctcat tggctctggt gggtttgggg atgtttacaa ggctcagttg  2880
aaggatggaa gtgttgtggc tatcaagaag ctgattcatg tcagcggcca aggggacagg  2940
gaattcactg ctgaaatgga gaccattggg aagatcaagc acaggaacct tgttcctctg  3000
ttgggatact gcaaggttgg ggaagagagg ctcttggttt atgagtacat gaaatatgga  3060
agcttagagg atgttcttca tgatccgaag aaagctggga tcaagttgaa ttggtcgatt  3120
aggaggaaaa ttgctattgg agctgctagg ggattgtctt ttcttcacca caattgtagc  3180
ccccacatca ttcatagaga catgaagtca agcaatgtgt tacttgatga aaacctggaa  3240
gctagagtct ctgattttgg aatggctagg catatgagtg ctatggatac acatttgagt  3300
gtgagcacac tggcaggcac accagggtat gttcctccgg agtactatga gagcttcaga  3360
tgctctacca aaggtgatgt ctacagttat ggtgtggttt tgttggagct gctaactggg  3420
aaaaggccaa cagattcggc tgattttggt gataataatc ttgttggatg ggttaaacaa  3480
catgccaagc tgaaaataag tgatattttt gacccagagc tcatgaagga agaccccaat  3540
ttggagatgg agcttttgca gcacctgaag attgcagttt cctgtttgga tgatcggcat  3600
tggagacgtc caacgatgat tcaagtgttg acaatgttca aggagattca ggcaggatct  3660
gggattgatt ctcagtcaac catagccaat gaagatgaca gtttcaatgc agttgaaatg  3720
gtggagatga gcattaaaga aacccctgaa ttgagcaagc attaggcaac aaattccgga  3780
agtgtcatgt ggattctttg ggaaacagac aagaagagag aaaaggagga gatgacggat  3840
tcagctcccc tcaaagtttt ttccttcctc tttgccgctt caaattattt cagacacaag  3900
ggggaaacgg ttaaaggggg aatgaatgcc tttgatgtat gtagtcttgt tattttatac  3960
aaaaaaaaaa agttgtttaa cttgtatata aacagcttca gttgttacca tctgtgtttt  4020
cctagaattt tcaaaagtac ttttctcatt cagatataat cctgaaaagg atctctgttc  4080
aatctggcga ccccagtgat ggcgactaag tggaggatct tttggccatt tctttaggcc  4140
tcttgatttg tttcccccat ttgatcaact gcaacttttg ctccgatttg cgatataatt  4200
tgtcaaaaca tgcttcttct aaaatcactc ataacataaa ttttcttgaa ttacaatttt  4260
ataccctccc ctccccaact tgttctgcgc cttctgaccc ttcttgtttt gtttgctagt  4320
ttaccctgta ggaaaaagta tcactctact caaatagtat tttcacctct tctggccata  4380
aataattttg gcctaattca g                                            4401
```

```
SEQ ID NO: 70          moltype = DNA  length = 2511
FEATURE                Location/Qualifiers
source                 1..2511
                       mol_type = other DNA
```

```
                         organism = Glycine max
SEQUENCE: 70
atggacgttc tcacgcaaat gaaaagcctc aaagagctcg cggtggcgtt caacgcgttc  60
cttggtcccc ttccggagtc tctgacgaag ctctccactt tagagtcgct ggatcttagc  120
tccaacaact tcagcggctc aatcccgaca acgctgtgcg gtggtgacgc tgggaataat  180
aatattctga aggaacttta cctgcagaac aaccggttca cgggttttat tccacccacg  240
ctcagcaact gttcaaacct cgttgctttg gacttgagtt tcaacttcct cacgggaact  300
attcctccaa gcctagggtc tctttccaag cttaaagact tgatcatctg gctcaaccag  360
ctccatggag aaataccgca ggagctcatg tatctgaaaa gcctcgagaa tttgatcctg  420
gatttcaacg acttgactgg gaacattccc tctgggcttg ttaactgcac caagctgaac  480
tggatctccc tctccaacaa caggctcagc ggcgagattc cgcggtggat tgggaagctt  540
tctaatctcg ccatacttaa gctcagtaat aactctttct ccggccggat tccgccggag  600
ctcggcgatt gtactagttt aatatggttg gatctgaata ctaatatgct caccgggccc  660
attccgccgg agctgttcaa gcagtcgggg aagatcgcgg tgaatttcat cagtgggaag  720
acgtatgtgt atataaagaa cgatgggagc aaagagtgtc atggtgcggg gaacttgctg  780
gagtttgccg ggatcagtca gcagcagttg aacaggattt cgacgaggaa cccgtgcaat  840
ttcactaggg tttatggagg taagttgcag ccaacgttta accataatgg ttctatgata  900
tttttggata tctcgcacaa catgttgtca gggagtattc ccaaggagat tggggccatg  960
tactatttgt acattctcaa tttgggtcat aataatgtgt ctgggagcat tcctcaagag  1020
cttgggaaga tgaagaatct caacatcctt gatctctcaa gtaatagact ggaggggcaa  1080
attcctcaga gtctcacggg gctttccttg ctcactgaga ttgacctgtc gaataacttg  1140
cttacgggga cgattcctga gtcgggtcaa tttgatactt tccctgcggc gagatttcag  1200
aacaactctg gtctctgtgg agttcctctc ggcccatgtg gttcggaccc ggcgaataac  1260
gggaatgcgc aacatatgaa gtctcacagg aggcaggctt ctctggtggg gagtgtggcc  1320
atgggtttgt tgttttccct cttctgcgtc tttggtttga tcattattgc cattgagacc  1380
aggaagagga ggaagaagaa ggaggctgct cttgaagcct atgctgatgg taatttgcat  1440
tcgggtcctg ccaacgtgag ctggaagcac accagtaccc gggaagcgct tagcataaac  1500
cttgcaacgt ttaagaggcc gctcaggagg cttacttttg cggaccttct tgacgctacc  1560
aatggctttc acaatgatag tctcattggc tctggtgggt ttggggatgt ttacaaggct  1620
cagttgaagg atggaagtgt tgtggctatc aagaagctga ttcatgtcag cggccaaggg  1680
gacagggaat tcactgctga aatggagacc attgggaaga tcaagcacag gaaccttgtt  1740
cctctgttgg gatactgcaa ggttggggaa gagaggctct tggtttatga gtacatgaaa  1800
tatggaagct tagaggatgt tcttcatgat ccgaagaaag ctgggatcaa gttgaattgg  1860
tcgattagga ggaaaattgc tattggagct gctaggggat tgtcttttct tcaccacaat  1920
tgtagccccc acatcattca tagagacatg aagtcaagca atgtgttact tgatgaaaac  1980
ctggaagcta gagtctctga ttttggaatg gctaggcata tgagtgctat ggatacacat  2040
ttgagtgtga gcacactggc aggcacacca gggtatgttc ctccggagta ctatgagagc  2100
ttcagatgct ctaccaaagg tgatgtctac agttatggtg tggttttgtt ggagctgcta  2160
actgggaaaa ggccaacaga ttcggctgat tttggtgata ataatcttgt tggatgggtt  2220
aaacaacatg ccaagctgaa aataagtgat atttttgacc cagagctcat gaaggaagac  2280
cccaatttgg agatggagct tttgcagcac ctgaagattg cagtttcctg tttggatgat  2340
cggcattgga gacgtccaac gatgattcaa gtgttgacaa tgttcaagga gattcaggca  2400
ggatctggga ttgattctca gtcaaccata gccaatgaag atgacagttt caatgcagtt  2460
gaaatggtgg agatgagcat taaagaaacc cctgaattga gcaagcatta g           2511

SEQ ID NO: 71            moltype = AA  length = 1184
FEATURE                  Location/Qualifiers
source                   1..1184
                         mol_type = protein
                         organism = Glycine max
SEQUENCE: 71
MKALYRSSLL LLFFLSVCSA SSSSVPTLQL LSFKNSLPNP TLLPNWLPNQ SPCSFTGITC  60
NDTQHLTSID LSGVPLTTNL TVIATFLLTL DNLQSLSLKS TNLSGPAAMP PPLSHSKCAS  120
TLTSLDLSQN ALSGSLNDMS FLSSCSNLQS LNLSSNLLEF DSSHWKLHLL VADFSYNKIS  180
GPGILPWLLN PEIEHLALKG NKVTGETDFS GSNSLQFLDL SSNNFSVTLP TFGECSSLEY  240
LDLSANKYFG DIARTLSPCK NLVYLNFSSN QFSGPVPSLP SGSLQFVYLA SNHFHGQIPL  300
PLADLCSTLL QLDLSSNNLS GALPEAFGAC TSLQSFDISS NLFAGALPMD VLTQMKSLKE  360
LAVAFNAFLG PLPESLTKLS TLESLDLSSN NFSGSIPTTL CGGDAGNNNI LKELYLQNNR  420
FTGFIPPTLS NCSNLVALDL SFNFLTGTIP PSLGSLSKLK DLIIWLNQLH GEIPQELMYL  480
KSLENLILDF NDLTGNIPSG LVNCTKLNWI SLSNNRLSGE IPRWIGKLSN LAILKLSNNS  540
FSGRIPPELG DCTSLIWLDL NTNMLTGPIP PELFKQSGKI AVNFISGKTY VYIKNDGSKE  600
CHGAGNLLEF AGISQQQLNR ISTRNPCNFT RVYGGKLQPT FNHNGSMIFL DISHNMLSGS  660
IPKEIGAMYY LYILNLGHNN VSGSIPQELG KMKNLNILDL SSNRLEGQIP QSLTGLSLLT  720
EIDLSNNLLT GTIPESGQFD TFPAARFQNN SGLCGVPLGP CGSDPANNGN AQHMKSHRRQ  780
ASLVGSVAMG LLFSLFCVFG LIIIAIETRK RRKKKEAALE AYADGNLHSG PANVSWKHTS  840
TREALSINLA TFKRPLRRLT FADLLDATNG FHNDSLIGSG GFGDVYKAQL KDGSVVAIKK  900
LIHVSGQGDR EFTAEMETIG KIKHRNLVPL LGYCKVGEER LLVYEYMKYG SLEDVLHDPK  960
KAGIKLNWSI RRKIAIGAAR GLSFLHHNCS PHIIHRDMKS SNVLLDENLE ARVSDFGMAR  1020
HMSAMDTHLS VSTLAGTPGY VPPEYYESFR CSTKGDVYSY GVVLLELLTG KRPTDSADFG  1080
DNNLVGWVKQ HAKLKISDIF DPELMKEDPN LEMELLQHLK IAVSCLDDRH WRRPTMIQVL  1140
TMFKEIQAGS GIDSQSTIAN EDDSFNAVEM VEMSIKETPE LSKH                   1184

SEQ ID NO: 72            moltype = AA  length = 1184
FEATURE                  Location/Qualifiers
source                   1..1184
                         mol_type = protein
                         organism = Glycine max
SEQUENCE: 72
MKALYRSSLL LLFFLSVCSA SSSSVPTLQL LSFKNSLPNP TLLPNWLPNQ SPCSFTGITC  60
```

```
NDTQHLTSID LSGVPLTTNL TVIATFLLTL DNLQSLSLKS TNLSGPAAMP PPLSHSKCAS  120
TLTSLDLSQN ALSGSLNDMS FLSSCSNLQS LNLSSNLLEF DSSHWKLHLL VADFSYNKIS  180
GPGILPWLLN PEIEHLALKG NKVTGETDFS GSNSLQFLDL SSNNFSVTLP TFGECSSLEY  240
LDLSANKYFG DIARTLSPCK SLVYLNFSSN QFSGPVPSLP SGSLQFVYLA SNHFHGQIPL  300
PLANLCSTLL QLDLSSNNLS GALPEAFGAC TSLQSFDISS NLFAGALPMD VLTQMKSLKE  360
LAVAFNAFLG PLPESLTKLS TLESLDLSSN NFSGSIPTTL CGGDAGNNNI LKELYLQNNR  420
FTGFIPPTLS NCSNLVALDL SFNFLTGTIP PSLGSLSKLK DLIIWLNQLH GEIPQELMYL  480
KSLENLILDF NDLTGNIPSG LVNCTKLNWI SLSNNRLSGE IPRWIGKLSN LAILKLSNNS  540
FSGRIPPELG DCTSLIWLDL NTNMLTGPIP PELFKQSGKI AVNFISGKTY VYIKNDGSKE  600
CHGAGNLLEF AGISQQQLNR ISTRNPCNFT RVYGGKLQPT FNHNGSMIFL DISHNMLSGS  660
IPKEIGAMYY LYILNLGHNN VSGSIPQELG KMKNLNILDL SSNRLEGQIP QSLTGLSLLT  720
EIDLSNNLLT GTIPESGQFD TFPAARFQNN SGLCGVPLGP CGSDPANNGN AQHMKSHRRQ  780
ASLVGSVAMG LLFSLFCVFG LIIIAIETRK RRKKKEAALE AYADGNLHSG PANVSWKHTS  840
TREALSINLA TFKRPLRRLT FADLLDATNG FHNDSLIGSG GFGDVYKAQL KDGSVVAIKK  900
LIHVSGQGDR EFTAEMETIG KIKHRNLVPL LGYCKVGEER LLVYEYMKYG SLEDVLHDPK  960
KAGIKLNWSI RRKIAIGAAR GLSFLHHNCS PHIIHRDMKS SNVLLDENLE ARVSDFGMAR  1020
HMSAMDTHLS VSTLAGTPGY VPPEYYESFR CSTKGDVYSY GVVLLELLTG KRPTDSADFG  1080
DNNLVGWVKQ HAKLKISDIF DPELMKEDPN LEMELLQHLK IAVSCLDDRH WRRPTMIQVL  1140
TMFKEIQAGS GIDSQSTIAN EDDSFNAVEM VEMSIKETPE LSKH                  1184

SEQ ID NO: 73           moltype = DNA  length = 213
FEATURE                 Location/Qualifiers
source                  1..213
                        mol_type = genomic DNA
                        organism = Glycine max
SEQUENCE: 73
acttttgact ctctctctct ctctctctac agtagtagta gtagtattca ttcatattca  60
tacttgatat catgtcacac acacactatc tctctctctc tctctctaat ggcagagcta  120
gctcagaccc ttaacacaga ccacagcctc tgagagaaac cactctcact ctcactctcc  180
ttaacctttc accttccata tctggcgaaa atg                               213

SEQ ID NO: 74           moltype = DNA  length = 133
FEATURE                 Location/Qualifiers
source                  1..133
                        mol_type = genomic DNA
                        organism = Glycine max
SEQUENCE: 74
gtagtattca ttcatattca tacttgatat catgtcacac acacactatc tctctctctc  60
tctctctaat ggcagagcta gctcagaccc ttaacacaga ccacagcctc tgagagaaac  120
cactctcact ctc                                                     133

SEQ ID NO: 75           moltype = DNA  length = 93
FEATURE                 Location/Qualifiers
source                  1..93
                        mol_type = genomic DNA
                        organism = Glycine max
SEQUENCE: 75
tacttgatat catgtcacac acacactatc tctctctctc tctctctaat ggcagagcta  60
gctcagaccc ttaacacaga ccacagcctc tga                               93

SEQ ID NO: 76           moltype = DNA  length = 53
FEATURE                 Location/Qualifiers
source                  1..53
                        mol_type = genomic DNA
                        organism = Glycine max
SEQUENCE: 76
acacactatc tctctctctc tctctctaat ggcagagcta gctcagaccc tta         53

SEQ ID NO: 77           moltype = DNA  length = 33
FEATURE                 Location/Qualifiers
source                  1..33
                        mol_type = genomic DNA
                        organism = Glycine max
SEQUENCE: 77
tctctctctc tctctctaat ggcagagcta gct                               33

SEQ ID NO: 78           moltype = DNA  length = 63
FEATURE                 Location/Qualifiers
source                  1..63
                        mol_type = genomic DNA
                        organism = Glycine max
SEQUENCE: 78
atgtcacaca cacactatct ctctctctct ctctctaatg gcagagctag ctcagaccct  60
taa                                                                63

SEQ ID NO: 79           moltype = DNA  length = 45
FEATURE                 Location/Qualifiers
source                  1..45
                        mol_type = genomic DNA
```

```
                         organism = Glycine max
SEQUENCE: 79
atggcagagc tagctcagac ccttaacaca gaccacagcc tctga                45

SEQ ID NO: 80            moltype = DNA  length = 4244
FEATURE                  Location/Qualifiers
source                   1..4244
                         mol_type = genomic DNA
                         organism = Glycine max
SEQUENCE: 80
gtagatacaa gtatggagga gagtggaaat aggaaaaaat agcttagaga gatttattta  60
cgaacaggaa gagtcacatg gcatgtgtcc agtcttccac atgataaata cccttcttac  120
cttccttact aggacttttg actctctctc tctctatcta tggtagtagt agtagtagta  180
ttcattcatt ctctctaatg gcagagctca caccctaaac acaaaccaga gcctctgaga  240
gaaacaacca caaactctcc cttaatcttg tcggtttcca tatctgctga aaatgaaagc  300
tctgtacaga agctctctct tgctcttgct cttgctcttc atctccgtgt gttttgcatc  360
ttcttcttct ccggtcactc agcaactcct aagcttcaaa aactctctcc cgaacccatc  420
cctgctcccc aactggctcc ctaaccaaag cccgtgcaca ttcagcggca tcagctgcaa  480
cgacacagag ctcacatcca tagacctcag ctccgtccct ctcagcacta acctaaccgt  540
catcgccagc ttcctcctta gcctggacca cctccagtca ctctccttaa aatccaccaa  600
cctctccggt cccgccgcca tgcctcctct ctcccactcc cagtgctcct cctcattaac  660
ctccctagat ctctcccaaa actccctctc tgcctccctc aacgacatgt cgtttctcgc  720
ctcctgctcc aacctccaat ccctcaacct ctcctccaac ctcctccaat tcggcccccc  780
gccccactgg aagctccacc acctccgctt cgccgacttc tcttacaaca agatttccgg  840
ccccggcgtc gtttcttggc ttctcaaccc cgtcatcgaa ctcctctctc tcaaaggcaa  900
caaagtcacc ggcgaaaccg acttctccgg ctcaatttct ctccagtatt tagacctttc  960
ttccaacaac ttttctgtta cgcttcctac tttcggcgag tgttcttcgc ttgagtattt  1020
ggacctctcc gctaacaagt acttgggcga cattgcacgc actctctccc cttgcaagag  1080
cctcgtttac cttaacgtct ccagcaacca gttctccggt ccggttcctt cccttccctc  1140
cggttcgcta cagtttgtgt accttgctgc aaaccacttc cacggccaga ttcctctctc  1200
cctcgccgac ctctgctcca ctctcctcca gctcgatctc tcctccaaca atctcaccgg  1260
cgctcttccc ggcgcgttcg gcgcgtgcac ttctcttcaa tcccttgaca tctccagcaa  1320
cctcttcgcc ggcgcgttgc cgatgtcggt tctcacgcaa atgaccagcc tgaaagagct  1380
cgcggttgcg ttcaacggct tcctcggtgc tctcccggag tctctgtcga agctctccgc  1440
tctggagttg ctggatctga gctccaacaa ctttagcggc tcaatccccg cctcgctgtg  1500
cggcggcggt gacgctggga ttaataataa tctgaaggaa ctttatctgc agaataaccg  1560
gttcacgggt tttattccgc ccacgctcag caactgttca aacctcgttg ctttggattt  1620
gagtttcaac ttcctcacgg ggactattcc tccgagccta gggtctcttt cgaatctcaa  1680
agacttcatc atctggctca accagctcca cggggagata ccgcaggagc tcatgtatct  1740
taaaagcctc gagaatttga tcctggattt caacgacttg actgggaaca ttccctctgg  1800
cctcgttaac tgcaccaagt tgaactggat ctccctctcc aacaacaggc tcagcggcga  1860
gattccgccg tggattggga agctttctaa tctcgccata ctcaagctca gcaataactc  1920
tttctccggc cggattccgc cggagctcgg cgactgtact agtttaatat ggttggatct  1980
gaatacaaat atgctcaccg ggcccattcc gccggagctg ttcaagcagt cggggaagat  2040
cgccgtgaat ttcatcagtg ggaagacgta tgtgtatata aagaacgatg ggagcaagga  2100
gtgccatggt gcggggaact tgcttgagtt tgcggggatc agtcagcagc agctgaacag  2160
gatttcgacg aggaacccct gcaatttcac tagggtttat ggaggtaagt tgcagccaac  2220
gtttaaccat aatggttcta tgatattttt ggatatctcg cacaacatgt tgtcagggag  2280
tattcccaag gagattgggg ccatgtacta tttgtacatt ctcaatttgg gtcacaataa  2340
tgtgtctggg agcattcctc aagagcttgg gaagatgaag aatctcaaca ttcttgatct  2400
gtcgaataat agactggagg gccaaattcc gcagagcctc acggggcttt ctttgctcac  2460
tgagattgac ttgtccaaca acttgcttac cgggacgatt cctgagtcgg gtcaatttga  2520
tactttccct gcggcgaagt ttcagaacaa ctctggtcta tgtggagttc ctctgggtcc  2580
gtgtggttcg gagccggcaa acaatggaaa tgcgcaacat atgaagtctc acaggaggca  2640
ggcttctctg gcggggagtg tggccatggg gttgttgttt tccctctttt gcgtctttgg  2700
tttgatcatt attgccattg agaccaggaa gaggaggaag aagaaggagg ctgctcttga  2760
agcctatggt gatggtaatt cccattcggg tccggccaat gtgagctgga agcacaccag  2820
tactcgggaa gctcttagca taaaccttgc aacatttgag aagccgctcc ggaagcttac  2880
ttttgcggac cttcttgacg ctaccaatgg ttttcacaac gacagtctca ttggctctgg  2940
cgggtttggg gatgtgtaca aggctcagtt gaaggatgga agtgttgtgg ctatcaagaa  3000
gctgattcat gttagcggac aaggggacag ggaattcacc gctgaaatgg agactattgg  3060
gaaaatcaag cacaggaacc ttgttcccct gttgggatac tgcaaggtag gggaagagag  3120
gctcttggtt tatgagtaca tgaaatatgg aagtttagag gatgttctac atgatcagaa  3180
gaaagctggg atcaagctga actgggccat taggcggaaa attgctattg gagctgctag  3240
gggattggct tttcttcacc acaattgtat cccccacatc attcatagag atatgaagtc  3300
gagcaatgtg ttacttgatg aaaacctgga agccagagtc tctgattttg gaatggctag  3360
gcttatgagt gctatggata cacatttgag tgtgagcaca ttggctggca caccggggta  3420
tgttcctccc gagtactatc agagcttcag atgctccaca aaaggtgatg tctacagtta  3480
tggtgtggtt ttgttggagc tgctaactgg gaaaaggcca acggactcgg ctgattttgg  3540
agataataat cttgttggat gggttaaaca acatgccaag ctgaaaatca gtgatatttt  3600
tgacccggag ctcatgaagg aagaccccaa tctggagatg gagcttttgc agcacttgaa  3660
gattgcggtt tcctgtttgg atgatcgacc gtggaggcgt ccgacgatga ttcaagtgat  3720
ggcaatgttc aaggagattc aggcgggatc cgggattgat tctcagtcaa ccatagccaa  3780
tgacgaggaa ggtttcaatg cagttgaaat ggtggagatg agcattaaag aagcccctga  3840
attgagcaag cattaggcat taaagtgtcg tgtggattct ttgggaaaca gacaagaaga  3900
gaggaggaga tgacggattc agctcccctc agttttttcc ttctttgccg cttcaaatta  3960
tttcagacat aagggaaaac ggttaaaagg ggaatgaatg cttttgatgt atgtattctt  4020
gttattttat acataaaaaa aagttgttta acttgtatat aaacagcttc agttgttacc  4080
atctgtgttt tcctagaatt ttcaaagtac ttttctcatt caaatataat cctgaaaagg  4140
```

-continued

```
ttctctgttc aatctgcgac cccagtgatg gcaactaagt ggatcaacag caacttttgc  4200
tccgatttgc gatataattt gtcaaaacat gcctctaaaa tcac                   4244

SEQ ID NO: 81          moltype = DNA  length = 3564
FEATURE                Location/Qualifiers
source                 1..3564
                       mol_type = other DNA
                       organism = Glycine max
SEQUENCE: 81
atgaaagctc tgtacagaag ctctctcttg ctcttgctct tgctcttcat ctccgtgtgt  60
tttgcatctt cttcttctcc ggtcactcag caactcctaa gcttcaaaaa ctctctcccg  120
aacccatccc tgctccccaa ctggctccct aaccaaagcc cgtgcacatt cagcggcatc  180
agctgcaacg acacagagct cacatccata gacctcagct ccgtccctct cagcactaac  240
ctaaccgtca tcgccagctt cctccttagc ctggaccacc tccagtcact ctccttaaaa  300
tccaccaacc tctccggtcc cgccgccatg cctcctctct cccactccca gtgctcctcc  360
tcattaacct ccctagatct ctcccaaaac tccctctctg cctccctcaa cgacatgtcg  420
tttctcgcct cctgctccaa cctccaatcc ctcaacctct cctccaacct cctccaattc  480
ggcccccgc cccactggaa gctccaccac ctccgcttcg ccgacttctc ttacaacaag  540
atttccggcc ccggcgtcgt ttcttggctt ctcaaccccg tcatcgaact cctctctctc  600
aaaggcaaca aagtcaccgg cgaaaccgac ttctccggct caatttctct ccagtattta  660
gacctttctt ccaacaactt ttctgttacg cttcctactt tcggcgagtg ttcttcgctt  720
gagtatttgg acctctccgc taacaagtac ttgggcgaca ttgcacgcac tctctcccct  780
tgcaagagcc tcgtttacct taacgtctcc agcaaccagt tctccggtcc ggttccttcc  840
cttccctccg gttcgctaca gtttgtgtac cttgctgcaa accacttcca cggccagatt  900
cctctctccc tcgccgacct ctgctccact ctcctccagc tcgatctctc ctccaacaat  960
ctcaccggcg ctcttcccgg cgcgttcggc gcgtgcactt ctcttcaatc ccttgacatc  1020
tccagcaacc tcttcgccgg cgcgttgccg atgtcggttc tcacgcaaat gaccagcctg  1080
aaagagctcg cggttgcgtt caacggcttc ctcggtgctc tcccggagtc tctgtcgaag  1140
ctctccgctc tggagttgct ggatctgagc tccaacaact ttagcggctc aatccccgcc  1200
tcgctgtgcg gcggcggtga cgctgggatt aataataatc tgaaggaact ttatctgcag  1260
aataaccggt tcacgggttt tattccgccc acgctcagca actgttcaaa cctcgttgct  1320
ttggatttga gtttcaactt cctcacgggg actattcctc cgagcctagg gtctctttcg  1380
aatctcaaag acttcatcat ctggctcaac cagctccacg gggagatacc gcaggagctc  1440
atgtatctta aaagcctcga gaatttgatc ctggatttca acgacttgac tgggaacatt  1500
ccctctggcc tcgttaactg caccaagttg aactggatct ccctctccaa caacaggctc  1560
agcggcgaga ttccgccgtg gattgggaag ctttctaatc tcgccatact caagctcagc  1620
aataactctt tctccggccg gattccgccg gagctcggcg actgtactag tttaatatgg  1680
ttggatctga atacaaatat gctcaccggg cccattccgc cggagctgtt caagcagtcg  1740
gggaagatcg ccgtgaattt catcagtggg aagacgtatg tgtatataaa gaacgatggg  1800
agcaaggagt gccatggtgc ggggaacttg cttgagtttg cggggatcag tcagcagcag  1860
ctgaacagga tttcgacgag gaacccctgc aatttcacta gggtttatgg aggtaagttg  1920
cagccaacgt ttaaccataa tggttctatg atatttttgg atatctcgca caacatgttg  1980
tcagggagta ttcccaagga gattggggcc atgtactatt tgtacattct caatttgggt  2040
cacaataatg tgtctgggag cattcctcaa gagcttggga agatgaagaa tctcaacatt  2100
cttgatctgt cgaataatag actggagggc caaattccgc agagcctcac ggggctttct  2160
ttgctcactg agattgactt gtccaacaac ttgcttaccg ggacgattcc tgagtcgggt  2220
caatttgata ctttccctgc ggcgaagttt cagaacaact ctggtctatg tggagttcct  2280
ctgggtccgt gtggttcgga gccggcaaac aatggaaatg cgcaacatat gaagtctcac  2340
aggaggcagg cttctctggc ggggagtgtg gccatggggt tgttgttttc cctcttttgc  2400
gtctttggtt tgatcattat tgccattgag accaggaaga ggaggaagaa gaaggaggct  2460
gctcttgaag cctatggtga tggtaattcc cattcgggtc cggccaatgt gagctggaag  2520
cacaccagta ctcgggaagc tcttagcata aaccttgcaa catttgagaa gccgctccgg  2580
aagcttactt ttgcggacct tcttgacgct accaatggtt ttcacaacga cagtctcatt  2640
ggctctggcg ggtttgggga tgtgtacaag gctcagttga aggatggaag tgttgtggct  2700
atcaagaagc tgattcatgt tagcggacaa ggggacaggg aattcaccgc tgaaatggag  2760
actattggga aaatcaagca caggaacctt gttcccctgt tgggatactg caaggtaggg  2820
gaagagaggc tcttggttta tgagtacatg aaatatggaa gtttagagga tgttctacat  2880
gatcagaaga aagctgggat caagctgaac tgggccatta ggcggaaaat tgctattgga  2940
gctgctaggg gattggcttt tcttcaccac aattgtatcc cccacatcat tcatagagat  3000
atgaagtcga gcaatgtgtt acttgatgaa aacctggaag ccagagtctc tgattttgga  3060
atggctaggc ttatgagtgc tatggataca catttgagtg tgagcacatt ggctggcaca  3120
ccggggtatg ttcctcccga gtactatcag agcttcagat gctccacaaa aggtgatgtc  3180
tacagttatg gtgtggtttt gttggagctg ctaactggga aaaggccaac ggactcggct  3240
gattttggag ataataatct tgttggatgg gttaaacaac atgccaagct gaaaatcagt  3300
gatatttttg acccggagct catgaaggaa gaccccaatc tggagatgga gcttttgcag  3360
cacttgaaga ttgcggtttc ctgtttggat gatcgaccgt ggaggcgtcc gacgatgatt  3420
caagtgatgg caatgttcaa ggagattcag gcgggatccg ggattgattc tcagtcaacc  3480
atagccaatg acgaggaagg tttcaatgca gttgaaatgg tggagatgag cattaaagaa  3540
gcccctgaat tgagcaagca ttag                                        3564

SEQ ID NO: 82          moltype = AA  length = 1187
FEATURE                Location/Qualifiers
source                 1..1187
                       mol_type = protein
                       organism = Glycine max
SEQUENCE: 82
MKALYRSSLL LLLLLFISVC FASSSSPVTQ QLLSFKNSLP NPSLLPNWLP NQSPCTFSGI  60
SCNDTELTSI DLSSVPLSTN LTVIASFLLS LDHLQSLSLK STNLSGPAAM PPLSHSQCSS  120
SLTSLDLSQN SLSASLNDMS FLASCSNLQS LNLSSNLLQF GPPPHWKLHH LRFADFSYNK  180
```

```
ISGPGVVSWL LNPVIELLSL KGNKVTGETD FSGSISLQYL DLSSNNFSVT LPTFGECSSL  240
EYLDLSANKY LGDIARTLSP CKSLVYLNVS SNQFSGPVPS LPSGSLQFVY LAANHFHGQI  300
PLSLADLCST LLQLDLSSNN LTGALPGAFG ACTSLQSLDI SSNLFAGALP MSVLTQMTSL  360
KELAVAFNGF LGALPESLSK LSALELLDLS SNNFSGSIPA SLCGGGDAGI NNNLKELYLQ  420
NNRFTGFIPP TLSNCSNLVA LDLSFNFLTG TIPPSLGSLS NLKDFIIWLN QLHGEIPQEL  480
MYLKSLENLI LDFNDLTGNI PSGLVNCTKL NWISLSNNRL SGEIPPWIGK LSNLAILKLS  540
NNSFSGRIPP ELGDCTSLIW LDLNTNMLTG PIPPELFKQS GKIAVNFISG KTYVYIKNDG  600
SKECHGAGNL LEFAGISQQQ LNRISTRNPC NFTRVYGGKL QPTFNHNGSM IFLDISHNML  660
SGSIPKEIGA MYYLYILNLG HNNVSGSIPQ ELGKMKNLNI LDLSNNRLEG QIPQSLTGLS  720
LLTEIDLSNN LLTGTIPESG QFDTFPAAKF QNNSGLCGVP LGPCGSEPAN NGNAQHMKSH  780
RRQASLAGSV AMGLLFSLFC VFGLIIIAIE TRKRRKKKEA ALEAYGDGNS HSGPANVSWK  840
HTSTREALSI NLATFEKPLR KLTFADLLDA TNGFHNDSLI GSGGFGDVYK AQLKDGSVVA  900
IKKLIHVSGQ GDREFTAEME TIGKIKHRNL VPLLGYCKVG EERLLVYEYM KYGSLEDVLH  960
DQKKAGIKLN WAIRRKIAIG AARGLAFLHH NCIPHIIHRD MKSSNVLLDE NLEARVSDFG  1020
MARLMSAMDT HLSVSTLAGT PGYVPPEYYQ SFRCSTKGDV YSYGVVLLEL LTGKRPTDSA  1080
DFGDNNLVGW VKQHAKLKIS DIFDPELMKE DPNLEMELLQ HLKIAVSCLD DRPWRRPTMI  1140
QVMAMFKEIQ AGSGIDSQST IANDEEGFNA VEMVEMSIKE APELSKH                1187

SEQ ID NO: 83          moltype = DNA  length = 267
FEATURE                Location/Qualifiers
source                 1..267
                       mol_type = genomic DNA
                       organism = Glycine max
SEQUENCE: 83
gtagatacaa gtatggagga gagtggaaat aggaaaaaat agcttagaga gatttattta  60
cgaacaggaa gagtcacatg gcatgtgtcc agtcttccac atgataaata cccttcttac  120
cttccttact aggacttttg actctctctc tctctatcta tggtagtagt agtagtagta  180
ttcattcatt ctctctaatg gcagagctca caccctaaac acaaaccaga gcctctgaga  240
gaaacaacca caaactctcc cttaatc                                      267

SEQ ID NO: 84          moltype = DNA  length = 188
FEATURE                Location/Qualifiers
source                 1..188
                       mol_type = genomic DNA
                       organism = Glycine max
SEQUENCE: 84
tagcttagag agatttattt acgaacagga agagtcacat ggcatgtgtc cagtcttcca  60
catgataaat acccttctta ccttccttac taggactttt gactctctct ctctctatct  120
atggtagtag tagtagtagt attcattcat tctctctaat ggcagagctc acaccctaaa  180
cacaaacc                                                           188

SEQ ID NO: 85          moltype = DNA  length = 128
FEATURE                Location/Qualifiers
source                 1..128
                       mol_type = genomic DNA
                       organism = Glycine max
SEQUENCE: 85
agagtcacat ggcatgtgtc cagtcttcca catgataaat acccttctta ccttccttac  60
taggactttt gactctctct ctctctatct atggtagtag tagtagtagt attcattcat  120
tctctcta                                                           128

SEQ ID NO: 86          moltype = DNA  length = 69
FEATURE                Location/Qualifiers
source                 1..69
                       mol_type = genomic DNA
                       organism = Glycine max
SEQUENCE: 86
catgataaat acccttctta ccttccttac taggactttt gactctctct ctctctatct  60
atggtagta                                                          69

SEQ ID NO: 87          moltype = DNA  length = 62
FEATURE                Location/Qualifiers
source                 1..62
                       mol_type = genomic DNA
                       organism = Glycine max
SEQUENCE: 87
gtagatacaa gtatggagga gagtggaaat aggaaaaaat agcttagaga gatttattta  60
cg                                                                 62

SEQ ID NO: 88          moltype = DNA  length = 64
FEATURE                Location/Qualifiers
source                 1..64
                       mol_type = genomic DNA
                       organism = Glycine max
SEQUENCE: 88
gacttttgac tctctctctc tctatctatg gtagtagtag tagtagtatt cattcattct  60
ctct                                                               64

SEQ ID NO: 89          moltype = DNA  length = 63
```

```
FEATURE                Location/Qualifiers
source                 1..63
                       mol_type = genomic DNA
                       organism = Glycine max
SEQUENCE: 89
agtagtagta gtagtattca ttcattctct ctaatggcag agctcacacc ctaaacacaa  60
acc                                                                63

SEQ ID NO: 90          moltype = DNA  length = 30
FEATURE                Location/Qualifiers
source                 1..30
                       mol_type = genomic DNA
                       organism = Glycine max
SEQUENCE: 90
atggaggaga gtggaaatag gaaaaaatag                                   30

SEQ ID NO: 91          moltype = DNA  length = 30
FEATURE                Location/Qualifiers
source                 1..30
                       mol_type = genomic DNA
                       organism = Glycine max
SEQUENCE: 91
atggcatgtg tccagtcttc cacatgataa                                   30

SEQ ID NO: 92          moltype = DNA  length = 97
FEATURE                Location/Qualifiers
source                 1..97
                       mol_type = genomic DNA
                       organism = Glycine max
SEQUENCE: 92
atgtgtccag tcttccacat gataaatacc cttcttacct tccttactag gacttttgac  60
tctctctctc tctatctatg gtagtagtag tagtagt                           97

SEQ ID NO: 93          moltype = DNA  length = 79
FEATURE                Location/Qualifiers
source                 1..79
                       mol_type = genomic DNA
                       organism = Glycine max
SEQUENCE: 93
atgataaata cccttcttac cttccttact aggacttttg actctctctc tctctatcta  60
tggtagtagt agtagtagt                                               79

SEQ ID NO: 94          moltype = DNA  length = 39
FEATURE                Location/Qualifiers
source                 1..39
                       mol_type = genomic DNA
                       organism = Glycine max
SEQUENCE: 94
atggtagtag tagtagtagt attcattcat tctctctaa                         39

SEQ ID NO: 95          moltype = DNA  length = 21
FEATURE                Location/Qualifiers
source                 1..21
                       mol_type = genomic DNA
                       organism = Glycine max
SEQUENCE: 95
atggcagagc tcacacccta a                                            21

SEQ ID NO: 96          moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 96
tacttgatat catgtcacac aca                                          23

SEQ ID NO: 97          moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 97
gagctagctc tgccattaga gag                                          23

SEQ ID NO: 98          moltype = DNA  length = 23
```

```
FEATURE                Location/Qualifiers
misc_feature           1..23
                       note = Synthetic oligonucleotide
source                 1..23
                       mol_type = other DNA
                       organism = synthetic construct
SEQUENCE: 98
tatttccact ctcctccata ctt                                             23

SEQ ID NO: 99          moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 99
ttcattctct ctaatggcag agc                                             23

SEQ ID NO: 100         moltype = DNA  length = 23
FEATURE                Location/Qualifiers
misc_feature           1..23
                       note = Synthetic oligonucleotide
source                 1..23
                       mol_type = other DNA
                       organism = synthetic construct
SEQUENCE: 100
ctactactac taccatagat aga                                             23

SEQ ID NO: 101         moltype = DNA  length = 4374
FEATURE                Location/Qualifiers
misc_feature           1..4374
                       note = Synthetic polynucleotide
source                 1..4374
                       mol_type = other DNA
                       organism = synthetic construct
SEQUENCE: 101
gacttttgac tctctctctc tctctctcta cagtagtagt agtagtattc attcatattc  60
aatctctctc tctctctctc taatggcaga gctagctcag acccttaaca cagaccacag  120
cctctgagag aaaccactct cactctcact ctccttaacc tttcaccttc catatctggc  180
gaaaatgaaa gctctgtaca gaagctctct cttgctcctc ttcttcctct ccgtctgttc  240
tgcatcttct tcttcggttc ccactctgca actcctaagc ttcaaaaact ctctcccgaa  300
cccaaccctg ctcccgaact ggctcccgaa ccaaagccca tgctcattca ccggcatcac  360
ctgcaacgac acccagcacc tcacttccat agacctctcc ggcgtccctc tcaccacaaa  420
cctcaccgtc atcgccacct tcctcctcac cctcgacaac ctccagtcac tctccttaaa  480
atccaccaac ctctccggcc ccgccgccat gcctcctcct ctctcccact ccaagtgcgc  540
ctccacatta acctccctag atctatcaca aaacgccctc tccggttccc tcaacgacat  600
gtcgtttctc tcctcctgct ccaacctcca atccctcaat ctctccagca accttcttga  660
attcgactcc tctcactgga agctccacct cctcgtcgcc gacttttcct acaacaagat  720
ttccggcccc ggtatcctcc cctggcttct caaccctgaa atcgaacacc tcgctctgaa  780
aggcaacaaa gtcaccggcg aaaccgactt ctccggttcc aattctctcc agtttttaga  840
cctttcttcc aacaactttt ctgttacgct tcctactttc ggcgagtgtt cttcgcttga  900
gtatttggac ctctccgcca acaagtactt cggcgacatt gctcgcactc tctcgccttg  960
caagaacctc gtttacttaa acttctccag caaccagttc tccggtccgg ttccttccct  1020
tccctccggt tcgctacagt tcgtgtacct tgcttcaaac cacttccacg gccagattcc  1080
tctccccctc gccgacctct gctccactct cctccagctc gatctctcct ccaacaacct  1140
ctcaggcgct ctcccgaagc cttcggcgct tgcacttctc ttcagtcctt cgacatctcc  1200
agcaacctct tcgccggtgc gctgcctatg gacgttctca cgcaaatgaa aagcctcaaa  1260
gagctcgcgg tggcgttcaa cgcgttcctt ggtcccctt c cggagtctct gacgaagctc  1320
tccactttag agtcgctgga tcttagctcc aacaacttca gcggctcaat cccgacaacg  1380
ctgtgcggtg gtgacgctgg gaataataat attctgaagg aactttacct gcagaacaac  1440
cggttcacgg gttttattcc acccacgctc agcaactgtt caaacctcgt tgctttggac  1500
ttgagtttca acttcctcac gggaactatt cctccaagcc tagggtctct ttccaagctt  1560
aaagacttga tcatctggct caaccagctc catggagaaa taccgcagga gctcatgtat  1620
ctgaaaagcc tcgagaattt gatcctggat ttcaacgact tgactgggaa cattccctct  1680
gggcttgtta actgcaccaa gctgaactgg atctccctct ccaacaacag gctcagcggc  1740
gagattccgc ggtggattgg gaagctttct aatctcgcca tacttaagct cagtaataac  1800
tctttctccg gccggattcc gccggagctc ggcgattgta ctagtttaat atggttggat  1860
ctgaatacta atatgctcac cgggcccatt ccgccggagc tgttcaagca gtcggggaag  1920
atcgcggtga atttcatcag tgggaagacg tatgtgtata taaagaacga tgggagcaaa  1980
gagtgtcatg gtgcggggaa cttgctggag tttgccggga tcagtcagca gcagttgaac  2040
aggatttcga cgaggaaccc gtgcaatttc actagggttt atggaggtaa gttgcagcca  2100
acgtttaacc ataatggttc tatgatattt ttggatatct cgcacaacat gttgtcaggg  2160
agtattccca aggagattgg ggccatgtac tatttgtaca ttctcaattt gggtcataat  2220
aatgtgtctg gagcattcc tcaagagctt gggaagatga agaatctcaa catccttgat  2280
ctctcaagta atagactgga ggggcaaatt cctcagagtc tcacggggct ttccttgctc  2340
actgagattg acctgtcgaa taacttgctt acggggacga ttcctgagtc gggtcaattt  2400
gatactttcc ctgcggcgag atttcagaac aactctggtc tctgtggagt tcctctcggc  2460
ccatgtggtt cggacccggc gaataacggg aatgcgcaac atatgaagtc tcacaggagg  2520
```

```
caggcttctc tggtggggag tgtggccatg ggtttgttgt tttccctctt ctgcgtcttt  2580
ggtttgatca ttattgccat tgagaccagg aagaggagga agaagaagga ggctgctctt  2640
gaagcctatg ctgatggtaa tttgcattcg ggtcctgcca acgtgagctg gaagcacacc  2700
agtacccggg aagcgcttag cataaacctt gcaacgttta agaggccgct caggaggctt  2760
acttttgcgg accttcttga cgctaccaat ggctttcaca atgatagtct cattggctct  2820
ggtgggtttg gggatgttta caaggctcag ttgaaggatg gaagtgttgt ggctatcaag  2880
aagctgattc atgtcagcgg ccaaggggac agggaattca ctgctgaaat ggagaccatt  2940
gggaagatca agcacaggaa ccttgttcct ctgttgggat actgcaaggt tggggaagag  3000
aggctcttgg tttatgagta catgaaatat ggaagcttag aggatgttct tcatgatccg  3060
aagaaagctg ggatcaagtt gaattggtcg attaggagga aaattgctat tggagctgct  3120
aggggattgt cttttcttca ccacaattgt agcccccaca tcattcatag agacatgaag  3180
tcaagcaatg tgttacttga tgaaaacctg gaagctagag tctctgattt tggaatggct  3240
aggcatatga gtgctatgga tacacatttg agtgtgagca cactggcagg cacaccaggg  3300
tatgttcctc cggagtacta tgagagcttc agatgctcta ccaaaggtga tgtctacagt  3360
tatggtgtgg ttttgttgga gctgctaact gggaaaaggc caacagattc ggctgatttt  3420
ggtgataata atcttgttgg atgggttaaa caacatgcca agctgaaaat aagtgatatt  3480
tttgacccag agctcatgaa ggaagacccc aatttggaga tggagctttt gcagcacctg  3540
aagattgcag tttcctgttt ggatgatcgg cattggagac gtccaacgat gattcaagtg  3600
ttgacaatgt tcaaggagat tcaggcagga tctgggattg attctcagtc aaccatagcc  3660
aatgaagatg acagtttcaa tgcagttgaa atggtggaga tgagcattaa agaaacccct  3720
gaattgagca agcattaggc aacaaattcc ggaagtgtca tgtggattct ttgggaaaca  3780
gacaagaaga gagaaaagga ggagatgacg gattcagctc ccctcaaagt tttttccttc  3840
ctctttgccg cttcaaatta tttcagacac aagggggaaa cggttaaagg gggaatgaat  3900
gcctttgatg tatgtagtct tgttatttta tacaaaaaaa aaaagttgtt taacttgtat  3960
ataaacagct tcagttgtta ccatctgtgt tttcctagaa ttttcaaaag tacttttctc  4020
attcagatat aatcctgaaa aggatctctg ttcaatctgg cgaccccagt gatggcgact  4080
aagtggagga tcttttggcc atttctttag gcctcttgat ttgtttcccc catttgatca  4140
actgcaactt ttgctccgat ttgcgatata atttgtcaaa acatgcttct tctaaaatca  4200
ctcataacat aaattttctt gaattacaat tttataccct cccctcccca acttgttctg  4260
cgccttctga cccttcttgt tttgtttgct agtttaccct gtaggaaaaa gtatcactct  4320
actcaaatag tattttcacc tcttctggcc ataaataatt ttggcctaat tcag        4374

SEQ ID NO: 102          moltype = DNA  length = 4393
FEATURE                 Location/Qualifiers
misc_feature            1..4393
                        note = Synthetic polynucleotide
source                  1..4393
                        mol_type = other DNA
                        organism = synthetic construct
SEQUENCE: 102
gacttttgac tctctctctc tctctctcta cagtagtagt agtagtattc attcatattc  60
atacttgata tcatgtcact atctctctct ctctctctct aatggcagag ctagctcaga  120
cccttaacac agaccacagc ctctgagaga aaccactctc actctcactc tccttaacct  180
ttcaccttcc atatctggcg aaaatgaaag ctctgtacag aagctctctc ttgctcctct  240
tcttcctctc cgtctgttct gcatcttctt cttcggttcc cactctgcaa ctcctaagct  300
tcaaaaactc tctcccgaac ccaaccctgc tcccgaactg gctcccgaac caaagcccat  360
gctcattcac cggcatcacc tgcaacgaca cccagcacct cacttccata gacctctccg  420
gcgtccctct caccacaaac ctcaccgtca tcgccacctt cctcctcacc ctcgacaacc  480
tccagtcact ctccttaaaa tccaccaacc tctccggccc cgccgccatg cctcctcctc  540
tctcccactc caagtgcgcc tccacattaa cctccctaga tctatcacaa aacgccctct  600
ccggttccct caacgacatg tcgtttctct cctcctgctc caacctccaa tccctcaatc  660
tctccagcaa ccttcttgaa ttcgactcct ctcactggaa gctccacctc ctcgtcgccg  720
acttttccta caacaagatt tccggccccg gtatcctccc ctggcttctc aaccctgaaa  780
tcgaacacct cgctctgaaa ggcaacaaag tcaccggcga aaccgacttc tccggttcca  840
attctctcca gtttttagac ctttcttcca acaacttttc tgttacgctt cctactttcg  900
gcgagtgttc ttcgcttgag tatttggacc tctccgccaa caagtacttc ggcgacattg  960
ctcgcactct ctcgccttgc aagaacctcg tttacttaaa cttctccagc aaccagttct  1020
ccggtccggt tccttccctt ccctccggtt cgctacagtt cgtgtacctt gcttcaaacc  1080
acttccacgg ccagattcct ctcccccctcg ccgacctctg ctccactctc ctccagctcg  1140
atctctcctc caacaacctc tcaggcgctc tcccgaagcc ttcggcgctt gcacttctct  1200
tcagtccttc gacatctcca gcaacctctt cgccggtgcg ctgcctatgg acgttctcac  1260
gcaaatgaaa agcctcaaag agctcgcggt ggcgttcaac gcgttccttg gtccccttcc  1320
ggagtctctg acgaagctct ccactttaga gtcgctggat cttagctcca acaacttcag  1380
cggctcaatc ccgacaacgc tgtgcggtgg tgacgctggg aataataata ttctgaagga  1440
actttacctg cagaacaacc ggttcacggg ttttattcca cccacgctca gcaactgttc  1500
aaacctcgtt gctttggact tgagtttcaa cttcctcacg ggaactattc ctccaagcct  1560
agggtctctt tccaagctta aagacttgat catctggctc aaccagctcc atggagaaat  1620
accgcaggag ctcatgtatc tgaaaagcct cgagaatttg atcctggatt tcaacgactt  1680
gactgggaac attccctctg ggcttgttaa ctgcaccaag ctgaactgga tctccctctc  1740
caacaacagg ctcagcggcg agattccgcg gtggattggg aagctttcta atctcgccat  1800
acttaagctc agtaataact ctttctccgg ccggattccg ccggagctcg gcgattgtac  1860
tagtttaata tggttggatc tgaatactaa tatgctcacc gggcccattc cgccggagct  1920
gttcaagcag tcggggaaga tcgcggtgaa tttcatcagt gggaagacgt atgtgtatat  1980
aaagaacgat gggagcaaag agtgtcatgg tgcggggaac ttgctggagt ttgccgggat  2040
cagtcagcag cagttgaaca ggatttcgac gaggaacccg tgcaatttca ctagggttta  2100
tggaggtaag ttgcagccaa cgtttaacca taatggttct atgatatttt tggatatctc  2160
gcacaacatg ttgtcaggga gtattcccaa ggagattggg gccatgtact atttgtacat  2220
tctcaatttg ggtcataata atgtgtctgg gagcattcct caagagcttg ggaagatgaa  2280
gaatctcaac atccttgatc tctcaagtaa tagactggag ggcaaattc ctcagagtct  2340
```

```
cacggggctt tccttgctca ctgagattga cctgtcgaat aacttgctta cggggacgat  2400
tcctgagtcg ggtcaatttg atactttccc tgcggcgaga tttcagaaca actctggtct  2460
ctgtggagtt cctctcggcc catgtggttc ggacccggcg aataacggga atgcgcaaca  2520
tatgaagtct cacaggaggc aggcttctct ggtggggagt gtggccatgg gtttgttgtt  2580
ttccctcttc tgcgtctttg gtttgatcat tattgccatt gagaccagga agaggaggaa  2640
gaagaaggag gctgctcttg aagcctatgc tgatggtaat ttgcattcgg gtcctgccaa  2700
cgtgagctgg aagcacacca gtacccggga agcgcttagc ataaaccttg caacgtttaa  2760
gaggccgctc aggaggctta cttttgcgga ccttcttgac gctaccaatg gctttcacaa  2820
tgatagtctc attggctctg gtgggtttgg ggatgtttac aaggctcagt tgaaggatgg  2880
aagtgttgtg gctatcaaga agctgattca tgtcagcggc caaggggaca gggaattcac  2940
tgctgaaatg gagaccattg ggaagatcaa gcacaggaac cttgttcctc tgttgggata  3000
ctgcaaggtt ggggaagaga ggctcttggt ttatgagtac atgaaatatg gaagcttaga  3060
ggatgttctt catgatccga agaaagctgg gatcaagttg aattggtcga ttaggaggaa  3120
aattgctatt ggagctgcta ggggattgtc ttttcttcac cacaattgta gcccccacat  3180
cattcataga gacatgaagt caagcaatgt gttacttgat gaaaacctgg aagctagagt  3240
ctctgatttt ggaatggcta ggcatatgag tgctatggat acacatttga gtgtgagcac  3300
actggcaggc acaccagggt atgttcctcc ggagtactat gagagcttca gatgctctac  3360
caaaggtgat gtctacagtt atggtgtggt tttgttggag ctgctaactg ggaaaaggcc  3420
aacagattcg gctgatttg gtgataataa tcttgttgga tgggttaaac aacatgccaa  3480
gctgaaaata agtgatattt ttgacccaga gctcatgaag gaagacccca atttggagat  3540
ggagcttttg cagcacctga agattgcagt ttcctgtttg gatgatcggc attggagacg  3600
tccaacgatg attcaagtgt tgacaatgtt caaggagatt caggcaggat ctgggattga  3660
ttctcagtca accatagcca atgaagatga cagtttcaat gcagttgaaa tggtggagat  3720
gagcattaaa gaaacccctg aattgagcaa gcattaggca acaaattccg gaagtgtcat  3780
gtggattctt tgggaaacag acaagaagag agaaaaggag gagatgacgg attcagctcc  3840
cctcaaagtt ttttccttcc tctttgccgc ttcaaattat ttcagacaca agggggaaac  3900
ggttaaaggg ggaatgaatg cctttgatgt atgtagtctt gttattttat acaaaaaaaa  3960
aaagttgttt aacttgtata taaacagctt cagttgttac catctgtgtt ttcctagaat  4020
tttcaaaagt actttctca ttcagatata atcctgaaaa ggatctctgt tcaatctggc  4080
gaccccagtg atggcgacta agtggaggat cttttggcca tttctttagg cctcttgatt  4140
tgtttccccc atttgatcaa ctgcaacttt tgctccgatt tgcgatataa tttgtcaaaa  4200
catgcttctt ctaaaatcac tcataacata aattttcttg aattacaatt ttataccctc  4260
ccctccccaa cttgttctgc gccttctgac ccttcttgtt ttgtttgcta gtttaccctg  4320
taggaaaaag tatcactcta ctcaaatagt attttcacct cttctggcca taaataattt  4380
tggcctaatt cag                                                     4393
```

```
SEQ ID NO: 103          moltype = DNA  length = 4384
FEATURE                 Location/Qualifiers
misc_feature            1..4384
                        note = Synthetic polynucleotide
source                  1..4384
                        mol_type = other DNA
                        organism = synthetic construct
SEQUENCE: 103
gacttttgac tctctctctc tctctctcta cagtagtagt agtagtattc attcatattc  60
atacttgata tcattctctc tctctctctc taatggcaga gctagctcag acccttaaca  120
cagaccacag cctctgagag aaaccactct cactctcact ctccttaacc tttcaccttc  180
catatctggc gaaaatgaaa gctctgtaca gaagctctct cttgctcctc ttcttcctct  240
ccgtctgttc tgcatcttct tctttcggttc ccactctgca actcctaagc ttcaaaaact  300
ctctcccgaa cccaaccctg ctcccgaact ggctcccgaa ccaaagccca tgctcattca  360
ccggcatcac ctgcaacgac acccagcacc tcacttccat agacctctcc ggcgtccctc  420
tcaccacaaa cctcaccgtc atcgccacct tcctcctcac cctcgacaac ctccagtcac  480
tctccttaaa atccaccaac ctctccggcc ccgccgccat gcctcctcct ctctcccact  540
ccaagtgcgc ctccacatta acctccctag atctatcaca aaacgccctc tccggttccc  600
tcaacgacat gtcgtttctc tcctcctgct ccaacctcca atccctcaat ctctccagca  660
accttcttga attcgactcc tctcactgga agctccacct cctcgtcgcc gacttttcct  720
acaacaagat ttccggcccc ggtatcctcc cctggcttct caaccctgaa atcgaacacc  780
tcgctctgaa aggcaacaaa gtcaccggcg aaaccgactt ctccggttcc aattctctcc  840
agtttttaga cctttcttcc aacaactttt ctgttacgct tcctactttc ggcgagtgtt  900
cttcgcttga gtatttggac ctctccgcca acaagtactt cggcgacatt gctcgcactc  960
tctcgccttg caagaacctc gtttacttaa acttctccag caaccagttc tccggtccgg  1020
ttccttccct tccctccggt tcgctacagt tcgtgtacct tgcttcaaac cacttccacg  1080
gccagattcc tctccccctc gccgacctct gctccactct cctccagctc gatctctcct  1140
ccaacaacct ctcaggcgct ctcccgaagc cttcggcgct tgcacttctc ttcagtcctt  1200
cgacatctcc agcaacctct tcgccggtgc gctgcctatg gacgttctca cgcaaatgaa  1260
aagcctcaaa gagctcgcgg tggcgttcaa cgcgttcctt ggtccccttc cggagtctct  1320
gacgaagctc tccactttag agtcgctgga tcttagctcc aacaacttca gcggctcaat  1380
cccgacaacg ctgtgcggtg gtgacgctgg gaataataat attctgaagg aactttacct  1440
gcagaacaac cggttcacgg gttttattcc acccacgctc agcaactgtt caaacctcgt  1500
tgctttggac ttgagtttca acttcctcac gggaactatt cctccaagcc tagggtctct  1560
ttccaagctt aaagacttga tcatctggct caaccagctc catggagaaa taccgcagga  1620
gctcatgtat ctgaaaagcc tcgagaattt gatcctggat ttcaacgact tgactgggaa  1680
cattccctct gggcttgtta actgcaccaa gctgaactgg atctccctct ccaacaacag  1740
gctcagcggc gagattccgc ggtggattgg gaagcttttct aatctcgcca tacttaagct  1800
cagtaataac tctttctccg gccggattcc gccggagctc ggcgattgta ctagtttaat  1860
atggttggat ctgaatacta atatgctcac cgggcccatt ccgccggagc tgttcaagca  1920
gtcggggaag atcgcggtga atttcatcag tgggaagacg tatgtgtata taaagaacga  1980
tgggagcaaa gagtgtcatg gtgcggggaa cttgctggag tttgccggga tcagtcagca  2040
gcagttgaac aggatttcga cgaggaaccc gtgcaatttc actagggttt atggaggtaa  2100
```

```
gttgcagcca acgtttaacc ataatggttc tatgatattt ttggatatct cgcacaacat  2160
gttgtcaggg agtattccca aggagattgg ggccatgtac tatttgtaca ttctcaattt  2220
gggtcataat aatgtgtctg ggagcattcc tcaagagctt gggaagatga agaatctcaa  2280
catccttgat ctctcaagta atagactgga ggggcaaatt cctcagagtc tcacggggct  2340
ttccttgctc actgagattg acctgtcgaa taacttgctt acggggacga ttcctgagtc  2400
gggtcaattt gatactttcc ctgcggcgag atttcagaac aactctggtc tctgtggagt  2460
tcctctcggc ccatgtggtt cggacccggc gaataacggg aatgcgcaac atatgaagtc  2520
tcacaggagg caggcttctc tggtggggag tgtggccatg ggtttgttgt tttccctctt  2580
ctgcgtcttt ggtttgatca ttattgccat tgagaccagg aagaggagga agaagaagga  2640
ggctgctctt gaagcctatg ctgatggtaa tttgcattcg ggtcctgcca acgtgagctg  2700
gaagcacacc agtacccggg aagcgcttag cataaacctt gcaacgttta agaggccgct  2760
caggaggctt acttttgcgg accttcttga cgctaccaat ggctttcaca atgatagtct  2820
cattggctct ggtgggtttg gggatgttta caaggctcag ttgaaggatg gaagtgttgt  2880
ggctatcaag aagctgattc atgtcagcgg ccaaggggac agggaattca ctgctgaaat  2940
ggagaccatt gggaagatca agcacaggaa ccttgttcct ctgttgggat actgcaaggt  3000
tggggaagag aggctcttgg tttatgagta catgaaatat ggaagcttag aggatgttct  3060
tcatgatccg aagaaagctg ggatcaagtt gaattggtcg attaggagga aaattgctat  3120
tggagctgct aggggattgt ctttcttca ccacaattgt agccccaca tcattcatag   3180
agacatgaag tcaagcaatg tgttacttga tgaaaacctg gaagctagag tctctgattt  3240
tggaatggct aggcatatga gtgctatgga tacacatttg agtgtgagca cactggcagg  3300
cacaccaggg tatgttcctc cggagtacta tgagagcttc agatgctcta ccaaaggtga  3360
tgtctacagt tatggtgtgg ttttgttgga gctgctaact gggaaaaggc caacagattc  3420
ggctgatttt ggtgataata atcttgttgg atgggttaaa caacatgcca agctgaaaat  3480
aagtgatatt tttgacccag agctcatgaa ggaagacccc aatttggaga tggagctttt  3540
gcagcacctg aagattgcag tttcctgttt ggatgatcgg cattggagac gtccaacgat  3600
gattcaagtg ttgacaatgt tcaaggagat tcaggcagga tctgggattg attctcagtc  3660
aaccatagcc aatgaagatg acagtttcaa tgcagttgaa atggtggaga tgagcattaa  3720
agaaacccct gaattgagca agcattaggc aacaaattcc ggaagtgtca tgtggattct  3780
ttgggaaaca gacaagaaga gagaaaagga ggagatgacg gattcagctc ccctcaaagt  3840
tttttccttc ctctttgccg cttcaaatta tttcagacac aagggggaaa cggttaaagg  3900
gggaatgaat gcctttgatg tatgtagtct tgttatttta tacaaaaaaa aaaagttgtt  3960
taacttgtat ataaacagct tcagttgtta ccatctgtgt tttcctagaa ttttcaaaag  4020
tacttttctc attcagatat aatcctgaaa aggatctctg ttcaatctgg cgaccccagt  4080
gatggcgact aagtggagga tcttttggcc atttctttag gcctcttgat ttgtttcccc  4140
catttgatca actgcaactt ttgctccgat ttgcgatata atttgtcaaa acatgcttct  4200
tctaaaatca ctcataacat aaattttctt gaattacaat tttataccct cccctcccca  4260
acttgttctg cgccttctga cccttcttgt tttgtttgct agtttaccct gtaggaaaaa  4320
gtatcactct actcaaatag tattttcacc tcttctggcc ataaataatt ttggcctaat  4380
tcag                                                              4384
```

```
SEQ ID NO: 104          moltype = DNA  length = 4393
FEATURE                 Location/Qualifiers
misc_feature            1..4393
                        note = Synthetic polynucleotide
source                  1..4393
                        mol_type = other DNA
                        organism = synthetic construct
SEQUENCE: 104
gacttttgac tctctctctc tctctctcta cagtagtagt agtagtattc attcatattc  60
atacttgata tcatgtcact atctctctct ctctctctct aatggcagag ctagctcaga  120
cccttaacac agaccacagc ctctgagaga aaccactctc actctcactc tccttaacct  180
ttcaccttcc atatctggcg aaaatgaaag ctctgtacag aagctctctc ttgctcctct  240
tcttcctctc cgtctgttct gcatcttctt cttcggttcc cactctgcaa ctcctaagct  300
tcaaaaactc tctcccgaac ccaaccctgc tcccgaactg gctcccgaac caaagcccat  360
gctcattcac cggcatcacc tgcaacgaca cccagcacct cacttccata gacctctccg  420
gcgtccctct caccacaaac ctcaccgtca tcgccacctt cctcctcacc ctcgacaacc  480
tccagtcact ctccttaaaa tccaccaacc tctccggccc cgccgccatg cctcctcctc  540
tctcccactc caagtgcgcc tccacattaa cctccctaga tctatcacaa aacgccctct  600
ccggttccct caacgacatg tcgtttctct cctcctgctc caacctccaa tccctcaatc  660
tctccagcaa ccttcttgaa ttcgactcct ctcactggaa gctccacctc ctcgtcgccg  720
acttttccta caacaagatt tccggccccg gtatcctccc ctggcttctc aaccctgaaa  780
tcgaacacct cgctctgaaa ggcaacaaag tcaccggcga aaccgacttc tccggttcca  840
attctctcca gtttttagac ctttcttcca acaacttttc tgttacgctt cctactttcg  900
gcgagtgttc ttcgcttgag tatttggacc tctccgccaa caagtacttc ggcgacattg  960
ctcgcactct ctcgccttgc aagaacctcg tttacttaaa cttctccagc aaccagttct  1020
ccggtccggt tccttccctt ccctccggtt cgctacagtt cgtgtacctt gcttcaaacc  1080
acttccacgg ccagattcct ctccccctcg ccgacctctg ctccactctc ctccagctcg  1140
atctctcctc caacaacctc tcaggcgctc tcccgaagcc ttcggcgctt gcacttctct  1200
tcagtccttc gacatctcca gcaacctctt cgccggtgcg ctgcctatgg acgttctcac  1260
gcaaatgaaa agcctcaaag agctcgcggt ggcgttcaac gcgttccttg gtccccttcc  1320
ggagtctctg acgaagctct ccactttaga gtcgctggat cttagctcca acaacttcag  1380
cggctcaatc ccgacaacgc tgtgcggtgg tgacgctggg aataataata ttctgaagga  1440
actttacctg cagaacaacc ggttcacggg ttttattcca cccacgctca gcaactgttc  1500
aaacctcgtt gctttggact tgagtttcaa cttcctcacg ggaactattc ctccaagcct  1560
agggtctctt tccaagctta aagacttgat catctggctc aaccagctcc atggagaaat  1620
accgcaggag ctcatgtatc tgaaaagcct cgagaatttg atcctggatt tcaacgactt  1680
gactgggaac attccctctg ggcttgttaa ctgcaccaag ctgaactgga tctccctctc  1740
caacaacagg ctcagcggcg agattccgcg gtggattggg aagctttcta atctcgccat  1800
acttaagctc agtaataact ctttctccgg ccggattccg ccggagctcg gcgattgtac  1860
```

tagtttaata tggttggatc tgaatactaa tatgctcacc gggcccattc cgccggagct 1920
gttcaagcag tcggggaaga tcgcggtgaa tttcatcagt gggaagacgt atgtgtatat 1980
aaagaacgat gggagcaaag agtgtcatgg tgcggggaac ttgctggagt ttgccgggat 2040
cagtcagcag cagttgaaca ggatttcgac gaggaacccg tgcaatttca ctagggttta 2100
tggaggtaag ttgcagccaa cgtttaacca taatggttct atgatatttt tggatatctc 2160
gcacaacatg ttgtcaggga gtattcccaa ggagattggg gccatgtact atttgtacat 2220
tctcaatttg ggtcataata atgtgtctgg gagcattcct caagagcttg ggaagatgaa 2280
gaatctcaac atccttgatc tctcaagtaa tagactggag gggcaaattc ctcagagtct 2340
cacggggctt tccttgctca ctgagattga cctgtcgaat aacttgctta cggggacgat 2400
tcctgagtcg ggtcaatttg atactttccc tgcggcgaga tttcagaaca actctggtct 2460
ctgtggagtt cctctcggcc catgtggttc ggacccggcg aataacggga atgcgcaaca 2520
tatgaagtct cacaggaggc aggcttctct ggtggggagt gtggccatgg gtttgttgtt 2580
ttccctcttc tgcgtctttg gtttgatcat tattgccatt gagaccagga agaggaggaa 2640
gaagaaggag gctgctcttg aagcctatgc tgatggtaat ttgcattcgg gtcctgccaa 2700
cgtgagctgg aagcacacca gtacccggga agcgcttagc ataaaccttg caacgtttaa 2760
gaggccgctc aggaggctta cttttgcgga ccttcttgac gctaccaatg gctttcacaa 2820
tgatagtctc attggctctg gtgggtttgg ggatgtttac aaggctcagt tgaaggatgg 2880
aagtgttgtg gctatcaaga agctgattca tgtcagcggc caaggggaca gggaattcac 2940
tgctgaaatg gagaccattg ggaagatcaa gcacaggaac cttgttcctc tgttgggata 3000
ctgcaaggtt ggggaagaga ggctcttggt ttatgagtac atgaaatatg gaagcttaga 3060
ggatgttctt catgatccga agaaagctgg gatcaagttg aattggtcga ttaggaggaa 3120
aattgctatt ggagctgcta ggggattgtc ttttcttcac cacaattgta gcccccacat 3180
cattcataga gacatgaagt caagcaatgt gttacttgat gaaaacctgg aagctagagt 3240
ctctgatttt ggaatggcta ggcatatgag tgctatggat acacatttga gtgtgagcac 3300
actggcaggc acaccagggt atgttcctcc ggagtactat gagagcttca gatgctctac 3360
caaaggtgat gtctacagtt atggtgtggt tttgttggag ctgctaactg ggaaaaggcc 3420
aacagattcg gctgatttg gtgataataa tcttgttgga tgggttaaac aacatgccaa 3480
gctgaaaata agtgatattt ttgacccaga gctcatgaag gaagacccca atttggagat 3540
ggagcttttg cagcacctga agattgcagt ttcctgtttg gatgatcggc attggagacg 3600
tccaacgatg attcaagtgt tgacaatgtt caaggagatt caggcaggat ctgggattga 3660
ttctcagtca accatagcca atgaagatga cagtttcaat gcagttgaaa tggtggagat 3720
gagcattaaa gaaacccctg aattgagcaa gcattaggca acaaattccg gaagtgtcat 3780
gtggattctt tgggaaacag acaagaagag agaaaaggag gagatgacgg attcagctcc 3840
cctcaaagtt ttttccttcc tctttgccgc ttcaaattat ttcagacaca agggggaaac 3900
ggttaaaggg ggaatgaatg cctttgatgt atgtagtctt gttattttat acaaaaaaaa 3960
aaagttgttt aacttgtata taaacagctt cagttgttac catctgtgtt ttcctagaat 4020
tttcaaaagt acttttctca ttcagatata atcctgaaaa ggatctctgt tcaatctggc 4080
gaccccagtg atggcgacta agtggaggat cttttggcca tttctttagg cctcttgatt 4140
tgtttccccc atttgatcaa ctgcaacttt tgctccgatt tgcgatataa tttgtcaaaa 4200
catgcttctt ctaaaatcac tcataacata aattttcttg aattacaatt ttataccctc 4260
ccctccccaa cttgttctgc gccttctgac ccttcttgtt ttgtttgcta gtttaccctg 4320
taggaaaaag tatcactcta ctcaaatagt attttcacct cttctggcca taaataattt 4380
tggcctaatt cag 4393

SEQ ID NO: 105 moltype = DNA length = 4389
FEATURE Location/Qualifiers
misc_feature 1..4389
note = Synthetic polynucleotide
source 1..4389
mol_type = other DNA
organism = synthetic construct
SEQUENCE: 105
gacttttgac tctctctctc tctctctcta cagtagtagt agtagtattc attcatattc 60
atacttgata tcatgtatct ctctctctct ctctctaatg gcagagctag ctcagaccct 120
taacacagac cacagcctct gagagaaacc actctcactc tcactctcct taacctttca 180
ccttccatat ctggcgaaaa tgaaagctct gtacagaagc tctctcttgc tcctcttctt 240
cctctccgtc tgttctgcat cttcttcttc ggttcccact ctgcaactcc taagcttcaa 300
aaactctctc ccgaacccaa ccctgctccc gaactggctc ccgaaccaaa gcccatgctc 360
attcaccggc atcacctgca acgacaccca gcacctcact tccatagacc tctccggcgt 420
ccctctcacc acaaacctca ccgtcatcgc caccttcctc ctcaccctcg acaacctcca 480
gtcactctcc ttaaaatcca ccaacctctc cggccccgcc gccatgcctc ctcctctctc 540
ccactccaag tgcgcctcca cattaacctc cctagatcta tcacaaaacg ccctctccgg 600
ttccctcaac gacatgtcgt ttctctcctc ctgctccaac ctccaatccc tcaatctctc 660
cagcaacctt cttgaattcg actcctctca ctggaagctc cacctcctcg tcgccgactt 720
ttcctacaac aagatttccg gccccggtat cctcccctgg cttctcaacc ctgaaatcga 780
acacctcgct ctgaaaggca acaaagtcac cggcgaaacc gacttctccg gttccaattc 840
tctccagttt ttagaccttt cttccaacaa cttttctgtt acgcttccta ctttcggcga 900
gtgttcttcg cttgagtatt tggacctctc cgccaacaag tacttcggcg acattgctcg 960
cactctctcg ccttgcaaga acctcgttta cttaaacttc tccagcaacc agttctccgg 1020
tccggttcct tcccttccct ccggttcgct acagttcgtg taccttgctt caaaccactt 1080
ccacggccag attcctctcc ccctcgccga cctctgctcc actctcctcc agctcgatct 1140
ctcctccaac aacctctcag gcgctctccc gaagccttcg gcgcttgcac ttctcttcag 1200
tccttcgaca tctccagcaa cctcttcgcc ggtgcgctgc ctatggacgt tctcacgcaa 1260
atgaaaagcc tcaaagagct cgcggtggcg ttcaacgcgt tccttggtcc ccttccggag 1320
tctctgacga agctctccac tttagagtcg ctggatctta gctccaacaa cttcagcggc 1380
tcaatcccga caacgctgtg cggtggtgac gctgggaata ataatattct gaaggaactt 1440
tacctgcaga acaaccggtt cacgggtttt attccaccca cgctcagcaa ctgttcaaac 1500
ctcgttgctt tggacttgag tttcaacttc ctcacgggaa ctattcctcc aagcctaggg 1560
tctctttcca agcttaaaga cttgatcatc tggctcaacc agctccatgg agaaataccg 1620

```
caggagctca tgtatctgaa aagcctcgag aatttgatcc tggatttcaa cgacttgact  1680
gggaacattc cctctgggct tgttaactgc accaagctga actggatctc cctctccaac  1740
aacaggctca gcggcgagat tccgcggtgg attgggaagc tttctaatct cgccatactt  1800
aagctcagta ataactcttt ctccggccgg attccgccgg agctcggcga ttgtactagt  1860
ttaatatggt tggatctgaa tactaatatg ctcaccgggc ccattccgcc ggagctgttc  1920
aagcagtcgg ggaagatcgc ggtgaatttc atcagtggga agacgtatgt gtatataaag  1980
aacgatggga gcaaagagtg tcatggtgcg gggaacttgc tggagttgc cgggatcagt  2040
cagcagcagt tgaacaggat ttcgacgagg aacccgtgca atttcactag ggtttatgga  2100
ggtaagttgc agccaacgtt taaccataat ggttctatga tatttttgga tatctcgcac  2160
aacatgttgt cagggagtat tcccaaggag attggggcca tgtactattt gtacattctc  2220
aatttgggtc ataataatgt gtctgggagc attcctcaag agcttgggaa gatgaagaat  2280
ctcaacatcc ttgatctctc aagtaataga ctggaggggc aaattcctca gagtctcacg  2340
gggctttcct tgctcactga gattgacctg tcgaataact tgcttacggg gacgattcct  2400
gagtcgggtc aatttgatac tttccctgcg gcgagatttc agaacaactc tggtctctgt  2460
ggagttcctc tcggcccatg tggttcggac ccggcgaata acgggaatgc gcaacatatg  2520
aagtctcaca ggaggcaggc ttctctggtg gggagtgtgg ccatgggttt gttgttttcc  2580
ctcttctgcg tctttggttt gatcattatt gccattgaga ccaggaagag gaggaagaag  2640
aaggaggctg ctcttgaagc ctatgctgat ggtaatttgc attcgggtcc tgccaacgtg  2700
agctggaagc acaccagtac ccgggaagcg cttagcataa accttgcaac gtttaagagg  2760
ccgctcagga ggcttacttt tgcggacctt cttgacgcta ccaatggctt tcacaatgat  2820
agtctcattg gctctggtgg gtttggggat gtttacaagg ctcagttgaa ggatggaagt  2880
gttgtggcta tcaagaagct gattcatgtc agcggccaag gggacaggga attcactgct  2940
gaaatggaga ccattgggaa gatcaagcac aggaaccttg ttcctctgtt gggatactgc  3000
aaggttgggg aagagaggct cttggtttat gagtacatga aatatggaag cttagaggat  3060
gttcttcatg atccgaagaa agctgggatc aagttgaatt ggtcgattag gaggaaaatt  3120
gctattggag ctgctagggg attgtctttt cttcaccaca attgtagccc ccacatcatt  3180
catagagaca tgaagtcaag caatgtgtta cttgatgaaa acctggaagc tagagtctct  3240
gattttggaa tggctaggca tatgagtgct atggatacac atttgagtgt gagcacactg  3300
gcaggcacac cagggtatgt tcctccggag tactatgaga gcttcagatg ctctaccaaa  3360
ggtgatgtct acagttatgg tgtggttttg ttggagctgc taactgggaa aaggccaaca  3420
gattcggctg attttggtga taataatctt gttggatggg ttaaacaaca tgccaagctg  3480
aaaataagtg atatttttga cccagagctc atgaaggaag accccaattt ggagatggag  3540
cttttgcagc acctgaagat tgcagtttcc tgtttggatg atcggcattg gagacgtcca  3600
acgatgattc aagtgttgac aatgttcaag gagattcagg caggatctgg gattgattct  3660
cagtcaacca tagccaatga agatgacagt ttcaatgcag ttgaaatggt ggagatgagc  3720
attaaagaaa cccctgaatt gagcaagcat taggcaacaa attccggaag tgtcatgtgg  3780
attctttggg aaacagacaa gaagagagaa aaggaggaga tgacggattc agctcccctc  3840
aaagtttttt ccttcctctt tgccgcttca aattatttca gacacaaggg ggaaacggtt  3900
aaagggggaa tgaatgcctt tgatgtatgt agtcttgtta ttttatacaa aaaaaaaaag  3960
ttgtttaact tgtatataaa cagcttcagt tgttaccatc tgtgttttcc tagaattttc  4020
aaaagtactt ttctcattca gatataatcc tgaaaaggat ctctgttcaa tctggcgacc  4080
ccagtgatgg cgactaagtg gaggatcttt tggccatttc tttaggcctc ttgatttgtt  4140
tcccccattt gatcaactgc aacttttgct ccgatttgcg atataatttg tcaaaacatg  4200
cttcttctaa aatcactcat aacataaatt ttcttgaatt acaattttat accctcccct  4260
ccccaacttg ttctgcgcct tctgaccctt cttgttttgt ttgctagttt accctgtagg  4320
aaaaagtatc actctactca aatagtattt tcacctcttc tggccataaa taattttggc  4380
ctaattcag                                                          4389

SEQ ID NO: 106          moltype = DNA  length = 4413
FEATURE                 Location/Qualifiers
misc_feature            1..4413
                        note = Synthetic polynucleotide
source                  1..4413
                        mol_type = other DNA
                        organism = synthetic construct
SEQUENCE: 106
gacttttgac tctctctctc tctctctcta cagtagtagt agtagtattc attcatattc  60
atacttgata tcatgtcaca cacatattca tacttgatat catgtcacta tctctctctc  120
tctggcagag ctagctcaga cccttaacac agaccacagc ctctgagaga aaccactctc  180
actctcactc tccttaacct ttcaccttcc atatctggcg aaaatgaaag ctctgtacag  240
aagctctctc ttgctcctct tcttcctctc cgtctgttct gcatcttctt cttcggttcc  300
cactctgcaa ctcctaagct tcaaaaactc tctcccgaac ccaaccctgc tcccgaactg  360
gctcccgaac caaagcccat gctcattcac cggcatcacc tgcaacgaca cccagcacct  420
cacttccata gacctctccg gcgtccctct caccacaaac ctcaccgtca tcgccacctt  480
cctcctcacc ctcgacaacc tccagtcact ctccttaaaa tccaccaacc tctccggccc  540
cgccgccatg cctcctcctc tctcccactc caagtgcgcc tccacattaa cctccctaga  600
tctatcacaa aacgccctct ccggttccct caacgacatg tcgtttctct cctcctgctc  660
caacctccaa tccctcaatc tctccagcaa ccttcttgaa ttcgactcct ctcactggaa  720
gctccacctc ctcgtcgccg acttttccta caacaagatt tccggccccg gtatcctccc  780
ctggcttctc aaccctgaaa tcgaacacct cgctctgaaa ggcaacaaag tcaccggcga  840
aaccgacttc tccggttcca attctctcca gtttttagac ctttcttcca acaacttttc  900
tgttacgctt cctactttcg gcgagtgttc ttcgcttgag tatttggacc tctccgccaa  960
caagtacttc ggcgacattg ctcgcactct ctcgccttgc aagaacctcg tttacttaaa  1020
cttctccagc aaccagttct ccggtccggt tccttccctt ccctccggtt cgctacagtt  1080
cgtgtacctt gcttcaaacc acttccacgg ccagattcct ctccccctcg ccgacctctg  1140
ctccactctc ctccagctcg atctctcctc caacaacctc tcaggcgctc tcccgaagcc  1200
ttcggcgctt gcacttctct tcagtccttc gacatctcca gcaacctctt cgccggtgcg  1260
ctgcctatgg acgttctcac gcaaatgaaa agcctcaaag agctcgcggt ggcgttcaac  1320
gcgttccttg gtccccttcc ggagtctctg acgaagctct ccactttaga gtcgctggat  1380
```

```
cttagctcca acaacttcag cggctcaatc ccgacaacgc tgtgcggtgg tgacgctggg  1440
aataataata ttctgaagga actttacctg cagaacaacc ggttcacggg ttttattcca  1500
cccacgctca gcaactgttc aaacctcgtt gctttggact tgagtttcaa cttcctcacg  1560
ggaactattc ctccaagcct agggtctctt tccaagctta aagacttgat catctggctc  1620
aaccagctcc atggagaaat accgcaggag ctcatgtatc tgaaaagcct cgagaatttg  1680
atcctggatt tcaacgactt gactgggaac attccctctg ggcttgttaa ctgcaccaag  1740
ctgaactgga tctccctctc caacaacagg ctcagcggcg agattccgcg gtggattggg  1800
aagctttcta atctcgccat acttaagctc agtaataact ctttctccgg ccggattccg  1860
ccggagctcg gcgattgtac tagtttaata tggttggatc tgaatactaa tatgctcacc  1920
gggcccattc cgccggagct gttcaagcag tcggggaaga tcgcggtgaa tttcatcagt  1980
gggaagacgt atgtgtatat aaagaacgat gggagcaaag agtgtcatgg tgcggggaac  2040
ttgctggagt ttgccgggat cagtcagcag cagttgaaca ggatttcgac gaggaacccg  2100
tgcaatttca ctagggttta tggaggtaag ttgcagccaa cgtttaacca taatggttct  2160
atgatatttt tggatatctc gcacaacatg ttgtcaggga gtattcccaa ggagattggg  2220
gccatgtact atttgtacat tctcaatttg ggtcataata atgtgtctgg gagcattcct  2280
caagagcttg ggaagatgaa gaatctcaac atccttgatc tctcaagtaa tagactggag  2340
gggcaaattc ctcagagtct cacggggctt tccttgctca ctgagattga cctgtcgaat  2400
aacttgctta cggggacgat tcctgagtcg ggtcaatttg atactttccc tgcggcgaga  2460
tttcagaaca actctggtct ctgtggagtt cctctcggcc catgtggttc ggacccggcg  2520
aataacggga atgcgcaaca tatgaagtct cacaggaggc aggcttctct ggtggggagt  2580
gtggccatgg gtttgttgtt ttccctcttc tgcgtctttg gtttgatcat tattgccatt  2640
gagaccagga agaggaggaa gaagaaggag gctgctcttg aagcctatgc tgatggtaat  2700
ttgcattcgg gtcctgccaa cgtgagctgg aagcacacca gtacccggga agcgcttagc  2760
ataaaccttg caacgtttaa gaggccgctc aggaggctta cttttgcgga ccttcttgac  2820
gctaccaatg gctttcacaa tgatagtctc attggctctg gtgggtttgg ggatgtttac  2880
aaggctcagt tgaaggatgg aagtgttgtg gctatcaaga agctgattca tgtcagcggc  2940
caaggggaca gggaattcac tgctgaaatg gagaccattg ggaagatcaa gcacaggaac  3000
cttgttcctc tgttgggata ctgcaaggtt ggggaagaga ggctcttggt ttatgagtac  3060
atgaaatatg gaagcttaga ggatgttctt catgatccga agaaagctgg gatcaagttg  3120
aattggtcga ttaggaggaa aattgctatt ggagctgcta ggggattgtc ttttcttcac  3180
cacaattgta gcccccacat cattcataga gacatgaagt caagcaatgt gttacttgat  3240
gaaaacctgg aagctagagt ctctgatttt ggaatggcta ggcatatgag tgctatggat  3300
acacatttga gtgtgagcac actggcaggc acaccagggt atgttcctcc ggagtactat  3360
gagagcttca gatgctctac caaaggtgat gtctacagtt atggtgtggt tttgttggag  3420
ctgctaactg ggaaaaggcc aacagattcg gctgattttg gtgataataa tcttgttgga  3480
tgggttaaac aacatgccaa gctgaaaata agtgatattt ttgacccaga gctcatgaag  3540
gaagacccca atttggagat ggagcttttg cagcacctga agattgcagt ttcctgtttg  3600
gatgatcggc attggagacg tccaacgatg attcaagtgt tgacaatgtt caaggagatt  3660
caggcaggat ctgggattga ttctcagtca accatagcca atgaagatga cagtttcaat  3720
gcagttgaaa tggtggagat gagcattaaa gaaacccctg aattgagcaa gcattaggca  3780
acaaattccg gaagtgtcat gtggattctt tgggaaacag acaagaagag agaaaaggag  3840
gagatgacgg attcagctcc cctcaaagtt ttttccttcc tctttgccgc ttcaaattat  3900
ttcagacaca agggggaaac ggttaaaggg ggaatgaatg cctttgatgt atgtagtctt  3960
gttattttat acaaaaaaaa aaagttgttt aacttgtata taaacagctt cagttgttac  4020
catctgtgtt ttcctagaat tttcaaaagt acttttctca ttcagatata atcctgaaaa  4080
ggatctctgt tcaatctggc gaccccagtg atggcgacta agtggaggat cttttggcca  4140
tttctttagg cctcttgatt tgtttccccc atttgatcaa ctgcaacttt tgctccgatt  4200
tgcgatataa tttgtcaaaa catgcttctt ctaaaatcac tcataacata aattttcttg  4260
aattacaatt ttataccctc ccctccccaa cttgttctgc gccttctgac ccttcttgtt  4320
ttgtttgcta gtttaccctg taggaaaaag tatcactcta ctcaaatagt attttcacct  4380
cttctggcca taaataattt tggcctaatt cag                              4413
```

```
SEQ ID NO: 107          moltype = DNA  length = 4389
FEATURE                 Location/Qualifiers
misc_feature            1..4389
                        note = Synthetic polynucleotide
source                  1..4389
                        mol_type = other DNA
                        organism = synthetic construct
SEQUENCE: 107
gactttgac tctctctctc tctctctcta cagtagtagt agtagtattc attcatattc  60
atacttgata tcatgtatct ctctctctct ctctctaatg gcagagctag ctcagaccct  120
taacacagac cacagcctct gagagaaacc actctcactc tcactctcct taacctttca  180
ccttccatat ctggcgaaaa tgaaagctct gtacagaagc tctctcttgc tcctcttctt  240
cctctccgtc tgttctgcat cttcttcttc ggttcccact ctgcaactcc taagcttcaa  300
aaactctctc ccgaacccaa ccctgctccc gaactggctc ccgaaccaaa gcccatgctc  360
attcaccggc atcacctgca acgacaccca gcacctcact tccatagacc tctccggcgt  420
ccctctcacc acaaacctca ccgtcatcgc caccttcctc ctcaccctcg acaacctcca  480
gtcactctcc ttaaaatcca ccaacctctc cggccccgcc gccatgcctc ctcctctctc  540
ccactccaag tgcgcctcca cattaacctc cctagatcta tcacaaaacg ccctctccgg  600
ttccctcaac gacatgtcgt ttctctcctc ctgctccaac ctccaatccc tcaatctctc  660
cagcaacctt cttgaattcg actcctctca ctggaagctc cacctcctcg tcgccgactt  720
ttcctacaac aagatttccg gccccggtat cctcccctgg cttctcaacc ctgaaatcga  780
acacctcgct ctgaaaggca acaaagtcac cggcgaaacc gacttctccg gttccaattc  840
tctccagttt ttagaccttt cttccaacaa cttttctgtt acgcttccta ctttcggcga  900
gtgttcttcg cttgagtatt tggacctctc cgccaacaag tacttcggcg acattgctcg  960
cactctctcg ccttgcaaga acctcgttta cttaaacttc tccagcaacc agttctccgg  1020
tccggttcct tcccttccct ccggttcgct acagttcgtg taccttgctt caaaccactt  1080
ccacggccag attcctctcc ccctcgccga cctctgctcc actctcctcc agctcgatct  1140
```

```
ctcctccaac aacctctcag gcgctctccc gaagccttcg gcgcttgcac ttctcttcag  1200
tccttcgaca tctccagcaa cctcttcgcc ggtgcgctgc ctatggacgt tctcacgcaa  1260
atgaaaagcc tcaaagagct cgcggtggcg ttcaacgcgt tccttggtcc ccttccggag  1320
tctctgacga agctctccac tttagagtcg ctggatctta gctccaacaa cttcagcggc  1380
tcaatcccga caacgctgtg cggtggtgac gctgggaata ataatattct gaaggaactt  1440
tacctgcaga acaaccggtt cacgggtttt attccaccca cgctcagcaa ctgttcaaac  1500
ctcgttgctt tggacttgag tttcaacttc ctcacgggaa ctattcctcc aagcctaggg  1560
tctctttcca agcttaaaga cttgatcatc tggctcaacc agctccatgg agaaataccg  1620
caggagctca tgtatctgaa aagcctcgag aatttgatcc tggatttcaa cgacttgact  1680
gggaacattc cctctgggct tgttaactgc accaagctga actggatctc cctctccaac  1740
aacaggctca gcggcgagat tccgcggtgg attgggaagc tttctaatct cgccatactt  1800
aagctcagta ataactcttt ctccggccgg attccgccgg agctcggcga ttgtactagt  1860
ttaatatggt tggatctgaa tactaatatg ctcaccgggc ccattccgcc ggagctgttc  1920
aagcagtcgg ggaagatcgc ggtgaatttc atcagtggga agacgtatgt gtatataaag  1980
aacgatggga gcaaagagtg tcatggtgcg gggaacttgc tggagtttgc cgggatcagt  2040
cagcagcagt tgaacaggat ttcgacgagg aacccgtgca atttcactag ggtttatgga  2100
ggtaagttgc agccaacgtt taaccataat ggttctatga tatttttgga tatctcgcac  2160
aacatgttgt cagggagtat tcccaaggag attggggcca tgtactattt gtacattctc  2220
aatttgggtc ataataatgt gtctgggagc attcctcaag agcttgggaa gatgaagaat  2280
ctcaacatcc ttgatctctc aagtaataga ctggaggggc aaattcctca gagtctcacg  2340
gggctttcct tgctcactga gattgacctg tcgaataact tgcttacggg gacgattcct  2400
gagtcgggtc aatttgatac tttccctgcg gcgagatttc agaacaactc tggtctctgt  2460
ggagttcctc tcggcccatg tggttcggac ccggcgaata acgggaatgc gcaacatatg  2520
aagtctcaca ggaggcaggc ttctctggtg gggagtgtgg ccatgggttt gttgtttcc  2580
ctcttctgcg tctttggttt gatcattatt gccattgaga ccaggaagag gaggaagaag  2640
aaggaggctg ctcttgaagc ctatgctgat ggtaatttgc attcgggtcc tgccaacgtg  2700
agctggaagc acaccagtac ccgggaagcg cttagcataa accttgcaac gtttaagagg  2760
ccgctcagga ggcttacttt tgcggacctt cttgacgcta ccaatggctt tcacaatgat  2820
agtctcattg gctctggtgg gtttggggat gtttacaagg ctcagttgaa ggatggaagt  2880
gttgtggcta tcaagaagct gattcatgtc agcggccaag gggacaggga attcactgct  2940
gaaatggaga ccattgggaa gatcaagcac aggaaccttg ttcctctgtt gggatactgc  3000
aaggttgggg aagagaggct cttggtttat gagtacatga aatatggaag cttagaggat  3060
gttcttcatg atccgaagaa agctgggatc aagttgaatt ggtcgattag gaggaaaatt  3120
gctattggag ctgctagggg attgtctttt cttcaccaca attgtagccc ccacatcatt  3180
catagagaca tgaagtcaag caatgtgtta cttgatgaaa acctggaagc tagagtctct  3240
gattttggaa tggctaggca tatgagtgct atggatacac atttgagtgt gagcacactg  3300
gcaggcacac cagggtatgt tcctccggag tactatgaga gcttcagatg ctctaccaaa  3360
ggtgatgtct acagttatgg tgtggttttg ttggagctgc taactgggaa aaggccaaca  3420
gattcggctg attttggtga taataatctt gttggatggg ttaaacaaca tgccaagctg  3480
aaaataagtg atatttttga cccagagctc atgaaggaag accccaattt ggagatggag  3540
cttttgcagc acctgaagat tgcagtttcc tgtttggatg atcggcattg gagacgtcca  3600
acgatgattc aagtgttgac aatgttcaag gagattcagg caggatctgg gattgattct  3660
cagtcaacca tagccaatga agatgacagt ttcaatgcag ttgaaatggt ggagatgagc  3720
attaaagaaa cccctgaatt gagcaagcat taggcaacaa attccggaag tgtcatgtgg  3780
attctttggg aaacagacaa gaagagagaa aaggaggaga tgacggattc agctcccctc  3840
aaagtttttt ccttcctctt tgccgcttca aattatttca gacacaaggg ggaaacggtt  3900
aaagggggaa tgaatgcctt tgatgtatgt agtcttgtta ttttatacaa aaaaaaaaag  3960
ttgtttaact tgtatataaa cagcttcagt tgttaccatc tgtgttttcc tagaattttc  4020
aaaagtactt ttctcattca gatataatcc tgaaaaggat ctctgttcaa tctggcgacc  4080
ccagtgatgg cgactaagtg gaggatcttt tggccatttc tttaggcctc ttgatttgtt  4140
tcccccattt gatcaactgc aacttttgct ccgatttgcg atataatttg tcaaaacatg  4200
cttcttctaa aatcactcat aacataaatt ttcttgaatt acaattttat accctcccct  4260
ccccaacttg ttctgcgcct tctgaccctt cttgttttgt ttgctagttt accctgtagg  4320
aaaaagtatc actctactca aatagtattt tcacctcttc tggccataaa taattttggc  4380
ctaattcag                                                          4389
```

```
SEQ ID NO: 108          moltype = DNA  length = 4237
FEATURE                 Location/Qualifiers
misc_feature            1..4237
                        note = Synthetic polynucleotide
source                  1..4237
                        mol_type = other DNA
                        organism = synthetic construct
SEQUENCE: 108
gtagatacaa ggagagtgga aataggaaaa aatagcttag agagatttat ttacgaacag  60
gaagagtcac atggcatgtg tccagtcttc cacatgataa ataccttct taccttcctt  120
actaggactt ttgactctct ctctctctat ctatggtagt agtagtagta gtattcattc  180
attctctcta atggcagagc tcacacccta aacacaaacc agagcctctg agagaaacaa  240
ccacaaactc tcccttaatc ttgtcggttt ccatatctgc tgaaaatgaa agctctgtac  300
agaagctctc tcttgctctt gctcttgctc ttcatctccg tgtgttttgc atcttcttct  360
tctccggtca ctcagcaact cctaagcttc aaaaactctc tcccgaaccc atccctgctc  420
cccaactggc tccctaacca aagcccgtgc acattcagcg gcatcagctg caacgacaca  480
gagctcacat ccatagacct cagctccgtc cctctcagca ctaacctaac cgtcatcgcc  540
agcttcctcc ttagcctgga ccacctccag tcactctcct taaaatccac caacctctcc  600
ggtcccgccg ccatgcctcc tctctcccac tcccagtgct cctcctcatt aacctcccta  660
gatctctccc aaaactccct ctctgcctcc ctcaacgaca tgtcgtttct cgcctcctgc  720
tccaacctcc aatccctcaa cctctcctcc aacctcctcc aattcggccc cccgccccac  780
tggaagctcc accacctccg cttcgccgac ttctcttaca acaagatttc cggccccggc  840
gtcgtttctt ggcttctcaa ccccgtcatc gaactcctct ctctcaaagg caacaaagtc  900
```

```
accggcgaaa ccgacttctc cggctcaatt tctctccagt atttagacct ttcttccaac  960
aacttttctg ttacgcttcc tactttcggc gagtgttctt cgcttgagta tttggacctc  1020
tccgctaaca agtacttggg cgacattgca cgcactctct ccccttgcaa gagcctcgtt  1080
taccttaacg tctccagcaa ccagttctcc ggtccggttc cttcccttcc ctccggttcg  1140
ctacagtttg tgtaccttgc tgcaaaccac ttccacggcc agattcctct ctccctcgcc  1200
gacctctgct ccactctcct ccagctcgat ctctcctcca acaatctcac cggcgctctt  1260
cccggcgcgt tcggcgcgtg cacttctctt caatcccttg acatctccag caacctcttc  1320
gccggcgcgt tgccgatgtc ggttctcacg caaatgacca gcctgaaaga gctcgcggtt  1380
gcgttcaacg gcttcctcgg tgctctcccg gagtctctgt cgaagctctc cgctctggag  1440
ttgctggatc tgagctccaa caactttagc ggctcaatcc ccgcctcgct gtgcggcggc  1500
ggtgacgctg ggattaataa taatctgaag gaactttatc tgcagaataa ccggttcacg  1560
ggttttattc cgcccacgct cagcaactgt tcaaacctcg ttgctttgga tttgagtttc  1620
aacttcctca cggggactat tcctccgagc ctagggtctc tttcgaatct caaagacttc  1680
atcatctggc tcaaccagct ccacggggag ataccgcagg agctcatgta tcttaaaagc  1740
ctcgagaatt tgatcctgga tttcaacgac ttgactggga acattccctc tggcctcgtt  1800
aactgcacca agttgaactg gatctccctc tccaacaaca ggctcagcgg cgagattccg  1860
ccgtggattg ggaagctttc taatctcgcc atactcaagc tcagcaataa ctctttctcc  1920
ggccggattc cgcccggagct cggcgactgt actagtttaa tatggttgga tctgaataca  1980
aatatgctca ccgggcccat tccgccggag ctgttcaagc agtcggggaa gatcgccgtg  2040
aatttcatca gtgggaagac gtatgtgtat ataaagaacg atgggagcaa ggagtgccat  2100
ggtgcgggga acttgcttga gtttgcgggg atcagtcagc agcagctgaa caggatttcg  2160
acgaggaacc cctgcaattt cactagggtt tatggaggta agttgcagcc aacgtttaac  2220
cataatggtt ctatgatatt tttggatatc tcgcacaaca tgttgtcagg gagtattccc  2280
aaggagattg gggccatgta ctatttgtac attctcaatt tgggtcacaa taatgtgtct  2340
gggagcattc ctcaagagct tgggaagatg aagaatctca acattcttga tctgtcgaat  2400
aatagactgg agggccaaat tccgcagagc ctcacggggc tttctttgct cactgagatt  2460
gacttgtcca acaacttgct taccgggacg attcctgagt cgggtcaatt tgatactttc  2520
cctgcggcga agtttcagaa caactctggt ctatgtggag ttcctctggg tccgtgtggt  2580
tcggagccgg caaacaatgg aaatgcgcaa catatgaagt ctcacaggag gcaggcttct  2640
ctggcgggga gtgtggccat ggggttgttg ttttccctct tttgcgtctt tggtttgatc  2700
attattgcca ttgagaccag gaagaggagg aagaagaagg aggctgctct tgaagcctat  2760
ggtgatggta attcccattc gggtccggcc aatgtgagct ggaagcacac cagtactcgg  2820
gaagctctta gcataaacct tgcaacattt gagaagccgc tccggaagct tacttttgcg  2880
gaccttcttg acgctaccaa tggttttcac aacgacagtc tcattggctc tggcgggttt  2940
ggggatgtgt acaaggctca gttgaaggat ggaagtgttg tggctatcaa gaagctgatt  3000
catgttagcg gacaagggga cagggaattc accgctgaaa tggagactat tgggaaaatc  3060
aagcacagga accttgttcc cctgttggga tactgcaagg taggggaaga gaggctcttg  3120
gtttatgagt acatgaaata tggaagttta gaggatgttc tacatgatca gaagaaagct  3180
gggatcaagc tgaactgggc cattaggcgg aaaattgcta ttggagctgc taggggattg  3240
tcttttcttc accacaattg tatcccccac atcattcata gagatatgaa gtcgagcaat  3300
gtgttacttg atgaaaacct ggaagccaga gtctctgatt ttggaatggc taggcttatg  3360
agtgctatgg atacacattt gagtgtgagc acattggctg gcacaccggg gtatgttcct  3420
cccgagtact atcagagctt cagatgctcc acaaaaggtg atgtctacag ttatggtgtg  3480
gttttgttgg agctgctaac tgggaaaagg ccaacggact cggctgattt tggagataat  3540
aatcttgttg gatgggttaa acaacatgcc aagctgaaaa tcagtgatat ttttgacccg  3600
gagctcatga aggaagaccc caatctggag atggagcttt tgcagcactt gaagattgcg  3660
gtttcctgtt tggatgatcg accgtggagg cgtccgacga tgattcaagt gatggcaatg  3720
ttcaaggaga ttcaggcggg atccgggatt gattctcagt caaccatagc caatgacgag  3780
gaaggtttca atgcagttga aatggtggag atgagcatta aagaagcccc tgaattgagc  3840
aagcattagg cattaaagtg tcgtgtggat tctttgggaa acagacaaga agagaggagg  3900
agatgacgga ttcagctccc ctcagttttt tccttctttg ccgcttcaaa ttatttcaga  3960
cataagggaa aacggttaaa aggggaatga atgcttttga tgtatgtatt cttgttattt  4020
tatacataaa aaaaagttgt ttaacttgta tataaacagc ttcagttgtt accatctgtg  4080
ttttcctaga attttcaaag tacttttctc attcaaatat aatcctgaaa aggttctctg  4140
ttcaatctgc gaccccagtg atggcaacta agtggatcaa cagcaacttt tgctccgatt  4200
tgcgatataa tttgtcaaaa catgcctcta aaatcac                           4237

SEQ ID NO: 109          moltype = DNA  length = 4220
FEATURE                 Location/Qualifiers
misc_feature            1..4220
                        note = Synthetic polynucleotide
source                  1..4220
                        mol_type = other DNA
                        organism = synthetic construct
SEQUENCE: 109
gtagatagga aaaaatagct tagagagatt tatttacgaa caggaagagt cacatggcat  60
gtgtccagtc ttccacatga taaataccct tcttaccttc cttactagga cttttgactc  120
tctctctctc tatctatggt agtagtagta gtagtattca ttcattctct ctaatggcag  180
agctcacacc ctaaacacaa accagagcct ctgagagaaa caaccacaaa ctctccctta  240
atcttgtcgg tttccatatc tgctgaaaat gaaagctctg tacagaagct ctctcttgct  300
cttgctcttg ctcttcatct ccgtgtgttt tgcatcttct tcttctccgg tcactcagca  360
actcctaagc ttcaaaaact ctctcccgaa cccatccctg ctccccaact ggctccctaa  420
ccaaagcccg tgcacattca gcggcatcag ctgcaacgac acagagctca catccataga  480
cctcagctcc gtccctctca gcactaacct aaccgtcatc gccagcttcc tccttagcct  540
ggaccacctc cagtcactct ccttaaaatc caccaacctc tccggtcccg ccgccatgcc  600
tcctctctcc cactcccagt gctcctcctc attaacctcc ctagatctct cccaaaactc  660
cctctctgcc tccctcaacg acatgtcgtt tctcgcctcc tgctccaacc tccaatccct  720
caacctctcc tccaacctcc tccaattcgg cccccgcccc cactggaagc tccaccacct  780
ccgcttcgcc gacttctctt acaacaagat ttccggcccc ggcgtcgttt cttggcttct  840
```

```
caaccccgtc atcgaactcc tctctctcaa aggcaacaaa gtcaccggcg aaaccgactt 900
ctccggctca atttctctcc agtatttaga cctttcttcc aacaactttt ctgttacgct 960
tcctactttc ggcgagtgtt cttcgcttga gtatttggac ctctccgcta acaagtactt 1020
gggcgacatt gcacgcactc tctccccttg caagagcctc gtttacctta acgtctccag 1080
caaccagttc tccggtccgg ttccttccct tccctccggt tcgctacagt ttgtgtacct 1140
tgctgcaaac cacttccacg gccagattcc tctctccctc gccgacctct gctccactct 1200
cctccagctc gatctctcct ccaacaatct caccggcgct cttcccggcg cgttcggcgc 1260
gtgcacttct cttcaatccc ttgacatctc cagcaacctc ttcgccggcg cgttgccgat 1320
gtcggttctc acgcaaatga ccagcctgaa agagctcgcg gttgcgttca acggcttcct 1380
cggtgctctc ccggagtctc tgtcgaagct ctccgctctg gagttgctgg atctgagctc 1440
caacaacttt agcggctcaa tccccgcctc gctgtgcggc ggcggtgacg ctgggattaa 1500
taataatctg aaggaacttt atctgcagaa taaccggttc acgggtttta ttccgcccac 1560
gctcagcaac tgttcaaacc tcgttgcttt ggatttgagt ttcaacttcc tcacggggac 1620
tattcctccg agcctagggt ctctttcgaa tctcaaagac ttcatcatct ggctcaacca 1680
gctccacggg gagataccgc aggagctcat gtatcttaaa agcctcgaga atttgatcct 1740
ggatttcaac gacttgactg ggaacattcc ctctggcctc gttaactgca ccaagttgaa 1800
ctggatctcc ctctccaaca acaggctcag cggcgagatt ccgccgtgga ttgggaagct 1860
ttctaatctc gccatactca agctcagcaa taactctttc tccggccgga ttccgccgga 1920
gctcggcgac tgtactagtt taatatggtt ggatctgaat acaaatatgc tcaccgggcc 1980
cattccgccg gagctgttca agcagtcggg gaagatcgcc gtgaatttca tcagtgggaa 2040
gacgtatgtg tatataaaga acgatgggag caaggagtgc catggtgcgg ggaacttgct 2100
tgagtttgcg gggatcagtc agcagcagct gaacaggatt tcgacgagga acccctgcaa 2160
tttcactagg gtttatggag gtaagttgca gccaacgttt aaccataatg gttctatgat 2220
atttttggat atctcgcaca acatgttgtc agggagtatt cccaaggaga ttggggccat 2280
gtactatttg tacattctca atttgggtca caataatgtg tctgggagca ttcctcaaga 2340
gcttgggaag atgaagaatc tcaacattct tgatctgtcg aataatagac tggagggcca 2400
aattccgcag agcctcacgg ggctttcttt gctcactgag attgacttgt ccaacaactt 2460
gcttaccggg acgattcctg agtcgggtca atttgatact ttccctgcgg cgaagtttca 2520
gaacaactct ggtctatgtg gagttcctct gggtccgtgt ggttcggagc cggcaaacaa 2580
tggaaatgcg caacatatga agtctcacag gaggcaggct tctctggcgg ggagtgtggc 2640
catggggttg ttgttttccc tcttttgcgt ctttggtttg atcattattg ccattgagac 2700
caggaagagg aggaagaaga aggaggctgc tcttgaagcc tatggtgatg gtaattccca 2760
ttcgggtccg gccaatgtga gctggaagca caccagtact cgggaagctc ttagcataaa 2820
ccttgcaaca tttgagaagc cgctccggaa gcttactttt gcggaccttc ttgacgctac 2880
caatggtttt cacaacgaca gtctcattgg ctctggcggg tttggggatg tgtacaaggc 2940
tcagttgaag gatggaagtg ttgtggctat caagaagctg attcatgtta gcggacaagg 3000
ggacagggaa ttcaccgctg aaatggagac tattgggaaa atcaagcaca ggaaccttgt 3060
tcccctgttg ggatactgca aggtagggga agagaggctc ttggtttatg agtacatgaa 3120
atatggaagt ttagaggatg ttctacatga tcagaagaaa gctgggatca agctgaactg 3180
ggccattagg cggaaaattg ctattggagc tgctagggga ttgtcttttc ttcaccacaa 3240
ttgtatcccc cacatcattc atagagatat gaagtcgagc aatgtgttac ttgatgaaaa 3300
cctggaagcc agagtctctg attttggaat ggctaggctt atgagtgcta tggatacaca 3360
tttgagtgtg agcacattgg ctggcacacc ggggtatgtt cctcccgagt actatcagag 3420
cttcagatgc tccacaaaag gtgatgtcta cagttatggt gtggttttgt tggagctgct 3480
aactgggaaa aggccaacgg actcggctga ttttggagat aataatcttg ttggatgggt 3540
taaacaacat gccaagctga aaatcagtga tatttttgac ccggagctca tgaaggaaga 3600
ccccaatctg gagatggagc ttttgcagca cttgaagatt gcggtttcct gtttggatga 3660
tcgaccgtgg aggcgtccga cgatgattca agtgatggca atgttcaagg agattcaggc 3720
gggatccggg attgattctc agtcaaccat agccaatgac gaggaaggtt tcaatgcagt 3780
tgaaatggtg gagatgagca ttaaagaagc ccctgaattg agcaagcatt aggcattaaa 3840
gtgtcgtgtg gattctttgg gaaacagaca agaagagagg aggagatgac ggattcagct 3900
cccctcagtt ttttccttct ttgccgcttc aaattatttc agacataagg gaaaacggtt 3960
aaaaggggaa tgaatgcttt tgatgtatgt attcttgtta ttttatacat aaaaaaaagt 4020
tgtttaactt gtatataaac agcttcagtt gttaccatct gtgttttcct agaattttca 4080
aagtactttt ctcattcaaa tataatcctg aaaaggttct ctgttcaatc tgcgacccca 4140
gtgatggcaa ctaagtggat caacagcaac ttttgctccg atttgcgata taatttgtca 4200
aaacatgcct ctaaaatcac                                             4220
```

```
SEQ ID NO: 110          moltype = DNA  length = 4237
FEATURE                 Location/Qualifiers
misc_feature            1..4237
                        note = Synthetic polynucleotide
source                  1..4237
                        mol_type = other DNA
                        organism = synthetic construct
SEQUENCE: 110
gtagatacaa ggagagtgga aataggaaaa aatagcttag agagatttat ttacgaacag 60
gaagagtcac atggcatgtg tccagtcttc cacatgataa ataccttctt taccttcctt 120
actaggactt ttgactctct ctctctctat ctatggtagt agtagtagta gtattcattc 180
attctctcta atggcagagc tcacacccta aacacaaacc agagcctctg agagaaacaa 240
ccacaaactc tcccttaatc ttgtcggttt ccatatctgc tgaaaatgaa agctctgtac 300
agaagctctc tcttgctctt gctcttgctc ttcatctccg tgtgttttgc atcttcttct 360
tctccggtca ctcagcaact cctaagcttc aaaaactctc tcccgaaccc atccctgctc 420
cccaactggc tccctaacca aagcccgtgc acattcagcg gcatcagctg caacgacaca 480
gagctcacat ccatagacct cagctccgtc cctctcagca ctaacctaac cgtcatcgcc 540
agcttcctcc ttagcctgga ccacctccag tcactctcct taaaatccac caacctctcc 600
ggtcccgccg ccatgcctcc tctctcccac tcccagtgct cctcctcatt aacctcccta 660
gatctctccc aaaactccct ctctgcctcc ctcaacgaca tgtcgtttct cgcctcctgc 720
tccaacctcc aatccctcaa cctctcctcc aacctcctcc aattcggccc cccgccccac 780
```

-continued

```
tggaagctcc accacctccg cttcgccgac ttctcttaca acaagatttc cggccccggc  840
gtcgtttctt ggcttctcaa ccccgtcatc gaactcctct ctctcaaagg caacaaagtc  900
accggcgaaa ccgacttctc cggctcaatt tctctccagt atttagacct ttcttccaac  960
aacttttctg ttacgcttcc tactttcggc gagtgttctt cgcttgagta tttggacctc  1020
tccgctaaca agtacttggg cgacattgca cgcactctct ccccttgcaa gagcctcgtt  1080
taccttaacg tctccagcaa ccagttctcc ggtccggttc cttcccttcc ctccggttcg  1140
ctacagtttg tgtaccttgc tgcaaaccac ttccacggcc agattcctct ctccctcgcc  1200
gacctctgct ccactctcct ccagctcgat ctctcctcca acaatctcac cggcgctctt  1260
cccggcgcgt tcggcgcgtg cacttctctt caatcccttg acatctccag caacctcttc  1320
gccggcgcgt tgccgatgtc ggttctcacg caaatgacca gcctgaaaga gctcgcggtt  1380
gcgttcaacg gcttcctcgg tgctctcccg gagtctctgt cgaagctctc cgctctggag  1440
ttgctggatc tgagctccaa caactttagc ggctcaatcc ccgcctcgct gtgcggcggc  1500
ggtgacgctg ggattaataa taatctgaag gaactttatc tgcagaataa ccggttcacg  1560
ggttttattc cgcccacgct cagcaactgt tcaaacctcg ttgctttgga tttgagtttc  1620
aacttcctca cggggactat tcctccgagc ctagggtctc tttcgaatct caaagacttc  1680
atcatctggc tcaaccagct ccacggggag ataccgcagg agctcatgta tcttaaaagc  1740
ctcgagaatt tgatcctgga tttcaacgac ttgactggga acattccctc tggcctcgtt  1800
aactgcacca agttgaactg gatctccctc tccaacaaca ggctcagcgg cgagattccg  1860
ccgtggattg ggaagctttc taatctcgcc atactcaagc tcagcaataa ctctttctcc  1920
ggccggattc cgccggagct cggcgactgt actagtttaa tatggttgga tctgaataca  1980
aatatgctca ccgggcccat tccgccggag ctgttcaagc agtcggggaa gatcgccgtg  2040
aatttcatca gtgggaagac gtatgtgtat ataaagaacg atgggagcaa ggagtgccat  2100
ggtgcgggga acttgcttga gtttgcgggg atcagtcagc agcagctgaa caggatttcg  2160
acgaggaacc cctgcaattt cactagggtt tatggaggta agttgcagcc aacgtttaac  2220
cataatggtt ctatgatatt tttggatatc tcgcacaaca tgttgtcagg gagtattccc  2280
aaggagattg gggccatgta ctatttgtac attctcaatt tgggtcacaa taatgtgtct  2340
gggagcattc ctcaagagct tgggaagatg aagaatctca acattcttga tctgtcgaat  2400
aatagactgg agggccaaat tccgcagagc ctcacggggc tttctttgct cactgagatt  2460
gacttgtcca acaacttgct taccgggacg attcctgagt cgggtcaatt tgatactttc  2520
cctgcggcga agtttcagaa caactctggt ctatgtggag ttcctctggg tccgtgtggt  2580
tcggagccgg caaacaatgg aaatgcgcaa catatgaagt ctcacaggag gcaggcttct  2640
ctggcgggga gtgtggccat ggggttgttg ttttccctct tttgcgtctt tggtttgatc  2700
attattgcca ttgagaccag gaagaggagg aagaagaagg aggctgctct tgaagcctat  2760
ggtgatggta attcccattc gggtccggcc aatgtgagct ggaagcacac cagtactcgg  2820
gaagctctta gcataaacct tgcaacattt gagaagccgc tccggaagct tacttttgcg  2880
gaccttcttg acgctaccaa tggttttcac aacgacagtc tcattggctc tggcgggttt  2940
ggggatgtgt acaaggctca gttgaaggat ggaagtgttg tggctatcaa gaagctgatt  3000
catgttagcg gacaagggga cagggaattc accgctgaaa tggagactat tgggaaaatc  3060
aagcacagga accttgttcc cctgttggga tactgcaagg taggggaaga gaggctcttg  3120
gtttatgagt acatgaaata tggaagttta gaggatgttc tacatgatca gaagaaagct  3180
gggatcaagc tgaactgggc cattaggcgg aaaattgcta ttggagctgc taggggattg  3240
tcttttcttc accacaattg tatcccccac atcattcata gagatatgaa gtcgagcaat  3300
gtgttacttg atgaaaacct ggaagccaga gtctctgatt ttggaatggc taggcttatg  3360
agtgctatgg atacacattt gagtgtgagc acattggctg gcacaccggg gtatgttcct  3420
cccgagtact atcagagctt cagatgctcc acaaaaggtg atgtctacag ttatggtgtg  3480
gttttgttgg agctgctaac tgggaaaagg ccaacggact cggctgattt tggagataat  3540
aatcttgttg gatgggttaa acaacatgcc aagctgaaaa tcagtgatat ttttgacccg  3600
gagctcatga aggaagaccc caatctggag atggagcttt tgcagcactt gaagattgcg  3660
gtttcctgtt tggatgatcg accgtggagg cgtccgacga tgattcaagt gatggcaatg  3720
ttcaaggaga ttcaggcggg atccgggatt gattctcagt caaccatagc caatgacgag  3780
gaaggtttca atgcagttga aatggtggag atgagcatta aagaagcccc tgaattgagc  3840
aagcattagg cattaaagtg tcgtgtggat tctttgggaa acagacaaga agagaggagg  3900
agatgacgga ttcagctccc ctcagttttt tccttctttg ccgcttcaaa ttatttcaga  3960
cataagggaa aacggttaaa aggggaatga atgcttttga tgtatgtatt cttgttattt  4020
tatacataaa aaaaagttgt ttaacttgta tataaacagc ttcagttgtt accatctgtg  4080
ttttcctaga attttcaaag tacttttctc attcaaatat aatcctgaaa aggttctctg  4140
ttcaatctgc gaccccagtg atggcaacta agtggatcaa cagcaacttt tgctccgatt  4200
tgcgatataa tttgtcaaaa catgcctcta aaatcac                           4237
```

```
SEQ ID NO: 111         moltype = DNA  length = 4045
FEATURE                Location/Qualifiers
misc_feature           1..4045
                       note = Synthetic polynucleotide
source                 1..4045
                       mol_type = other DNA
                       organism = synthetic construct
SEQUENCE: 111
gtagatactc acaccctaaa cacaaaccag agcctctgag agaaacaacc acaaactctc  60
ccttaatctt gtcggtttcc atatctgctg aaaatgaaag ctctgtacag aagctctctc  120
ttgctcttgc tcttgctctt catctccgtg tgttttgcat cttcttcttc tccggtcact  180
cagcaactcc taagcttcaa aaactctctc ccgaacccat ccctgctccc caactggctc  240
cctaaccaaa gcccgtgcac attcagcggc atcagctgca acgacacaga gctcacatcc  300
atagacctca gctccgtccc tctcagcact aacctaaccg tcatcgccag cttcctcctt  360
agcctggacc acctccagtc actctcctta aaatccacca acctctccgg tcccgccgcc  420
atgcctcctc tctcccactc ccagtgctcc tcctcattaa cctccctaga tctctcccaa  480
aactccctct ctgcctccct caacgacatg tcgtttctcg cctcctgctc caacctccaa  540
tccctcaacc tctcctccaa cctcctccaa ttcggccccc cgccccactg gaagctccac  600
cacctccgct tcgccgactt ctcttacaac aagatttccg gccccggcgt cgtttcttgg  660
cttctcaacc ccgtcatcga actcctctct ctcaaaggca acaaagtcac cggcgaaacc  720
```

```
gacttctccg gctcaatttc tctccagtat ttagaccttt cttccaacaa cttttctgtt  780
acgcttccta ctttcggcga gtgttcttcg cttgagtatt tggacctctc cgctaacaag  840
tacttgggcg acattgcacg cactctctcc ccttgcaaga gcctcgttta ccttaacgtc  900
tccagcaacc agttctccgg tccggttcct tcccttccct ccggttcgct acagtttgtg  960
taccttgctg caaaccactt ccacggccag attcctctct ccctcgccga cctctgctcc  1020
actctcctcc agctcgatct ctcctccaac aatctcaccg gcgctcttcc cggcgcgttc  1080
ggcgcgtgca cttctcttca atcccttgac atctccagca acctcttcgc cggcgcgttg  1140
ccgatgtcgg ttctcacgca aatgaccagc ctgaaagagc tcgcggttgc gttcaacggc  1200
ttcctcggtg ctctcccgga gtctctgtcg aagctctccg ctctggagtt gctggatctg  1260
agctccaaca actttagcgg ctcaatcccc gcctcgctgt gcggcggcgg tgacgctggg  1320
attaataata atctgaagga actttatctg cagaataacc ggttcacggg ttttattccg  1380
cccacgctca gcaactgttc aaacctcgtt gctttggatt tgagtttcaa cttcctcacg  1440
gggactattc ctccgagcct agggtctctt tcgaatctca aagacttcat catctggctc  1500
aaccagctcc acggggagat accgcaggag ctcatgtatc ttaaaagcct cgagaatttg  1560
atcctggatt tcaacgactt gactgggaac attccctctg gcctcgttaa ctgcaccaag  1620
ttgaactgga tctccctctc caacaacagg ctcagcggcg agattccgcc gtggattggg  1680
aagctttcta atctcgccat actcaagctc agcaataact ctttctccgg ccggattccg  1740
ccggagctcg gcgactgtac tagtttaata tggttggatc tgaatacaaa tatgctcacc  1800
gggcccattc cgccggagct gttcaagcag tcggggaaga tcgccgtgaa tttcatcagt  1860
gggaagacgt atgtgtatat aaagaacgat gggagcaagg agtgccatgg tgcggggaac  1920
ttgcttgagt ttgcggggat cagtcagcag cagctgaaca ggatttcgac gaggaacccc  1980
tgcaatttca ctagggttta tggaggtaag ttgcagccaa cgtttaacca taatggttct  2040
atgatatttt tggatatctc gcacaacatg ttgtcaggga gtattcccaa ggagattggg  2100
gccatgtact atttgtacat tctcaatttg ggtcacaata atgtgtctgg gagcattcct  2160
caagagcttg ggaagatgaa gaatctcaac attcttgatc tgtcgaataa tagactggag  2220
ggccaaattc cgcagagcct cacggggctt tctttgctca ctgagattga cttgtccaac  2280
aacttgctta ccgggacgat tcctgagtcg ggtcaatttg atactttccc tgcggcgaag  2340
tttcagaaca actctggtct atgtggagtt cctctgggtc cgtgtggttc ggagccggca  2400
aacaatggaa atgcgcaaca tatgaagtct cacaggaggc aggcttctct ggcggggagt  2460
gtggccatgg ggttgttgtt ttccctcttt tgcgtctttg gtttgatcat tattgccatt  2520
gagaccagga agaggaggaa gaagaaggag gctgctcttg aagcctatgg tgatggtaat  2580
tcccattcgg gtccggccaa tgtgagctgg aagcacacca gtactcggga agctcttagc  2640
ataaaccttg caacatttga gaagccgctc cggaagctta cttttgcgga ccttcttgac  2700
gctaccaatg gttttcacaa cgacagtctc attggctctg gcgggtttgg ggatgtgtac  2760
aaggctcagt tgaaggatgg aagtgttgtg gctatcaaga agctgattca tgttagcgga  2820
caaggggaca gggaattcac cgctgaaatg gagactattg ggaaaatcaa gcacaggaac  2880
cttgttcccc tgttgggata ctgcaaggta ggggaagaga ggctcttggt ttatgagtac  2940
atgaaatatg gaagtttaga ggatgttcta catgatcaga agaaagctgg gatcaagctg  3000
aactgggcca ttaggcggaa aattgctatt ggagctgcta ggggattgtc ttttcttcac  3060
cacaattgta tcccccacat cattcataga gatatgaagt cgagcaatgt gttacttgat  3120
gaaaacctgg aagccagagt ctctgatttt ggaatggcta ggcttatgag tgctatggat  3180
acacatttga gtgtgagcac attggctggc acaccggggt atgttcctcc cgagtactat  3240
cagagcttca gatgctccac aaaaggtgat gtctacagtt atggtgtggt tttgttggag  3300
ctgctaactg ggaaaaggcc aacggactcg gctgattttg gagataataa tcttgttgga  3360
tgggttaaac aacatgccaa gctgaaaatc agtgatattt ttgacccgga gctcatgaag  3420
gaagacccca atctggagat ggagcttttg cagcacttga agattgcggt ttcctgtttg  3480
gatgatcgac cgtggaggcg tccgacgatg attcaagtga tggcaatgtt caaggagatt  3540
caggcgggat ccgggattga ttctcagtca accatagcca atgacgagga aggtttcaat  3600
gcagttgaaa tggtggagat gagcattaaa gaagcccctg aattgagcaa gcattaggca  3660
ttaaagtgtc gtgtggattc tttgggaaac agacaagaag agaggaggag atgacggatt  3720
cagctcccct cagttttttc cttctttgcc gcttcaaatt atttcagaca taagggaaaa  3780
cggttaaaag gggaatgaat gcttttgatg tatgtattct tgttatttta tacataaaaa  3840
aaagttgttt aacttgtata taaacagctt cagttgttac catctgtgtt ttcctagaat  3900
tttcaaagta cttttctcat tcaaatataa tcctgaaaag gttctctgtt caatctgcga  3960
ccccagtgat ggcaactaag tggatcaaca gcaacttttg ctccgatttg cgatataatt  4020
tgtcaaaaca tgcctctaaa atcac                                         4045
```

```
SEQ ID NO: 112          moltype = DNA  length = 4236
FEATURE                 Location/Qualifiers
misc_feature            1..4236
                        note = Synthetic polynucleotide
source                  1..4236
                        mol_type = other DNA
                        organism = synthetic construct
SEQUENCE: 112
gtagatacag gagagtggaa ataggaaaaa atagcttaga gagatttatt tacgaacagg  60
aagagtcaca tggcatgtgt ccagtcttcc acatgataaa taccccttctt accttcctta  120
ctaggacttt tgactctctc tctctctatc tatggtagta gtagtagtag tattcattca  180
ttctctctaa tggcagagct cacaccctaa acacaaacca gagcctctga gagaaacaac  240
cacaaactct cccttaatct tgtcggtttc catatctgct gaaaatgaaa gctctgtaca  300
gaagctctct cttgctcttg ctcttgctct tcatctccgt gtgttttgca tcttcttctt  360
ctccggtcac tcagcaactc ctaagcttca aaaactctct cccgaaccca tccctgctcc  420
ccaactggct ccctaaccaa agcccgtgca cattcagcgg catcagctgc aacgacacag  480
agctcacatc catagacctc agctccgtcc ctctcagcac taacctaacc gtcatcgcca  540
gcttcctcct tagcctggac cacctccagt cactctcctt aaaatccacc aacctctccg  600
gtcccgccgc catgcctcct ctctcccact cccagtgctc ctcctcatta acctccctag  660
atctctccca aaactccctc tctgcctccc tcaacgacat gtcgtttctc gcctcctgct  720
ccaacctcca atccctcaac ctctcctcca acctcctcca attcggcccc ccgccccact  780
ggaagctcca ccacctccgc ttcgccgact tctcttacaa caagatttcc ggccccggcg  840
```

```
tcgtttcttg gcttctcaac cccgtcatcg aactcctctc tctcaaaggc aacaaagtca  900
ccggcgaaac cgacttctcc ggctcaattt ctctccagta tttagacctt tcttccaaca  960
acttttctgt tacgcttcct actttcggcg agtgttcttc gcttgagtat ttggacctct  1020
ccgctaacaa gtacttgggc gacattgcac gcactctctc cccttgcaag agcctcgttt  1080
accttaacgt ctccagcaac cagttctccg gtccggttcc ttcccttccc tccggttcgc  1140
tacagtttgt gtaccttgct gcaaaccact tccacggcca gattcctctc tccctcgccg  1200
acctctgctc cactctcctc cagctcgatc tctcctccaa caatctcacc ggcgctcttc  1260
ccggcgcgtt cggcgcgtgc acttctcttc aatcccttga catctccagc aacctcttcg  1320
ccggcgcgtt gccgatgtcg gttctcacgc aaatgaccag cctgaaagag ctcgcggttg  1380
cgttcaacgg cttcctcggt gctctcccgg agtctctgtc gaagctctcc gctctggagt  1440
tgctggatct gagctccaac aactttagcg gctcaatccc cgcctcgctg tgcggcggcg  1500
gtgacgctgg gattaataat aatctgaagg aactttatct gcagaataac cggttcacgg  1560
gttttattcc gcccacgctc agcaactgtt caaacctcgt tgctttggat ttgagtttca  1620
acttcctcac ggggactatt cctccgagcc tagggtctct ttcgaatctc aaagacttca  1680
tcatctggct caaccagctc cacggggaga taccgcagga gctcatgtat cttaaaagcc  1740
tcgagaattt gatcctggat ttcaacgact tgactgggaa cattccctct ggcctcgtta  1800
actgcaccaa gttgaactgg atctccctct ccaacaacag gctcagcggc gagattccgc  1860
cgtggattgg gaagctttct aatctcgcca tactcaagct cagcaataac tctttctccg  1920
gccggattcc gccggagctc ggcgactgta ctagtttaat atggttggat ctgaatacaa  1980
atatgctcac cgggcccatt ccgccggagc tgttcaagca gtcggggaag atcgccgtga  2040
atttcatcag tgggaagacg tatgtgtata taaagaacga tgggagcaag gagtgccatg  2100
gtgcggggaa cttgcttgag tttgcgggga tcagtcagca gcagctgaac aggatttcga  2160
cgaggaaccc ctgcaatttc actagggttt atggaggtaa gttgcagcca acgtttaacc  2220
ataatggttc tatgatattt ttggatatct cgcacaacat gttgtcaggg agtattccca  2280
aggagattgg ggccatgtac tatttgtaca ttctcaattt gggtcacaat aatgtgtctg  2340
ggagcattcc tcaagagctt gggaagatga agaatctcaa cattcttgat ctgtcgaata  2400
atagactgga gggccaaatt ccgcagagcc tcacggggct ttctttgctc actgagattg  2460
acttgtccaa caacttgctt accgggacga ttcctgagtc gggtcaattt gatactttcc  2520
ctgcggcgaa gtttcagaac aactctggtc tatgtggagt tcctctgggt ccgtgtggtt  2580
cggagccggc aaacaatgga aatgcgcaac atatgaagtc tcacaggagg caggcttctc  2640
tggcggggag tgtggccatg gggttgttgt tttccctctt ttgcgtcttt ggtttgatca  2700
ttattgccat tgagaccagg aagaggagga agaagaagga ggctgctctt gaagcctatg  2760
gtgatggtaa ttcccattcg ggtccggcca atgtgagctg gaagcacacc agtactcggg  2820
aagctcttag cataaacctt gcaacatttg agaagccgct ccggaagctt acttttgcgg  2880
accttcttga cgctaccaat ggttttcaca acgacagtct cattggctct ggcgggtttg  2940
gggatgtgta caaggctcag ttgaaggatg gaagtgttgt ggctatcaag aagctgattc  3000
atgttagcgg acaaggggac agggaattca ccgctgaaat ggagactatt gggaaaatca  3060
agcacaggaa ccttgttccc ctgttgggat actgcaaggt aggggaagag aggctcttgg  3120
tttatgagta catgaaatat ggaagtttag aggatgttct acatgatcag aagaaagctg  3180
ggatcaagct gaactgggcc attaggcgga aaattgctat tggagctgct aggggattgt  3240
cttttcttca ccacaattgt atcccccaca tcattcatag agatatgaag tcgagcaatg  3300
tgttacttga tgaaaacctg gaagccagag tctctgattt tggaatggct aggcttatga  3360
gtgctatgga tacacatttg agtgtgagca cattggctgg cacaccgggg tatgttcctc  3420
ccgagtacta tcagagcttc agatgctcca caaaaggtga tgtctacagt tatggtgtgg  3480
ttttgttgga gctgctaact gggaaaaggc caacggactc ggctgatttt ggagataata  3540
atcttgttgg atgggttaaa caacatgcca agctgaaaat cagtgatatt tttgacccgg  3600
agctcatgaa ggaagacccc aatctggaga tggagctttt gcagcacttg aagattgcgg  3660
tttcctgttt ggatgatcga ccgtggaggc gtccgacgat gattcaagtg atggcaatgt  3720
tcaaggagat tcaggcggga tccgggattg attctcagtc aaccatagcc aatgacgagg  3780
aaggtttcaa tgcagttgaa atggtggaga tgagcattaa agaagcccct gaattgagca  3840
agcattaggc attaaagtgt cgtgtggatt ctttgggaaa cagacaagaa gagaggagga  3900
gatgacggat tcagctcccc tcagtttttt ccttctttgc cgcttcaaat tatttcagac  3960
ataagggaaa acggttaaaa ggggaatgaa tgcttttgat gtatgtattc ttgttatttt  4020
atacataaaa aaaagttgtt taacttgtat ataaacagct tcagttgtta ccatctgtgt  4080
tttcctagaa ttttcaaagt acttttctca ttcaaatata atcctgaaaa ggttctctgt  4140
tcaatctgcg accccagtga tggcaactaa gtggatcaac agcaactttt gctccgattt  4200
gcgatataat ttgtcaaaac atgcctctaa aatcac                            4236

SEQ ID NO: 113          moltype = DNA  length = 4160
FEATURE                 Location/Qualifiers
misc_feature            1..4160
                        note = Synthetic polynucleotide
source                  1..4160
                        mol_type = other DNA
                        organism = synthetic construct
SEQUENCE: 113
gtgtccagtc ttccacatga taaataccct tcttaccttc cttactagga cttttgactc  60
tctctctctc tatctatggt agtagtagta gtagtattca ttcattctct ctaatggcag  120
agctcacacc ctaaacacaa accagagcct ctgagagaaa caaccacaaa ctctccctta  180
atcttgtcgg tttccatatc tgctgaaaat gaaagctctg tacagaagct ctctcttgct  240
cttgctcttg ctcttcatct ccgtgtgttt tgcatcttct tcttctccgg tcactcagca  300
actcctaagc ttcaaaaact ctctcccgaa cccatccctg ctccccaact ggctccctaa  360
ccaaagcccg tgcacattca gcggcatcag ctgcaacgac acagagctca catccataga  420
cctcagctcc gtccctctca gcactaacct aaccgtcatc gccagcttcc tccttagcct  480
ggaccacctc cagtcactct ccttaaaatc caccaacctc tccggtcccg ccgccatgcc  540
tcctctctcc cactcccagt gctcctcctc attaacctcc ctagatctct cccaaaactc  600
cctctctgcc tccctcaacg acatgtcgtt tctcgcctcc tgctccaacc tccaatccct  660
caacctctcc tccaacctcc tccaattcgg cccccgccc cactggaagc tccaccacct  720
ccgcttcgcc gacttctctt acaacaagat ttccggcccc ggcgtcgttt cttggcttct  780
```

```
caaccccgtc atcgaactcc tctctctcaa aggcaacaaa gtcaccggcg aaaccgactt  840
ctccggctca atttctctcc agtatttaga cctttcttcc aacaactttt ctgttacgct  900
tcctactttc ggcgagtgtt cttcgcttga gtatttggac ctctccgcta acaagtactt  960
gggcgacatt gcacgcactc tctccccttg caagagcctc gtttacctta acgtctccag  1020
caaccagttc tccggtccgg ttccttccct tccctccggt tcgctacagt ttgtgtacct  1080
tgctgcaaac cacttccacg gccagattcc tctctccctc gccgacctct gctccactct  1140
cctccagctc gatctctcct ccaacaatct caccggcgct cttcccggcg cgttcggcgc  1200
gtgcacttct cttcaatccc ttgacatctc cagcaacctc ttcgccggcg cgttgccgat  1260
gtcggttctc acgcaaatga ccagcctgaa agagctcgcg gttgcgttca acggcttcct  1320
cggtgctctc ccggagtctc tgtcgaagct ctccgctctg gagttgctgg atctgagctc  1380
caacaacttt agcggctcaa tccccgcctc gctgtgcggc ggcggtgacg ctgggattaa  1440
taataatctg aaggaacttt atctgcagaa taaccggttc acgggtttta ttccgcccac  1500
gctcagcaac tgttcaaacc tcgttgcttt ggatttgagt ttcaacttcc tcacggggac  1560
tattcctccg agcctagggt ctctttcgaa tctcaaagac ttcatcatct ggctcaacca  1620
gctccacggg gagataccgc aggagctcat gtatcttaaa agcctcgaga atttgatcct  1680
ggatttcaac gacttgactg ggaacattcc ctctggcctc gttaactgca ccaagttgaa  1740
ctggatctcc ctctccaaca acaggctcag cggcgagatt ccgccgtgga ttgggaagct  1800
ttctaatctc gccatactca agctcagcaa taactctttc tccggccgga ttccgccgga  1860
gctcggcgac tgtactagtt taatatggtt ggatctgaat acaaatatgc tcaccgggcc  1920
cattccgccg gagctgttca agcagtcggg gaagatcgcc gtgaatttca tcagtgggaa  1980
gacgtatgtg tatataaaga acgatgggag caaggagtgc catggtgcgg ggaacttgct  2040
tgagtttgcg gggatcagtc agcagcagct gaacaggatt tcgacgagga acccctgcaa  2100
tttcactagg gtttatggag gtaagttgca gccaacgttt aaccataatg gttctatgat  2160
atttttggat atctcgcaca acatgttgtc agggagtatt cccaaggaga ttggggccat  2220
gtactatttg tacattctca atttgggtca caataatgtg tctgggagca ttcctcaaga  2280
gcttgggaag atgaagaatc tcaacattct tgatctgtcg aataatagac tggagggcca  2340
aattccgcag agcctcacgg ggctttcttt gctcactgag attgacttgt ccaacaactt  2400
gcttaccggg acgattcctg agtcgggtca atttgatact ttccctgcgg cgaagtttca  2460
gaacaactct ggtctatgtg gagttcctct gggtccgtgt ggttcggagc cggcaaacaa  2520
tggaaatgcg caacatatga agtctcacag gaggcaggct tctctggcgg ggagtgtggc  2580
catggggttg ttgttttccc tcttttgcgt ctttggtttg atcattattg ccattgagac  2640
caggaagagg aggaagaaga aggaggctgc tcttgaagcc tatggtgatg gtaattccca  2700
ttcgggtccg gccaatgtga gctggaagca caccagtact cgggaagctc ttagcataaa  2760
ccttgcaaca tttgagaagc cgctccggaa gcttactttt gcggaccttc ttgacgctac  2820
caatggtttt cacaacgaca gtctcattgg ctctggcggg tttggggatg tgtacaaggc  2880
tcagttgaag gatggaagtg ttgtggctat caagaagctg attcatgtta gcggacaagg  2940
ggacagggaa ttcaccgctg aaatggagac tattgggaaa atcaagcaca ggaaccttgt  3000
tcccctgttg ggatactgca aggtagggga agagaggctc ttggtttatg agtacatgaa  3060
atatggaagt ttagaggatg ttctacatga tcagaagaaa gctgggatca agctgaactg  3120
ggccattagg cggaaaattg ctattggagc tgctagggga ttgtcttttc ttcaccacaa  3180
ttgtatcccc cacatcattc atagagatat gaagtcgagc aatgtgttac ttgatgaaaa  3240
cctggaagcc agagtctctg attttggaat ggctaggctt atgagtgcta tggatacaca  3300
tttgagtgtg agcacattgg ctggcacacc ggggtatgtt cctcccgagt actatcagag  3360
cttcagatgc tccacaaaag gtgatgtcta cagttatggt gtggttttgt tggagctgct  3420
aactgggaaa aggccaacgg actcggctga ttttggagat aataatcttg ttggatgggt  3480
taaacaacat gccaagctga aaatcagtga tatttttgac ccggagctca tgaaggaaga  3540
ccccaatctg gagatggagc ttttgcagca cttgaagatt gcggtttcct gtttggatga  3600
tcgaccgtgg aggcgtccga cgatgattca agtgatggca atgttcaagg agattcaggc  3660
gggatccggg attgattctc agtcaaccat agccaatgac gaggaaggtt tcaatgcagt  3720
tgaaatggtg gagatgagca ttaaagaagc ccctgaattg agcaagcatt aggcattaaa  3780
gtgtcgtgtg gattctttgg gaaacagaca agaagagagg aggagatgac ggattcagct  3840
cccctcagtt ttttccttct ttgccgcttc aaattatttc agacataagg gaaaacggtt  3900
aaaaggggaa tgaatgcttt tgatgtatgt attcttgtta ttttatacat aaaaaaaagt  3960
tgtttaactt gtatataaac agcttcagtt gttaccatct gtgttttcct agaattttca  4020
aagtactttt ctcattcaaa tataatcctg aaaaggttct ctgttcaatc tgcgacccca  4080
gtgatggcaa ctaagtggat caacagcaac ttttgctccg atttgcgata taatttgtca  4140
aaacatgcct ctaaaatcac                                              4160

SEQ ID NO: 114          moltype = DNA  length = 4240
FEATURE                 Location/Qualifiers
misc_feature            1..4240
                        note = Synthetic polynucleotide
source                  1..4240
                        mol_type = other DNA
                        organism = synthetic construct
SEQUENCE: 114
gtagatacat ggaggagagt ggaaatagga aaaaatagct tagagagatt tatttacgaa  60
caggaagagt cacatggcat gtgtccagtc ttccacatga taaataccct tcttaccttc  120
cttactagga cttttgactc tctctctctc tatctatggt agtagtagta gtagtattca  180
ttcattctct ctaatggcag agctcacacc ctaaacacaa accagagcct ctgagagaaa  240
caaccacaaa ctctccctta atcttgtcgg tttccatatc tgctgaaaat gaaagctctg  300
tacagaagct ctctcttgct cttgctcttg ctcttcatct ccgtgtgttt tgcatcttct  360
tcttctccgg tcactcagca actcctaagc ttcaaaaact ctctcccgaa cccatccctg  420
ctccccaact ggctccctaa ccaaagcccg tgcacattca gcggcatcag ctgcaacgac  480
acagagctca catccataga cctcagctcc gtccctctca gcactaacct aaccgtcatc  540
gccagcttcc tccttagcct ggaccacctc cagtcactct ccttaaaatc caccaacctc  600
tccggtcccg ccgccatgcc tcctctctcc cactcccagt gctcctcctc attaacctcc  660
ctagatctct cccaaaactc cctctctgcc tccctcaacg acatgtcgtt tctcgcctcc  720
tgctccaacc tccaatccct caacctctcc tccaacctcc tccaattcgg ccccccgccc  780
```

```
cactggaagc tccaccacct ccgcttcgcc gacttctctt acaacaagat ttccggcccc  840
ggcgtcgttt cttggcttct caaccccgtc atcgaactcc tctctctcaa aggcaacaaa  900
gtcaccggcg aaaccgactt ctccggctca atttctctcc agtatttaga cctttcttcc  960
aacaactttt ctgttacgct tcctactttc ggcgagtgtt cttcgcttga gtatttggac  1020
ctctccgcta acaagtactt gggcgacatt gcacgcactc tctccccttg caagagcctc  1080
gtttacctta acgtctccag caaccagttc tccggtccgg ttccttccct tccctccggt  1140
tcgctacagt ttgtgtacct tgctgcaaac cacttccacg gccagattcc tctctccctc  1200
gccgacctct gctccactct cctccagctc gatctctcct ccaacaatct caccggcgct  1260
cttccccggcg cgttcggcgc gtgcacttct cttcaatccc ttgacatctc cagcaacctc  1320
ttcgccggcg cgttgccgat gtcggttctc acgcaaatga ccagcctgaa agagctcgcg  1380
gttgcgttca acggcttcct cggtgctctc ccggagtctc tgtcgaagct ctccgctctg  1440
gagttgctgg atctgagctc caacaacttt agcggctcaa tccccgcctc gctgtgcggc  1500
ggcggtgacg ctgggattaa taataatctg aaggaacttt atctgcagaa taaccggttc  1560
acgggtttta ttccgcccac gctcagcaac tgttcaaacc tcgttgcttt ggatttgagt  1620
ttcaacttcc tcacggggac tattcctccg agcctagggt ctctttcgaa tctcaaagac  1680
ttcatcatct ggctcaacca gctccacggg gagataccgc aggagctcat gtatcttaaa  1740
agcctcgaga atttgatcct ggatttcaac gacttgactg ggaacattcc ctctggcctc  1800
gttaactgca ccaagttgaa ctggatctcc ctctccaaca acaggctcag cggcgagatt  1860
ccgccgtgga ttgggaagct ttctaatctc gccatactca agctcagcaa taactctttc  1920
tccggccgga ttccgccgga gctcggcgac tgtactagtt taatatggtt ggatctgaat  1980
acaaatatgc tcaccgggcc cattccgccg gagctgttca agcagtcggg gaagatcgcc  2040
gtgaatttca tcagtgggaa gacgtatgtg tatataaaga acgatgggag caaggagtgc  2100
catggtgcgg ggaacttgct tgagtttgcg gggatcagtc agcagcagct gaacaggatt  2160
tcgacgagga accccctgcaa tttcactagg gtttatggag gtaagttgca gccaacgttt  2220
aaccataatg gttctatgat atttttggat atctcgcaca acatgttgtc agggagtatt  2280
cccaaggaga ttggggccat gtactatttg tacattctca atttgggtca caataatgtg  2340
tctgggagca ttcctcaaga gcttgggaag atgaagaatc tcaacattct tgatctgtcg  2400
aataatagac tggagggcca aattccgcag agcctcacgg ggctttcttt gctcactgag  2460
attgacttgt ccaacaactt gcttaccggg acgattcctg agtcgggtca atttgatact  2520
ttccctgcgg cgaagtttca gaacaactct ggtctatgtg gagttcctct gggtccgtgt  2580
ggttcggagc cggcaaacaa tggaaatgcg caacatatga agtctcacag gaggcaggct  2640
tctctggcgg ggagtgtggc catggggttg ttgttttccc tcttttgcgt ctttggtttg  2700
atcattattg ccattgagac caggaagagg aggaagaaga aggaggctgc tcttgaagcc  2760
tatggtgatg gtaattccca ttcgggtccg gccaatgtga gctggaagca caccagtact  2820
cgggaagctc ttagcataaa ccttgcaaca tttgagaagc cgctccggaa gcttactttt  2880
gcggaccttc ttgacgctac caatggtttt cacaacgaca gtctcattgg ctctggcggg  2940
tttggggatg tgtacaaggc tcagttgaag gatggaagtg ttgtggctat caagaagctg  3000
attcatgtta gcggacaagg ggacagggaa ttcaccgctg aaatggagac tattgggaaa  3060
atcaagcaca ggaaccttgt tcccctgttg ggatactgca aggtagggga agagaggctc  3120
ttggtttatg agtacatgaa atatggaagt ttagaggatg ttctacatga tcagaagaaa  3180
gctgggatca agctgaactg ggccattagg cggaaaattg ctattggagc tgctagggga  3240
ttgtcttttc ttcaccacaa ttgtatcccc cacatcattc atagagatat gaagtcgagc  3300
aatgtgttac ttgatgaaaa cctggaagcc agagtctctg attttggaat ggctaggctt  3360
atgagtgcta tggatacaca tttgagtgtg agcacattgg ctggcacacc ggggtatgtt  3420
cctccccgagt actatcagag cttcagatgc tccacaaaag gtgatgtcta cagttatggt  3480
gtggttttgt tggagctgct aactgggaaa aggccaacgg actcggctga ttttggagat  3540
aataatcttg ttggatgggt taaacaacat gccaagctga aatcagtga tatttttgac  3600
ccggagctca tgaaggaaga ccccaatctg gagatggagc ttttgcagca cttgaagatt  3660
gcggtttcct gtttggatga tcgaccgtgg aggcgtccga cgatgattca agtgatggca  3720
atgttcaagg agattcaggc gggatccggg attgattctc agtcaaccat agccaatgac  3780
gaggaaggtt tcaatgcagt tgaaatggtg gagatgagca ttaaagaagc ccctgaattg  3840
agcaagcatt aggcattaaa gtgtcgtgtg gattctttgg gaaacagaca agaagagagg  3900
aggagatgac ggattcagct cccctcagtt ttttccttct ttgccgcttc aaattatttc  3960
agacataagg gaaaacggtt aaaaggggaa tgaatgcttt tgatgtatgt attcttgtta  4020
ttttatacat aaaaaaaagt tgtttaactt gtatataaac agcttcagtt gttaccatct  4080
gtgttttcct agaattttca aagtactttt ctcattcaaa tataatcctg aaaaggttct  4140
ctgttcaatc tgcgaccccca gtgatggcaa ctaagtggat caacagcaac ttttgctccg  4200
atttgcgata taatttgtca aaacatgcct ctaaaatcac                        4240
```

```
SEQ ID NO: 115         moltype = DNA  length = 4234
FEATURE                Location/Qualifiers
misc_feature           1..4234
                       note = Synthetic polynucleotide
source                 1..4234
                       mol_type = other DNA
                       organism = synthetic construct
SEQUENCE: 115
gtagatagga gagtggaaat aggaaaaaat agcttagaga gatttattta cgaacaggaa  60
gagtcacatg gcatgtgtcc agtcttccac atgataaata cccttcttac cttccttact  120
aggacttttg actctctctc tctctatcta tggtagtagt agtagtagta ttcattcatt  180
ctctctaatg gcagagctca caccctaaac acaaaccaga gcctctgaga gaaacaacca  240
caaactctcc cttaatcttg tcggtttcca tatctgctga aaatgaaagc tctgtacaga  300
agctctctct tgctcttgct cttgctcttc atctccgtgt gttttgcatc ttcttcttct  360
ccggtcactc agcaactcct aagcttcaaa aactctctcc cgaacccatc cctgctcccc  420
aactggctcc ctaaccaaag cccgtgcaca ttcagcggca tcagctgcaa cgacacagag  480
ctcacatcca tagacctcag ctccgtccct ctcagcacta acctaaccgt catcgccagc  540
ttcctcctta gcctggacca cctccagtca ctctccttaa aatccaccaa cctctccggt  600
cccgccgcca tgcctcctct ctcccactcc cagtgctcct cctcattaac ctccctagat  660
ctctcccaaa actccctctc tgcctccctc aacgacatgt cgtttctcgc ctcctgctcc  720
```

```
aacctccaat ccctcaacct ctcctccaac ctcctccaat tcggcccccc gccccactgg  780
aagctccacc acctccgctt cgccgacttc tcttacaaca agatttccgg ccccggcgtc  840
gtttcttggc ttctcaaccc cgtcatcgaa ctcctctctc tcaaaggcaa caaagtcacc  900
ggcgaaaccg acttctccgg ctcaatttct ctccagtatt tagacctttc ttccaacaac  960
ttttctgtta cgcttcctac tttcggcgag tgttcttcgc ttgagtattt ggacctctcc  1020
gctaacaagt acttgggcga cattgcacgc actctctccc cttgcaagag cctcgtttac  1080
cttaacgtct ccagcaacca gttctccggt ccggttcctt cccttccctc cggttcgcta  1140
cagtttgtgt accttgctgc aaaccacttc cacggccaga ttcctctctc cctcgccgac  1200
ctctgctcca ctctcctcca gctcgatctc tcctccaaca atctcaccgg cgctcttccc  1260
ggcgcgttcg gcgcgtgcac ttctcttcaa tcccttgaca tctccagcaa cctcttcgcc  1320
ggcgcgttgc cgatgtcggt tctcacgcaa atgaccagcc tgaaagagct cgcggttgcg  1380
ttcaacggct tcctcggtgc tctcccggag tctctgtcga agctctccgc tctggagttg  1440
ctggatctga gctccaacaa ctttagcggc tcaatccccg cctcgctgtg cggcggcggt  1500
gacgctggga ttaataataa tctgaaggaa ctttatctgc agaataaccg gttcacgggt  1560
tttattccgc ccacgctcag caactgttca aacctcgttg ctttggattt gagtttcaac  1620
ttcctcacgg ggactattcc tccgagccta gggtctcttt cgaatctcaa agacttcatc  1680
atctggctca accagctcca cggggagata ccgcaggagc tcatgtatct taaaagcctc  1740
gagaatttga tcctggattt caacgacttg actgggaaca ttccctctgg cctcgttaac  1800
tgcaccaagt tgaactggat ctccctctcc aacaacaggc tcagcggcga gattccgccg  1860
tggattggga agctttctaa tctcgccata ctcaagctca gcaataactc tttctccggc  1920
cggattccgc cggagctcgg cgactgtact agtttaatat ggttggatct gaatacaaat  1980
atgctcaccg ggcccattcc gccggagctg ttcaagcagt cggggaagat cgccgtgaat  2040
ttcatcagtg ggaagacgta tgtgtatata aagaacgatg ggagcaagga gtgccatggt  2100
gcggggaact tgcttgagtt tgcggggatc agtcagcagc agctgaacag gatttcgacg  2160
aggaacccct gcaatttcac tagggtttat ggaggtaagt tgcagccaac gtttaaccat  2220
aatggttcta tgatattttt ggatatctcg cacaacatgt tgtcagggag tattcccaag  2280
gagattgggg ccatgtacta tttgtacatt ctcaatttgg gtcacaataa tgtgtctggg  2340
agcattcctc aagagcttgg gaagatgaag aatctcaaca ttcttgatct gtcgaataat  2400
agactggagg gccaaattcc gcagagcctc acggggcttt ctttgctcac tgagattgac  2460
ttgtccaaca acttgcttac cgggacgatt cctgagtcgg gtcaatttga tactttccct  2520
gcggcgaagt ttcagaacaa ctctggtcta tgtggagttc ctctgggtcc gtgtggttcg  2580
gagccggcaa acaatggaaa tgcgcaacat atgaagtctc acaggaggca ggcttctctg  2640
gcggggagtg tggccatggg gttgttgttt tccctctttt gcgtctttgg tttgatcatt  2700
attgccattg agaccaggaa gaggaggaag aagaaggagg ctgctcttga agcctatggt  2760
gatggtaatt cccattcggg tccggccaat gtgagctgga agcacaccag tactcgggaa  2820
gctcttagca taaaccttgc aacatttgag aagccgctcc ggaagcttac ttttgcggac  2880
cttcttgacg ctaccaatgg ttttcacaac gacagtctca ttggctctgg cgggtttggg  2940
gatgtgtaca aggctcagtt gaaggatgga agtgttgtgg ctatcaagaa gctgattcat  3000
gttagcggac aaggggacag ggaattcacc gctgaaatgg agactattgg gaaaatcaag  3060
cacaggaacc ttgttcccct gttgggatac tgcaaggtag gggaagagag gctcttggtt  3120
tatgagtaca tgaaatatgg aagtttagag gatgttctac atgatcagaa gaaagctggg  3180
atcaagctga actgggccat taggcggaaa attgctattg gagctgctag ggggattgtct  3240
tttcttcacc acaattgtat cccccacatc attcatagag atatgaagtc gagcaatgtg  3300
ttacttgatg aaaacctgga agccagagtc tctgattttg gaatggctag gcttatgagt  3360
gctatggata cacatttgag tgtgagcaca ttggctggca caccggggta tgttcctccc  3420
gagtactatc agagcttcag atgctccaca aaaggtgatg tctacagtta tggtgtggtt  3480
ttgttggagc tgctaactgg gaaaaggcca acggactcgg ctgattttgg agataataat  3540
cttgttggat gggttaaaca acatgccaag ctgaaaatca gtgatatttt tgacccggag  3600
ctcatgaagg aagaccccaa tctggagatg gagcttttgc agcacttgaa gattgcggtt  3660
tcctgtttgg atgatcgacc gtggaggcgt ccgacgatga ttcaagtgat ggcaatgttc  3720
aaggagattc aggcgggatc cgggattgat tctcagtcaa ccatagccaa tgacgaggaa  3780
ggtttcaatg cagttgaaat ggtggagatg agcattaaag aagcccctga attgagcaag  3840
cattaggcat taaagtgtcg tgtggattct ttgggaaaca gacaagaaga gaggaggaga  3900
tgacggattc agctcccctc agtttttctc ttctttgccg cttcaaatta tttcagacat  3960
aagggaaaac ggttaaaagg ggaatgaatg cttttgatgt atgtattctt gttattttat  4020
acataaaaaa aagttgttta acttgtatat aaacagcttc agttgttacc atctgtgttt  4080
tcctagaatt ttcaaagtac ttttctcatt caaatataat cctgaaaagg ttctctgttc  4140
aatctgcgac cccagtgatg gcaactaagt ggatcaacag caacttttgc tccgatttgc  4200
gatataattt gtcaaaacat gcctctaaaa tcac                             4234
```

```
SEQ ID NO: 116          moltype = DNA  length = 4092
FEATURE                 Location/Qualifiers
misc_feature            1..4092
                        note = Synthetic polynucleotide
source                  1..4092
                        mol_type = other DNA
                        organism = synthetic construct
SEQUENCE: 116
gtagataatg gtagtagtag tagtagtatt cattcattct ctctaatggc agagctcaca  60
ccctaaacac aaaccagagc ctctgagaga aacaaccaca aactctccct taatcttgtc  120
ggtttccata tctgctgaaa atgaaagctc tgtacagaag ctctctcttg ctcttgctct  180
tgctcttcat ctccgtgtgt tttgcatctt cttcttctcc ggtcactcag caactcctaa  240
gcttcaaaaa ctctctcccg aacccatccc tgctccccaa ctggctccct aaccaaagcc  300
cgtgcacatt cagcggcatc agctgcaacg acacagagct cacatccata gacctcagct  360
ccgtccctct cagcactaac ctaaccgtca tcgccagctt cctccttagc ctggaccacc  420
tccagtcact ctccttaaaa tccaccaacc tctccggtcc cgccgccatg cctcctctct  480
cccactccca gtgctcctcc tcattaacct ccctagatct ctcccaaaac tccctctctg  540
cctccctcaa cgacatgtcg tttctcgcct cctgctccaa cctccaatcc ctcaacctct  600
cctccaacct cctccaattc ggcccccccgc cccactggaa gctccaccac ctccgcttcg  660
```

```
ccgacttctc ttacaacaag atttccggcc ccggcgtcgt ttcttggctt ctcaaccccg  720
tcatcgaact cctctctctc aaaggcaaca aagtcaccgg cgaaaccgac ttctccggct  780
caatttctct ccagtattta gacctttctt ccaacaactt ttctgttacg cttcctactt  840
tcggcgagtg ttcttcgctt gagtatttgg acctctccgc taacaagtac ttgggcgaca  900
ttgcacgcac tctctcccct tgcaagagcc tcgtttacct taacgtctcc agcaaccagt  960
tctccggtcc ggttccttcc cttccctccg gttcgctaca gtttgtgtac cttgctgcaa  1020
accacttcca cggccagatt cctctctccc tcgccgacct ctgctccact ctcctccagc  1080
tcgatctctc ctccaacaat ctcaccggcg ctcttcccgg cgcgttcggc gcgtgcactt  1140
ctcttcaatc ccttgacatc tccagcaacc tcttcgccgg cgcgttgccg atgtcggttc  1200
tcacgcaaat gaccagcctg aaagagctcg cggttgcgtt caacggcttc ctcggtgctc  1260
tcccggagtc tctgtcgaag ctctccgctc tggagttgct ggatctgagc tccaacaact  1320
ttagcggctc aatccccgcc tcgctgtgcg gcggcggtga cgctgggatt aataataatc  1380
tgaaggaact ttatctgcag aataaccggt tcacgggttt tattccgccc acgctcagca  1440
actgttcaaa cctcgttgct ttggatttga gtttcaactt cctcacgggg actattcctc  1500
cgagcctagg gtctctttcg aatctcaaag acttcatcat ctggctcaac cagctccacg  1560
gggagatacc gcaggagctc atgtatctta aaagcctcga gaatttgatc ctggatttca  1620
acgacttgac tgggaacatt ccctctggcc tcgttaactg caccaagttg aactggatct  1680
ccctctccaa caacaggctc agcggcgaga ttccgccgtg gattgggaag ctttctaatc  1740
tcgccatact caagctcagc aataactctt tctccggccg gattccgccg gagctcggcg  1800
actgtactag tttaatatgg ttggatctga atacaaatat gctcaccggg cccattccgc  1860
cggagctgtt caagcagtcg gggaagatcg ccgtgaattt catcagtggg aagacgtatg  1920
tgtatataaa gaacgatggg agcaaggagt gccatggtgc ggggaacttg cttgagtttg  1980
cggggatcag tcagcagcag ctgaacagga tttcgacgag gaacccctgc aatttcacta  2040
gggtttatgg aggtaagttg cagccaacgt ttaaccataa tggttctatg atatttttgg  2100
atatctcgca caacatgttg tcagggagta ttcccaagga gattggggcc atgtactatt  2160
tgtacattct caatttgggt cacaataatg tgtctgggag cattcctcaa gagcttggga  2220
agatgaagaa tctcaacatt cttgatctgt cgaataatag actggagggc caaattccgc  2280
agagcctcac ggggctttct ttgctcactg agattgactt gtccaacaac ttgcttaccg  2340
ggacgattcc tgagtcgggt caatttgata ctttccctgc ggcgaagttt cagaacaact  2400
ctggtctatg tggagttcct ctgggtccgt gtggttcgga gccggcaaac aatggaaatg  2460
cgcaacatat gaagtctcac aggaggcagg cttctctggc ggggagtgtg gccatggggt  2520
tgttgttttc cctcttttgc gtctttggtt tgatcattat tgccattgag accaggaaga  2580
ggaggaagaa gaaggaggct gctcttgaag cctatggtga tggtaattcc cattcgggtc  2640
cggccaatgt gagctggaag cacaccagta ctcgggaagc tcttagcata aaccttgcaa  2700
catttgagaa gccgctccgg aagcttactt ttgcggacct tcttgacgct accaatggtt  2760
ttcacaacga cagtctcatt ggctctggcg ggtttgggga tgtgtacaag gctcagttga  2820
aggatggaag tgttgtggct atcaagaagc tgattcatgt tagcggacaa ggggacaggg  2880
aattcaccgc tgaaatggag actattggga aaatcaagca caggaacctt gttcccctgt  2940
tgggatactg caaggtaggg gaagagaggc tcttggttta tgagtacatg aaatatggaa  3000
gtttagagga tgttctacat gatcagaaga aagctgggat caagctgaac tgggccatta  3060
ggcggaaaat tgctattgga gctgctaggg gattgtcttt tcttcaccac aattgtatcc  3120
cccacatcat tcatagagat atgaagtcga gcaatgtgtt acttgatgaa aacctggaag  3180
ccagagtctc tgattttgga atggctaggc ttatgagtgc tatggataca catttgagtg  3240
tgagcacatt ggctggcaca ccggggtatg ttcctcccga gtactatcag agcttcagat  3300
gctccacaaa aggtgatgtc tacagttatg gtgtggtttt gttggagctg ctaactggga  3360
aaaggccaac ggactcggct gattttggag ataataatct tgttggatgg gttaaacaac  3420
atgccaagct gaaaatcagt gatatttttg acccggagct catgaaggaa gaccccaatc  3480
tggagatgga gcttttgcag cacttgaaga ttgcggtttc ctgtttggat gatcgaccgt  3540
ggaggcgtcc gacgatgatt caagtgatgg caatgttcaa ggagattcag gcgggatccg  3600
ggattgattc tcagtcaacc atagccaatg acgaggaagg tttcaatgca gttgaaatgg  3660
tggagatgag cattaaagaa gcccctgaat tgagcaagca ttaggcatta aagtgtcgtg  3720
tggattcttt gggaaacaga caagaagaga ggaggagatg acggattcag ctcccctcag  3780
ttttttcctt ctttgccgct tcaaattatt tcagacataa gggaaaacgg ttaaaagggg  3840
aatgaatgct tttgatgtat gtattcttgt tattttatac ataaaaaaaa gttgtttaac  3900
ttgtatataa acagcttcag ttgttaccat ctgtgttttc ctagaatttt caaagtactt  3960
ttctcattca aatataatcc tgaaaaggtt ctctgttcaa tctgcgaccc cagtgatggc  4020
aactaagtgg atcaacagca acttttgctc cgatttgcga tataatttgt caaaacatgc  4080
ctctaaaatc ac                                                      4092
```

```
SEQ ID NO: 117         moltype = DNA  length = 4215
FEATURE                Location/Qualifiers
misc_feature           1..4215
                       note = Synthetic polynucleotide
source                 1..4215
                       mol_type = other DNA
                       organism = synthetic construct
SEQUENCE: 117
gtagatggag agtggaaata ggaaaaaata gcttagagag atttatttac gaacaggaag  60
agtcacatgg catgtgtcca gtcttccaca tgataaatac ccttcttacc ttccttacta  120
ggacttttga ctctctctct ctctatggta gtagtagtag tagtattcat tcattctctc  180
acaccctaaa cacaaaccag agcctctgag agaaacaacc acaaactctc ccttaatctt  240
gtcggtttcc atatctgctg aaaatgaaag ctctgtacag aagctctctc ttgctcttgc  300
tcttgctctt catctccgtg tgttttgcat cttcttcttc tccggtcact cagcaactcc  360
taagcttcaa aaactctctc ccgaacccat ccctgctccc caactggctc cctaaccaaa  420
gcccgtgcac attcagcggc atcagctgca acgacacaga gctcacatcc atagacctca  480
gctccgtccc tctcagcact aacctaaccg tcatcgccag cttcctcctt agcctggacc  540
acctccagtc actctcctta aaatccacca acctctccgg tcccgccgcc atgcctcctc  600
tctcccactc ccagtgctcc tcctcattaa cctccctaga tctctcccaa aactccctct  660
ctgcctccct caacgacatg tcgtttctcg cctcctgctc caacctccaa tccctcaacc  720
```

-continued

```
tctcctccaa cctcctccaa ttcggccccc cgccccactg gaagctccac cacctccgct  780
tcgccgactt ctcttacaac aagatttccg gccccggcgt cgtttcttgg cttctcaacc  840
ccgtcatcga actcctctct ctcaaaggca acaaagtcac cggcgaaacc gacttctccg  900
gctcaatttc tctccagtat ttagaccttt cttccaacaa cttttctgtt acgcttccta  960
ctttcggcga gtgttcttcg cttgagtatt tggacctctc cgctaacaag tacttgggcg  1020
acattgcacg cactctctcc ccttgcaaga gcctcgttta ccttaacgtc tccagcaacc  1080
agttctccgg tccggttcct tcccttccct ccggttcgct acagtttgtg taccttgctg  1140
caaaccactt ccacggccag attcctctct ccctcgccga cctctgctcc actctcctcc  1200
agctcgatct ctcctccaac aatctcaccg gcgctcttcc cggcgcgttc ggcgcgtgca  1260
cttctcttca atcccttgac atctccagca acctcttcgc cggcgcgttg ccgatgtcgg  1320
ttctcacgca aatgaccagc ctgaaagagc tcgcggttgc gttcaacggc ttcctcggtg  1380
ctctcccgga gtctctgtcg aagctctccg ctctggagtt gctggatctg agctccaaca  1440
actttagcgg ctcaatcccc gcctcgctgt gcggcggcgg tgacgctggg attaataata  1500
atctgaagga actttatctg cagaataacc ggttcacggg ttttattccg cccacgctca  1560
gcaactgttc aaacctcgtt gctttggatt tgagtttcaa cttcctcacg ggactattc  1620
ctccgagcct agggtctctt tcgaatctca aagacttcat catctggctc aaccagctcc  1680
acggggagat accgcaggag ctcatgtatc ttaaaagcct cgagaatttg atcctggatt  1740
tcaacgactt gactgggaac attccctctg gcctcgttaa ctgcaccaag ttgaactgga  1800
tctccctctc caacaacagg ctcagcggcg agattccgcc gtggattggg aagctttcta  1860
atctcgccat actcaagctc agcaataact ctttctccgg ccggattccg ccggagctcg  1920
gcgactgtac tagtttaata tggttggatc tgaatacaaa tatgctcacc gggcccattc  1980
cgcccggagct gttcaagcag tcggggaaga tcgccgtgaa tttcatcagt gggaagacgt  2040
atgtgtatat aaagaacgat gggagcaagg agtgccatgg tgcggggaac ttgcttgagt  2100
ttgcggggat cagtcagcag cagctgaaca ggatttcgac gaggaacccc tgcaatttca  2160
ctagggttta tggaggtaag ttgcagccaa cgtttaacca taatggttct atgatatttt  2220
tggatatctc gcacaacatg ttgtcaggga gtattcccaa ggagattggg gccatgtact  2280
atttgtacat tctcaatttg ggtcacaata atgtgtctgg gagcattcct caagagcttg  2340
ggaagatgaa gaatctcaac attcttgatc tgtcgaataa tagactggag ggccaaattc  2400
cgcagagcct cacggggctt tctttgctca ctgagattga cttgtccaac aacttgctta  2460
ccgggacgat tcctgagtcg ggtcaatttg atactttccc tgcggcgaag tttcagaaca  2520
actctggtct atgtggagtt cctctgggtc cgtgtggttc ggagccggca aacaatggaa  2580
atgcgcaaca tatgaagtct cacaggaggc aggcttctct ggcggggagt gtggccatgg  2640
ggttgttgtt ttccctcttt tgcgtctttg gtttgatcat tattgccatt gagaccagga  2700
agaggaggaa gaagaaggag gctgctcttg aagcctatgg tgatggtaat tcccattcgg  2760
gtccggccaa tgtgagctgg aagcacacca gtactcggga agctcttagc ataaaccttg  2820
caacatttga gaagccgctc cggaagctta cttttgcgga ccttcttgac gctaccaatg  2880
gttttcacaa cgacagtctc attggctctg gcgggtttgg ggatgtgtac aaggctcagt  2940
tgaaggatgg aagtgttgtg gctatcaaga agctgattca tgttagcgga caaggggaca  3000
gggaattcac cgctgaaatg gagactattg ggaaaatcaa gcacaggaac cttgttcccc  3060
tgttgggata ctgcaaggta ggggaagaga ggctcttggt ttatgagtac atgaaatatg  3120
gaagtttaga ggatgttcta catgatcaga agaaagctgg gatcaagctg aactgggcca  3180
ttaggcggaa aattgctatt ggagctgcta ggggattgtc ttttcttcac cacaattgta  3240
tcccccacat cattcataga gatatgaagt cgagcaatgt gttacttgat gaaaacctgg  3300
aagccagagt ctctgatttt ggaatggcta ggcttatgag tgctatggat acacatttga  3360
gtgtgagcac attggctggc acaccggggt atgttcctcc cgagtactat cagagcttca  3420
gatgctccac aaaaggtgat gtctacagtt atggtgtggt tttgttggag ctgctaactg  3480
ggaaaaggcc aacggactcg gctgattttg gagataataa tcttgttgga tgggttaaac  3540
aacatgccaa gctgaaaatc agtgatattt ttgacccgga gctcatgaag gaagacccca  3600
atctggagat ggagcttttg cagcacttga agattgcggt ttcctgtttg gatgatcgac  3660
cgtggaggcg tccgacgatg attcaagtga tggcaatgtt caaggagatt caggcgggat  3720
ccgggattga ttctcagtca accatagcca atgacgagga aggtttcaat gcagttgaaa  3780
tggtggagat gagcattaaa gaagcccctg aattgagcaa gcattaggca ttaaagtgtc  3840
gtgtggattc tttgggaaac agacaagaag agaggaggag atgacggatt cagctcccct  3900
cagtttttc cttctttgcc gcttcaaatt atttcagaca taagggaaaa cggttaaaag  3960
gggaatgaat gcttttgatg tatgtattct tgttatttta tacataaaaa aaagttgttt  4020
aacttgtata taaacagctt cagttgttac catctgtgtt ttcctagaat tttcaaagta  4080
cttttctcat tcaaatataa tcctgaaaag gttctctgtt caatctgcga ccccagtgat  4140
ggcaactaag tggatcaaca gcaacttttg ctccgatttg cgatataatt tgtcaaaaca  4200
tgcctctaaa atcac                                                  4215
```